(12) United States Patent
Keller et al.

(10) Patent No.: US 9,790,554 B2
(45) Date of Patent: Oct. 17, 2017

(54) COMPLEX SETS OF MIRNAS AS NON-INVASIVE BIOMARKERS FOR KIDNEY CANCER

(75) Inventors: Andreas Keller, Püttlingen (DE); Markus Beier, Weinheim (DE); Eckart Meese, Hütschenhausen (DE); Petra Leidinger, Wadern-Nunkirchen (DE); Anke Wendschlag, Mannheim (DE)

(73) Assignee: Hummingbird Diagnostics GmbH, Heidelberg (DE)

( * ) Notice: Subject to any disclaimer, the term of this patent is extended or adjusted under 35 U.S.C. 154(b) by 245 days.

(21) Appl. No.: 14/239,263

(22) PCT Filed: Aug. 3, 2012

(86) PCT No.: PCT/EP2012/065277
§ 371 (c)(1),
(2), (4) Date: Feb. 18, 2014

(87) PCT Pub. No.: WO2013/026684
PCT Pub. Date: Feb. 28, 2013

(65) Prior Publication Data
US 2014/0193822 A1    Jul. 10, 2014

(30) Foreign Application Priority Data

Aug. 19, 2011    (EP) ..................... 11178149

(51) Int. Cl.
| C40B 30/04 | (2006.01) |
| C12Q 1/68 | (2006.01) |
| C12N 15/11 | (2006.01) |
| C07H 21/02 | (2006.01) |

(52) U.S. Cl.
CPC ..... *C12Q 1/6886* (2013.01); *C12Q 2600/158* (2013.01); *C12Q 2600/178* (2013.01)

(58) Field of Classification Search
CPC ........... C12C 1/6886; C12C 2600/158; C12C 2600/178
See application file for complete search history.

(56) References Cited

FOREIGN PATENT DOCUMENTS

WO    WO 2010/145035    * 12/2010 ............. C40B 40/60

* cited by examiner

*Primary Examiner* — Reza Ghafoorian
(74) *Attorney, Agent, or Firm* — Kilpatrick Townsend & Stockton LLP

(57) ABSTRACT

The present invention relates to non-invasive methods, kits and means for diagnosing and/or prognosing of kidney cancer in a body fluid sample from a subject. Further, the present invention relates to set of polynucleotides or sets of primer pairs for detecting sets of miRNAs for diagnosing and/or prognosing of kidney cancer in a body fluid sample from a subject. In addition, the present invention relates to sets of miRNAs for diagnosing and/or prognosing of kidney cancer in a body fluid sample from a subject.

6 Claims, 40 Drawing Sheets

Figure 1

| SEQ ID NO | miRNA | median g1 | median g2 | qmedian | logqmedian | wmw_rawp | wmw_adjp | ttest_raw p | ttest_adjp | AUC |
|---|---|---|---|---|---|---|---|---|---|---|
| 1 | hsa-miR-106a | 14166 | 4325 | 3.28 | 1.19 | 3.70E-06 | 1.74E-04 | 5.09E-11 | 4.31E-08 | 0.96 |
| 2 | hsa-miR-20b | 6078 | 1812 | 3.36 | 1.21 | 7.39E-07 | 1.74E-04 | 1.71E-10 | 7.25E-08 | 0.99 |
| 3 | hsa-miR-523 | 132 | 40 | 3.29 | 1.19 | 3.38E-06 | 1.74E-04 | 5.59E-10 | 1.58E-07 | 0.96 |
| 4 | hsa-miR-640 | 151 | 7 | 22.44 | 3.11 | 2.15E-06 | 1.74E-04 | 1.42E-09 | 3.01E-07 | 0.97 |
| 5 | hsa-miR-1251 | 194 | 83 | 2.34 | 0.85 | 6.21E-09 | 5.26E-06 | 2.80E-09 | 4.75E-07 | 0.98 |
| 6 | hsa-miR-20a | 7876 | 1963 | 4.01 | 1.39 | 1.37E-06 | 1.74E-04 | 5.80E-09 | 8.20E-07 | 0.98 |
| 7 | hsa-miR-17 | 10953 | 4967 | 2.21 | 0.79 | 1.77E-05 | 3.87E-04 | 1.22E-07 | 1.40E-05 | 0.92 |
| 8 | hsa-miR-34a* | 136 | 1 | 102.14 | 4.63 | 3.67E-06 | 1.74E-04 | 1.42E-07 | 1.40E-05 | 0.96 |
| 9 | hsa-miR-496 | 123 | 66 | 1.87 | 0.62 | 2.93E-06 | 1.74E-04 | 1.49E-07 | 1.40E-05 | 0.96 |
| 10 | hsa-let-7d* | 69 | 332 | 0.21 | -1.58 | 2.93E-06 | 1.74E-04 | 3.07E-07 | 2.61E-05 | 0.04 |
| 11 | hsa-miR-19b | 11562 | 17175 | 0.67 | -0.40 | 7.37E-06 | 2.19E-04 | 4.57E-07 | 3.53E-05 | 0.06 |
| 12 | hsa-miR-518a-3p | 96 | 1 | 95.79 | 4.56 | 3.21E-05 | 5.23E-04 | 5.10E-07 | 3.60E-05 | 0.91 |
| 13 | hsa-miR-516b | 57 | 1 | 57.10 | 4.04 | 1.78E-05 | 3.87E-04 | 5.80E-07 | 3.78E-05 | 0.92 |
| 14 | hsa-miR-367* | 110 | 25 | 4.47 | 1.50 | 4.69E-05 | 6.75E-04 | 6.27E-07 | 3.80E-05 | 0.90 |
| 15 | hsa-miR-93 | 6841 | 2745 | 2.49 | 0.91 | 2.09E-05 | 3.96E-04 | 7.64E-07 | 4.32E-05 | 0.92 |
| 16 | hsa-miR-891b | 123 | 15 | 8.23 | 2.11 | 5.19E-06 | 2.02E-04 | 8.56E-07 | 4.52E-05 | 0.95 |
| 17 | hsa-miR-450b-5p | 95 | 48 | 1.98 | 0.69 | 5.25E-06 | 2.02E-04 | 9.60E-07 | 4.52E-05 | 0.95 |
| 18 | hsa-miR-1260 | 2295 | 4913 | 0.47 | -0.76 | 4.17E-06 | 1.86E-04 | 9.27E-07 | 4.52E-05 | 0.05 |
| 19 | hsa-miR-221* | 151 | 73 | 2.08 | 0.73 | 2.30E-06 | 1.74E-04 | 1.74E-06 | 7.78E-05 | 0.92 |
| 20 | hsa-miR-224 | 34 | 107 | 0.32 | -1.13 | 2.92E-06 | 1.74E-04 | 2.01E-06 | 8.54E-05 | 0.04 |
| 21 | hsa-miR-32* | 51 | 8 | 6.33 | 1.84 | 5.59E-05 | 7.53E-04 | 2.34E-06 | 9.44E-05 | 0.90 |
| 22 | hsa-miR-934 | 128 | 43 | 2.97 | 1.09 | 2.40E-05 | 4.20E-04 | 2.82E-06 | 1.09E-04 | 0.92 |
| 23 | hsa-miR-654-5p | 250 | 127 | 1.97 | 0.68 | 5.34E-05 | 7.31E-04 | 3.28E-06 | 1.18E-04 | 0.90 |
| 24 | hsa-miR-554 | 133 | 36 | 3.69 | 1.31 | 4.12E-05 | 6.13E-04 | 3.38E-06 | 1.18E-04 | 0.90 |
| 25 | hsa-miR-633 | 128 | 30 | 4.29 | 1.46 | 3.38E-06 | 1.74E-04 | 3.47E-06 | 1.18E-04 | 0.96 |
| 26 | hsa-miR-580 | 68 | 140 | 0.48 | -0.72 | 2.30E-06 | 1.74E-04 | 5.66E-06 | 1.85E-04 | 0.08 |
| 27 | hsa-miR-106b | 19895 | 10468 | 1.90 | 0.64 | 6.14E-05 | 7.89E-04 | 6.11E-06 | 1.92E-04 | 0.89 |
| 28 | hsa-miR-548m | 1 | 91 | 0.01 | -4.51 | 1.60E-05 | 3.87E-04 | 8.59E-06 | 2.60E-04 | 0.08 |
| 29 | hsa-miR-606 | 126 | 36 | 3.48 | 1.25 | 2.86E-06 | 1.74E-04 | 1.05E-05 | 3.08E-04 | 0.92 |
| 30 | hsa-miR-216b | 234 | 88 | 2.65 | 0.98 | 1.61E-05 | 3.87E-04 | 1.50E-05 | 4.23E-04 | 0.93 |
| 31 | hsa-miR-425* | 91 | 181 | 0.50 | -0.69 | 2.66E-04 | 1.93E-03 | 1.58E-05 | 4.31E-04 | 0.14 |
| 32 | hsa-miR-139-3p | 92 | 53 | 1.74 | 0.55 | 6.62E-06 | 2.19E-04 | 1.98E-05 | 5.25E-04 | 0.91 |
| 33 | hsa-miR-103 | 10287 | 4023 | 2.56 | 0.94 | 1.27E-04 | 1.27E-03 | 2.06E-05 | 5.30E-04 | 0.88 |
| 34 | hsa-miR-607 | 132 | 68 | 1.96 | 0.67 | 1.55E-04 | 1.43E-03 | 2.20E-05 | 5.49E-04 | 0.87 |
| 35 | hsa-miR-200a* | 118 | 53 | 2.23 | 0.80 | 3.85E-05 | 5.83E-04 | 2.36E-05 | 5.71E-04 | 0.91 |
| 36 | hsa-miR-561 | 72 | 20 | 3.55 | 1.27 | 9.99E-05 | 1.07E-03 | 2.49E-05 | 5.72E-04 | 0.88 |
| 37 | hsa-miR-1298 | 84 | 30 | 2.86 | 1.05 | 5.90E-05 | 7.82E-04 | 2.50E-05 | 5.72E-04 | 0.87 |
| 38 | hsa-miR-25* | 71 | 140 | 0.51 | -0.68 | 4.39E-06 | 1.86E-04 | 2.65E-05 | 5.75E-04 | 0.09 |
| 39 | hsa-miR-373 | 1 | 71 | 0.01 | -4.26 | 2.95E-07 | 1.25E-04 | 2.62E-05 | 5.75E-04 | 0.03 |
| 40 | hsa-miR-409-5p | 111 | 72 | 1.54 | 0.43 | 1.86E-04 | 1.59E-03 | 3.28E-05 | 6.94E-04 | 0.87 |
| 41 | hsa-miR-18a | 2413 | 1155 | 2.09 | 0.74 | 2.74E-05 | 4.65E-04 | 3.40E-05 | 7.02E-04 | 0.91 |
| 42 | hsa-miR-624 | 88 | 159 | 0.55 | -0.59 | 8.17E-05 | 9.24E-04 | 3.66E-05 | 7.39E-04 | 0.13 |
| 43 | hsa-miR-652 | 2096 | 1037 | 2.02 | 0.70 | 1.84E-04 | 1.59E-03 | 3.95E-05 | 7.55E-04 | 0.87 |
| 44 | hsa-miR-646 | 369 | 179 | 2.06 | 0.72 | 1.97E-05 | 3.96E-04 | 3.90E-05 | 7.55E-04 | 0.92 |
| 45 | hsa-miR-505 | 37 | 104 | 0.36 | -1.03 | 1.45E-04 | 1.37E-03 | 4.01E-05 | 7.55E-04 | 0.13 |
| 46 | hsa-miR-302f | 1 | 70 | 0.01 | -4.25 | 7.01E-06 | 2.19E-04 | 4.26E-05 | 7.72E-04 | 0.07 |
| 47 | hsa-miR-218-1* | 125 | 51 | 2.44 | 0.89 | 3.56E-05 | 5.48E-04 | 4.28E-05 | 7.72E-04 | 0.88 |

Figure 1 (cont.)

| 48 | hsa-miR-595 | 139 | 37 | 3.81 | 1.34 | 6.96E-04 | 3.62E-03 | 4.40E-05 | 7.77E-04 | 0.83 |
|---|---|---|---|---|---|---|---|---|---|---|
| 49 | hsa-miR-499-3p | 142 | 92 | 1.54 | 0.43 | 8.89E-05 | 9.92E-04 | 5.65E-05 | 8.55E-04 | 0.89 |
| 50 | hsa-miR-513a-3p | 73 | 26 | 2.82 | 1.04 | 2.06E-04 | 1.72E-03 | 5.87E-05 | 8.55E-04 | 0.87 |
| 51 | hsa-miR-512-5p | 84 | 27 | 3.07 | 1.12 | 2.66E-04 | 1.93E-03 | 5.57E-05 | 8.55E-04 | 0.86 |
| 52 | hsa-miR-604 | 99 | 26 | 3.85 | 1.35 | 6.90E-05 | 8.25E-04 | 6.07E-05 | 8.55E-04 | 0.89 |
| 53 | hsa-miR-513a-5p | 49 | 139 | 0.35 | -1.04 | 1.65E-04 | 1.49E-03 | 6.15E-05 | 8.55E-04 | 0.13 |
| 54 | hsa-miR-92a | 16394 | 11562 | 1.42 | 0.35 | 6.82E-05 | 8.25E-04 | 5.99E-05 | 8.55E-04 | 0.89 |
| 55 | hsa-miR-556-5p | 182 | 108 | 1.69 | 0.52 | 1.31E-04 | 1.27E-03 | 5.30E-05 | 8.55E-04 | 0.86 |
| 56 | hsa-miR-596 | 104 | 50 | 2.07 | 0.73 | 1.14E-04 | 1.17E-03 | 5.95E-05 | 8.55E-04 | 0.88 |
| 57 | hsa-miR-411 | 88 | 40 | 2.19 | 0.78 | 1.14E-04 | 1.17E-03 | 5.79E-05 | 8.55E-04 | 0.88 |
| 58 | hsa-miR-454 | 258 | 105 | 2.45 | 0.90 | 4.47E-04 | 2.71E-03 | 5.07E-05 | 8.55E-04 | 0.85 |
| 59 | hsa-miR-593* | 413 | 208 | 1.99 | 0.69 | 6.47E-05 | 8.19E-04 | 5.96E-05 | 8.55E-04 | 0.89 |
| 60 | hsa-miR-28-3p | 161 | 325 | 0.49 | -0.70 | 6.90E-05 | 8.25E-04 | 5.92E-05 | 8.55E-04 | 0.11 |
| 61 | hsa-miR-127-5p | 182 | 79 | 2.30 | 0.83 | 1.74E-05 | 3.87E-04 | 5.06E-05 | 8.55E-04 | 0.89 |
| 62 | hsa-miR-1233 | 142 | 80 | 1.78 | 0.58 | 2.09E-05 | 3.96E-04 | 6.75E-05 | 8.85E-04 | 0.89 |
| 63 | hsa-miR-328 | 61 | 219 | 0.28 | -1.28 | 5.00E-05 | 6.95E-04 | 6.57E-05 | 8.85E-04 | 0.13 |
| 64 | hsa-miR-525-3p | 106 | 57 | 1.86 | 0.62 | 3.56E-05 | 5.48E-04 | 6.78E-05 | 8.85E-04 | 0.88 |
| 65 | hsa-miR-33b | 204 | 97 | 2.11 | 0.75 | 1.19E-05 | 3.38E-04 | 6.58E-05 | 8.85E-04 | 0.90 |
| 66 | hsa-miR-33a | 154 | 89 | 1.72 | 0.55 | 1.46E-04 | 1.37E-03 | 7.10E-05 | 9.13E-04 | 0.88 |
| 67 | hsa-miR-139-5p | 213 | 142 | 1.50 | 0.41 | 1.12E-04 | 1.17E-03 | 7.28E-05 | 9.22E-04 | 0.86 |
| 68 | hsa-miR-1283 | 145 | 79 | 1.84 | 0.61 | 1.65E-04 | 1.49E-03 | 7.69E-05 | 9.59E-04 | 0.87 |
| 69 | hsa-miR-34b* | 68 | 118 | 0.58 | -0.54 | 6.62E-06 | 2.19E-04 | 7.93E-05 | 9.74E-04 | 0.09 |
| 70 | hsa-miR-491-3p | 128 | 67 | 1.91 | 0.65 | 1.86E-04 | 1.59E-03 | 9.38E-05 | 1.14E-03 | 0.87 |
| 71 | hsa-miR-518d-3p | 108 | 42 | 2.60 | 0.96 | 1.31E-04 | 1.27E-03 | 9.58E-05 | 1.14E-03 | 0.86 |
| 72 | hsa-miR-216a | 251 | 164 | 1.53 | 0.43 | 1.74E-05 | 3.87E-04 | 9.76E-05 | 1.15E-03 | 0.89 |
| 73 | hsa-miR-1227 | 78 | 200 | 0.39 | -0.94 | 6.90E-05 | 8.25E-04 | 1.02E-04 | 1.19E-03 | 0.11 |
| 74 | hsa-miR-132* | 1 | 48 | 0.02 | -3.87 | 1.56E-06 | 1.74E-04 | 1.19E-04 | 1.30E-03 | 0.06 |
| 75 | hsa-miR-936 | 60 | 148 | 0.41 | -0.90 | 7.84E-05 | 9.04E-04 | 1.16E-04 | 1.30E-03 | 0.11 |
| 76 | hsa-miR-488 | 1 | 66 | 0.02 | -3.80 | 2.21E-05 | 4.07E-04 | 1.19E-04 | 1.30E-03 | 0.09 |
| 77 | hsa-miR-455-5p | 31 | 83 | 0.38 | -0.98 | 2.98E-04 | 2.09E-03 | 1.17E-04 | 1.30E-03 | 0.14 |
| 78 | hsa-miR-558 | 127 | 43 | 2.93 | 1.07 | 3.35E-04 | 2.17E-03 | 1.15E-04 | 1.30E-03 | 0.85 |
| 79 | hsa-miR-491-5p | 120 | 222 | 0.54 | -0.62 | 1.46E-04 | 1.37E-03 | 1.24E-04 | 1.31E-03 | 0.13 |
| 80 | hsa-miR-105 | 59 | 11 | 5.49 | 1.70 | 4.72E-04 | 2.82E-03 | 1.23E-04 | 1.31E-03 | 0.84 |
| 81 | hsa-miR-192 | 5661 | 9165 | 0.62 | -0.48 | 2.36E-05 | 4.20E-04 | 1.25E-04 | 1.31E-03 | 0.08 |
| 82 | hsa-miR-664 | 249 | 903 | 0.28 | -1.29 | 2.42E-05 | 4.20E-04 | 1.34E-04 | 1.39E-03 | 0.08 |
| 83 | hsa-miR-145 | 152 | 460 | 0.33 | -1.11 | 6.08E-05 | 7.89E-04 | 1.41E-04 | 1.44E-03 | 0.10 |
| 84 | hsa-miR-517c | 17 | 70 | 0.24 | -1.43 | 2.10E-05 | 3.96E-04 | 1.57E-04 | 1.59E-03 | 0.08 |
| 85 | hsa-miR-483-3p | 24 | 128 | 0.19 | -1.66 | 3.67E-04 | 2.31E-03 | 1.63E-04 | 1.62E-03 | 0.15 |
| 86 | hsa-miR-1284 | 43 | 124 | 0.34 | -1.07 | 9.46E-05 | 1.04E-03 | 1.68E-04 | 1.65E-03 | 0.11 |
| 87 | hsa-miR-1261 | 1 | 67 | 0.02 | -3.82 | 1.67E-05 | 3.87E-04 | 1.73E-04 | 1.68E-03 | 0.08 |
| 88 | hsa-miR-650 | 164 | 96 | 1.72 | 0.54 | 3.36E-04 | 2.17E-03 | 1.86E-04 | 1.76E-03 | 0.85 |
| 89 | hsa-miR-1538 | 95 | 146 | 0.65 | -0.43 | 9.08E-07 | 1.74E-04 | 1.87E-04 | 1.76E-03 | 0.07 |
| 90 | hsa-miR-555 | 56 | 10 | 5.54 | 1.71 | 5.89E-04 | 3.14E-03 | 1.88E-04 | 1.76E-03 | 0.84 |
| 91 | hsa-miR-653 | 57 | 105 | 0.55 | -0.60 | 5.00E-05 | 6.95E-04 | 1.89E-04 | 1.76E-03 | 0.13 |
| 92 | hsa-miR-568 | 139 | 71 | 1.96 | 0.67 | 9.16E-04 | 4.43E-03 | 2.01E-04 | 1.83E-03 | 0.82 |
| 93 | hsa-miR-548a-5p | 32 | 1 | 32.33 | 3.48 | 2.21E-04 | 1.78E-03 | 2.01E-04 | 1.83E-03 | 0.86 |
| 94 | hsa-miR-181a-2* | 99 | 242 | 0.41 | -0.90 | 1.01E-04 | 1.07E-03 | 2.08E-04 | 1.87E-03 | 0.12 |
| 95 | hsa-miR-1296 | 74 | 26 | 2.85 | 1.05 | 2.64E-04 | 1.93E-03 | 2.18E-04 | 1.90E-03 | 0.86 |
| 96 | hsa-miR-655 | 79 | 25 | 3.09 | 1.13 | 1.02E-03 | 4.72E-03 | 2.14E-04 | 1.90E-03 | 0.82 |
| 97 | hsa-miR-628-3p | 179 | 341 | 0.53 | -0.64 | 1.86E-04 | 1.59E-03 | 2.18E-04 | 1.90E-03 | 0.13 |
| 98 | hsa-miR-1305 | 136 | 35 | 3.93 | 1.37 | 7.49E-06 | 2.19E-04 | 2.35E-04 | 2.03E-03 | 0.94 |
| 99 | hsa-miR-181d | 28 | 79 | 0.36 | -1.01 | 3.36E-04 | 2.17E-03 | 2.38E-04 | 2.04E-03 | 0.15 |
| 100 | hsa-miR-30c-1* | 69 | 160 | 0.43 | -0.85 | 5.46E-04 | 2.98E-03 | 2.56E-04 | 2.17E-03 | 0.17 |
| 101 | hsa-miR-208b | 116 | 60 | 1.93 | 0.66 | 5.00E-04 | 2.93E-03 | 2.75E-04 | 2.31E-03 | 0.84 |
| 102 | hsa-miR-99b | 156 | 274 | 0.57 | -0.56 | 2.99E-05 | 4.97E-04 | 2.83E-04 | 2.34E-03 | 0.12 |

Figure 1 (cont.)

| 103 | hsa-miR-548p | 191 | 89 | 2.15 | 0.77 | 2.50E-04 | 1.91E-03 | 2.84E-04 | 2.34E-03 | 0.86 |
|---|---|---|---|---|---|---|---|---|---|---|
| 104 | hsa-miR-570 | 117 | 59 | 2.00 | 0.69 | 3.16E-04 | 2.16E-03 | 2.87E-04 | 2.34E-03 | 0.84 |
| 105 | hsa-miR-612 | 101 | 63 | 1.59 | 0.46 | 2.37E-04 | 1.86E-03 | 3.02E-04 | 2.44E-03 | 0.85 |
| 106 | hsa-miR-96* | 246 | 173 | 1.42 | 0.35 | 2.35E-03 | 8.68E-03 | 3.15E-04 | 2.52E-03 | 0.80 |
| 107 | hsa-miR-505* | 177 | 269 | 0.66 | -0.42 | 4.77E-04 | 2.83E-03 | 3.25E-04 | 2.53E-03 | 0.17 |
| 108 | hsa-miR-193b* | 40 | 159 | 0.25 | -1.39 | 3.50E-04 | 2.25E-03 | 3.23E-04 | 2.53E-03 | 0.15 |
| 109 | hsa-miR-143* | 169 | 83 | 2.03 | 0.71 | 1.41E-03 | 5.98E-03 | 3.25E-04 | 2.53E-03 | 0.82 |
| 110 | hsa-miR-380* | 124 | 68 | 1.84 | 0.61 | 4.17E-04 | 2.56E-03 | 3.59E-04 | 2.77E-03 | 0.83 |
| 111 | hsa-miR-374a | 450 | 235 | 1.92 | 0.65 | 2.02E-03 | 7.69E-03 | 3.75E-04 | 2.87E-03 | 0.81 |
| 112 | hsa-miR-548i | 12 | 52 | 0.23 | -1.49 | 3.15E-04 | 2.16E-03 | 3.92E-04 | 2.97E-03 | 0.15 |
| 113 | hsa-miR-1272 | 177 | 103 | 1.71 | 0.54 | 5.46E-04 | 2.98E-03 | 3.97E-04 | 2.98E-03 | 0.83 |
| 114 | hsa-miR-559 | 92 | 41 | 2.24 | 0.81 | 9.20E-04 | 4.43E-03 | 4.05E-04 | 3.01E-03 | 0.83 |
| 115 | hsa-miR-548c-3p | 64 | 20 | 3.21 | 1.17 | 1.02E-03 | 4.72E-03 | 4.28E-04 | 3.12E-03 | 0.82 |
| 116 | hsa-miR-1321 | 3 | 70 | 0.04 | -3.26 | 6.23E-06 | 2.19E-04 | 4.30E-04 | 3.12E-03 | 0.06 |
| 117 | hsa-miR-892a | 23 | 66 | 0.35 | -1.04 | 3.35E-04 | 2.17E-03 | 4.28E-04 | 3.12E-03 | 0.15 |
| 118 | hsa-miR-302a | 6 | 69 | 0.08 | -2.48 | 5.74E-04 | 3.10E-03 | 4.42E-04 | 3.17E-03 | 0.17 |
| 119 | hsa-let-7a* | 10 | 65 | 0.15 | -1.90 | 2.56E-04 | 1.92E-03 | 4.83E-04 | 3.44E-03 | 0.14 |
| 120 | hsa-miR-620 | 23 | 51 | 0.45 | -0.79 | 7.13E-04 | 3.66E-03 | 4.89E-04 | 3.46E-03 | 0.17 |
| 121 | hsa-miR-548n | 57 | 8 | 6.78 | 1.91 | 1.86E-03 | 7.44E-03 | 4.98E-04 | 3.49E-03 | 0.81 |
| 122 | hsa-miR-144 | 3906 | 2745 | 1.42 | 0.35 | 3.48E-03 | 1.19E-02 | 5.02E-04 | 3.49E-03 | 0.79 |
| 123 | hsa-miR-188-3p | 190 | 104 | 1.83 | 0.61 | 5.46E-04 | 2.98E-03 | 5.12E-04 | 3.53E-03 | 0.83 |
| 124 | hsa-miR-658 | 42 | 144 | 0.29 | -1.23 | 1.44E-05 | 3.83E-04 | 5.37E-04 | 3.67E-03 | 0.10 |
| 125 | hsa-miR-154 | 1 | 49 | 0.02 | -3.89 | 2.35E-06 | 1.74E-04 | 5.55E-04 | 3.68E-03 | 0.06 |
| 126 | hsa-miR-939 | 63 | 139 | 0.45 | -0.80 | 2.37E-04 | 1.86E-03 | 5.49E-04 | 3.68E-03 | 0.15 |
| 127 | hsa-miR-1226* | 245 | 147 | 1.67 | 0.51 | 1.56E-03 | 6.41E-03 | 5.54E-04 | 3.68E-03 | 0.81 |
| 128 | hsa-miR-495 | 128 | 64 | 2.00 | 0.69 | 5.46E-04 | 2.98E-03 | 5.50E-04 | 3.68E-03 | 0.83 |
| 129 | hsa-miR-1274a | 187 | 346 | 0.54 | -0.62 | 1.03E-03 | 4.72E-03 | 5.61E-04 | 3.69E-03 | 0.18 |
| 130 | hsa-miR-31* | 237 | 86 | 2.75 | 1.01 | 2.50E-04 | 1.91E-03 | 5.87E-04 | 3.83E-03 | 0.86 |
| 131 | hsa-miR-32 | 186 | 102 | 1.82 | 0.60 | 1.44E-05 | 3.83E-04 | 6.30E-04 | 4.08E-03 | 0.90 |
| 132 | hsa-miR-9* | 136 | 78 | 1.75 | 0.56 | 1.20E-03 | 5.31E-03 | 6.64E-04 | 4.12E-03 | 0.82 |
| 133 | hsa-miR-769-3p | 12 | 53 | 0.23 | -1.47 | 3.96E-04 | 2.47E-03 | 6.66E-04 | 4.12E-03 | 0.15 |
| 134 | hsa-miR-147b | 57 | 24 | 2.37 | 0.86 | 1.33E-03 | 5.76E-03 | 6.53E-04 | 4.12E-03 | 0.81 |
| 135 | hsa-miR-20a* | 200 | 133 | 1.50 | 0.41 | 2.09E-05 | 3.96E-04 | 6.64E-04 | 4.12E-03 | 0.89 |
| 136 | hsa-miR-340 | 223 | 353 | 0.63 | -0.46 | 4.69E-05 | 6.75E-04 | 6.54E-04 | 4.12E-03 | 0.10 |
| 137 | hsa-miR-296-5p | 221 | 527 | 0.42 | -0.87 | 6.99E-06 | 2.19E-04 | 6.60E-04 | 4.12E-03 | 0.06 |
| 138 | hsa-miR-1270 | 43 | 102 | 0.43 | -0.85 | 2.37E-04 | 1.86E-03 | 7.36E-04 | 4.41E-03 | 0.15 |
| 139 | hsa-miR-19a* | 91 | 14 | 6.37 | 1.85 | 1.38E-03 | 5.91E-03 | 7.29E-04 | 4.41E-03 | 0.82 |
| 140 | hsa-miR-1909 | 136 | 213 | 0.64 | -0.45 | 5.00E-04 | 2.93E-03 | 7.38E-04 | 4.41E-03 | 0.16 |
| 141 | hsa-miR-1246 | 2 | 65 | 0.03 | -3.52 | 7.55E-05 | 8.90E-04 | 7.26E-04 | 4.41E-03 | 0.12 |
| 142 | hsa-miR-411* | 82 | 43 | 1.93 | 0.66 | 4.22E-04 | 2.58E-03 | 7.34E-04 | 4.41E-03 | 0.85 |
| 143 | hsa-let-7d | 4226 | 2807 | 1.51 | 0.41 | 2.00E-03 | 7.69E-03 | 7.44E-04 | 4.41E-03 | 0.81 |
| 144 | hsa-miR-18b | 546 | 266 | 2.05 | 0.72 | 3.56E-05 | 5.48E-04 | 7.96E-04 | 4.69E-03 | 0.88 |
| 145 | hsa-miR-515-5p | 239 | 153 | 1.56 | 0.45 | 2.99E-04 | 2.09E-03 | 8.27E-04 | 4.80E-03 | 0.86 |
| 146 | hsa-miR-1224-5p | 39 | 91 | 0.43 | -0.85 | 1.12E-03 | 5.09E-03 | 8.23E-04 | 4.80E-03 | 0.18 |
| 147 | hsa-let-7g* | 177 | 122 | 1.45 | 0.37 | 1.03E-03 | 4.72E-03 | 8.75E-04 | 5.05E-03 | 0.82 |
| 148 | hsa-miR-552 | 33 | 96 | 0.35 | -1.05 | 2.05E-04 | 1.72E-03 | 8.83E-04 | 5.06E-03 | 0.15 |
| 149 | hsa-miR-508-5p | 167 | 82 | 2.04 | 0.71 | 5.30E-04 | 2.98E-03 | 8.89E-04 | 5.06E-03 | 0.84 |
| 150 | hsa-miR-545* | 47 | 11 | 4.43 | 1.49 | 1.65E-03 | 6.70E-03 | 9.09E-04 | 5.13E-03 | 0.81 |
| 151 | hsa-miR-1291 | 182 | 114 | 1.60 | 0.47 | 1.20E-03 | 5.31E-03 | 9.13E-04 | 5.13E-03 | 0.82 |
| 152 | hsa-miR-346 | 96 | 135 | 0.71 | -0.34 | 1.56E-03 | 6.41E-03 | 9.35E-04 | 5.20E-03 | 0.19 |
| 153 | hsa-miR-24-2* | 235 | 141 | 1.66 | 0.51 | 3.50E-03 | 1.19E-02 | 9.38E-04 | 5.20E-03 | 0.79 |
| 154 | hsa-miR-484 | 8278 | 13074 | 0.63 | -0.46 | 2.96E-03 | 1.04E-02 | 9.55E-04 | 5.26E-03 | 0.21 |
| 155 | hsa-miR-720 | 4671 | 12225 | 0.38 | -0.96 | 9.86E-05 | 1.07E-03 | 9.92E-04 | 5.43E-03 | 0.12 |
| 156 | hsa-miR-503 | 420 | 257 | 1.64 | 0.49 | 5.29E-04 | 2.98E-03 | 1.00E-03 | 5.46E-03 | 0.84 |
| 157 | hsa-miR-219-2-3p | 10 | 80 | 0.12 | -2.10 | 3.53E-04 | 2.25E-03 | 1.03E-03 | 5.46E-03 | 0.15 |

Figure 1 (cont.)

| | | | | | | | | | | |
|---|---|---|---|---|---|---|---|---|---|---|
| 158 | hsa-miR-30c | 1795 | 3101 | 0.58 | -0.55 | 2.48E-04 | 1.91E-03 | 1.04E-03 | 5.46E-03 | 0.14 |
| 159 | hsa-miR-1180 | 71 | 170 | 0.42 | -0.87 | 6.23E-04 | 3.28E-03 | 1.02E-03 | 5.46E-03 | 0.18 |
| 160 | hsa-miR-487b | 90 | 49 | 1.85 | 0.61 | 8.26E-04 | 4.12E-03 | 1.04E-03 | 5.46E-03 | 0.83 |
| 161 | hsa-miR-422a | 145 | 330 | 0.44 | -0.82 | 3.49E-03 | 1.19E-02 | 1.03E-03 | 5.46E-03 | 0.21 |
| 162 | hsa-miR-29a | 760 | 1041 | 0.73 | -0.32 | 1.53E-04 | 1.43E-03 | 1.11E-03 | 5.79E-03 | 0.13 |
| 163 | hsa-miR-509-3-5p | 394 | 171 | 2.31 | 0.84 | 2.74E-04 | 1.97E-03 | 1.13E-03 | 5.87E-03 | 0.84 |
| 164 | hsa-miR-217 | 212 | 111 | 1.91 | 0.65 | 2.10E-04 | 1.73E-03 | 1.14E-03 | 5.87E-03 | 0.87 |
| 165 | hsa-miR-26b* | 23 | 71 | 0.32 | -1.14 | 5.09E-04 | 2.94E-03 | 1.18E-03 | 6.05E-03 | 0.16 |
| 166 | hsa-miR-1825 | 47 | 116 | 0.41 | -0.90 | 1.64E-03 | 6.68E-03 | 1.19E-03 | 6.07E-03 | 0.19 |
| 167 | hsa-miR-214* | 85 | 29 | 2.98 | 1.09 | 8.24E-04 | 4.12E-03 | 1.28E-03 | 6.51E-03 | 0.83 |
| 168 | hsa-miR-24-1* | 162 | 119 | 1.37 | 0.31 | 8.42E-03 | 2.30E-02 | 1.32E-03 | 6.65E-03 | 0.76 |
| 169 | hsa-miR-1306 | 29 | 85 | 0.34 | -1.07 | 8.71E-04 | 4.29E-03 | 1.32E-03 | 6.65E-03 | 0.17 |
| 170 | hsa-miR-99a* | 44 | 92 | 0.48 | -0.73 | 1.14E-03 | 5.17E-03 | 1.37E-03 | 6.79E-03 | 0.18 |
| 171 | hsa-miR-1248 | 57 | 1 | 42.37 | 3.75 | 2.54E-04 | 1.92E-03 | 1.37E-03 | 6.79E-03 | 0.86 |
| 172 | hsa-miR-450b-3p | 59 | 23 | 2.58 | 0.95 | 4.65E-03 | 1.48E-02 | 1.40E-03 | 6.91E-03 | 0.78 |
| 173 | hsa-miR-517* | 276 | 187 | 1.48 | 0.39 | 8.71E-04 | 4.29E-03 | 1.44E-03 | 7.08E-03 | 0.83 |
| 174 | hsa-miR-587 | 68 | 159 | 0.43 | -0.85 | 2.87E-03 | 1.02E-02 | 1.45E-03 | 7.08E-03 | 0.21 |
| 175 | hsa-miR-574-5p | 1266 | 421 | 3.00 | 1.10 | 1.85E-05 | 3.92E-04 | 1.46E-03 | 7.09E-03 | 0.92 |
| 176 | hsa-miR-544 | 64 | 17 | 3.67 | 1.30 | 6.46E-03 | 1.86E-02 | 1.50E-03 | 7.25E-03 | 0.77 |
| 177 | hsa-miR-99a | 127 | 254 | 0.50 | -0.69 | 2.48E-03 | 8.97E-03 | 1.53E-03 | 7.34E-03 | 0.20 |
| 178 | hsa-miR-152 | 251 | 381 | 0.66 | -0.42 | 3.35E-04 | 2.17E-03 | 1.54E-03 | 7.36E-03 | 0.15 |
| 179 | hsa-miR-17* | 1000 | 601 | 1.66 | 0.51 | 4.72E-04 | 2.82E-03 | 1.59E-03 | 7.53E-03 | 0.85 |
| 180 | hsa-miR-96 | 261 | 142 | 1.84 | 0.61 | 3.85E-03 | 1.29E-02 | 1.72E-03 | 8.06E-03 | 0.79 |
| 181 | hsa-miR-30a | 423 | 839 | 0.50 | -0.68 | 1.29E-04 | 1.27E-03 | 1.72E-03 | 8.06E-03 | 0.12 |
| 182 | hsa-miR-490-3p | 111 | 46 | 2.41 | 0.88 | 1.56E-03 | 6.41E-03 | 1.79E-03 | 8.36E-03 | 0.81 |
| 183 | hsa-miR-549 | 96 | 52 | 1.85 | 0.61 | 1.61E-02 | 3.77E-02 | 1.85E-03 | 8.57E-03 | 0.74 |
| 184 | hsa-miR-802 | 122 | 75 | 1.63 | 0.49 | 8.07E-04 | 4.10E-03 | 1.96E-03 | 8.99E-03 | 0.82 |
| 185 | hsa-miR-1267 | 50 | 80 | 0.62 | -0.47 | 2.05E-04 | 1.72E-03 | 1.95E-03 | 8.99E-03 | 0.15 |
| 186 | hsa-miR-410 | 132 | 88 | 1.50 | 0.41 | 1.35E-02 | 3.35E-02 | 2.05E-03 | 9.33E-03 | 0.74 |
| 187 | hsa-miR-302b | 1 | 47 | 0.02 | -3.85 | 7.89E-05 | 9.04E-04 | 2.17E-03 | 9.82E-03 | 0.13 |
| 188 | hsa-miR-28-5p | 374 | 573 | 0.65 | -0.43 | 3.35E-04 | 2.17E-03 | 2.21E-03 | 9.88E-03 | 0.15 |
| 189 | hsa-miR-196b | 1 | 44 | 0.02 | -3.79 | 5.07E-04 | 2.94E-03 | 2.20E-03 | 9.88E-03 | 0.18 |
| 190 | hsa-miR-34c-5p | 91 | 64 | 1.41 | 0.34 | 3.33E-03 | 1.15E-02 | 2.21E-03 | 9.88E-03 | 0.79 |
| 191 | hsa-miR-515-3p | 2 | 40 | 0.04 | -3.15 | 7.95E-04 | 4.06E-03 | 2.23E-03 | 9.88E-03 | 0.17 |
| 192 | hsa-miR-1302 | 55 | 12 | 4.64 | 1.54 | 3.97E-03 | 1.32E-02 | 2.28E-03 | 1.00E-02 | 0.78 |
| 193 | hsa-miR-671-3p | 46 | 94 | 0.49 | -0.72 | 1.92E-03 | 7.44E-03 | 2.28E-03 | 1.00E-02 | 0.19 |
| 194 | hsa-miR-767-5p | 269 | 137 | 1.97 | 0.68 | 1.92E-03 | 7.44E-03 | 2.31E-03 | 1.01E-02 | 0.81 |
| 195 | hsa-miR-197 | 601 | 1420 | 0.42 | -0.86 | 2.65E-04 | 1.93E-03 | 2.33E-03 | 1.01E-02 | 0.14 |
| 196 | hsa-miR-629 | 42 | 332 | 0.13 | -2.08 | 5.84E-03 | 1.74E-02 | 2.40E-03 | 1.04E-02 | 0.23 |
| 197 | hsa-miR-1225-5p | 97 | 179 | 0.54 | -0.61 | 4.04E-03 | 1.34E-02 | 2.42E-03 | 1.04E-02 | 0.22 |
| 198 | hsa-miR-188-5p | 162 | 94 | 1.73 | 0.55 | 5.62E-03 | 1.69E-02 | 2.58E-03 | 1.10E-02 | 0.77 |
| 199 | hsa-miR-298 | 191 | 113 | 1.69 | 0.52 | 4.59E-03 | 1.48E-02 | 2.61E-03 | 1.11E-02 | 0.77 |
| 200 | hsa-miR-539 | 16 | 42 | 0.37 | -0.99 | 2.06E-03 | 7.78E-03 | 2.61E-03 | 1.11E-02 | 0.20 |
| 201 | hsa-miR-125a-5p | 219 | 604 | 0.36 | -1.01 | 9.16E-04 | 4.43E-03 | 2.67E-03 | 1.13E-02 | 0.18 |
| 202 | hsa-miR-548a-3p | 125 | 76 | 1.65 | 0.50 | 4.66E-03 | 1.48E-02 | 2.71E-03 | 1.13E-02 | 0.78 |
| 203 | hsa-miR-92b | 329 | 425 | 0.77 | -0.26 | 8.45E-03 | 2.30E-02 | 2.70E-03 | 1.13E-02 | 0.24 |
| 204 | hsa-miR-518e* | 232 | 156 | 1.49 | 0.40 | 1.41E-03 | 5.98E-03 | 2.73E-03 | 1.13E-02 | 0.82 |
| 205 | hsa-miR-513b | 62 | 24 | 2.61 | 0.96 | 5.07E-03 | 1.57E-02 | 2.78E-03 | 1.15E-02 | 0.78 |
| 206 | hsa-miR-660 | 588 | 403 | 1.46 | 0.38 | 1.10E-02 | 2.85E-02 | 2.82E-03 | 1.16E-02 | 0.75 |
| 207 | hsa-miR-1908 | 1059 | 2346 | 0.45 | -0.80 | 1.82E-03 | 7.31E-03 | 2.96E-03 | 1.21E-02 | 0.19 |
| 208 | hsa-miR-200c* | 68 | 103 | 0.67 | -0.41 | 1.50E-03 | 6.26E-03 | 2.99E-03 | 1.22E-02 | 0.20 |
| 209 | hsa-miR-635 | 165 | 96 | 1.72 | 0.54 | 4.59E-03 | 1.48E-02 | 3.06E-03 | 1.24E-02 | 0.77 |
| 210 | hsa-miR-199b-3p | 174 | 98 | 1.76 | 0.57 | 3.33E-03 | 1.15E-02 | 3.06E-03 | 1.24E-02 | 0.78 |
| 211 | hsa-miR-492 | 111 | 67 | 1.67 | 0.51 | 2.99E-03 | 1.05E-02 | 3.12E-03 | 1.25E-02 | 0.79 |
| 212 | hsa-miR-885-3p | 180 | 368 | 0.49 | -0.71 | 2.02E-03 | 7.69E-03 | 3.14E-03 | 1.26E-02 | 0.19 |

Figure 1 (cont.)

| | | | | | | | | | |
|---|---|---|---|---|---|---|---|---|---|
| 213 | hsa-miR-92a-2* | 1 | 45 | 0.03 | -3.46 | 6.75E-04 | 3.53E-03 | 3.30E-03 | 1.32E-02 | 0.17 |
| 214 | hsa-miR-603 | 210 | 125 | 1.69 | 0.52 | 1.56E-03 | 6.41E-03 | 3.44E-03 | 1.36E-02 | 0.81 |
| 215 | hsa-let-7b* | 13 | 57 | 0.22 | -1.52 | 2.63E-03 | 9.49E-03 | 3.55E-03 | 1.40E-02 | 0.21 |
| 216 | hsa-miR-382 | 23 | 70 | 0.32 | -1.13 | 2.03E-03 | 7.69E-03 | 3.62E-03 | 1.41E-02 | 0.20 |
| 217 | hsa-miR-379* | 74 | 119 | 0.62 | -0.47 | 1.69E-03 | 6.81E-03 | 3.61E-03 | 1.41E-02 | 0.20 |
| 218 | hsa-let-7e* | 25 | 73 | 0.34 | -1.08 | 5.11E-03 | 1.57E-02 | 3.66E-03 | 1.43E-02 | 0.22 |
| 219 | hsa-miR-520f | 1 | 43 | 0.02 | -3.75 | 1.10E-03 | 5.04E-03 | 3.69E-03 | 1.43E-02 | 0.19 |
| 220 | hsa-miR-377 | 211 | 142 | 1.49 | 0.40 | 5.65E-03 | 1.69E-02 | 3.75E-03 | 1.45E-02 | 0.77 |
| 221 | hsa-miR-1912 | 217 | 156 | 1.39 | 0.33 | 1.48E-03 | 6.22E-03 | 3.89E-03 | 1.49E-02 | 0.81 |
| 222 | hsa-miR-452* | 695 | 258 | 2.70 | 0.99 | 2.98E-04 | 2.09E-03 | 4.14E-03 | 1.57E-02 | 0.86 |
| 223 | hsa-miR-146a | 225 | 398 | 0.56 | -0.57 | 4.23E-03 | 1.38E-02 | 4.14E-03 | 1.57E-02 | 0.22 |
| 224 | hsa-miR-183* | 125 | 262 | 0.48 | -0.74 | 1.90E-03 | 7.44E-03 | 4.12E-03 | 1.57E-02 | 0.20 |
| 225 | hsa-miR-219-1-3p | 61 | 28 | 2.20 | 0.79 | 6.75E-03 | 1.92E-02 | 4.24E-03 | 1.60E-02 | 0.77 |
| 226 | hsa-miR-509-3p | 2 | 40 | 0.06 | -2.83 | 5.74E-04 | 3.10E-03 | 4.32E-03 | 1.62E-02 | 0.17 |
| 227 | hsa-miR-512-3p | 41 | 65 | 0.63 | -0.46 | 1.00E-02 | 2.63E-02 | 4.38E-03 | 1.62E-02 | 0.25 |
| 228 | hsa-miR-146a* | 134 | 87 | 1.54 | 0.43 | 1.48E-02 | 3.56E-02 | 4.35E-03 | 1.62E-02 | 0.74 |
| 229 | hsa-miR-632 | 44 | 88 | 0.50 | -0.70 | 9.20E-04 | 4.43E-03 | 4.37E-03 | 1.62E-02 | 0.17 |
| 230 | hsa-miR-361-5p | 520 | 800 | 0.65 | -0.43 | 2.12E-03 | 7.92E-03 | 4.40E-03 | 1.62E-02 | 0.20 |
| 231 | hsa-miR-1265 | 11 | 1 | 10.61 | 2.36 | 1.28E-02 | 3.22E-02 | 4.44E-03 | 1.63E-02 | 0.74 |
| 232 | hsa-miR-133a | 84 | 39 | 2.18 | 0.78 | 3.63E-04 | 2.30E-03 | 4.49E-03 | 1.64E-02 | 0.84 |
| 233 | hsa-miR-185 | 29628 | 38642 | 0.77 | -0.27 | 8.68E-03 | 2.35E-02 | 4.52E-03 | 1.64E-02 | 0.25 |
| 234 | hsa-miR-92b* | 146 | 275 | 0.53 | -0.63 | 1.90E-03 | 7.44E-03 | 4.59E-03 | 1.66E-02 | 0.20 |
| 235 | hsa-miR-1288 | 136 | 86 | 1.59 | 0.46 | 3.71E-03 | 1.25E-02 | 4.61E-03 | 1.66E-02 | 0.78 |
| 236 | hsa-miR-548j | 1 | 49 | 0.02 | -3.76 | 6.08E-04 | 3.22E-03 | 4.64E-03 | 1.67E-02 | 0.17 |
| 237 | hsa-miR-365 | 101 | 161 | 0.63 | -0.46 | 4.24E-03 | 1.38E-02 | 4.73E-03 | 1.69E-02 | 0.22 |
| 238 | hsa-miR-18b* | 104 | 169 | 0.62 | -0.48 | 4.66E-03 | 1.48E-02 | 4.78E-03 | 1.70E-02 | 0.22 |
| 239 | hsa-miR-1279 | 10 | 51 | 0.19 | -1.68 | 3.19E-03 | 1.11E-02 | 4.81E-03 | 1.71E-02 | 0.21 |
| 240 | hsa-miR-425 | 12225 | 16394 | 0.75 | -0.29 | 5.72E-03 | 1.71E-02 | 4.90E-03 | 1.73E-02 | 0.23 |
| 241 | hsa-miR-576-3p | 18 | 60 | 0.30 | -1.21 | 1.90E-03 | 7.44E-03 | 4.93E-03 | 1.74E-02 | 0.19 |
| 242 | hsa-miR-431 | 245 | 139 | 1.76 | 0.56 | 8.10E-03 | 2.21E-02 | 5.05E-03 | 1.76E-02 | 0.76 |
| 243 | hsa-miR-518b | 145 | 114 | 1.27 | 0.24 | 2.74E-03 | 9.79E-03 | 5.07E-03 | 1.76E-02 | 0.80 |
| 244 | hsa-miR-124 | 164 | 105 | 1.56 | 0.45 | 5.10E-03 | 1.57E-02 | 5.08E-03 | 1.76E-02 | 0.77 |
| 245 | hsa-miR-26a-1* | 29 | 74 | 0.39 | -0.95 | 6.11E-03 | 1.81E-02 | 5.15E-03 | 1.78E-02 | 0.23 |
| 246 | hsa-miR-571 | 75 | 48 | 1.55 | 0.44 | 1.15E-02 | 2.93E-02 | 5.49E-03 | 1.89E-02 | 0.75 |
| 247 | hsa-miR-199b-5p | 22 | 62 | 0.35 | -1.06 | 2.43E-03 | 8.88E-03 | 5.53E-03 | 1.90E-02 | 0.20 |
| 248 | hsa-miR-103-as | 208 | 156 | 1.33 | 0.29 | 1.92E-02 | 4.38E-02 | 5.59E-03 | 1.91E-02 | 0.73 |
| 249 | hsa-miR-219-5p | 60 | 10 | 6.03 | 1.80 | 2.12E-03 | 7.92E-03 | 5.63E-03 | 1.91E-02 | 0.80 |
| 250 | hsa-miR-223 | 2400 | 3906 | 0.61 | -0.49 | 5.33E-03 | 1.63E-02 | 5.63E-03 | 1.91E-02 | 0.22 |
| 251 | hsa-miR-301a | 493 | 334 | 1.47 | 0.39 | 6.26E-03 | 1.82E-02 | 5.84E-03 | 1.97E-02 | 0.76 |
| 252 | hsa-miR-769-5p | 18 | 51 | 0.36 | -1.03 | 4.80E-03 | 1.52E-02 | 6.10E-03 | 2.05E-02 | 0.22 |
| 253 | hsa-miR-1207-5p | 387 | 899 | 0.43 | -0.84 | 1.02E-03 | 4.72E-03 | 6.27E-03 | 2.10E-02 | 0.18 |
| 254 | hsa-miR-369-3p | 29 | 80 | 0.36 | -1.01 | 5.61E-03 | 1.69E-02 | 6.29E-03 | 2.10E-02 | 0.23 |
| 255 | hsa-miR-519b-5p | 205 | 132 | 1.56 | 0.44 | 2.13E-03 | 7.92E-03 | 6.42E-03 | 2.14E-02 | 0.79 |
| 256 | hsa-miR-324-5p | 502 | 354 | 1.42 | 0.35 | 1.42E-02 | 3.47E-02 | 6.55E-03 | 2.17E-02 | 0.74 |
| 257 | hsa-miR-597 | 107 | 52 | 2.06 | 0.72 | 6.75E-03 | 1.92E-02 | 6.67E-03 | 2.19E-02 | 0.77 |
| 258 | hsa-miR-564 | 211 | 125 | 1.68 | 0.52 | 3.36E-04 | 2.17E-03 | 6.65E-03 | 2.19E-02 | 0.85 |
| 259 | hsa-miR-140-5p | 21 | 77 | 0.27 | -1.30 | 5.07E-03 | 1.57E-02 | 6.80E-03 | 2.23E-02 | 0.22 |
| 260 | hsa-miR-432 | 1 | 27 | 0.04 | -3.28 | 5.24E-04 | 2.98E-03 | 6.83E-03 | 2.23E-02 | 0.19 |
| 261 | hsa-miR-153 | 146 | 91 | 1.61 | 0.48 | 6.26E-03 | 1.82E-02 | 6.86E-03 | 2.23E-02 | 0.76 |
| 262 | hsa-miR-215 | 412 | 665 | 0.62 | -0.48 | 8.25E-04 | 4.12E-03 | 6.91E-03 | 2.23E-02 | 0.17 |
| 263 | hsa-miR-1914 | 33 | 84 | 0.40 | -0.92 | 2.69E-03 | 9.65E-03 | 6.92E-03 | 2.23E-02 | 0.20 |
| 264 | hsa-miR-183 | 436 | 709 | 0.62 | -0.49 | 6.46E-03 | 1.86E-02 | 7.12E-03 | 2.29E-02 | 0.23 |
| 265 | hsa-miR-671-5p | 87 | 41 | 2.14 | 0.76 | 1.25E-02 | 3.16E-02 | 7.31E-03 | 2.32E-02 | 0.75 |
| 266 | hsa-miR-508-3p | 11 | 56 | 0.19 | -1.67 | 7.88E-03 | 2.17E-02 | 7.28E-03 | 2.32E-02 | 0.24 |
| 267 | hsa-miR-362-3p | 228 | 407 | 0.56 | -0.58 | 7.39E-03 | 2.06E-02 | 7.31E-03 | 2.32E-02 | 0.24 |

Figure 1 (cont.)

| 268 | hsa-miR-556-3p | 4 | 38 | 0.11 | -2.17 | 2.01E-03 | 7.69E-03 | 7.40E-03 | 2.34E-02 | 0.20 |
|---|---|---|---|---|---|---|---|---|---|---|
| 269 | hsa-miR-1324 | 143 | 102 | 1.40 | 0.34 | 1.61E-02 | 3.77E-02 | 7.58E-03 | 2.39E-02 | 0.74 |
| 270 | hsa-miR-770-5p | 62 | 107 | 0.58 | -0.54 | 6.26E-03 | 1.82E-02 | 7.71E-03 | 2.42E-02 | 0.24 |
| 271 | hsa-miR-409-3p | 64 | 189 | 0.34 | -1.09 | 9.25E-03 | 2.45E-02 | 7.73E-03 | 2.42E-02 | 0.24 |
| 272 | hsa-miR-629* | 110 | 210 | 0.52 | -0.65 | 6.92E-03 | 1.95E-02 | 7.89E-03 | 2.46E-02 | 0.24 |
| 273 | hsa-miR-509-5p | 359 | 185 | 1.94 | 0.66 | 5.30E-04 | 2.98E-03 | 7.91E-03 | 2.46E-02 | 0.84 |
| 274 | hsa-miR-551a | 60 | 103 | 0.58 | -0.54 | 1.33E-03 | 5.76E-03 | 7.96E-03 | 2.46E-02 | 0.19 |
| 275 | hsa-miR-548e | 59 | 108 | 0.54 | -0.61 | 5.12E-03 | 1.57E-02 | 8.26E-03 | 2.55E-02 | 0.22 |
| 276 | hsa-miR-518f | 84 | 125 | 0.67 | -0.40 | 1.75E-02 | 4.07E-02 | 8.35E-03 | 2.57E-02 | 0.26 |
| 277 | hsa-miR-520c-3p | 1 | 31 | 0.03 | -3.44 | 5.63E-03 | 1.69E-02 | 8.47E-03 | 2.58E-02 | 0.24 |
| 278 | hsa-miR-548o | 160 | 119 | 1.34 | 0.29 | 1.92E-02 | 4.38E-02 | 8.46E-03 | 2.58E-02 | 0.73 |
| 279 | hsa-miR-520c-5p | 167 | 123 | 1.36 | 0.30 | 2.39E-03 | 8.76E-03 | 8.48E-03 | 2.58E-02 | 0.79 |
| 280 | hsa-miR-141* | 126 | 71 | 1.78 | 0.58 | 7.07E-03 | 1.99E-02 | 8.70E-03 | 2.63E-02 | 0.77 |
| 281 | hsa-miR-194* | 68 | 102 | 0.67 | -0.40 | 6.26E-03 | 1.82E-02 | 8.72E-03 | 2.63E-02 | 0.24 |
| 282 | hsa-miR-424 | 272 | 441 | 0.62 | -0.48 | 1.36E-02 | 3.35E-02 | 8.81E-03 | 2.64E-02 | 0.26 |
| 283 | hsa-miR-1275 | 83 | 146 | 0.57 | -0.57 | 5.10E-03 | 1.57E-02 | 8.80E-03 | 2.64E-02 | 0.23 |
| 284 | hsa-miR-181c* | 90 | 55 | 1.64 | 0.49 | 6.76E-03 | 1.92E-02 | 9.07E-03 | 2.71E-02 | 0.77 |
| 285 | hsa-miR-126 | 3161 | 2096 | 1.51 | 0.41 | 4.41E-02 | 8.63E-02 | 9.15E-03 | 2.72E-02 | 0.70 |
| 286 | hsa-miR-151-3p | 530 | 889 | 0.60 | -0.52 | 2.87E-03 | 1.02E-02 | 9.27E-03 | 2.75E-02 | 0.21 |
| 287 | hsa-miR-942 | 10 | 47 | 0.22 | -1.51 | 1.47E-03 | 6.19E-03 | 9.48E-03 | 2.80E-02 | 0.19 |
| 288 | hsa-miR-330-3p | 482 | 302 | 1.60 | 0.47 | 1.20E-03 | 5.31E-03 | 9.60E-03 | 2.83E-02 | 0.82 |
| 289 | hsa-miR-200c | 110 | 137 | 0.80 | -0.22 | 2.06E-02 | 4.65E-02 | 9.64E-03 | 2.83E-02 | 0.27 |
| 290 | hsa-miR-601 | 1 | 39 | 0.03 | -3.37 | 4.27E-03 | 1.39E-02 | 9.86E-03 | 2.88E-02 | 0.23 |
| 291 | hsa-miR-23b | 4007 | 5279 | 0.76 | -0.28 | 3.08E-03 | 1.08E-02 | 9.88E-03 | 2.88E-02 | 0.21 |
| 292 | hsa-miR-625* | 278 | 366 | 0.76 | -0.28 | 1.31E-02 | 3.27E-02 | 9.95E-03 | 2.89E-02 | 0.25 |
| 293 | hsa-miR-1253 | 106 | 42 | 2.54 | 0.93 | 1.36E-02 | 3.35E-02 | 1.00E-02 | 2.90E-02 | 0.74 |
| 294 | hsa-miR-423-5p | 3309 | 6689 | 0.49 | -0.70 | 4.84E-03 | 1.52E-02 | 1.02E-02 | 2.93E-02 | 0.22 |
| 295 | hsa-miR-522* | 191 | 105 | 1.82 | 0.60 | 2.35E-03 | 8.68E-03 | 1.04E-02 | 3.00E-02 | 0.80 |
| 296 | hsa-miR-185* | 6 | 33 | 0.18 | -1.70 | 4.24E-03 | 1.38E-02 | 1.05E-02 | 3.00E-02 | 0.22 |
| 297 | hsa-miR-1238 | 27 | 63 | 0.43 | -0.84 | 1.00E-02 | 2.63E-02 | 1.07E-02 | 3.04E-02 | 0.25 |
| 298 | hsa-miR-376b | 105 | 68 | 1.55 | 0.44 | 1.61E-02 | 3.77E-02 | 1.07E-02 | 3.04E-02 | 0.74 |
| 299 | hsa-miR-553 | 13 | 52 | 0.24 | -1.42 | 1.38E-03 | 5.91E-03 | 1.08E-02 | 3.06E-02 | 0.18 |
| 300 | hsa-miR-23a | 4671 | 6836 | 0.68 | -0.38 | 1.01E-02 | 2.63E-02 | 1.13E-02 | 3.16E-02 | 0.25 |
| 301 | hsa-miR-566 | 119 | 74 | 1.61 | 0.47 | 1.92E-03 | 7.44E-03 | 1.13E-02 | 3.16E-02 | 0.81 |
| 302 | hsa-miR-1269 | 66 | 104 | 0.63 | -0.46 | 1.75E-02 | 4.07E-02 | 1.13E-02 | 3.16E-02 | 0.26 |
| 303 | hsa-miR-613 | 1 | 40 | 0.02 | -3.69 | 2.21E-04 | 1.78E-03 | 1.13E-02 | 3.16E-02 | 0.14 |
| 304 | hsa-miR-342-5p | 149 | 266 | 0.56 | -0.58 | 7.40E-03 | 2.06E-02 | 1.13E-02 | 3.16E-02 | 0.24 |
| 305 | hsa-miR-521 | 61 | 41 | 1.46 | 0.38 | 3.68E-02 | 7.43E-02 | 1.15E-02 | 3.19E-02 | 0.71 |
| 306 | hsa-miR-297 | 84 | 146 | 0.57 | -0.56 | 1.12E-02 | 2.87E-02 | 1.18E-02 | 3.26E-02 | 0.25 |
| 307 | hsa-miR-137 | 126 | 55 | 2.27 | 0.82 | 1.23E-02 | 3.11E-02 | 1.24E-02 | 3.42E-02 | 0.74 |
| 308 | hsa-miR-455-3p | 191 | 117 | 1.64 | 0.49 | 5.65E-03 | 1.69E-02 | 1.27E-02 | 3.50E-02 | 0.77 |
| 309 | hsa-miR-15b* | 84 | 131 | 0.64 | -0.45 | 9.28E-03 | 2.45E-02 | 1.29E-02 | 3.54E-02 | 0.25 |
| 310 | hsa-miR-615-3p | 41 | 75 | 0.55 | -0.59 | 6.46E-03 | 1.86E-02 | 1.30E-02 | 3.55E-02 | 0.23 |
| 311 | hsa-miR-1278 | 89 | 42 | 2.10 | 0.74 | 3.16E-04 | 2.16E-03 | 1.30E-02 | 3.55E-02 | 0.84 |
| 312 | hsa-miR-186 | 55 | 111 | 0.50 | -0.70 | 7.64E-03 | 2.11E-02 | 1.32E-02 | 3.57E-02 | 0.24 |
| 313 | hsa-miR-545 | 143 | 83 | 1.71 | 0.54 | 7.42E-02 | 1.34E-01 | 1.33E-02 | 3.61E-02 | 0.68 |
| 314 | hsa-miR-34c-3p | 152 | 91 | 1.67 | 0.51 | 8.09E-03 | 2.21E-02 | 1.33E-02 | 3.61E-02 | 0.76 |
| 315 | hsa-miR-1204 | 14 | 55 | 0.25 | -1.39 | 1.01E-03 | 4.72E-03 | 1.34E-02 | 3.61E-02 | 0.18 |
| 316 | hsa-miR-421 | 160 | 126 | 1.27 | 0.24 | 4.42E-02 | 8.63E-02 | 1.34E-02 | 3.61E-02 | 0.70 |
| 317 | hsa-miR-1303 | 54 | 85 | 0.64 | -0.45 | 1.02E-02 | 2.65E-02 | 1.38E-02 | 3.69E-02 | 0.25 |
| 318 | hsa-miR-644 | 16 | 49 | 0.33 | -1.11 | 9.12E-03 | 2.44E-02 | 1.42E-02 | 3.73E-02 | 0.24 |
| 319 | hsa-miR-1271 | 317 | 242 | 1.31 | 0.27 | 7.67E-02 | 1.37E-01 | 1.41E-02 | 3.73E-02 | 0.68 |
| 320 | hsa-miR-381 | 127 | 108 | 1.18 | 0.17 | 1.61E-02 | 3.77E-02 | 1.42E-02 | 3.73E-02 | 0.74 |
| 321 | hsa-miR-627 | 219 | 177 | 1.23 | 0.21 | 1.48E-02 | 3.57E-02 | 1.42E-02 | 3.73E-02 | 0.74 |
| 322 | hsa-miR-1247 | 76 | 42 | 1.82 | 0.60 | 1.36E-02 | 3.35E-02 | 1.42E-02 | 3.73E-02 | 0.74 |

Figure 1 (cont.)

| | | | | | | | | | | |
|---|---|---|---|---|---|---|---|---|---|---|
| 323 | hsa-miR-489 | 289 | 181 | 1.60 | 0.47 | 9.91E-02 | 1.69E-01 | 1.40E-02 | 3.73E-02 | 0.66 |
| 324 | hsa-miR-135b | 13 | 49 | 0.25 | -1.37 | 7.13E-03 | 2.00E-02 | 1.43E-02 | 3.74E-02 | 0.24 |
| 325 | hsa-miR-518c* | 86 | 107 | 0.80 | -0.23 | 3.68E-02 | 7.43E-02 | 1.46E-02 | 3.81E-02 | 0.29 |
| 326 | hsa-miR-135a | 1 | 25 | 0.04 | -3.21 | 1.15E-03 | 5.20E-03 | 1.47E-02 | 3.84E-02 | 0.19 |
| 327 | hsa-miR-548d-5p | 1 | 34 | 0.03 | -3.52 | 4.07E-04 | 2.52E-03 | 1.49E-02 | 3.86E-02 | 0.17 |
| 328 | hsa-miR-574-3p | 1939 | 3551 | 0.55 | -0.60 | 8.79E-03 | 2.37E-02 | 1.55E-02 | 4.02E-02 | 0.24 |
| 329 | hsa-miR-186* | 151 | 105 | 1.44 | 0.37 | 1.76E-02 | 4.08E-02 | 1.58E-02 | 4.07E-02 | 0.73 |
| 330 | hsa-miR-654-3p | 52 | 19 | 2.79 | 1.03 | 8.84E-03 | 2.37E-02 | 1.59E-02 | 4.08E-02 | 0.76 |
| 331 | hsa-miR-206 | 7 | 46 | 0.16 | -1.86 | 6.51E-03 | 1.86E-02 | 1.59E-02 | 4.08E-02 | 0.24 |
| 332 | hsa-miR-144* | 970 | 544 | 1.78 | 0.58 | 1.02E-03 | 4.72E-03 | 1.60E-02 | 4.08E-02 | 0.82 |
| 333 | hsa-miR-589* | 115 | 149 | 0.77 | -0.26 | 4.59E-03 | 1.48E-02 | 1.61E-02 | 4.08E-02 | 0.23 |
| 334 | hsa-miR-135a* | 19 | 54 | 0.35 | -1.06 | 9.20E-03 | 2.45E-02 | 1.61E-02 | 4.08E-02 | 0.24 |
| 335 | hsa-let-7f-1* | 35 | 67 | 0.52 | -0.66 | 1.54E-02 | 3.70E-02 | 1.62E-02 | 4.10E-02 | 0.26 |
| 336 | hsa-miR-1290 | 9 | 36 | 0.24 | -1.41 | 3.08E-02 | 6.48E-02 | 1.63E-02 | 4.10E-02 | 0.29 |
| 337 | hsa-miR-214 | 417 | 203 | 2.06 | 0.72 | 2.48E-03 | 8.97E-03 | 1.67E-02 | 4.21E-02 | 0.80 |
| 338 | hsa-miR-593 | 1 | 38 | 0.03 | -3.65 | 1.22E-03 | 5.35E-03 | 1.69E-02 | 4.25E-02 | 0.19 |
| 339 | hsa-miR-196a* | 197 | 126 | 1.57 | 0.45 | 6.26E-03 | 1.82E-02 | 1.71E-02 | 4.26E-02 | 0.76 |
| 340 | hsa-miR-30d* | 94 | 67 | 1.39 | 0.33 | 1.36E-02 | 3.35E-02 | 1.70E-02 | 4.26E-02 | 0.74 |
| 341 | hsa-miR-548b-5p | 11 | 36 | 0.31 | -1.18 | 1.58E-02 | 3.76E-02 | 1.72E-02 | 4.27E-02 | 0.26 |
| 342 | hsa-miR-222* | 95 | 65 | 1.46 | 0.38 | 6.27E-02 | 1.16E-01 | 1.74E-02 | 4.31E-02 | 0.68 |
| 343 | hsa-miR-483-5p | 172 | 257 | 0.67 | -0.40 | 2.06E-02 | 4.65E-02 | 1.78E-02 | 4.39E-02 | 0.27 |
| 344 | hsa-miR-1307 | 114 | 173 | 0.66 | -0.42 | 1.55E-02 | 3.70E-02 | 1.87E-02 | 4.62E-02 | 0.26 |
| 345 | hsa-miR-1276 | 65 | 38 | 1.71 | 0.54 | 2.48E-02 | 5.44E-02 | 1.90E-02 | 4.66E-02 | 0.72 |
| 346 | hsa-miR-1231 | 123 | 181 | 0.68 | -0.39 | 9.28E-03 | 2.45E-02 | 1.90E-02 | 4.66E-02 | 0.25 |
| 347 | hsa-miR-518d-5p | 210 | 145 | 1.45 | 0.37 | 6.92E-03 | 1.95E-02 | 1.96E-02 | 4.80E-02 | 0.76 |
| 348 | hsa-miR-148b | 819 | 740 | 1.11 | 0.10 | 1.12E-01 | 1.86E-01 | 1.98E-02 | 4.81E-02 | 0.66 |
| 349 | hsa-miR-625 | 96 | 208 | 0.46 | -0.77 | 2.48E-02 | 5.44E-02 | 1.98E-02 | 4.81E-02 | 0.28 |
| 350 | hsa-miR-517a | 59 | 15 | 3.98 | 1.38 | 1.20E-02 | 3.05E-02 | 1.99E-02 | 4.82E-02 | 0.75 |
| 351 | hsa-miR-379 | 21 | 63 | 0.33 | -1.10 | 1.60E-02 | 3.77E-02 | 2.04E-02 | 4.93E-02 | 0.26 |
| 352 | hsa-miR-23a* | 5 | 1 | 4.95 | 1.60 | 9.62E-01 | 9.67E-01 | 5.72E-01 | 6.79E-01 | 0.49 |
| 353 | hsa-miR-27a | 346 | 383 | 0.90 | -0.10 | 8.44E-01 | 8.86E-01 | 4.17E-01 | 5.37E-01 | 0.52 |
| 354 | hsa-miR-125b-2* | 51 | 63 | 0.80 | -0.22 | 1.26E-01 | 2.04E-01 | 6.69E-02 | 1.24E-01 | 0.35 |
| 355 | hsa-miR-1294 | 5 | 13 | 0.39 | -0.93 | 6.46E-01 | 7.31E-01 | 6.65E-01 | 7.53E-01 | 0.46 |
| 356 | hsa-miR-609 | 1 | 18 | 0.05 | -2.91 | 2.26E-02 | 5.05E-02 | 2.50E-02 | 5.70E-02 | 0.30 |
| 357 | hsa-miR-598 | 61 | 65 | 0.95 | -0.05 | 8.09E-01 | 8.60E-01 | 7.05E-01 | 7.82E-01 | 0.47 |

Figure 2

| Signature | SEQ-ID NOs | miRNA -identifiers | Acc | Spec | Sens |
|---|---|---|---|---|---|
| SNRCC-1 | 25, 8, 16 | hsa-miR-633, hsa-miR-34a*, hsa-miR-891b | 94.7% | 96.6% | 92.9% |
| SNRCC-2 | 8, 16 | hsa-miR-34a*, hsa-miR-891b | 94.3% | 96.0% | 92.6% |
| SNRCC-3 | 13, 14, 16 | hsa-miR-516b, hsa-miR-367*, hsa-miR-891b | 93.9% | 95.1% | 92.6% |
| SNRCC-4 | 18, 19, 26 | hsa-miR-1260, hsa-miR-221*, hsa-miR-580 | 93.7% | 92.3% | 95.1% |
| SNRCC-5 | 16, 11 | hsa-miR-891b, hsa-miR-19b | 92.9% | 92.9% | 92.9% |
| SNRCC-6 | 12, 14, 16 | hsa-miR-518a-3p, hsa-miR-367*, hsa-miR-891b | 92.9% | 93.1% | 92.6% |
| SNRCC-7 | 2, 5, 7 | hsa-miR-20b, hsa-miR-1251, hsa-miR-17 | 92.6% | 87.4% | 97.7% |
| SNRCC-8 | 13, 16 | hsa-miR-516b, hsa-miR-891b | 92.0% | 91.4% | 92.6% |
| SNRCC-9 | 8, 16, 17 | hsa-miR-34a*, hsa-miR-891b, hsa-miR-450b-5p | 92.0% | 92.3% | 91.7% |
| SNRCC-10 | 1, 8, 16 | hsa-miR-106a, hsa-miR-34a*, hsa-miR-891b | 91.9% | 90.9% | 92.9% |
| SNRCC-11 | 12, 15, 16 | hsa-miR-518a-3p, hsa-miR-93, hsa-miR-891b | 91.9% | 91.7% | 92.0% |
| SNRCC-12 | 5, 1, 2 | hsa-miR-1251, hsa-miR-106a, hsa-miR-20b | 91.9% | 86.0% | 97.7% |
| SNRCC-13 | 23, 24, 26 | hsa-miR-654-5p, hsa-miR-554, hsa-miR-580 | 91.7% | 93.1% | 90.3% |
| SNRCC-14 | 3, 5, 6 | hsa-miR-523, hsa-miR-1251, hsa-miR-20a | 91.6% | 83.7% | 99.4% |
| SNRCC-15 | 13, 15, 16 | hsa-miR-516b, hsa-miR-93, hsa-miR-891b | 91.6% | 90.3% | 92.9% |
| SNRCC-16 | 5, 2, 6 | hsa-miR-1251, hsa-miR-20b, hsa-miR-20a | 91.4% | 84.6% | 98.3% |
| SNRCC-17 | 8, 10, 11 | hsa-miR-34a*, hsa-let-7d*, hsa-miR-19b | 91.4% | 92.3% | 90.6% |
| SNRCC-18 | 6, 3, 8 | hsa-miR-20a, hsa-miR-523, hsa-miR-34a* | 91.3% | 88.9% | 93.7% |
| SNRCC-19 | 4, 8, 10 | hsa-miR-640, hsa-miR-34a*, hsa-let-7d* | 91.3% | 93.4% | 89.1% |
| SNRCC-20 | 8, 16, 74 | hsa-miR-34a*, hsa-miR-891b, hsa-miR-132* | 91.3% | 89.7% | 92.9% |
| SNRCC-21 | 8, 10, 12 | hsa-miR-34a*, hsa-let-7d*, hsa-miR-518a-3p | 91.1% | 92.6% | 89.7% |
| SNRCC-22 | 14, 16, 18 | hsa-miR-367*, hsa-miR-891b, hsa-miR-1260 | 91.1% | 89.4% | 92.9% |
| SNRCC-23 | 18, 26, 33 | hsa-miR-1260, hsa-miR-580, hsa-miR-103 | 91.1% | 88.0% | 94.3% |
| SNRCC-24 | 2, 5 | hsa-miR-20b, hsa-miR-1251 | 91.0% | 86.0% | 96.0% |
| SNRCC-25 | 8, 11, 12 | hsa-miR-34a*, hsa-miR-19b, hsa-miR-518a-3p | 91.0% | 90.3% | 91.7% |
| SNRCC-26 | 22, 24, 26 | hsa-miR-934, hsa-miR-554, hsa-miR-580 | 91.0% | 91.1% | 90.9% |
| SNRCC-27 | 8, 10 | hsa-miR-34a*, hsa-let-7d* | 90.9% | 96.0% | 85.7% |
| SNRCC-28 | 14, 16 | hsa-miR-367*, hsa-miR-891b | 90.7% | 93.1% | 88.3% |
| SNRCC-29 | 10, 12, 14 | hsa-let-7d*, hsa-miR-518a-3p, hsa-miR-367* | 90.7% | 90.3% | 91.1% |
| SNRCC-30 | 14, 15, 16 | hsa-miR-367*, hsa-miR-93, hsa-miR-891b | 90.7% | 89.1% | 92.3% |
| SNRCC-31 | 5, 39, 2 | hsa-miR-1251, hsa-miR-373, hsa-miR-20b | 90.7% | 86.6% | 94.9% |
| SNRCC-32 | 15, 18, 26 | hsa-miR-93, hsa-miR-1260, hsa-miR-580 | 90.7% | 89.1% | 92.3% |
| SNRCC-33 | 2, 5, 4 | hsa-miR-20b, hsa-miR-1251, hsa-miR-640 | 90.6% | 87.7% | 93.4% |
| SNRCC-34 | 2, 3, 8 | hsa-miR-20b, hsa-miR-523, hsa-miR-34a* | 90.4% | 87.7% | 93.1% |
| SNRCC-35 | 12, 13, 16 | hsa-miR-518a-3p, hsa-miR-516b, hsa-miR-891b | 90.4% | 89.1% | 91.7% |
| SNRCC-36 | 38, 16, 11 | hsa-miR-25*, hsa-miR-891b, hsa-miR-19b | 90.4% | 88.0% | 92.9% |
| SNRCC-37 | 10, 11, 14 | hsa-let-7d*, hsa-miR-19b, hsa-miR-367* | 90.3% | 88.9% | 91.7% |
| SNRCC-38 | 8, 18, 16 | hsa-miR-34a*, hsa-miR-1260, hsa-miR-891b | 90.3% | 87.7% | 92.9% |
| SNRCC-39 | 8, 10, 25 | hsa-miR-34a*, hsa-let-7d*, hsa-miR-633 | 90.3% | 92.0% | 88.6% |
| SNRCC-40 | 13, 16, 17 | hsa-miR-516b, hsa-miR-891b, hsa-miR-450b-5p | 90.3% | 90.6% | 90.0% |

Figure 2 (cont.)

| SNRCC-41 | 4, 8 | hsa-miR-640, hsa-miR-34a* | 90.1% | 94.3% | 86.0% |
|---|---|---|---|---|---|
| SNRCC-42 | 3, 5 | hsa-miR-523, hsa-miR-1251 | 90.1% | 84.3% | 96.0% |
| SNRCC-43 | 4, 5, 8 | hsa-miR-640, hsa-miR-1251, hsa-miR-34a* | 90.1% | 91.1% | 89.1% |
| SNRCC-44 | 20, 3, 8 | hsa-miR-224, hsa-miR-523, hsa-miR-34a* | 90.1% | 84.6% | 95.7% |
| SNRCC-45 | 1, 16 | hsa-miR-106a, hsa-miR-891b | 90.0% | 87.7% | 92.3% |
| SNRCC-46 | 2, 3, 5 | hsa-miR-20b, hsa-miR-523, hsa-miR-1251 | 90.0% | 81.4% | 98.6% |
| SNRCC-47 | 125, 16, 17 | hsa-miR-154, hsa-miR-891b, hsa-miR-450b-5p | 90.0% | 87.4% | 92.6% |
| SNRCC-48 | 3, 4, 8 | hsa-miR-523, hsa-miR-640, hsa-miR-34a* | 90.0% | 90.0% | 90.0% |
| SNRCC-49 | 25, 8 | hsa-miR-633, hsa-miR-34a* | 89.9% | 89.7% | 90.0% |
| SNRCC-50 | 16, 19 | hsa-miR-891b, hsa-miR-221* | 89.9% | 88.6% | 91.1% |
| SNRCC-51 | 3, 5, 7 | hsa-miR-523, hsa-miR-1251, hsa-miR-17 | 89.9% | 81.1% | 98.6% |
| SNRCC-52 | 11, 12, 14 | hsa-miR-19b, hsa-miR-518a-3p, hsa-miR-367* | 89.9% | 90.0% | 89.7% |
| SNRCC-53 | 8, 11 | hsa-miR-34a*, hsa-miR-19b | 89.7% | 88.6% | 90.9% |
| SNRCC-54 | 10, 18, 26 | hsa-let-7d*, hsa-miR-1260, hsa-miR-580 | 89.7% | 87.4% | 92.0% |
| SNRCC-55 | 8, 9, 11 | hsa-miR-34a*, hsa-miR-496, hsa-miR-19b | 89.6% | 88.3% | 90.9% |
| SNRCC-56 | 39, 2, 3 | hsa-miR-373, hsa-miR-20b, hsa-miR-523 | 89.6% | 80.3% | 98.9% |
| SNRCC-57 | 16, 18, 19 | hsa-miR-891b, hsa-miR-1260, hsa-miR-221* | 89.6% | 86.3% | 92.9% |
| SNRCC-58 | 1, 3, 5 | hsa-miR-106a, hsa-miR-523, hsa-miR-1251 | 89.6% | 79.4% | 99.7% |
| SNRCC-59 | 16, 137 | hsa-miR-891b, hsa-miR-296-5p | 89.4% | 89.7% | 89.1% |
| SNRCC-60 | 10, 11 | hsa-let-7d*, hsa-miR-19b | 89.4% | 88.3% | 90.6% |
| SNRCC-61 | 4, 10, 3 | hsa-miR-640, hsa-let-7d*, hsa-miR-523 | 89.4% | 87.7% | 91.1% |
| SNRCC-62 | 7, 8, 11 | hsa-miR-17, hsa-miR-34a*, hsa-miR-19b | 89.4% | 87.1% | 91.7% |
| SNRCC-63 | 8, 10, 19 | hsa-miR-34a*, hsa-let-7d*, hsa-miR-221* | 89.4% | 91.7% | 87.1% |
| SNRCC-64 | 12, 14, 15 | hsa-miR-518a-3p, hsa-miR-367*, hsa-miR-93 | 89.4% | 86.3% | 92.6% |
| SNRCC-65 | 14, 16, 17 | hsa-miR-367*, hsa-miR-891b, hsa-miR-450b-5p | 89.4% | 93.1% | 85.7% |
| SNRCC-66 | 23, 25, 26 | hsa-miR-654-5p, hsa-miR-633, hsa-miR-580 | 89.4% | 92.3% | 86.6% |
| SNRCC-67 | 6, 4, 8 | hsa-miR-20a, hsa-miR-640, hsa-miR-34a* | 89.3% | 88.9% | 89.7% |
| SNRCC-68 | 8, 9, 10 | hsa-miR-34a*, hsa-miR-496, hsa-let-7d* | 89.3% | 91.7% | 86.9% |
| SNRCC-69 | 39, 6, 3 | hsa-miR-373, hsa-miR-20a, hsa-miR-523 | 89.3% | 80.0% | 98.6% |
| SNRCC-70 | 5, 1, 6 | hsa-miR-1251, hsa-miR-106a, hsa-miR-20a | 89.1% | 83.1% | 95.1% |
| SNRCC-71 | 6, 8, 10 | hsa-miR-20a, hsa-miR-34a*, hsa-let-7d* | 89.1% | 90.6% | 87.7% |
| SNRCC-72 | 9, 10, 11 | hsa-miR-496, hsa-let-7d*, hsa-miR-19b | 89.1% | 88.6% | 89.7% |
| SNRCC-73 | 3, 25, 8 | hsa-miR-523, hsa-miR-633, hsa-miR-34a* | 89.1% | 86.3% | 92.0% |
| SNRCC-74 | 11, 14, 15 | hsa-miR-19b, hsa-miR-367*, hsa-miR-93 | 89.1% | 85.4% | 92.9% |
| SNRCC-75 | 18, 38, 16 | hsa-miR-1260, hsa-miR-25*, hsa-miR-891b | 89.1% | 85.7% | 92.6% |
| SNRCC-76 | 16, 11, 98 | hsa-miR-891b, hsa-miR-19b, hsa-miR-1305 | 89.0% | 86.3% | 91.7% |
| SNRCC-77 | 5, 6, 8 | hsa-miR-1251, hsa-miR-20a, hsa-miR-34a* | 89.0% | 85.4% | 92.6% |
| SNRCC-78 | 4, 9, 10 | hsa-miR-640, hsa-miR-496, hsa-let-7d* | 89.0% | 87.1% | 90.9% |
| SNRCC-79 | 3, 8, 19 | hsa-miR-523, hsa-miR-34a*, hsa-miR-221* | 89.0% | 86.0% | 92.0% |
| SNRCC-80 | 10, 11, 13 | hsa-let-7d*, hsa-miR-19b, hsa-miR-516b | 89.0% | 87.1% | 90.9% |
| SNRCC-81 | 11, 12, 13 | hsa-miR-19b, hsa-miR-518a-3p, hsa-miR-516b | 89.0% | 90.9% | 87.1% |
| SNRCC-82 | 10, 13, 14 | hsa-let-7d*, hsa-miR-516b, hsa-miR-367* | 89.0% | 88.9% | 89.1% |
| SNRCC-83 | 16, 17, 11 | hsa-miR-891b, hsa-miR-450b-5p, hsa-miR-19b | 89.0% | 86.0% | 92.0% |
| SNRCC-84 | 8, 19, 20 | hsa-miR-34a*, hsa-miR-221*, hsa-miR-224 | 89.0% | 84.3% | 93.7% |
| SNRCC-85 | 10, 19, 26 | hsa-let-7d*, hsa-miR-221*, hsa-miR-580 | 89.0% | 91.4% | 86.6% |
| SNRCC-86 | 125, 16 | hsa-miR-154, hsa-miR-891b | 88.9% | 87.1% | 90.6% |

Figure 2 (cont.)

| SNRCC-87 | 4, 10 | hsa-miR-640, hsa-let-7d* | 88.9% | 88.0% | 89.7% |
|---|---|---|---|---|---|
| SNRCC-88 | 5, 7, 8 | hsa-miR-1251, hsa-miR-17, hsa-miR-34a* | 88.9% | 86.3% | 91.4% |
| SNRCC-89 | 8, 20, 25 | hsa-miR-34a*, hsa-miR-224, hsa-miR-633 | 88.9% | 85.1% | 92.6% |
| SNRCC-90 | 15, 19, 26 | hsa-miR-93, hsa-miR-221*, hsa-miR-580 | 88.9% | 88.0% | 89.7% |
| SNRCC-91 | 24, 26, 28 | hsa-miR-554, hsa-miR-580, hsa-miR-548m | 88.9% | 94.0% | 83.7% |
| SNRCC-92 | 16, 137, 11 | hsa-miR-891b, hsa-miR-296-5p, hsa-miR-19b | 88.7% | 88.9% | 88.6% |
| SNRCC-93 | 3, 8, 10 | hsa-miR-523, hsa-miR-34a*, hsa-let-7d* | 88.7% | 90.3% | 87.1% |
| SNRCC-94 | 5, 7, 9 | hsa-miR-1251, hsa-miR-17, hsa-miR-496 | 88.7% | 81.7% | 95.7% |
| SNRCC-95 | 3, 8, 18 | hsa-miR-523, hsa-miR-34a*, hsa-miR-1260 | 88.7% | 82.9% | 94.6% |
| SNRCC-96 | 11, 13, 14 | hsa-miR-19b, hsa-miR-516b, hsa-miR-367* | 88.7% | 86.6% | 90.9% |
| SNRCC-97 | 14, 17, 18 | hsa-miR-367*, hsa-miR-450b-5p, hsa-miR-1260 | 88.7% | 78.9% | 98.6% |
| SNRCC-98 | 8, 19, 25 | hsa-miR-34a*, hsa-miR-221*, hsa-miR-633 | 88.7% | 87.1% | 90.3% |
| SNRCC-99 | 22, 23, 26 | hsa-miR-934, hsa-miR-654-5p, hsa-miR-580 | 88.7% | 87.7% | 89.7% |
| SNRCC-100 | 18, 26, 30 | hsa-miR-1260, hsa-miR-580, hsa-miR-216b | 88.7% | 88.9% | 88.6% |
| SNRCC-101 | 26, 27, 28 | hsa-miR-580, hsa-miR-106b, hsa-miR-548m | 88.7% | 91.1% | 86.3% |
| SNRCC-102 | 3, 1, 8 | hsa-miR-523, hsa-miR-106a, hsa-miR-34a* | 88.6% | 84.9% | 92.3% |
| SNRCC-103 | 4, 7, 8 | hsa-miR-640, hsa-miR-17, hsa-miR-34a* | 88.6% | 87.7% | 89.4% |
| SNRCC-104 | 3, 10, 19 | hsa-miR-523, hsa-let-7d*, hsa-miR-221* | 88.6% | 84.6% | 92.6% |
| SNRCC-105 | 4, 10, 19 | hsa-miR-640, hsa-let-7d*, hsa-miR-221* | 88.6% | 87.7% | 89.4% |
| SNRCC-106 | 22, 25, 26 | hsa-miR-934, hsa-miR-633, hsa-miR-580 | 88.6% | 86.6% | 90.6% |
| SNRCC-107 | 6, 8 | hsa-miR-20a, hsa-miR-34a* | 88.4% | 87.4% | 89.4% |
| SNRCC-108 | 18, 16 | hsa-miR-1260, hsa-miR-891b | 88.4% | 84.6% | 92.3% |
| SNRCC-109 | 38, 16 | hsa-miR-25*, hsa-miR-891b | 88.4% | 84.6% | 92.3% |
| SNRCC-110 | 8, 18, 74 | hsa-miR-34a*, hsa-miR-1260, hsa-miR-132* | 88.4% | 83.7% | 93.1% |
| SNRCC-111 | 6, 4, 10 | hsa-miR-20a, hsa-miR-640, hsa-let-7d* | 88.4% | 86.6% | 90.3% |
| SNRCC-112 | 25, 1, 8 | hsa-miR-633, hsa-miR-106a, hsa-miR-34a* | 88.4% | 84.6% | 92.3% |
| SNRCC-113 | 10, 12, 13 | hsa-let-7d*, hsa-miR-518a-3p, hsa-miR-516b | 88.4% | 91.4% | 85.4% |
| SNRCC-114 | 13, 15, 17 | hsa-miR-516b, hsa-miR-93, hsa-miR-450b-5p | 88.4% | 82.0% | 94.9% |
| SNRCC-115 | 5, 8 | hsa-miR-1251, hsa-miR-34a* | 88.3% | 89.7% | 86.9% |
| SNRCC-116 | 8, 17 | hsa-miR-34a*, hsa-miR-450b-5p | 88.3% | 90.9% | 85.7% |
| SNRCC-117 | 8, 19 | hsa-miR-34a*, hsa-miR-221* | 88.3% | 88.0% | 88.6% |
| SNRCC-118 | 8, 10, 20 | hsa-miR-34a*, hsa-let-7d*, hsa-miR-224 | 88.3% | 86.9% | 89.7% |
| SNRCC-119 | 3, 4, 5 | hsa-miR-523, hsa-miR-640, hsa-miR-1251 | 88.1% | 86.3% | 90.0% |
| SNRCC-120 | 5, 6, 7 | hsa-miR-1251, hsa-miR-20a, hsa-miR-17 | 88.1% | 79.1% | 97.1% |
| SNRCC-121 | 4, 8, 19 | hsa-miR-640, hsa-miR-34a*, hsa-miR-221* | 88.1% | 90.0% | 86.3% |
| SNRCC-122 | 9, 11, 13 | hsa-miR-496, hsa-miR-19b, hsa-miR-516b | 88.1% | 88.6% | 87.7% |
| SNRCC-123 | 15, 16, 19 | hsa-miR-93, hsa-miR-891b, hsa-miR-221* | 88.1% | 83.4% | 92.9% |
| SNRCC-124 | 38, 16, 17 | hsa-miR-25*, hsa-miR-891b, hsa-miR-450b-5p | 88.1% | 84.6% | 91.7% |
| SNRCC-125 | 125, 18, 16 | hsa-miR-154, hsa-miR-1260, hsa-miR-891b | 88.0% | 83.7% | 92.3% |
| SNRCC-126 | 10, 18, 19 | hsa-let-7d*, hsa-miR-1260, hsa-miR-221* | 88.0% | 83.1% | 92.9% |
| SNRCC-127 | 15, 16, 17 | hsa-miR-93, hsa-miR-891b, hsa-miR-450b-5p | 88.0% | 84.6% | 91.4% |
| SNRCC-128 | 25, 18, 16 | hsa-miR-633, hsa-miR-1260, hsa-miR-891b | 88.0% | 86.6% | 89.4% |
| SNRCC-129 | 18, 19, 33 | hsa-miR-1260, hsa-miR-221*, hsa-miR-103 | 88.0% | 83.4% | 92.6% |
| SNRCC-130 | 19, 25, 26 | hsa-miR-221*, hsa-miR-633, hsa-miR-580 | 88.0% | 85.7% | 90.3% |
| SNRCC-131 | 24, 26, 27 | hsa-miR-554, hsa-miR-580, hsa-miR-106b | 88.0% | 90.9% | 85.1% |
| SNRCC-132 | 11, 14 | hsa-miR-19b, hsa-miR-367* | 87.9% | 83.4% | 92.3% |

Figure 2 (cont.)

| SNRCC-133 | 74, 18, 16 | hsa-miR-132*, hsa-miR-1260, hsa-miR-891b | 87.9% | 85.4% | 90.3% |
|---|---|---|---|---|---|
| SNRCC-134 | 74, 125, 16 | hsa-miR-132*, hsa-miR-154, hsa-miR-891b | 87.9% | 85.7% | 90.0% |
| SNRCC-135 | 16, 74, 137 | hsa-miR-891b, hsa-miR-132*, hsa-miR-296-5p | 87.9% | 85.1% | 90.6% |
| SNRCC-136 | 7, 8, 10 | hsa-miR-17, hsa-miR-34a*, hsa-let-7d* | 87.9% | 88.0% | 87.7% |
| SNRCC-137 | 10, 11, 12 | hsa-let-7d*, hsa-miR-19b, hsa-miR-518a-3p | 87.9% | 86.3% | 89.4% |
| SNRCC-138 | 16, 17, 19 | hsa-miR-891b, hsa-miR-450b-5p, hsa-miR-221* | 87.9% | 84.9% | 90.9% |
| SNRCC-139 | 16, 18, 20 | hsa-miR-891b, hsa-miR-1260, hsa-miR-224 | 87.9% | 81.7% | 94.0% |
| SNRCC-140 | 10, 12 | hsa-let-7d*, hsa-miR-518a-3p | 87.7% | 87.7% | 87.7% |
| SNRCC-141 | 15, 16 | hsa-miR-93, hsa-miR-891b | 87.7% | 85.7% | 89.7% |
| SNRCC-142 | 16, 74 | hsa-miR-891b, hsa-miR-132* | 87.7% | 85.4% | 90.0% |
| SNRCC-143 | 5, 6, 9 | hsa-miR-1251, hsa-miR-20a, hsa-miR-496 | 87.7% | 80.0% | 95.4% |
| SNRCC-144 | 6, 9, 10 | hsa-miR-20a, hsa-miR-496, hsa-let-7d* | 87.7% | 84.0% | 91.4% |
| SNRCC-145 | 10, 25, 26 | hsa-let-7d*, hsa-miR-633, hsa-miR-580 | 87.7% | 90.3% | 85.1% |
| SNRCC-146 | 1, 3, 4 | hsa-miR-106a, hsa-miR-523, hsa-miR-640 | 87.7% | 85.1% | 90.3% |
| SNRCC-147 | 3, 8 | hsa-miR-523, hsa-miR-34a* | 87.6% | 85.1% | 90.0% |
| SNRCC-148 | 5, 6 | hsa-miR-1251, hsa-miR-20a | 87.6% | 81.7% | 93.4% |
| SNRCC-149 | 7, 8 | hsa-miR-17, hsa-miR-34a* | 87.6% | 86.9% | 88.3% |
| SNRCC-150 | 2, 4, 8 | hsa-miR-20b, hsa-miR-640, hsa-miR-34a* | 87.6% | 86.0% | 89.1% |
| SNRCC-151 | 2, 6, 8 | hsa-miR-20b, hsa-miR-20a, hsa-miR-34a* | 87.6% | 84.0% | 91.1% |
| SNRCC-152 | 125, 38, 16 | hsa-miR-154, hsa-miR-25*, hsa-miR-891b | 87.6% | 84.3% | 90.9% |
| SNRCC-153 | 20, 1, 8 | hsa-miR-224, hsa-miR-106a, hsa-miR-34a* | 87.6% | 82.0% | 93.1% |
| SNRCC-154 | 8, 9, 12 | hsa-miR-34a*, hsa-miR-496, hsa-miR-518a-3p | 87.6% | 87.1% | 88.0% |
| SNRCC-155 | 39, 1, 3 | hsa-miR-373, hsa-miR-106a, hsa-miR-523 | 87.6% | 78.3% | 96.9% |
| SNRCC-156 | 10, 19 | hsa-let-7d*, hsa-miR-221* | 87.4% | 84.3% | 90.6% |
| SNRCC-157 | 6, 7, 8 | hsa-miR-20a, hsa-miR-17, hsa-miR-34a* | 87.4% | 85.7% | 89.1% |
| SNRCC-158 | 5, 8, 9 | hsa-miR-1251, hsa-miR-34a*, hsa-miR-496 | 87.4% | 87.1% | 87.7% |
| SNRCC-159 | 1, 8, 17 | hsa-miR-106a, hsa-miR-34a*, hsa-miR-450b-5p | 87.4% | 84.0% | 90.9% |
| SNRCC-160 | 10, 20, 3 | hsa-let-7d*, hsa-miR-224, hsa-miR-523 | 87.4% | 80.6% | 94.3% |
| SNRCC-161 | 10, 15, 26 | hsa-let-7d*, hsa-miR-93, hsa-miR-580 | 87.4% | 90.6% | 84.3% |
| SNRCC-162 | 16, 19, 20 | hsa-miR-891b, hsa-miR-221*, hsa-miR-224 | 87.4% | 82.6% | 92.3% |
| SNRCC-163 | 16, 17 | hsa-miR-891b, hsa-miR-450b-5p | 87.3% | 88.3% | 86.3% |
| SNRCC-164 | 18, 26 | hsa-miR-1260, hsa-miR-580 | 87.3% | 84.6% | 90.0% |
| SNRCC-165 | 1, 5, 7 | hsa-miR-106a, hsa-miR-1251, hsa-miR-17 | 87.3% | 79.7% | 94.9% |
| SNRCC-166 | 5, 6, 4 | hsa-miR-1251, hsa-miR-20a, hsa-miR-640 | 87.3% | 86.0% | 88.6% |
| SNRCC-167 | 25, 1, 16 | hsa-miR-633, hsa-miR-106a, hsa-miR-891b | 87.3% | 84.3% | 90.3% |
| SNRCC-168 | 8, 18, 17 | hsa-miR-34a*, hsa-miR-1260, hsa-miR-450b-5p | 87.3% | 82.9% | 91.7% |
| SNRCC-169 | 10, 15, 19 | hsa-let-7d*, hsa-miR-93, hsa-miR-221* | 87.3% | 84.6% | 90.0% |
| SNRCC-170 | 5, 39, 1 | hsa-miR-1251, hsa-miR-373, hsa-miR-106a | 87.3% | 86.3% | 88.3% |
| SNRCC-171 | 15, 16, 18 | hsa-miR-93, hsa-miR-891b, hsa-miR-1260 | 87.3% | 82.6% | 92.0% |
| SNRCC-172 | 25, 26, 28 | hsa-miR-633, hsa-miR-580, hsa-miR-548m | 87.3% | 89.1% | 85.4% |
| SNRCC-173 | 16, 74, 98 | hsa-miR-891b, hsa-miR-132*, hsa-miR-1305 | 87.1% | 82.6% | 91.7% |
| SNRCC-174 | 16, 137, 98 | hsa-miR-891b, hsa-miR-296-5p, hsa-miR-1305 | 87.1% | 85.7% | 88.6% |
| SNRCC-175 | 1, 18, 16 | hsa-miR-106a, hsa-miR-1260, hsa-miR-891b | 87.1% | 82.9% | 91.4% |
| SNRCC-176 | 5, 6, 39 | hsa-miR-1251, hsa-miR-20a, hsa-miR-373 | 87.1% | 83.4% | 90.9% |
| SNRCC-177 | 21, 23, 24 | hsa-miR-32*, hsa-miR-654-5p, hsa-miR-554 | 87.1% | 86.6% | 87.7% |
| SNRCC-178 | 5, 7, 15 | hsa-miR-1251, hsa-miR-17, hsa-miR-93 | 87.0% | 80.9% | 93.1% |

Figure 2 (cont.)

| | | | | | |
|---|---|---|---|---|---|
| SNRCC-179 | 14, 15, 17 | hsa-miR-367*, hsa-miR-93, hsa-miR-450b-5p | 87.0% | 80.3% | 93.7% |
| SNRCC-180 | 19, 26, 33 | hsa-miR-221*, hsa-miR-580, hsa-miR-103 | 87.0% | 89.4% | 84.6% |
| SNRCC-181 | 6, 3 | hsa-miR-20a, hsa-miR-523 | 86.9% | 77.7% | 96.0% |
| SNRCC-182 | 2, 3, 6 | hsa-miR-20b, hsa-miR-523, hsa-miR-20a | 86.9% | 77.7% | 96.0% |
| SNRCC-183 | 6, 3, 4 | hsa-miR-20a, hsa-miR-523, hsa-miR-640 | 86.9% | 81.1% | 92.6% |
| SNRCC-184 | 26, 29, 89 | hsa-miR-580, hsa-miR-606, hsa-miR-1538 | 86.9% | 84.0% | 89.7% |
| SNRCC-185 | 5, 7, 10 | hsa-miR-1251, hsa-miR-17, hsa-let-7d* | 86.9% | 82.6% | 91.1% |
| SNRCC-186 | 1, 6, 3 | hsa-miR-106a, hsa-miR-20a, hsa-miR-523 | 86.7% | 76.6% | 96.9% |
| SNRCC-187 | 1, 4, 5 | hsa-miR-106a, hsa-miR-640, hsa-miR-1251 | 86.7% | 87.4% | 86.0% |
| SNRCC-188 | 4, 5, 7 | hsa-miR-640, hsa-miR-1251, hsa-miR-17 | 86.7% | 83.1% | 90.3% |
| SNRCC-189 | 6, 8, 9 | hsa-miR-20a, hsa-miR-34a*, hsa-miR-496 | 86.7% | 82.9% | 90.6% |
| SNRCC-190 | 9, 10, 12 | hsa-miR-496, hsa-let-7d*, hsa-miR-518a-3p | 86.7% | 85.4% | 88.0% |
| SNRCC-191 | 9, 10, 13 | hsa-miR-496, hsa-let-7d*, hsa-miR-516b | 86.7% | 85.1% | 88.3% |
| SNRCC-192 | 1, 16, 17 | hsa-miR-106a, hsa-miR-891b, hsa-miR-450b-5p | 86.7% | 82.6% | 90.9% |
| SNRCC-193 | 7, 19, 26 | hsa-miR-17, hsa-miR-221*, hsa-miR-580 | 86.7% | 82.9% | 90.6% |
| SNRCC-194 | 23, 24, 25 | hsa-miR-654-5p, hsa-miR-554, hsa-miR-633 | 86.7% | 87.7% | 85.7% |
| SNRCC-195 | 24, 25, 26 | hsa-miR-554, hsa-miR-633, hsa-miR-580 | 86.7% | 88.3% | 85.1% |
| SNRCC-196 | 2, 3, 4 | hsa-miR-20b, hsa-miR-523, hsa-miR-640 | 86.7% | 82.0% | 91.4% |
| SNRCC-197 | 1, 8 | hsa-miR-106a, hsa-miR-34a* | 86.6% | 84.9% | 88.3% |
| SNRCC-198 | 16, 17, 74 | hsa-miR-891b, hsa-miR-450b-5p, hsa-miR-132* | 86.6% | 81.4% | 91.7% |
| SNRCC-199 | 74, 38, 16 | hsa-miR-132*, hsa-miR-25*, hsa-miR-891b | 86.6% | 84.3% | 88.9% |
| SNRCC-200 | 26, 29, 74 | hsa-miR-580, hsa-miR-606, hsa-miR-132* | 86.6% | 84.3% | 88.9% |
| SNRCC-201 | 10, 19, 25 | hsa-let-7d*, hsa-miR-221*, hsa-miR-633 | 86.6% | 84.0% | 89.1% |
| SNRCC-202 | 19, 26, 30 | hsa-miR-221*, hsa-miR-580, hsa-miR-216b | 86.6% | 90.3% | 82.9% |
| SNRCC-203 | 26, 30, 33 | hsa-miR-580, hsa-miR-216b, hsa-miR-103 | 86.6% | 92.3% | 80.9% |
| SNRCC-204 | 17, 11 | hsa-miR-450b-5p, hsa-miR-19b | 86.4% | 80.6% | 92.3% |
| SNRCC-205 | 16, 17, 98 | hsa-miR-891b, hsa-miR-450b-5p, hsa-miR-1305 | 86.4% | 86.3% | 86.6% |
| SNRCC-206 | 3, 6, 7 | hsa-miR-523, hsa-miR-20a, hsa-miR-17 | 86.4% | 77.4% | 95.4% |
| SNRCC-207 | 16, 17, 137 | hsa-miR-891b, hsa-miR-450b-5p, hsa-miR-296-5p | 86.4% | 85.7% | 87.1% |
| SNRCC-208 | 19, 175, 26 | hsa-miR-221*, hsa-miR-574-5p, hsa-miR-580 | 86.4% | 86.9% | 86.0% |
| SNRCC-209 | 7, 8, 9 | hsa-miR-17, hsa-miR-34a*, hsa-miR-496 | 86.4% | 83.7% | 89.1% |
| SNRCC-210 | 7, 10, 11 | hsa-miR-17, hsa-let-7d*, hsa-miR-19b | 86.4% | 81.1% | 91.7% |
| SNRCC-211 | 5, 4, 9 | hsa-miR-1251, hsa-miR-640, hsa-miR-496 | 86.3% | 87.7% | 84.9% |
| SNRCC-212 | 14, 15, 18 | hsa-miR-367*, hsa-miR-93, hsa-miR-1260 | 86.3% | 74.9% | 97.7% |
| SNRCC-213 | 18, 16, 17 | hsa-miR-1260, hsa-miR-891b, hsa-miR-450b-5p | 86.3% | 80.3% | 92.3% |
| SNRCC-214 | 23, 26, 27 | hsa-miR-654-5p, hsa-miR-580, hsa-miR-106b | 86.3% | 85.1% | 87.4% |
| SNRCC-215 | 23, 24 | hsa-miR-654-5p, hsa-miR-554 | 86.1% | 85.4% | 86.9% |
| SNRCC-216 | 26, 28 | hsa-miR-580, hsa-miR-548m | 86.1% | 87.4% | 84.9% |
| SNRCC-217 | 18, 16, 137 | hsa-miR-1260, hsa-miR-891b, hsa-miR-296-5p | 86.1% | 82.0% | 90.3% |
| SNRCC-218 | 1, 8, 18 | hsa-miR-106a, hsa-miR-34a*, hsa-miR-1260 | 86.1% | 79.4% | 92.9% |
| SNRCC-219 | 17, 11, 69 | hsa-miR-450b-5p, hsa-miR-19b, hsa-miR-34b* | 86.1% | 87.1% | 85.1% |
| SNRCC-220 | 10, 3 | hsa-let-7d*, hsa-miR-523 | 86.0% | 81.7% | 90.3% |
| SNRCC-221 | 1, 3 | hsa-miR-106a, hsa-miR-523 | 86.0% | 78.0% | 94.0% |
| SNRCC-222 | 3, 4, 19 | hsa-miR-523, hsa-miR-640, hsa-miR-221* | 86.0% | 82.9% | 89.1% |
| SNRCC-223 | 2, 6, 39 | hsa-miR-20b, hsa-miR-20a, hsa-miR-373 | 86.0% | 79.4% | 92.6% |
| SNRCC-224 | 6, 18, 33 | hsa-miR-20a, hsa-miR-1260, hsa-miR-103 | 86.0% | 74.9% | 97.1% |

Figure 2 (cont.)

| | | | | | |
|---|---|---|---|---|---|
| SNRCC-225 | 30, 7, 26 | hsa-miR-216b, hsa-miR-17, hsa-miR-580 | 86.0% | 86.3% | 85.7% |
| SNRCC-226 | 8, 9 | hsa-miR-34a*, hsa-miR-496 | 85.9% | 88.9% | 82.9% |
| SNRCC-227 | 2, 39, 4 | hsa-miR-20b, hsa-miR-373, hsa-miR-640 | 85.9% | 79.7% | 92.0% |
| SNRCC-228 | 39, 9, 10 | hsa-miR-373, hsa-miR-496, hsa-let-7d* | 85.9% | 86.3% | 85.4% |
| SNRCC-229 | 1, 2, 4 | hsa-miR-106a, hsa-miR-20b, hsa-miR-640 | 85.9% | 83.1% | 88.6% |
| SNRCC-230 | 25, 26, 27 | hsa-miR-633, hsa-miR-580, hsa-miR-106b | 85.9% | 86.0% | 85.7% |
| SNRCC-231 | 5, 39 | hsa-miR-1251, hsa-miR-373 | 85.7% | 83.1% | 88.3% |
| SNRCC-232 | 39, 6 | hsa-miR-373, hsa-miR-20a | 85.7% | 82.0% | 89.4% |
| SNRCC-233 | 2, 6, 10 | hsa-miR-20b, hsa-miR-20a, hsa-let-7d* | 85.7% | 81.1% | 90.3% |
| SNRCC-234 | 26, 30, 41 | hsa-miR-580, hsa-miR-216b, hsa-miR-18a | 85.7% | 88.0% | 83.4% |
| SNRCC-235 | 6, 10 | hsa-miR-20a, hsa-let-7d* | 85.6% | 81.1% | 90.0% |
| SNRCC-236 | 13, 14 | hsa-miR-516b, hsa-miR-367* | 85.6% | 83.4% | 87.7% |
| SNRCC-237 | 23, 26 | hsa-miR-654-5p, hsa-miR-580 | 85.6% | 86.0% | 85.1% |
| SNRCC-238 | 24, 26 | hsa-miR-554, hsa-miR-580 | 85.6% | 89.4% | 81.7% |
| SNRCC-239 | 26, 89, 74 | hsa-miR-580, hsa-miR-1538, hsa-miR-132* | 85.6% | 84.3% | 86.9% |
| SNRCC-240 | 13, 14, 17 | hsa-miR-516b, hsa-miR-367*, hsa-miR-450b-5p | 85.6% | 84.6% | 86.6% |
| SNRCC-241 | 19, 26, 29 | hsa-miR-221*, hsa-miR-580, hsa-miR-606 | 85.6% | 87.4% | 83.7% |
| SNRCC-242 | 4, 6 | hsa-miR-640, hsa-miR-20a | 85.4% | 81.7% | 89.1% |
| SNRCC-243 | 1, 6, 4 | hsa-miR-106a, hsa-miR-20a, hsa-miR-640 | 85.4% | 82.6% | 88.3% |
| SNRCC-244 | 6, 4, 9 | hsa-miR-20a, hsa-miR-640, hsa-miR-496 | 85.4% | 82.9% | 88.0% |
| SNRCC-245 | 6, 10, 15 | hsa-miR-20a, hsa-let-7d*, hsa-miR-93 | 85.4% | 82.0% | 88.9% |
| SNRCC-246 | 4, 8, 20 | hsa-miR-640, hsa-miR-34a*, hsa-miR-224 | 85.4% | 85.1% | 85.7% |
| SNRCC-247 | 9, 10, 25 | hsa-miR-496, hsa-let-7d*, hsa-miR-633 | 85.4% | 84.9% | 86.0% |
| SNRCC-248 | 5, 7 | hsa-miR-1251, hsa-miR-17 | 85.3% | 76.9% | 93.7% |
| SNRCC-249 | 4, 19 | hsa-miR-640, hsa-miR-221* | 85.3% | 85.7% | 84.9% |
| SNRCC-250 | 1, 4 | hsa-miR-106a, hsa-miR-640 | 85.3% | 84.6% | 86.0% |
| SNRCC-251 | 7, 10, 19 | hsa-miR-17, hsa-let-7d*, hsa-miR-221* | 85.3% | 84.6% | 86.0% |
| SNRCC-252 | 10, 19, 20 | hsa-let-7d*, hsa-miR-221*, hsa-miR-224 | 85.3% | 80.9% | 89.7% |
| SNRCC-253 | 25, 8, 18 | hsa-miR-633, hsa-miR-34a*, hsa-miR-1260 | 85.3% | 79.4% | 91.1% |
| SNRCC-254 | 2, 4 | hsa-miR-20b, hsa-miR-640 | 85.1% | 81.1% | 89.1% |
| SNRCC-255 | 13, 14, 15 | hsa-miR-516b, hsa-miR-367*, hsa-miR-93 | 85.1% | 78.6% | 91.7% |
| SNRCC-256 | 39, 1, 6 | hsa-miR-373, hsa-miR-106a, hsa-miR-20a | 85.1% | 80.3% | 90.0% |
| SNRCC-257 | 8, 17, 74 | hsa-miR-34a*, hsa-miR-450b-5p, hsa-miR-132* | 85.1% | 86.6% | 83.7% |
| SNRCC-258 | 10, 13 | hsa-let-7d*, hsa-miR-516b | 85.0% | 84.0% | 86.0% |
| SNRCC-259 | 2, 5, 10 | hsa-miR-20b, hsa-miR-1251, hsa-let-7d* | 85.0% | 80.0% | 90.0% |
| SNRCC-260 | 6, 3, 10 | hsa-miR-20a, hsa-miR-523, hsa-let-7d* | 85.0% | 78.3% | 91.7% |
| SNRCC-261 | 10, 3, 25 | hsa-let-7d*, hsa-miR-523, hsa-miR-633 | 85.0% | 81.1% | 88.9% |
| SNRCC-262 | 1, 2, 3 | hsa-miR-106a, hsa-miR-20b, hsa-miR-523 | 85.0% | 75.4% | 94.6% |
| SNRCC-263 | 19, 33 | hsa-miR-221*, hsa-miR-103 | 84.9% | 86.0% | 83.7% |
| SNRCC-264 | 26, 29 | hsa-miR-580, hsa-miR-606 | 84.9% | 84.6% | 85.1% |
| SNRCC-265 | 3, 4, 7 | hsa-miR-523, hsa-miR-640, hsa-miR-17 | 84.9% | 80.3% | 89.4% |
| SNRCC-266 | 5, 6, 15 | hsa-miR-1251, hsa-miR-20a, hsa-miR-93 | 84.9% | 78.6% | 91.1% |
| SNRCC-267 | 3, 25, 1 | hsa-miR-523, hsa-miR-633, hsa-miR-106a | 84.9% | 73.4% | 96.3% |
| SNRCC-268 | 15, 17, 19 | hsa-miR-93, hsa-miR-450b-5p, hsa-miR-221* | 84.9% | 74.9% | 94.9% |
| SNRCC-269 | 17, 18, 19 | hsa-miR-450b-5p, hsa-miR-1260, hsa-miR-221* | 84.9% | 78.6% | 91.1% |
| SNRCC-270 | 4, 9 | hsa-miR-640, hsa-miR-496 | 84.7% | 86.3% | 83.1% |

Figure 2 (cont.)

| | | | | | |
|---|---|---|---|---|---|
| SNRCC-271 | 25, 26 | hsa-miR-633, hsa-miR-580 | 84.7% | 83.7% | 85.7% |
| SNRCC-272 | 5, 1 | hsa-miR-1251, hsa-miR-106a | 84.7% | 81.1% | 88.3% |
| SNRCC-273 | 2, 4, 6 | hsa-miR-20b, hsa-miR-640, hsa-miR-20a | 84.7% | 77.7% | 91.7% |
| SNRCC-274 | 61, 56, 65 | hsa-miR-127-5p, hsa-miR-596, hsa-miR-33b | 84.7% | 84.0% | 85.4% |
| SNRCC-275 | 38, 16, 137 | hsa-miR-25*, hsa-miR-891b, hsa-miR-296-5p | 84.7% | 86.0% | 83.4% |
| SNRCC-276 | 12, 13, 14 | hsa-miR-518a-3p, hsa-miR-516b, hsa-miR-367* | 84.7% | 82.3% | 87.1% |
| SNRCC-277 | 39, 4, 10 | hsa-miR-373, hsa-miR-640, hsa-let-7d* | 84.7% | 83.4% | 86.0% |
| SNRCC-278 | 24, 25, 28 | hsa-miR-554, hsa-miR-633, hsa-miR-548m | 84.7% | 90.9% | 78.6% |
| SNRCC-279 | 8, 20 | hsa-miR-34a*, hsa-miR-224 | 84.6% | 80.6% | 88.6% |
| SNRCC-280 | 25, 26, 89 | hsa-miR-633, hsa-miR-580, hsa-miR-1538 | 84.6% | 81.4% | 87.7% |
| SNRCC-281 | 137, 11, 98 | hsa-miR-296-5p, hsa-miR-19b, hsa-miR-1305 | 84.6% | 83.4% | 85.7% |
| SNRCC-282 | 6, 39, 4 | hsa-miR-20a, hsa-miR-373, hsa-miR-640 | 84.6% | 80.3% | 88.9% |
| SNRCC-283 | 10, 20, 26 | hsa-let-7d*, hsa-miR-224, hsa-miR-580 | 84.6% | 85.1% | 84.0% |
| SNRCC-284 | 15, 18, 33 | hsa-miR-93, hsa-miR-1260, hsa-miR-103 | 84.6% | 75.1% | 94.0% |
| SNRCC-285 | 11, 12 | hsa-miR-19b, hsa-miR-518a-3p | 84.4% | 87.7% | 81.1% |
| SNRCC-286 | 12, 14 | hsa-miR-518a-3p, hsa-miR-367* | 84.4% | 81.7% | 87.1% |
| SNRCC-287 | 15, 17 | hsa-miR-93, hsa-miR-450b-5p | 84.4% | 72.6% | 96.3% |
| SNRCC-288 | 17, 11, 98 | hsa-miR-450b-5p, hsa-miR-19b, hsa-miR-1305 | 84.4% | 80.9% | 88.0% |
| SNRCC-289 | 26, 29, 9 | hsa-miR-580, hsa-miR-606, hsa-miR-496 | 84.4% | 83.1% | 85.7% |
| SNRCC-290 | 26, 9 | hsa-miR-580, hsa-miR-496 | 84.3% | 84.0% | 84.6% |
| SNRCC-291 | 5, 4 | hsa-miR-1251, hsa-miR-640 | 84.3% | 87.1% | 81.4% |
| SNRCC-292 | 6, 7, 10 | hsa-miR-20a, hsa-miR-17, hsa-let-7d* | 84.3% | 78.6% | 90.0% |
| SNRCC-293 | 89, 19, 175 | hsa-miR-1538, hsa-miR-221*, hsa-miR-574-5p | 84.3% | 74.6% | 94.0% |
| SNRCC-294 | 11, 12, 15 | hsa-miR-19b, hsa-miR-518a-3p, hsa-miR-93 | 84.3% | 83.7% | 84.9% |
| SNRCC-295 | 5, 39, 4 | hsa-miR-1251, hsa-miR-373, hsa-miR-640 | 84.3% | 85.1% | 83.4% |
| SNRCC-296 | 26, 30 | hsa-miR-580, hsa-miR-216b | 84.1% | 88.6% | 79.7% |
| SNRCC-297 | 15, 18, 19 | hsa-miR-93, hsa-miR-1260, hsa-miR-221* | 84.1% | 75.4% | 92.9% |
| SNRCC-298 | 3, 4 | hsa-miR-523, hsa-miR-640 | 84.0% | 81.1% | 86.9% |
| SNRCC-299 | 60, 56, 65 | hsa-miR-28-3p, hsa-miR-596, hsa-miR-33b | 84.0% | 84.9% | 83.1% |
| SNRCC-300 | 9, 10, 3 | hsa-miR-496, hsa-let-7d*, hsa-miR-523 | 84.0% | 78.9% | 89.1% |
| SNRCC-301 | 25, 26, 9 | hsa-miR-633, hsa-miR-580, hsa-miR-496 | 84.0% | 84.0% | 84.0% |
| SNRCC-302 | 5, 10 | hsa-miR-1251, hsa-let-7d* | 83.9% | 81.4% | 86.3% |
| SNRCC-303 | 11, 69 | hsa-miR-19b, hsa-miR-34b* | 83.9% | 83.4% | 84.3% |
| SNRCC-304 | 10, 15, 18 | hsa-let-7d*, hsa-miR-93, hsa-miR-1260 | 83.9% | 77.7% | 90.0% |
| SNRCC-305 | 22, 23, 24 | hsa-miR-934, hsa-miR-654-5p, hsa-miR-554 | 83.9% | 83.1% | 84.6% |
| SNRCC-306 | 15, 26, 30 | hsa-miR-93, hsa-miR-580, hsa-miR-216b | 83.9% | 86.3% | 81.4% |
| SNRCC-307 | 19, 26, 35 | hsa-miR-221*, hsa-miR-580, hsa-miR-200a* | 83.9% | 84.9% | 82.9% |
| SNRCC-308 | 25, 26, 29 | hsa-miR-633, hsa-miR-580, hsa-miR-606 | 83.9% | 82.0% | 85.7% |
| SNRCC-309 | 4, 7 | hsa-miR-640, hsa-miR-17 | 83.7% | 81.1% | 86.3% |
| SNRCC-310 | 10, 25 | hsa-let-7d*, hsa-miR-633 | 83.7% | 82.6% | 84.9% |
| SNRCC-311 | 2, 3 | hsa-miR-20b, hsa-miR-523 | 83.7% | 73.4% | 94.0% |
| SNRCC-312 | 17, 74, 98 | hsa-miR-450b-5p, hsa-miR-132*, hsa-miR-1305 | 83.7% | 74.0% | 93.4% |
| SNRCC-313 | 30, 175, 26 | hsa-miR-216b, hsa-miR-574-5p, hsa-miR-580 | 83.7% | 88.6% | 78.9% |
| SNRCC-314 | 12, 13, 15 | hsa-miR-518a-3p, hsa-miR-516b, hsa-miR-93 | 83.7% | 82.6% | 84.9% |
| SNRCC-315 | 20, 23, 24 | hsa-miR-224, hsa-miR-654-5p, hsa-miR-554 | 83.7% | 81.4% | 86.0% |
| SNRCC-316 | 39, 10, 20 | hsa-miR-373, hsa-let-7d*, hsa-miR-224 | 83.7% | 83.4% | 84.0% |

Figure 2 (cont.)

| | | | | | |
|---|---|---|---|---|---|
| SNRCC-317 | 56, 65 | hsa-miR-596, hsa-miR-33b | 83.6% | 83.4% | 83.7% |
| SNRCC-318 | 10, 3, 1 | hsa-let-7d*, hsa-miR-523, hsa-miR-106a | 83.6% | 78.0% | 89.1% |
| SNRCC-319 | 60, 61, 65 | hsa-miR-28-3p, hsa-miR-127-5p, hsa-miR-33b | 83.6% | 83.4% | 83.7% |
| SNRCC-320 | 75, 83, 94 | hsa-miR-936, hsa-miR-145, hsa-miR-181a-2* | 83.6% | 82.3% | 84.9% |
| SNRCC-321 | 6, 10, 18 | hsa-miR-20a, hsa-let-7d*, hsa-miR-1260 | 83.6% | 77.1% | 90.0% |
| SNRCC-322 | 4, 10, 20 | hsa-miR-640, hsa-let-7d*, hsa-miR-224 | 83.6% | 81.1% | 86.0% |
| SNRCC-323 | 1, 18, 17 | hsa-miR-106a, hsa-miR-1260, hsa-miR-450b-5p | 83.6% | 72.3% | 94.9% |
| SNRCC-324 | 39, 1, 2 | hsa-miR-373, hsa-miR-106a, hsa-miR-20b | 83.6% | 77.1% | 90.0% |
| SNRCC-325 | 18, 19, 21 | hsa-miR-1260, hsa-miR-221*, hsa-miR-32* | 83.6% | 77.7% | 89.4% |
| SNRCC-326 | 20, 3 | hsa-miR-224, hsa-miR-523 | 83.4% | 73.7% | 93.1% |
| SNRCC-327 | 26, 9, 74 | hsa-miR-580, hsa-miR-496, hsa-miR-132* | 83.4% | 82.3% | 84.6% |
| SNRCC-328 | 7, 175, 26 | hsa-miR-17, hsa-miR-574-5p, hsa-miR-580 | 83.4% | 80.0% | 86.9% |
| SNRCC-329 | 11, 98, 116 | hsa-miR-19b, hsa-miR-1305, hsa-miR-1321 | 83.4% | 77.7% | 89.1% |
| SNRCC-330 | 137, 11, 125 | hsa-miR-296-5p, hsa-miR-19b, hsa-miR-154 | 83.4% | 81.1% | 85.7% |
| SNRCC-331 | 11, 13, 15 | hsa-miR-19b, hsa-miR-516b, hsa-miR-93 | 83.4% | 78.6% | 88.3% |
| SNRCC-332 | 23, 24, 27 | hsa-miR-654-5p, hsa-miR-554, hsa-miR-106b | 83.4% | 82.6% | 84.3% |
| SNRCC-333 | 10, 15 | hsa-let-7d*, hsa-miR-93 | 83.3% | 82.3% | 84.3% |
| SNRCC-334 | 3, 25 | hsa-miR-523, hsa-miR-633 | 83.3% | 76.0% | 90.6% |
| SNRCC-335 | 4, 6, 7 | hsa-miR-640, hsa-miR-20a, hsa-miR-17 | 83.3% | 79.1% | 87.4% |
| SNRCC-336 | 18, 17, 137 | hsa-miR-1260, hsa-miR-450b-5p, hsa-miR-296-5p | 83.3% | 79.1% | 87.4% |
| SNRCC-337 | 10, 25, 1 | hsa-let-7d*, hsa-miR-633, hsa-miR-106a | 83.3% | 80.3% | 86.3% |
| SNRCC-338 | 39, 4, 9 | hsa-miR-373, hsa-miR-640, hsa-miR-496 | 83.3% | 81.1% | 85.4% |
| SNRCC-339 | 16, 17, 20 | hsa-miR-891b, hsa-miR-450b-5p, hsa-miR-224 | 83.3% | 81.7% | 84.9% |
| SNRCC-340 | 8, 18 | hsa-miR-34a*, hsa-miR-1260 | 83.1% | 76.3% | 90.0% |
| SNRCC-341 | 39, 1 | hsa-miR-373, hsa-miR-106a | 83.1% | 81.4% | 84.9% |
| SNRCC-342 | 5, 6, 10 | hsa-miR-1251, hsa-miR-20a, hsa-let-7d* | 83.1% | 76.3% | 90.0% |
| SNRCC-343 | 98, 11, 125 | hsa-miR-1305, hsa-miR-19b, hsa-miR-154 | 83.1% | 77.4% | 88.9% |
| SNRCC-344 | 7, 9, 10 | hsa-miR-17, hsa-miR-496, hsa-let-7d* | 83.1% | 77.1% | 89.1% |
| SNRCC-345 | 5, 10, 15 | hsa-miR-1251, hsa-let-7d*, hsa-miR-93 | 83.1% | 80.9% | 85.4% |
| SNRCC-346 | 6, 39, 9 | hsa-miR-20a, hsa-miR-373, hsa-miR-496 | 83.1% | 73.7% | 92.6% |
| SNRCC-347 | 18, 19, 20 | hsa-miR-1260, hsa-miR-221*, hsa-miR-224 | 83.1% | 73.7% | 92.6% |
| SNRCC-348 | 20, 26, 29 | hsa-miR-224, hsa-miR-580, hsa-miR-606 | 83.1% | 82.9% | 83.4% |
| SNRCC-349 | 10, 18 | hsa-let-7d*, hsa-miR-1260 | 83.0% | 77.4% | 88.6% |
| SNRCC-350 | 60, 58, 65 | hsa-miR-28-3p, hsa-miR-454, hsa-miR-33b | 83.0% | 83.4% | 82.6% |
| SNRCC-351 | 21, 23, 25 | hsa-miR-32*, hsa-miR-654-5p, hsa-miR-633 | 83.0% | 81.1% | 84.9% |
| SNRCC-352 | 22, 23, 25 | hsa-miR-934, hsa-miR-654-5p, hsa-miR-633 | 83.0% | 80.3% | 85.7% |
| SNRCC-353 | 39, 2 | hsa-miR-373, hsa-miR-20b | 82.9% | 79.4% | 86.3% |
| SNRCC-354 | 89, 7, 19 | hsa-miR-1538, hsa-miR-17, hsa-miR-221* | 82.9% | 73.1% | 92.6% |
| SNRCC-355 | 9, 11, 12 | hsa-miR-496, hsa-miR-19b, hsa-miR-518a-3p | 82.9% | 83.4% | 82.3% |
| SNRCC-356 | 7, 15, 19 | hsa-miR-17, hsa-miR-93, hsa-miR-221* | 82.9% | 74.6% | 91.1% |
| SNRCC-357 | 23, 25 | hsa-miR-654-5p, hsa-miR-633 | 82.7% | 77.4% | 88.0% |
| SNRCC-358 | 39, 10 | hsa-miR-373, hsa-let-7d* | 82.7% | 84.6% | 80.9% |
| SNRCC-359 | 2, 7, 10 | hsa-miR-20b, hsa-miR-17, hsa-let-7d* | 82.7% | 79.4% | 86.0% |
| SNRCC-360 | 6, 7, 33 | hsa-miR-20a, hsa-miR-17, hsa-miR-103 | 82.7% | 72.9% | 92.6% |
| SNRCC-361 | 7, 10 | hsa-miR-17, hsa-let-7d* | 82.6% | 80.0% | 85.1% |
| SNRCC-362 | 11, 13 | hsa-miR-19b, hsa-miR-516b | 82.6% | 79.7% | 85.4% |

Figure 2 (cont.)

| SNRCC-363 | 12, 15 | hsa-miR-518a-3p, hsa-miR-93 | 82.6% | 73.7% | 91.4% |
|---|---|---|---|---|---|
| SNRCC-364 | 15, 19 | hsa-miR-93, hsa-miR-221* | 82.6% | 76.0% | 89.1% |
| SNRCC-365 | 19, 26 | hsa-miR-221*, hsa-miR-580 | 82.6% | 80.0% | 85.1% |
| SNRCC-366 | 11, 69, 46 | hsa-miR-19b, hsa-miR-34b*, hsa-miR-302f | 82.6% | 82.9% | 82.3% |
| SNRCC-367 | 4, 9, 3 | hsa-miR-640, hsa-miR-496, hsa-miR-523 | 82.6% | 79.7% | 85.4% |
| SNRCC-368 | 3, 1, 18 | hsa-miR-523, hsa-miR-106a, hsa-miR-1260 | 82.6% | 70.6% | 94.6% |
| SNRCC-369 | 20, 3, 1 | hsa-miR-224, hsa-miR-523, hsa-miR-106a | 82.6% | 73.4% | 91.7% |
| SNRCC-370 | 7, 18, 19 | hsa-miR-17, hsa-miR-1260, hsa-miR-221* | 82.6% | 76.9% | 88.3% |
| SNRCC-371 | 3, 25, 18 | hsa-miR-523, hsa-miR-633, hsa-miR-1260 | 82.6% | 74.0% | 91.1% |
| SNRCC-372 | 20, 3, 25 | hsa-miR-224, hsa-miR-523, hsa-miR-633 | 82.6% | 71.4% | 93.7% |
| SNRCC-373 | 6, 39, 10 | hsa-miR-20a, hsa-miR-373, hsa-let-7d* | 82.6% | 80.9% | 84.3% |
| SNRCC-374 | 7, 18, 33 | hsa-miR-17, hsa-miR-1260, hsa-miR-103 | 82.6% | 69.1% | 96.0% |
| SNRCC-375 | 19, 20, 26 | hsa-miR-221*, hsa-miR-224, hsa-miR-580 | 82.6% | 80.9% | 84.3% |
| SNRCC-376 | 83, 94 | hsa-miR-145, hsa-miR-181a-2* | 82.4% | 85.7% | 79.1% |
| SNRCC-377 | 9, 10 | hsa-miR-496, hsa-let-7d* | 82.4% | 80.9% | 84.0% |
| SNRCC-378 | 18, 19 | hsa-miR-1260, hsa-miR-221* | 82.4% | 77.7% | 87.1% |
| SNRCC-379 | 24, 25 | hsa-miR-554, hsa-miR-633 | 82.4% | 82.0% | 82.9% |
| SNRCC-380 | 56, 58, 65 | hsa-miR-596, hsa-miR-454, hsa-miR-33b | 82.4% | 80.0% | 84.9% |
| SNRCC-381 | 73, 83, 94 | hsa-miR-1227, hsa-miR-145, hsa-miR-181a-2* | 82.4% | 88.3% | 76.6% |
| SNRCC-382 | 4, 20, 3 | hsa-miR-640, hsa-miR-224, hsa-miR-523 | 82.3% | 80.6% | 84.0% |
| SNRCC-383 | 83, 144, 155 | hsa-miR-145, hsa-miR-18b, hsa-miR-720 | 82.3% | 83.7% | 80.9% |
| SNRCC-384 | 9, 11 | hsa-miR-496, hsa-miR-19b | 82.1% | 80.6% | 83.7% |
| SNRCC-385 | 83, 155 | hsa-miR-145, hsa-miR-720 | 82.1% | 82.3% | 82.0% |
| SNRCC-386 | 11, 98, 69 | hsa-miR-19b, hsa-miR-1305, hsa-miR-34b* | 82.1% | 83.4% | 80.9% |
| SNRCC-387 | 6, 15, 33 | hsa-miR-20a, hsa-miR-93, hsa-miR-103 | 82.1% | 74.6% | 89.7% |
| SNRCC-388 | 22, 24, 25 | hsa-miR-934, hsa-miR-554, hsa-miR-633 | 82.1% | 80.3% | 84.0% |
| SNRCC-389 | 46, 7, 19 | hsa-miR-302f, hsa-miR-17, hsa-miR-221* | 82.1% | 75.1% | 89.1% |
| SNRCC-390 | 26, 89 | hsa-miR-580, hsa-miR-1538 | 82.0% | 75.7% | 88.3% |
| SNRCC-391 | 74, 98 | hsa-miR-132*, hsa-miR-1305 | 82.0% | 73.4% | 90.6% |
| SNRCC-392 | 26, 33 | hsa-miR-580, hsa-miR-103 | 82.0% | 84.0% | 80.0% |
| SNRCC-393 | 7, 9, 11 | hsa-miR-17, hsa-miR-496, hsa-miR-19b | 82.0% | 75.1% | 88.9% |
| SNRCC-394 | 9, 3, 25 | hsa-miR-496, hsa-miR-523, hsa-miR-633 | 82.0% | 74.9% | 89.1% |
| SNRCC-395 | 15, 17, 18 | hsa-miR-93, hsa-miR-450b-5p, hsa-miR-1260 | 82.0% | 71.1% | 92.9% |
| SNRCC-396 | 20, 25, 26 | hsa-miR-224, hsa-miR-633, hsa-miR-580 | 82.0% | 82.6% | 81.4% |
| SNRCC-397 | 25, 27, 28 | hsa-miR-633, hsa-miR-106b, hsa-miR-548m | 82.0% | 84.3% | 79.7% |
| SNRCC-398 | 26, 33, 35 | hsa-miR-580, hsa-miR-103, hsa-miR-200a* | 82.0% | 85.4% | 78.6% |
| SNRCC-399 | 18, 33, 44 | hsa-miR-1260, hsa-miR-103, hsa-miR-646 | 82.0% | 74.3% | 89.7% |
| SNRCC-400 | 137, 155 | hsa-miR-296-5p, hsa-miR-720 | 81.9% | 83.4% | 80.3% |
| SNRCC-401 | 98, 69, 46 | hsa-miR-1305, hsa-miR-34b*, hsa-miR-302f | 81.9% | 76.3% | 87.4% |
| SNRCC-402 | 19, 22, 23 | hsa-miR-221*, hsa-miR-934, hsa-miR-654-5p | 81.9% | 80.3% | 83.4% |
| SNRCC-403 | 75, 82, 83 | hsa-miR-936, hsa-miR-664, hsa-miR-145 | 81.7% | 81.7% | 81.7% |
| SNRCC-404 | 15, 26 | hsa-miR-93, hsa-miR-580 | 81.6% | 82.3% | 80.9% |
| SNRCC-405 | 60, 61, 56 | hsa-miR-28-3p, hsa-miR-127-5p, hsa-miR-596 | 81.6% | 78.0% | 85.1% |
| SNRCC-406 | 74, 98, 11 | hsa-miR-132*, hsa-miR-1305, hsa-miR-19b | 81.6% | 74.9% | 88.3% |
| SNRCC-407 | 74, 98, 116 | hsa-miR-132*, hsa-miR-1305, hsa-miR-1321 | 81.6% | 75.1% | 88.0% |
| SNRCC-408 | 21, 22, 25 | hsa-miR-32*, hsa-miR-934, hsa-miR-633 | 81.6% | 77.1% | 86.0% |

Figure 2 (cont.)

| | | | | | |
|---|---|---|---|---|---|
| SNRCC-409 | 24, 27, 28 | hsa-miR-554, hsa-miR-106b, hsa-miR-548m | 81.6% | 85.7% | 77.4% |
| SNRCC-410 | 69, 46 | hsa-miR-34b*, hsa-miR-302f | 81.4% | 80.9% | 82.0% |
| SNRCC-411 | 137, 11, 46 | hsa-miR-296-5p, hsa-miR-19b, hsa-miR-302f | 81.4% | 82.3% | 80.6% |
| SNRCC-412 | 58, 82, 144 | hsa-miR-454, hsa-miR-664, hsa-miR-18b | 81.4% | 78.3% | 84.6% |
| SNRCC-413 | 21, 24, 25 | hsa-miR-32*, hsa-miR-554, hsa-miR-633 | 81.4% | 80.9% | 82.0% |
| SNRCC-414 | 47, 56 | hsa-miR-218-1*, hsa-miR-596 | 81.3% | 74.0% | 88.6% |
| SNRCC-415 | 10, 20 | hsa-let-7d*, hsa-miR-224 | 81.3% | 78.3% | 84.3% |
| SNRCC-416 | 25, 28 | hsa-miR-633, hsa-miR-548m | 81.3% | 85.4% | 77.1% |
| SNRCC-417 | 2, 6 | hsa-miR-20b, hsa-miR-20a | 81.3% | 70.3% | 92.3% |
| SNRCC-418 | 144, 155, 175 | hsa-miR-18b, hsa-miR-720, hsa-miR-574-5p | 81.3% | 86.0% | 76.6% |
| SNRCC-419 | 19, 21, 23 | hsa-miR-221*, hsa-miR-32*, hsa-miR-654-5p | 81.3% | 77.7% | 84.9% |
| SNRCC-420 | 137, 11 | hsa-miR-296-5p, hsa-miR-19b | 81.1% | 77.7% | 84.6% |
| SNRCC-421 | 6, 9 | hsa-miR-20a, hsa-miR-496 | 81.1% | 69.4% | 92.9% |
| SNRCC-422 | 25, 1 | hsa-miR-633, hsa-miR-106a | 81.1% | 69.7% | 92.6% |
| SNRCC-423 | 17, 74, 11 | hsa-miR-450b-5p, hsa-miR-132*, hsa-miR-19b | 81.1% | 74.3% | 88.0% |
| SNRCC-424 | 1, 2, 15 | hsa-miR-106a, hsa-miR-20b, hsa-miR-93 | 81.1% | 72.6% | 89.7% |
| SNRCC-425 | 26, 27 | hsa-miR-580, hsa-miR-106b | 81.0% | 83.1% | 78.9% |
| SNRCC-426 | 17, 74 | hsa-miR-450b-5p, hsa-miR-132* | 81.0% | 73.4% | 88.6% |
| SNRCC-427 | 74, 137, 98 | hsa-miR-132*, hsa-miR-296-5p, hsa-miR-1305 | 81.0% | 72.0% | 90.0% |
| SNRCC-428 | 137, 98, 125 | hsa-miR-296-5p, hsa-miR-1305, hsa-miR-154 | 81.0% | 76.0% | 86.0% |
| SNRCC-429 | 18, 38, 17 | hsa-miR-1260, hsa-miR-25*, hsa-miR-450b-5p | 81.0% | 77.7% | 84.3% |
| SNRCC-430 | 26, 30, 35 | hsa-miR-580, hsa-miR-216b, hsa-miR-200a* | 81.0% | 85.7% | 76.3% |
| SNRCC-431 | 33, 44, 60 | hsa-miR-103, hsa-miR-646, hsa-miR-28-3p | 80.9% | 80.6% | 81.1% |
| SNRCC-432 | 56, 65, 73 | hsa-miR-596, hsa-miR-33b, hsa-miR-1227 | 80.9% | 87.4% | 74.3% |
| SNRCC-433 | 58, 82, 83 | hsa-miR-454, hsa-miR-664, hsa-miR-145 | 80.9% | 81.1% | 80.6% |
| SNRCC-434 | 9, 20, 3 | hsa-miR-496, hsa-miR-224, hsa-miR-523 | 80.9% | 72.6% | 89.1% |
| SNRCC-435 | 10, 20, 25 | hsa-let-7d*, hsa-miR-224, hsa-miR-633 | 80.9% | 75.7% | 86.0% |
| SNRCC-436 | 17, 19, 20 | hsa-miR-450b-5p, hsa-miR-221*, hsa-miR-224 | 80.9% | 70.0% | 91.7% |
| SNRCC-437 | 19, 20, 21 | hsa-miR-221*, hsa-miR-224, hsa-miR-32* | 80.9% | 73.1% | 88.6% |
| SNRCC-438 | 89, 19 | hsa-miR-1538, hsa-miR-221* | 80.7% | 71.1% | 90.3% |
| SNRCC-439 | 75, 82 | hsa-miR-936, hsa-miR-664 | 80.7% | 80.9% | 80.6% |
| SNRCC-440 | 7, 19 | hsa-miR-17, hsa-miR-221* | 80.7% | 73.7% | 87.7% |
| SNRCC-441 | 25, 18 | hsa-miR-633, hsa-miR-1260 | 80.7% | 71.1% | 90.3% |
| SNRCC-442 | 46, 89, 19 | hsa-miR-302f, hsa-miR-1538, hsa-miR-221* | 80.7% | 76.0% | 85.4% |
| SNRCC-443 | 98, 11, 46 | hsa-miR-1305, hsa-miR-19b, hsa-miR-302f | 80.7% | 80.3% | 81.1% |
| SNRCC-444 | 58, 83, 144 | hsa-miR-454, hsa-miR-145, hsa-miR-18b | 80.7% | 80.0% | 81.4% |
| SNRCC-445 | 20, 21, 24 | hsa-miR-224, hsa-miR-32*, hsa-miR-554 | 80.7% | 81.1% | 80.3% |
| SNRCC-446 | 19, 30, 33 | hsa-miR-221*, hsa-miR-216b, hsa-miR-103 | 80.7% | 81.1% | 80.3% |
| SNRCC-447 | 9, 3 | hsa-miR-496, hsa-miR-523 | 80.6% | 70.9% | 90.3% |
| SNRCC-448 | 7, 26 | hsa-miR-17, hsa-miR-580 | 80.6% | 78.9% | 82.3% |
| SNRCC-449 | 39, 4 | hsa-miR-373, hsa-miR-640 | 80.6% | 81.4% | 79.7% |
| SNRCC-450 | 22, 24 | hsa-miR-934, hsa-miR-554 | 80.6% | 81.4% | 79.7% |
| SNRCC-451 | 74, 18, 38 | hsa-miR-132*, hsa-miR-1260, hsa-miR-25* | 80.6% | 80.0% | 81.1% |
| SNRCC-452 | 74, 137, 11 | hsa-miR-132*, hsa-miR-296-5p, hsa-miR-19b | 80.6% | 76.9% | 84.3% |
| SNRCC-453 | 2, 6, 18 | hsa-miR-20b, hsa-miR-20a, hsa-miR-1260 | 80.6% | 71.7% | 89.4% |
| SNRCC-454 | 7, 10, 18 | hsa-miR-17, hsa-let-7d*, hsa-miR-1260 | 80.6% | 75.1% | 86.0% |

Figure 2 (cont.)

| | | | | | |
|---|---|---|---|---|---|
| SNRCC-455 | 25, 1, 18 | hsa-miR-633, hsa-miR-106a, hsa-miR-1260 | 80.6% | 69.1% | 92.0% |
| SNRCC-456 | 38, 17, 11 | hsa-miR-25*, hsa-miR-450b-5p, hsa-miR-19b | 80.6% | 72.9% | 88.3% |
| SNRCC-457 | 12, 13 | hsa-miR-518a-3p, hsa-miR-516b | 80.4% | 83.7% | 77.1% |
| SNRCC-458 | 14, 15 | hsa-miR-367*, hsa-miR-93 | 80.4% | 73.4% | 87.4% |
| SNRCC-459 | 26, 33, 41 | hsa-miR-580, hsa-miR-103, hsa-miR-18a | 80.4% | 84.6% | 76.3% |
| SNRCC-460 | 26, 35, 41 | hsa-miR-580, hsa-miR-200a*, hsa-miR-18a | 80.4% | 80.9% | 80.0% |
| SNRCC-461 | 11, 69, 116 | hsa-miR-19b, hsa-miR-34b*, hsa-miR-1321 | 80.4% | 82.9% | 78.0% |
| SNRCC-462 | 74, 125, 38 | hsa-miR-132*, hsa-miR-154, hsa-miR-25* | 80.4% | 77.1% | 83.7% |
| SNRCC-463 | 82, 83, 94 | hsa-miR-664, hsa-miR-145, hsa-miR-181a-2* | 80.4% | 84.6% | 76.3% |
| SNRCC-464 | 10, 20, 1 | hsa-let-7d*, hsa-miR-224, hsa-miR-106a | 80.4% | 78.9% | 82.0% |
| SNRCC-465 | 98, 116, 125 | hsa-miR-1305, hsa-miR-1321, hsa-miR-154 | 80.4% | 73.7% | 87.1% |
| SNRCC-466 | 1, 2, 6 | hsa-miR-106a, hsa-miR-20b, hsa-miR-20a | 80.4% | 69.7% | 91.1% |
| SNRCC-467 | 74, 38 | hsa-miR-132*, hsa-miR-25* | 80.3% | 80.9% | 79.7% |
| SNRCC-468 | 175, 26 | hsa-miR-574-5p, hsa-miR-580 | 80.3% | 79.4% | 81.1% |
| SNRCC-469 | 7, 33 | hsa-miR-17, hsa-miR-103 | 80.3% | 73.4% | 87.1% |
| SNRCC-470 | 1, 6 | hsa-miR-106a, hsa-miR-20a | 80.3% | 70.0% | 90.6% |
| SNRCC-471 | 11, 125, 46 | hsa-miR-19b, hsa-miR-154, hsa-miR-302f | 80.3% | 82.3% | 78.3% |
| SNRCC-472 | 5, 39, 9 | hsa-miR-1251, hsa-miR-373, hsa-miR-496 | 80.3% | 76.9% | 83.7% |
| SNRCC-473 | 18, 19, 22 | hsa-miR-1260, hsa-miR-221*, hsa-miR-934 | 80.3% | 74.3% | 86.3% |
| SNRCC-474 | 1, 2 | hsa-miR-106a, hsa-miR-20b | 80.1% | 69.7% | 90.6% |
| SNRCC-475 | 18, 17 | hsa-miR-1260, hsa-miR-450b-5p | 80.1% | 71.7% | 88.6% |
| SNRCC-476 | 38, 17 | hsa-miR-25*, hsa-miR-450b-5p | 80.1% | 78.3% | 82.0% |
| SNRCC-477 | 56, 58, 63 | hsa-miR-596, hsa-miR-454, hsa-miR-328 | 80.1% | 80.6% | 79.7% |
| SNRCC-478 | 2, 6, 15 | hsa-miR-20b, hsa-miR-20a, hsa-miR-93 | 80.1% | 69.4% | 90.9% |
| SNRCC-479 | 18, 20, 22 | hsa-miR-1260, hsa-miR-224, hsa-miR-934 | 80.1% | 75.1% | 85.1% |
| SNRCC-480 | 11, 125 | hsa-miR-19b, hsa-miR-154 | 80.0% | 80.0% | 80.0% |
| SNRCC-481 | 75, 83 | hsa-miR-936, hsa-miR-145 | 80.0% | 77.4% | 82.6% |
| SNRCC-482 | 26, 9, 89 | hsa-miR-580, hsa-miR-496, hsa-miR-1538 | 80.0% | 74.3% | 85.7% |
| SNRCC-483 | 20, 22, 24 | hsa-miR-224, hsa-miR-934, hsa-miR-554 | 80.0% | 80.3% | 79.7% |
| SNRCC-484 | 98, 125 | hsa-miR-1305, hsa-miR-154 | 79.9% | 78.0% | 81.7% |
| SNRCC-485 | 19, 25 | hsa-miR-221*, hsa-miR-633 | 79.9% | 75.1% | 84.6% |
| SNRCC-486 | 27, 28 | hsa-miR-106b, hsa-miR-548m | 79.9% | 80.6% | 79.1% |
| SNRCC-487 | 21, 22, 24 | hsa-miR-32*, hsa-miR-934, hsa-miR-554 | 79.9% | 78.9% | 80.9% |
| SNRCC-488 | 2, 15 | hsa-miR-20b, hsa-miR-93 | 79.7% | 69.1% | 90.3% |
| SNRCC-489 | 1, 6, 7 | hsa-miR-106a, hsa-miR-20a, hsa-miR-17 | 79.7% | 72.6% | 86.9% |
| SNRCC-490 | 4, 19, 20 | hsa-miR-640, hsa-miR-221*, hsa-miR-224 | 79.7% | 78.0% | 81.4% |
| SNRCC-491 | 17, 18, 21 | hsa-miR-450b-5p, hsa-miR-1260, hsa-miR-32* | 79.7% | 73.7% | 85.7% |
| SNRCC-492 | 23, 25, 27 | hsa-miR-654-5p, hsa-miR-633, hsa-miR-106b | 79.7% | 73.4% | 86.0% |
| SNRCC-493 | 74, 11, 116 | hsa-miR-132*, hsa-miR-19b, hsa-miR-1321 | 79.6% | 78.3% | 80.9% |
| SNRCC-494 | 65, 73, 82 | hsa-miR-33b, hsa-miR-1227, hsa-miR-664 | 79.6% | 84.9% | 74.3% |
| SNRCC-495 | 63, 75, 83 | hsa-miR-328, hsa-miR-936, hsa-miR-145 | 79.6% | 80.6% | 78.6% |
| SNRCC-496 | 18, 74, 137 | hsa-miR-1260, hsa-miR-132*, hsa-miR-296-5p | 79.6% | 72.6% | 86.6% |
| SNRCC-497 | 75, 82, 94 | hsa-miR-936, hsa-miR-664, hsa-miR-181a-2* | 79.6% | 81.4% | 77.7% |
| SNRCC-498 | 20, 25, 1 | hsa-miR-224, hsa-miR-633, hsa-miR-106a | 79.6% | 71.4% | 87.7% |
| SNRCC-499 | 19, 20, 23 | hsa-miR-221*, hsa-miR-224, hsa-miR-654-5p | 79.6% | 73.4% | 85.7% |
| SNRCC-500 | 18, 30, 33 | hsa-miR-1260, hsa-miR-216b, hsa-miR-103 | 79.6% | 75.7% | 83.4% |

Figure 2 (cont.)

| SNRCC-501 | 18, 33, 41 | hsa-miR-1260, hsa-miR-103, hsa-miR-18a | 79.6% | 70.0% | 89.1% |
|---|---|---|---|---|---|
| SNRCC-502 | 98, 11 | hsa-miR-1305, hsa-miR-19b | 79.4% | 76.9% | 82.0% |
| SNRCC-503 | 61, 65 | hsa-miR-127-5p, hsa-miR-33b | 79.4% | 80.3% | 78.6% |
| SNRCC-504 | 2, 6, 7 | hsa-miR-20b, hsa-miR-20a, hsa-miR-17 | 79.4% | 71.7% | 87.1% |
| SNRCC-505 | 9, 10, 20 | hsa-miR-496, hsa-let-7d*, hsa-miR-224 | 79.4% | 75.7% | 83.1% |
| SNRCC-506 | 155, 161, 195 | hsa-miR-720, hsa-miR-422a, hsa-miR-197 | 79.4% | 80.6% | 78.3% |
| SNRCC-507 | 89, 74, 18 | hsa-miR-1538, hsa-miR-132*, hsa-miR-1260 | 79.3% | 77.7% | 80.9% |
| SNRCC-508 | 61, 58, 65 | hsa-miR-127-5p, hsa-miR-454, hsa-miR-33b | 79.3% | 72.0% | 86.6% |
| SNRCC-509 | 73, 82, 94 | hsa-miR-1227, hsa-miR-664, hsa-miR-181a-2* | 79.3% | 84.9% | 73.7% |
| SNRCC-510 | 82, 83, 155 | hsa-miR-664, hsa-miR-145, hsa-miR-720 | 79.3% | 81.4% | 77.1% |
| SNRCC-511 | 83, 137, 155 | hsa-miR-145, hsa-miR-296-5p, hsa-miR-720 | 79.3% | 80.3% | 78.3% |
| SNRCC-512 | 61, 56, 63 | hsa-miR-127-5p, hsa-miR-596, hsa-miR-328 | 79.1% | 80.3% | 78.0% |
| SNRCC-513 | 56, 65, 63 | hsa-miR-596, hsa-miR-33b, hsa-miR-328 | 79.1% | 80.3% | 78.0% |
| SNRCC-514 | 69, 46, 116 | hsa-miR-34b*, hsa-miR-302f, hsa-miR-1321 | 79.1% | 80.3% | 78.0% |
| SNRCC-515 | 137, 98, 46 | hsa-miR-296-5p, hsa-miR-1305, hsa-miR-302f | 79.1% | 76.6% | 81.7% |
| SNRCC-516 | 15, 33, 44 | hsa-miR-93, hsa-miR-103, hsa-miR-646 | 79.1% | 75.1% | 83.1% |
| SNRCC-517 | 60, 83 | hsa-miR-28-3p, hsa-miR-145 | 79.0% | 83.1% | 74.9% |
| SNRCC-518 | 89, 74, 38 | hsa-miR-1538, hsa-miR-132*, hsa-miR-25* | 79.0% | 78.0% | 80.0% |
| SNRCC-519 | 6, 15 | hsa-miR-20a, hsa-miR-93 | 78.9% | 68.0% | 89.7% |
| SNRCC-520 | 20, 26 | hsa-miR-224, hsa-miR-580 | 78.9% | 76.9% | 80.9% |
| SNRCC-521 | 18, 33 | hsa-miR-1260, hsa-miR-103 | 78.9% | 70.6% | 87.1% |
| SNRCC-522 | 17, 98, 69 | hsa-miR-450b-5p, hsa-miR-1305, hsa-miR-34b* | 78.9% | 76.6% | 81.1% |
| SNRCC-523 | 82, 83, 144 | hsa-miR-664, hsa-miR-145, hsa-miR-18b | 78.9% | 80.9% | 76.9% |
| SNRCC-524 | 6, 15, 18 | hsa-miR-20a, hsa-miR-93, hsa-miR-1260 | 78.9% | 67.7% | 90.0% |
| SNRCC-525 | 155, 175, 195 | hsa-miR-720, hsa-miR-574-5p, hsa-miR-197 | 78.9% | 79.1% | 78.6% |
| SNRCC-526 | 19, 21, 22 | hsa-miR-221*, hsa-miR-32*, hsa-miR-934 | 78.9% | 75.4% | 82.3% |
| SNRCC-527 | 144, 155 | hsa-miR-18b, hsa-miR-720 | 78.7% | 83.1% | 74.3% |
| SNRCC-528 | 155, 175 | hsa-miR-720, hsa-miR-574-5p | 78.7% | 81.1% | 76.3% |
| SNRCC-529 | 19, 22 | hsa-miR-221*, hsa-miR-934 | 78.7% | 70.9% | 86.6% |
| SNRCC-530 | 7, 19, 175 | hsa-miR-17, hsa-miR-221*, hsa-miR-574-5p | 78.7% | 72.0% | 85.4% |
| SNRCC-531 | 9, 12, 13 | hsa-miR-496, hsa-miR-518a-3p, hsa-miR-516b | 78.7% | 84.6% | 72.9% |
| SNRCC-532 | 15, 19, 30 | hsa-miR-93, hsa-miR-221*, hsa-miR-216b | 78.7% | 74.3% | 83.1% |
| SNRCC-533 | 4, 20 | hsa-miR-640, hsa-miR-224 | 78.6% | 79.7% | 77.4% |
| SNRCC-534 | 33, 41, 60 | hsa-miR-103, hsa-miR-18a, hsa-miR-28-3p | 78.6% | 76.9% | 80.3% |
| SNRCC-535 | 11, 116, 89 | hsa-miR-19b, hsa-miR-1321, hsa-miR-1538 | 78.6% | 72.3% | 84.9% |
| SNRCC-536 | 137, 11, 69 | hsa-miR-296-5p, hsa-miR-19b, hsa-miR-34b* | 78.6% | 82.9% | 74.3% |
| SNRCC-537 | 18, 21, 22 | hsa-miR-1260, hsa-miR-32*, hsa-miR-934 | 78.6% | 74.9% | 82.3% |
| SNRCC-538 | 58, 83, 137 | hsa-miR-454, hsa-miR-145, hsa-miR-296-5p | 78.4% | 72.9% | 84.0% |
| SNRCC-539 | 82, 144, 155 | hsa-miR-664, hsa-miR-18b, hsa-miR-720 | 78.4% | 82.6% | 74.3% |
| SNRCC-540 | 155, 161, 175 | hsa-miR-720, hsa-miR-422a, hsa-miR-574-5p | 78.4% | 79.1% | 77.7% |
| SNRCC-541 | 18, 19, 30 | hsa-miR-1260, hsa-miR-221*, hsa-miR-216b | 78.4% | 73.4% | 83.4% |
| SNRCC-542 | 33, 44 | hsa-miR-103, hsa-miR-646 | 78.3% | 80.0% | 76.6% |
| SNRCC-543 | 29, 9, 74 | hsa-miR-606, hsa-miR-496, hsa-miR-132* | 78.3% | 74.0% | 82.6% |
| SNRCC-544 | 38, 137, 11 | hsa-miR-25*, hsa-miR-296-5p, hsa-miR-19b | 78.3% | 80.3% | 76.3% |
| SNRCC-545 | 137, 69, 46 | hsa-miR-296-5p, hsa-miR-34b*, hsa-miR-302f | 78.3% | 76.6% | 80.0% |
| SNRCC-546 | 19, 25, 29 | hsa-miR-221*, hsa-miR-633, hsa-miR-606 | 78.3% | 70.3% | 86.3% |

Figure 2 (cont.)

| SNRCC-547 | 13, 15 | hsa-miR-516b, hsa-miR-93 | 78.1% | 69.7% | 86.6% |
|---|---|---|---|---|---|
| SNRCC-548 | 1, 2, 7 | hsa-miR-106a, hsa-miR-20b, hsa-miR-17 | 78.1% | 70.3% | 86.0% |
| SNRCC-549 | 30, 33, 44 | hsa-miR-216b, hsa-miR-103, hsa-miR-646 | 78.1% | 78.3% | 78.0% |
| SNRCC-550 | 89, 30, 19 | hsa-miR-1538, hsa-miR-216b, hsa-miR-221* | 78.1% | 70.6% | 85.7% |
| SNRCC-551 | 47, 56, 58 | hsa-miR-218-1*, hsa-miR-596, hsa-miR-454 | 78.1% | 70.0% | 86.3% |
| SNRCC-552 | 137, 144, 155 | hsa-miR-296-5p, hsa-miR-18b, hsa-miR-720 | 78.1% | 80.9% | 75.4% |
| SNRCC-553 | 19, 20, 25 | hsa-miR-221*, hsa-miR-224, hsa-miR-633 | 78.1% | 69.4% | 86.9% |
| SNRCC-554 | 65, 73 | hsa-miR-33b, hsa-miR-1227 | 78.0% | 88.0% | 68.0% |
| SNRCC-555 | 98, 46 | hsa-miR-1305, hsa-miR-302f | 78.0% | 78.6% | 77.4% |
| SNRCC-556 | 224, 253 | hsa-miR-183*, hsa-miR-1207-5p | 78.0% | 82.3% | 73.7% |
| SNRCC-557 | 18, 74 | hsa-miR-1260, hsa-miR-132* | 78.0% | 79.4% | 76.6% |
| SNRCC-558 | 18, 38, 137 | hsa-miR-1260, hsa-miR-25*, hsa-miR-296-5p | 78.0% | 74.3% | 81.7% |
| SNRCC-559 | 2, 7, 18 | hsa-miR-20b, hsa-miR-17, hsa-miR-1260 | 78.0% | 71.1% | 84.9% |
| SNRCC-560 | 82, 137, 155 | hsa-miR-664, hsa-miR-296-5p, hsa-miR-720 | 78.0% | 79.1% | 76.9% |
| SNRCC-561 | 144, 155, 161 | hsa-miR-18b, hsa-miR-720, hsa-miR-422a | 78.0% | 78.9% | 77.1% |
| SNRCC-562 | 11, 46 | hsa-miR-19b, hsa-miR-302f | 77.9% | 84.3% | 71.4% |
| SNRCC-563 | 18, 17, 74 | hsa-miR-1260, hsa-miR-450b-5p, hsa-miR-132* | 77.9% | 70.9% | 84.9% |
| SNRCC-564 | 17, 137, 11 | hsa-miR-450b-5p, hsa-miR-296-5p, hsa-miR-19b | 77.9% | 74.3% | 81.4% |
| SNRCC-565 | 61, 65, 63 | hsa-miR-127-5p, hsa-miR-33b, hsa-miR-328 | 77.9% | 82.6% | 73.1% |
| SNRCC-566 | 63, 73, 83 | hsa-miR-328, hsa-miR-1227, hsa-miR-145 | 77.9% | 84.9% | 70.9% |
| SNRCC-567 | 98, 125, 46 | hsa-miR-1305, hsa-miR-154, hsa-miR-302f | 77.9% | 74.6% | 81.1% |
| SNRCC-568 | 83, 155, 161 | hsa-miR-145, hsa-miR-720, hsa-miR-422a | 77.9% | 76.9% | 78.9% |
| SNRCC-569 | 21, 22, 23 | hsa-miR-32*, hsa-miR-934, hsa-miR-654-5p | 77.9% | 77.1% | 78.6% |
| SNRCC-570 | 1, 18 | hsa-miR-106a, hsa-miR-1260 | 77.7% | 66.3% | 89.1% |
| SNRCC-571 | 125, 18, 17 | hsa-miR-154, hsa-miR-1260, hsa-miR-450b-5p | 77.7% | 70.6% | 84.9% |
| SNRCC-572 | 89, 7, 175 | hsa-miR-1538, hsa-miR-17, hsa-miR-574-5p | 77.7% | 72.0% | 83.4% |
| SNRCC-573 | 20, 22 | hsa-miR-224, hsa-miR-934 | 77.6% | 72.3% | 82.9% |
| SNRCC-574 | 9, 74 | hsa-miR-496, hsa-miR-132* | 77.6% | 78.6% | 76.6% |
| SNRCC-575 | 9, 74, 18 | hsa-miR-496, hsa-miR-132*, hsa-miR-1260 | 77.6% | 76.6% | 78.6% |
| SNRCC-576 | 63, 82, 83 | hsa-miR-328, hsa-miR-664, hsa-miR-145 | 77.6% | 84.0% | 71.1% |
| SNRCC-577 | 1, 6, 15 | hsa-miR-106a, hsa-miR-20a, hsa-miR-93 | 77.6% | 64.9% | 90.3% |
| SNRCC-578 | 19, 20, 22 | hsa-miR-221*, hsa-miR-224, hsa-miR-934 | 77.6% | 70.0% | 85.1% |
| SNRCC-579 | 22, 25 | hsa-miR-934, hsa-miR-633 | 77.4% | 71.7% | 83.1% |
| SNRCC-580 | 46, 7 | hsa-miR-302f, hsa-miR-17 | 77.4% | 72.3% | 82.6% |
| SNRCC-581 | 30, 33 | hsa-miR-216b, hsa-miR-103 | 77.4% | 78.6% | 76.3% |
| SNRCC-582 | 17, 74, 137 | hsa-miR-450b-5p, hsa-miR-132*, hsa-miR-296-5p | 77.4% | 74.0% | 80.9% |
| SNRCC-583 | 7, 10, 15 | hsa-miR-17, hsa-let-7d*, hsa-miR-93 | 77.4% | 74.0% | 80.9% |
| SNRCC-584 | 155, 163, 175 | hsa-miR-720, hsa-miR-509-3-5p, hsa-miR-574-5p | 77.4% | 80.3% | 74.6% |
| SNRCC-585 | 20, 21, 23 | hsa-miR-224, hsa-miR-32*, hsa-miR-654-5p | 77.4% | 71.1% | 83.7% |
| SNRCC-586 | 82, 83 | hsa-miR-664, hsa-miR-145 | 77.3% | 78.3% | 76.3% |
| SNRCC-587 | 47, 61, 56 | hsa-miR-218-1*, hsa-miR-127-5p, hsa-miR-596 | 77.3% | 70.6% | 84.0% |
| SNRCC-588 | 2, 7, 15 | hsa-miR-20b, hsa-miR-17, hsa-miR-93 | 77.3% | 69.1% | 85.4% |
| SNRCC-589 | 98, 69, 116 | hsa-miR-1305, hsa-miR-34b*, hsa-miR-1321 | 77.3% | 73.7% | 80.9% |
| SNRCC-590 | 17, 20, 21 | hsa-miR-450b-5p, hsa-miR-224, hsa-miR-32* | 77.3% | 69.4% | 85.1% |
| SNRCC-591 | 56, 63 | hsa-miR-596, hsa-miR-328 | 77.1% | 76.6% | 77.7% |
| SNRCC-592 | 18, 20 | hsa-miR-1260, hsa-miR-224 | 77.1% | 68.3% | 86.0% |

Figure 2 (cont.)

| SNRCC-593 | 15, 33 | hsa-miR-93, hsa-miR-103 | 77.1% | 74.9% | 79.4% |
|---|---|---|---|---|---|
| SNRCC-594 | 222, 294 | hsa-miR-452*, hsa-miR-423-5p | 77.1% | 80.6% | 73.7% |
| SNRCC-595 | 46, 89, 7 | hsa-miR-302f, hsa-miR-1538, hsa-miR-17 | 77.1% | 72.3% | 82.0% |
| SNRCC-596 | 17, 137, 69 | hsa-miR-450b-5p, hsa-miR-296-5p, hsa-miR-34b* | 77.1% | 77.1% | 77.1% |
| SNRCC-597 | 6, 7, 15 | hsa-miR-20a, hsa-miR-17, hsa-miR-93 | 77.1% | 70.6% | 83.7% |
| SNRCC-598 | 4, 9, 20 | hsa-miR-640, hsa-miR-496, hsa-miR-224 | 77.1% | 75.4% | 78.9% |
| SNRCC-599 | 83, 144, 161 | hsa-miR-145, hsa-miR-18b, hsa-miR-422a | 77.1% | 75.4% | 78.9% |
| SNRCC-600 | 17, 18, 20 | hsa-miR-450b-5p, hsa-miR-1260, hsa-miR-224 | 77.1% | 68.9% | 85.4% |
| SNRCC-601 | 15, 18, 44 | hsa-miR-93, hsa-miR-1260, hsa-miR-646 | 77.1% | 66.0% | 88.3% |
| SNRCC-602 | 82, 137 | hsa-miR-664, hsa-miR-296-5p | 77.0% | 78.9% | 75.1% |
| SNRCC-603 | 19, 20 | hsa-miR-221*, hsa-miR-224 | 77.0% | 67.7% | 86.3% |
| SNRCC-604 | 21, 23 | hsa-miR-32*, hsa-miR-654-5p | 77.0% | 71.1% | 82.9% |
| SNRCC-605 | 22, 23 | hsa-miR-934, hsa-miR-654-5p | 77.0% | 78.3% | 75.7% |
| SNRCC-606 | 125, 38, 17 | hsa-miR-154, hsa-miR-25*, hsa-miR-450b-5p | 77.0% | 74.0% | 80.0% |
| SNRCC-607 | 60, 58, 83 | hsa-miR-28-3p, hsa-miR-454, hsa-miR-145 | 77.0% | 76.6% | 77.4% |
| SNRCC-608 | 116, 46, 89 | hsa-miR-1321, hsa-miR-302f, hsa-miR-1538 | 77.0% | 79.1% | 74.9% |
| SNRCC-609 | 18, 20, 21 | hsa-miR-1260, hsa-miR-224, hsa-miR-32* | 77.0% | 70.3% | 83.7% |
| SNRCC-610 | 17, 98 | hsa-miR-450b-5p, hsa-miR-1305 | 76.9% | 72.3% | 81.4% |
| SNRCC-611 | 11, 46, 89 | hsa-miR-19b, hsa-miR-302f, hsa-miR-1538 | 76.9% | 81.7% | 72.0% |
| SNRCC-612 | 65, 73, 75 | hsa-miR-33b, hsa-miR-1227, hsa-miR-936 | 76.9% | 82.0% | 71.7% |
| SNRCC-613 | 11, 125, 89 | hsa-miR-19b, hsa-miR-154, hsa-miR-1538 | 76.9% | 76.3% | 77.4% |
| SNRCC-614 | 60, 82, 83 | hsa-miR-28-3p, hsa-miR-664, hsa-miR-145 | 76.9% | 80.3% | 73.4% |
| SNRCC-615 | 14, 17 | hsa-miR-367*, hsa-miR-450b-5p | 76.7% | 74.9% | 78.6% |
| SNRCC-616 | 125, 18, 38 | hsa-miR-154, hsa-miR-1260, hsa-miR-25* | 76.7% | 73.7% | 79.7% |
| SNRCC-617 | 63, 75, 82 | hsa-miR-328, hsa-miR-936, hsa-miR-664 | 76.7% | 79.1% | 74.3% |
| SNRCC-618 | 98, 46, 116 | hsa-miR-1305, hsa-miR-302f, hsa-miR-1321 | 76.7% | 73.7% | 79.7% |
| SNRCC-619 | 60, 83, 137 | hsa-miR-28-3p, hsa-miR-145, hsa-miR-296-5p | 76.7% | 75.7% | 77.7% |
| SNRCC-620 | 2, 15, 18 | hsa-miR-20b, hsa-miR-93, hsa-miR-1260 | 76.7% | 65.7% | 87.7% |
| SNRCC-621 | 83, 137, 161 | hsa-miR-145, hsa-miR-296-5p, hsa-miR-422a | 76.7% | 74.3% | 79.1% |
| SNRCC-622 | 30, 7, 19 | hsa-miR-216b, hsa-miR-17, hsa-miR-221* | 76.7% | 73.4% | 80.0% |
| SNRCC-623 | 60, 61 | hsa-miR-28-3p, hsa-miR-127-5p | 76.6% | 70.0% | 83.1% |
| SNRCC-624 | 58, 82 | hsa-miR-454, hsa-miR-664 | 76.6% | 69.1% | 84.0% |
| SNRCC-625 | 82, 94 | hsa-miR-664, hsa-miR-181a-2* | 76.6% | 83.4% | 69.7% |
| SNRCC-626 | 74, 11 | hsa-miR-132*, hsa-miR-19b | 76.6% | 71.7% | 81.4% |
| SNRCC-627 | 19, 33, 35 | hsa-miR-221*, hsa-miR-103, hsa-miR-200a* | 76.6% | 75.7% | 77.4% |
| SNRCC-628 | 18, 33, 43 | hsa-miR-1260, hsa-miR-103, hsa-miR-652 | 76.6% | 68.6% | 84.6% |
| SNRCC-629 | 73, 82 | hsa-miR-1227, hsa-miR-664 | 76.4% | 81.1% | 71.7% |
| SNRCC-630 | 19, 21 | hsa-miR-221*, hsa-miR-32* | 76.4% | 69.4% | 83.4% |
| SNRCC-631 | 26, 35 | hsa-miR-580, hsa-miR-200a* | 76.4% | 78.3% | 74.6% |
| SNRCC-632 | 1, 7 | hsa-miR-106a, hsa-miR-17 | 76.4% | 72.6% | 80.3% |
| SNRCC-633 | 60, 56 | hsa-miR-28-3p, hsa-miR-596 | 76.3% | 77.7% | 74.9% |
| SNRCC-634 | 89, 74 | hsa-miR-1538, hsa-miR-132* | 76.3% | 76.9% | 75.7% |
| SNRCC-635 | 82, 144 | hsa-miR-664, hsa-miR-18b | 76.3% | 77.4% | 75.1% |
| SNRCC-636 | 15, 18 | hsa-miR-93, hsa-miR-1260 | 76.3% | 65.1% | 87.4% |
| SNRCC-637 | 6, 7, 9 | hsa-miR-20a, hsa-miR-17, hsa-miR-496 | 76.3% | 65.4% | 87.1% |
| SNRCC-638 | 7, 15, 33 | hsa-miR-17, hsa-miR-93, hsa-miR-103 | 76.3% | 70.3% | 82.3% |

Figure 2 (cont.)

| | | | | | |
|---|---|---|---|---|---|
| SNRCC-639 | 137, 69 | hsa-miR-296-5p, hsa-miR-34b* | 76.1% | 77.1% | 75.1% |
| SNRCC-640 | 17, 137, 98 | hsa-miR-450b-5p, hsa-miR-296-5p, hsa-miR-1305 | 76.1% | 72.9% | 79.4% |
| SNRCC-641 | 175, 201, 207 | hsa-miR-574-5p, hsa-miR-125a-5p, hsa-miR-1908 | 76.1% | 78.0% | 74.3% |
| SNRCC-642 | 30, 19 | hsa-miR-216b, hsa-miR-221* | 76.0% | 72.0% | 80.0% |
| SNRCC-643 | 25, 27 | hsa-miR-633, hsa-miR-106b | 76.0% | 66.3% | 85.7% |
| SNRCC-644 | 60, 56, 58 | hsa-miR-28-3p, hsa-miR-596, hsa-miR-454 | 76.0% | 76.6% | 75.4% |
| SNRCC-645 | 65, 63, 73 | hsa-miR-33b, hsa-miR-328, hsa-miR-1227 | 76.0% | 86.9% | 65.1% |
| SNRCC-646 | 137, 98, 116 | hsa-miR-296-5p, hsa-miR-1305, hsa-miR-1321 | 76.0% | 72.9% | 79.1% |
| SNRCC-647 | 73, 83 | hsa-miR-1227, hsa-miR-145 | 75.9% | 83.4% | 68.3% |
| SNRCC-648 | 33, 43, 60 | hsa-miR-103, hsa-miR-652, hsa-miR-28-3p | 75.9% | 76.3% | 75.4% |
| SNRCC-649 | 11, 46, 116 | hsa-miR-19b, hsa-miR-302f, hsa-miR-1321 | 75.9% | 76.9% | 74.9% |
| SNRCC-650 | 58, 65, 63 | hsa-miR-454, hsa-miR-33b, hsa-miR-328 | 75.9% | 78.9% | 72.9% |
| SNRCC-651 | 56, 58, 73 | hsa-miR-596, hsa-miR-454, hsa-miR-1227 | 75.9% | 77.7% | 74.0% |
| SNRCC-652 | 65, 75, 82 | hsa-miR-33b, hsa-miR-936, hsa-miR-664 | 75.9% | 76.0% | 75.7% |
| SNRCC-653 | 82, 83, 137 | hsa-miR-664, hsa-miR-145, hsa-miR-296-5p | 75.9% | 77.1% | 74.6% |
| SNRCC-654 | 58, 65 | hsa-miR-454, hsa-miR-33b | 75.7% | 68.6% | 82.9% |
| SNRCC-655 | 6, 18 | hsa-miR-20a, hsa-miR-1260 | 75.7% | 63.1% | 88.3% |
| SNRCC-656 | 43, 47 | hsa-miR-652, hsa-miR-218-1* | 75.7% | 80.0% | 71.4% |
| SNRCC-657 | 2, 7 | hsa-miR-20b, hsa-miR-17 | 75.7% | 69.7% | 81.7% |
| SNRCC-658 | 43, 58, 82 | hsa-miR-652, hsa-miR-454, hsa-miR-664 | 75.7% | 70.9% | 80.6% |
| SNRCC-659 | 44, 58, 82 | hsa-miR-646, hsa-miR-454, hsa-miR-664 | 75.7% | 68.6% | 82.9% |
| SNRCC-660 | 30, 19, 175 | hsa-miR-216b, hsa-miR-221*, hsa-miR-574-5p | 75.7% | 72.3% | 79.1% |
| SNRCC-661 | 82, 137, 144 | hsa-miR-664, hsa-miR-296-5p, hsa-miR-18b | 75.7% | 74.9% | 76.6% |
| SNRCC-662 | 24, 25, 27 | hsa-miR-554, hsa-miR-633, hsa-miR-106b | 75.7% | 71.7% | 79.7% |
| SNRCC-663 | 224, 253, 294 | hsa-miR-183*, hsa-miR-1207-5p, hsa-miR-423-5p | 75.7% | 81.1% | 70.3% |
| SNRCC-664 | 6, 7 | hsa-miR-20a, hsa-miR-17 | 75.6% | 67.4% | 83.7% |
| SNRCC-665 | 155, 161 | hsa-miR-720, hsa-miR-422a | 75.6% | 75.4% | 75.7% |
| SNRCC-666 | 17, 19 | hsa-miR-450b-5p, hsa-miR-221* | 75.6% | 66.3% | 84.9% |
| SNRCC-667 | 58, 65, 73 | hsa-miR-454, hsa-miR-33b, hsa-miR-1227 | 75.6% | 80.0% | 71.1% |
| SNRCC-668 | 11, 116, 125 | hsa-miR-19b, hsa-miR-1321, hsa-miR-154 | 75.6% | 75.7% | 75.4% |
| SNRCC-669 | 137, 11, 116 | hsa-miR-296-5p, hsa-miR-19b, hsa-miR-1321 | 75.6% | 73.7% | 77.4% |
| SNRCC-670 | 19, 20, 29 | hsa-miR-221*, hsa-miR-224, hsa-miR-606 | 75.6% | 71.4% | 79.7% |
| SNRCC-671 | 65, 63 | hsa-miR-33b, hsa-miR-328 | 75.4% | 82.0% | 68.9% |
| SNRCC-672 | 19, 175 | hsa-miR-221*, hsa-miR-574-5p | 75.4% | 68.0% | 82.9% |
| SNRCC-673 | 18, 21 | hsa-miR-1260, hsa-miR-32* | 75.4% | 74.0% | 76.9% |
| SNRCC-674 | 43, 60, 56 | hsa-miR-652, hsa-miR-28-3p, hsa-miR-596 | 75.4% | 71.1% | 79.7% |
| SNRCC-675 | 74, 125, 18 | hsa-miR-132*, hsa-miR-154, hsa-miR-1260 | 75.4% | 74.6% | 76.3% |
| SNRCC-676 | 73, 75, 83 | hsa-miR-1227, hsa-miR-936, hsa-miR-145 | 75.4% | 76.9% | 74.0% |
| SNRCC-677 | 20, 22, 23 | hsa-miR-224, hsa-miR-934, hsa-miR-654-5p | 75.4% | 72.0% | 78.9% |
| SNRCC-678 | 46, 30, 7 | hsa-miR-302f, hsa-miR-216b, hsa-miR-17 | 75.4% | 72.6% | 78.3% |
| SNRCC-679 | 46, 116 | hsa-miR-302f, hsa-miR-1321 | 75.3% | 77.1% | 73.4% |
| SNRCC-680 | 47, 60, 56 | hsa-miR-218-1*, hsa-miR-28-3p, hsa-miR-596 | 75.3% | 72.3% | 78.3% |
| SNRCC-681 | 60, 58, 82 | hsa-miR-28-3p, hsa-miR-454, hsa-miR-664 | 75.3% | 71.7% | 78.9% |
| SNRCC-682 | 17, 19, 21 | hsa-miR-450b-5p, hsa-miR-221*, hsa-miR-32* | 75.3% | 65.4% | 85.1% |
| SNRCC-683 | 74, 137 | hsa-miR-132*, hsa-miR-296-5p | 75.1% | 70.3% | 80.0% |
| SNRCC-684 | 83, 144 | hsa-miR-145, hsa-miR-18b | 75.1% | 73.1% | 77.1% |

Figure 2 (cont.)

| SNRCC-685 | 125, 46, 89 | hsa-miR-154, hsa-miR-302f, hsa-miR-1538 | 75.1% | 76.9% | 73.4% |
|---|---|---|---|---|---|
| SNRCC-686 | 137, 155, 161 | hsa-miR-296-5p, hsa-miR-720, hsa-miR-422a | 75.1% | 72.9% | 77.4% |
| SNRCC-687 | 144, 155, 163 | hsa-miR-18b, hsa-miR-720, hsa-miR-509-3-5p | 75.1% | 76.6% | 73.7% |
| SNRCC-688 | 7, 33, 41 | hsa-miR-17, hsa-miR-103, hsa-miR-18a | 75.1% | 68.9% | 81.4% |
| SNRCC-689 | 29, 74 | hsa-miR-606, hsa-miR-132* | 75.0% | 71.4% | 78.6% |
| SNRCC-690 | 20, 1 | hsa-miR-224, hsa-miR-106a | 75.0% | 68.0% | 82.0% |
| SNRCC-691 | 253, 294 | hsa-miR-1207-5p, hsa-miR-423-5p | 75.0% | 73.4% | 76.6% |
| SNRCC-692 | 9, 89, 74 | hsa-miR-496, hsa-miR-1538, hsa-miR-132* | 75.0% | 74.3% | 75.7% |
| SNRCC-693 | 73, 75, 82 | hsa-miR-1227, hsa-miR-936, hsa-miR-664 | 75.0% | 77.1% | 72.9% |
| SNRCC-694 | 7, 15, 18 | hsa-miR-17, hsa-miR-93, hsa-miR-1260 | 75.0% | 70.3% | 79.7% |

Figure 5a

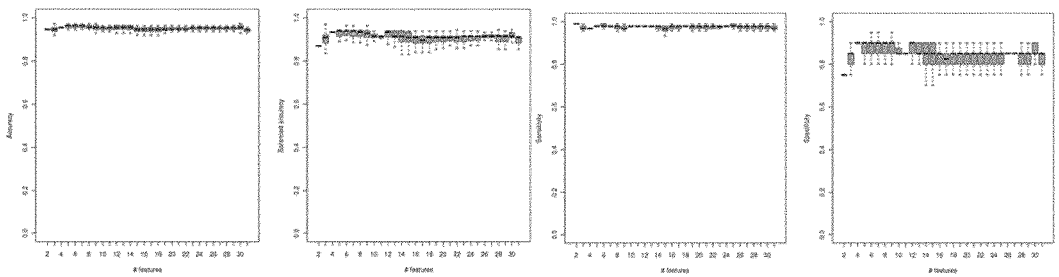

Figure 5b

| Signature | # miRNAs | miRNAs | Accuracy |
|---|---|---|---|
| SNRCC-lin1 | 2 | hsa-miR-27a, hsa-miR-23a | 94.4% |
| SNRCC-lin2 | 3 | hsa-miR-574-3p, hsa-miR-23a*, hsa-miR-125b-2* | 94.6% |
| SNRCC-lin3 | 4 | hsa-miR-574-3p, hsa-miR-23a*, hsa-miR-1260, hsa-miR-1247 | 95.7% |
| SNRCC-lin4 | 5 | hsa-miR-1296, hsa-miR-1246, hsa-miR-23a*, hsa-miR-516b, hsa-miR-720 | 96.1% |
| SNRCC-lin5 | 6 | hsa-miR-595, hsa-miR-574-3p, hsa-miR-185, hsa-miR-23a*, hsa-miR-1260, hsa-miR-1247 | 96.0% |
| SNRCC-lin6 | 7 | hsa-miR-595, hsa-miR-574-3p, hsa-miR-423-5p, hsa-miR-185, hsa-miR-23a*, hsa-miR-1260, hsa-miR-1247 | 95.8% |
| SNRCC-lin7 | 8 | hsa-miR-595, hsa-miR-574-3p, hsa-miR-423-5p, hsa-miR-185, hsa-miR-23a*, hsa-miR-516b, hsa-miR-1260, hsa-miR-1247, | 95.5% |
| SNRCC-lin8 | 9 | hsa-miR-595, hsa-miR-574-3p, hsa-miR-423-5p, hsa-miR-185, hsa-miR-23a*, hsa-miR-516b, hsa-miR-1260, hsa-miR-1247 | 94.7% |
| SNRCC-lin9 | 10 | hsa-miR-19b, hsa-miR-595, hsa-miR-574-3p, hsa-miR-1296, hsa-miR-23a*, hsa-miR-1274a, hsa-miR-516b, hsa-miR-1294, hsa-miR-598 | 95.1% |
| SNRCC-rbf1 | 2 | hsa-miR-27a, hsa-miR-23a | 94.2% |
| SNRCC-rbf2 | 3 | hsa-miR-19b, hsa-miR-23a*, hsa-miR-1294 | 94.9% |
| SNRCC-rbf3 | 4 | hsa-miR-574-3p, hsa-miR-23a*, hsa-miR-1260, hsa-miR-1247 | 95.3% |
| SNRCC-rbf4 | 5 | hsa-miR-1296, hsa-miR-1246, hsa-miR-23a*, hsa-miR-516b, hsa-miR-720 | 96.2% |
| SNRCC-rbf5 | 6 | hsa-miR-1296, hsa-miR-1246, hsa-miR-23a*, hsa-miR-516b, hsa-miR-1294, hsa-miR-720 | 96.1% |
| SNRCC-rbf6 | 7 | hsa-miR-19b, hsa-miR-574-3p, hsa-miR-23a*, hsa-miR-1265, hsa-miR-516b, hsa-miR-1294, hsa-miR-720 | 95.6% |
| SNRCC-rbf7 | 8 | hsa-miR-19b, hsa-miR-574-3p, hsa-miR-609, hsa-miR-23a*, hsa-miR-1265, hsa-miR-516b, hsa-miR-1294, hsa-miR-720, | 95.7% |
| SNRCC-rbf8 | 9 | hsa-miR-19b, hsa-miR-574-3p, hsa-miR-609, hsa-miR-545*, hsa-miR-23a*, hsa-miR-1265, hsa-miR-516b, hsa-miR-1294 | 95.7% |
| SNRCC-rbf9 | 10 | hsa-miR-19b, hsa-miR-595, hsa-miR-574-3p, hsa-miR-1296, hsa-miR-23a*, hsa-miR-1274a, hsa-miR-516b, hsa-miR-1294, hsa-miR-598 | 95.5% |

Figure 6

| SEQ ID NO | miRNA | median g1 | median g2 | qmedian | ttest rawp | ttest adjp | AUC | limma rawp | limma adjp |
|---|---|---|---|---|---|---|---|---|---|
| 16 | hsa-miR-891b | 92 | 22 | 4.15 | 3.59E-11 | 3.04E-08 | 0.03 | 3.42E-12 | 1.45E-09 |
| 11 | hsa-miR-19b | 10929 | 25257 | 0.43 | 8.55E-11 | 3.63E-08 | 0.90 | 4.95E-06 | 8.57E-05 |
| 10 | hsa-let-7d* | 75 | 279 | 0.27 | 3.91E-10 | 1.10E-07 | 0.96 | 5.14E-10 | 7.27E-08 |
| 26 | hsa-miR-580 | 46 | 84 | 0.54 | 4.95E-09 | 1.05E-06 | 0.83 | 3.61E-04 | 2.13E-03 |
| 240 | hsa-miR-425 | 14077 | 24285 | 0.58 | 7.23E-09 | 1.23E-06 | 0.84 | 1.64E-03 | 6.84E-03 |
| 4 | hsa-miR-640 | 96 | 21 | 4.62 | 2.30E-08 | 3.25E-06 | 0.06 | 1.36E-11 | 3.85E-09 |
| 8 | hsa-miR-34a* | 94 | 19 | 5.04 | 3.59E-08 | 4.03E-06 | 0.02 | 1.30E-16 | 1.10E-13 |
| 18 | hsa-miR-1260 | 2592 | 7482 | 0.35 | 4.28E-08 | 4.03E-06 | 0.91 | 3.50E-06 | 6.92E-05 |
| 81 | hsa-miR-192 | 5727 | 12474 | 0.46 | 4.21E-08 | 4.03E-06 | 0.90 | 7.93E-06 | 1.18E-04 |
| 28 | hsa-miR-548m | 20 | 64 | 0.32 | 5.96E-08 | 5.05E-06 | 0.90 | 2.86E-07 | 1.15E-05 |
| 24 | hsa-miR-554 | 93 | 29 | 3.23 | 7.31E-08 | 5.64E-06 | 0.08 | 3.33E-08 | 2.17E-06 |
| 52 | hsa-miR-604 | 85 | 25 | 3.35 | 8.39E-08 | 5.93E-06 | 0.04 | 1.09E-10 | 2.30E-08 |
| 300 | hsa-miR-23a | 4274 | 11874 | 0.36 | 1.20E-07 | 7.85E-06 | 0.89 | 8.36E-06 | 1.22E-04 |
| 233 | hsa-miR-185 | 25520 | 45036 | 0.57 | 2.03E-07 | 1.23E-05 | 0.78 | 2.68E-03 | 1.01E-02 |
| 117 | hsa-miR-892a | 23 | 47 | 0.49 | 4.39E-07 | 2.48E-05 | 0.90 | 4.49E-06 | 8.20E-05 |
| 85 | hsa-miR-483-3p | 31 | 78 | 0.40 | 5.07E-07 | 2.53E-05 | 0.85 | 1.61E-05 | 1.97E-04 |
| 291 | hsa-miR-23b | 3337 | 9067 | 0.37 | 4.97E-07 | 2.53E-05 | 0.89 | 2.74E-06 | 5.95E-05 |
| 3 | hsa-miR-523 | 84 | 32 | 2.60 | 7.29E-07 | 3.43E-05 | 0.12 | 1.48E-06 | 3.80E-05 |
| 358 | hsa-miR-744 | 565 | 1388 | 0.41 | 7.93E-07 | 3.54E-05 | 0.90 | 9.61E-07 | 2.72E-05 |
| 154 | hsa-miR-484 | 7388 | 19631 | 0.38 | 8.36E-07 | 3.54E-05 | 0.87 | 9.30E-06 | 1.31E-04 |
| 14 | hsa-miR-367* | 51 | 26 | 1.92 | 1.01E-06 | 3.90E-05 | 0.16 | 3.64E-04 | 2.13E-03 |
| 301 | hsa-miR-566 | 94 | 49 | 1.93 | 9.78E-07 | 3.90E-05 | 0.10 | 3.30E-06 | 6.84E-05 |
| 313 | hsa-miR-545 | 119 | 54 | 2.21 | 1.28E-06 | 4.73E-05 | 0.14 | 2.41E-05 | 2.67E-04 |
| 13 | hsa-miR-516b | 39 | 16 | 2.43 | 1.45E-06 | 4.86E-05 | 0.11 | 6.42E-07 | 1.94E-05 |
| 137 | hsa-miR-296-5p | 267 | 736 | 0.36 | 1.39E-06 | 4.86E-05 | 0.86 | 7.52E-06 | 1.14E-04 |
| 158 | hsa-miR-30c | 1905 | 3839 | 0.50 | 1.49E-06 | 4.86E-05 | 0.82 | 3.93E-04 | 2.27E-03 |
| 82 | hsa-miR-664 | 282 | 1185 | 0.24 | 1.67E-06 | 5.21E-05 | 0.89 | 2.25E-07 | 9.53E-06 |
| 118 | hsa-miR-302a | 17 | 47 | 0.37 | 1.72E-06 | 5.21E-05 | 0.89 | 1.27E-07 | 5.98E-06 |
| 46 | hsa-miR-302f | 19 | 52 | 0.37 | 2.33E-06 | 6.43E-05 | 0.90 | 3.72E-07 | 1.43E-05 |
| 83 | hsa-miR-145 | 150 | 558 | 0.27 | 2.35E-06 | 6.43E-05 | 0.88 | 4.10E-07 | 1.45E-05 |
| 105 | hsa-miR-612 | 79 | 37 | 2.17 | 2.27E-06 | 6.43E-05 | 0.15 | 5.19E-05 | 5.00E-04 |
| 100 | hsa-miR-30c-1* | 46 | 105 | 0.43 | 2.50E-06 | 6.63E-05 | 0.83 | 1.10E-04 | 8.67E-04 |
| 359 | hsa-miR-151-5p | 5019 | 10652 | 0.47 | 2.80E-06 | 7.19E-05 | 0.85 | 9.30E-05 | 7.74E-04 |
| 155 | hsa-miR-720 | 4108 | 13648 | 0.30 | 3.13E-06 | 7.81E-05 | 0.90 | 4.72E-07 | 1.54E-05 |
| 65 | hsa-miR-33b | 154 | 62 | 2.49 | 3.28E-06 | 7.87E-05 | 0.10 | 8.56E-08 | 4.27E-06 |
| 181 | hsa-miR-30a | 304 | 1056 | 0.29 | 3.34E-06 | 7.87E-05 | 0.91 | 2.12E-08 | 1.64E-06 |
| 5 | hsa-miR-1251 | 128 | 55 | 2.31 | 4.41E-06 | 9.83E-05 | 0.07 | 2.95E-09 | 3.57E-07 |
| 12 | hsa-miR-518a-3p | 59 | 18 | 3.22 | 4.39E-06 | 9.83E-05 | 0.09 | 1.44E-08 | 1.22E-06 |
| 78 | hsa-miR-558 | 87 | 32 | 2.75 | 4.66E-06 | 1.01E-04 | 0.12 | 4.46E-06 | 8.20E-05 |
| 19 | hsa-miR-221* | 102 | 44 | 2.31 | 5.32E-06 | 1.05E-04 | 0.10 | 2.19E-07 | 9.53E-06 |

Figure 6 (cont.)

| | | | | | | | | | |
|---|---|---|---|---|---|---|---|---|---|
| 23 | hsa-miR-654-5p | 178 | 83 | 2.13 | 5.14E-06 | 1.05E-04 | 0.07 | 5.80E-09 | 6.15E-07 |
| 131 | hsa-miR-32 | 141 | 58 | 2.43 | 5.33E-06 | 1.05E-04 | 0.14 | 1.63E-05 | 1.97E-04 |
| 360 | hsa-miR-16 | 16826 | 27296 | 0.62 | 5.24E-06 | 1.05E-04 | 0.78 | 1.85E-03 | 7.54E-03 |
| 147 | hsa-let-7g* | 128 | 78 | 1.64 | 5.87E-06 | 1.13E-04 | 0.15 | 6.11E-05 | 5.46E-04 |
| 56 | hsa-miR-596 | 68 | 37 | 1.85 | 6.49E-06 | 1.22E-04 | 0.13 | 2.43E-05 | 2.67E-04 |
| 361 | hsa-miR-194 | 6765 | 13973 | 0.48 | 6.86E-06 | 1.26E-04 | 0.81 | 7.56E-04 | 3.75E-03 |
| 362 | hsa-miR-19a | 2783 | 5624 | 0.49 | 7.42E-06 | 1.34E-04 | 0.80 | 2.74E-04 | 1.69E-03 |
| 363 | hsa-miR-1281 | 80 | 158 | 0.51 | 7.95E-06 | 1.41E-04 | 0.80 | 6.87E-04 | 3.53E-03 |
| 196 | hsa-miR-629 | 91 | 320 | 0.29 | 1.02E-05 | 1.73E-04 | 0.84 | 1.38E-05 | 1.75E-04 |
| 294 | hsa-miR-423-5p | 2759 | 8686 | 0.32 | 1.01E-05 | 1.73E-04 | 0.91 | 6.72E-08 | 3.80E-06 |
| 364 | hsa-miR-7-1* | 293 | 529 | 0.55 | 1.05E-05 | 1.74E-04 | 0.85 | 1.70E-04 | 1.18E-03 |
| 40 | hsa-miR-409-5p | 83 | 46 | 1.80 | 1.12E-05 | 1.83E-04 | 0.17 | 8.24E-04 | 3.99E-03 |
| 87 | hsa-miR-1261 | 18 | 48 | 0.38 | 1.19E-05 | 1.87E-04 | 0.86 | 5.25E-06 | 8.91E-05 |
| 113 | hsa-miR-1272 | 142 | 63 | 2.25 | 1.18E-05 | 1.87E-04 | 0.13 | 6.19E-06 | 9.97E-05 |
| 32 | hsa-miR-139-3p | 75 | 38 | 1.99 | 1.25E-05 | 1.93E-04 | 0.07 | 1.01E-08 | 9.48E-07 |
| 365 | hsa-miR-532-3p | 3327 | 9019 | 0.37 | 1.39E-05 | 2.11E-04 | 0.88 | 3.51E-06 | 6.92E-05 |
| 366 | hsa-miR-93* | 929 | 3065 | 0.30 | 1.46E-05 | 2.18E-04 | 0.90 | 2.35E-08 | 1.66E-06 |
| 79 | hsa-miR-491-5p | 91 | 144 | 0.63 | 1.56E-05 | 2.28E-04 | 0.84 | 1.60E-04 | 1.13E-03 |
| 367 | hsa-miR-128 | 607 | 922 | 0.66 | 1.69E-05 | 2.44E-04 | 0.83 | 1.58E-04 | 1.13E-03 |
| 288 | hsa-miR-330-3p | 357 | 174 | 2.05 | 1.80E-05 | 2.55E-04 | 0.12 | 1.82E-05 | 2.12E-04 |
| 136 | hsa-miR-340 | 177 | 361 | 0.49 | 1.95E-05 | 2.68E-04 | 0.85 | 1.52E-05 | 1.90E-04 |
| 368 | hsa-miR-182 | 4641 | 8980 | 0.52 | 1.96E-05 | 2.68E-04 | 0.82 | 1.11E-04 | 8.67E-04 |
| 74 | hsa-miR-132* | 14 | 37 | 0.40 | 2.04E-05 | 2.74E-04 | 0.88 | 1.29E-06 | 3.41E-05 |
| 98 | hsa-miR-1305 | 82 | 29 | 2.85 | 2.19E-05 | 2.86E-04 | 0.13 | 4.55E-06 | 8.20E-05 |
| 164 | hsa-miR-217 | 150 | 70 | 2.14 | 2.19E-05 | 2.86E-04 | 0.15 | 2.32E-04 | 1.50E-03 |
| 63 | hsa-miR-328 | 62 | 163 | 0.38 | 2.32E-05 | 2.98E-04 | 0.85 | 1.35E-05 | 1.75E-04 |
| 39 | hsa-miR-373 | 21 | 53 | 0.41 | 2.40E-05 | 3.04E-04 | 0.87 | 1.81E-06 | 4.53E-05 |
| 153 | hsa-miR-24-2* | 155 | 79 | 1.96 | 2.57E-05 | 3.13E-04 | 0.13 | 7.11E-06 | 1.10E-04 |
| 339 | hsa-miR-196a* | 141 | 75 | 1.89 | 2.53E-05 | 3.13E-04 | 0.17 | 1.12E-04 | 8.67E-04 |
| 369 | hsa-miR-30d | 5661 | 11836 | 0.48 | 2.58E-05 | 3.13E-04 | 0.81 | 4.94E-04 | 2.65E-03 |
| 130 | hsa-miR-31* | 175 | 49 | 3.53 | 3.03E-05 | 3.61E-04 | 0.13 | 8.07E-07 | 2.36E-05 |
| 195 | hsa-miR-197 | 605 | 2119 | 0.29 | 3.12E-05 | 3.67E-04 | 0.88 | 8.26E-08 | 4.27E-06 |
| 108 | hsa-miR-193b* | 34 | 93 | 0.37 | 3.32E-05 | 3.85E-04 | 0.82 | 2.34E-04 | 1.50E-03 |
| 230 | hsa-miR-361-5p | 390 | 1313 | 0.30 | 3.39E-05 | 3.88E-04 | 0.84 | 1.79E-05 | 2.11E-04 |
| 188 | hsa-miR-28-5p | 377 | 678 | 0.56 | 3.53E-05 | 3.98E-04 | 0.87 | 3.32E-05 | 3.40E-04 |
| 370 | hsa-miR-191 | 11739 | 19616 | 0.60 | 3.57E-05 | 3.98E-04 | 0.74 | 5.41E-03 | 1.77E-02 |
| 112 | hsa-miR-548i | 22 | 41 | 0.54 | 3.68E-05 | 4.05E-04 | 0.89 | 2.15E-06 | 5.22E-05 |
| 129 | hsa-miR-1274a | 147 | 318 | 0.46 | 3.98E-05 | 4.33E-04 | 0.84 | 4.60E-05 | 4.53E-04 |
| 250 | hsa-miR-223 | 1801 | 6179 | 0.29 | 4.05E-05 | 4.35E-04 | 0.82 | 5.37E-05 | 5.11E-04 |
| 371 | hsa-let-7f | 450 | 1133 | 0.40 | 4.52E-05 | 4.79E-04 | 0.78 | 1.16E-03 | 5.14E-03 |
| 372 | hsa-miR-582-3p | 72 | 108 | 0.67 | 5.33E-05 | 5.58E-04 | 0.78 | 3.24E-03 | 1.15E-02 |
| 373 | hsa-miR-25 | 6715 | 11952 | 0.56 | 5.40E-05 | 5.59E-04 | 0.76 | 5.62E-03 | 1.82E-02 |
| 88 | hsa-miR-650 | 129 | 59 | 2.16 | 6.01E-05 | 6.14E-04 | 0.12 | 2.53E-06 | 5.92E-05 |
| 374 | hsa-miR-22 | 8077 | 12241 | 0.66 | 6.38E-05 | 6.37E-04 | 0.74 | 5.19E-03 | 1.71E-02 |
| 375 | hsa-miR-199a-5p | 234 | 570 | 0.41 | 6.38E-05 | 6.37E-04 | 0.84 | 3.18E-04 | 1.90E-03 |

Figure 6 (cont.)

| | | | | | | | | | |
|---|---|---|---|---|---|---|---|---|---|
| 25 | hsa-miR-633 | 68 | 28 | 2.43 | 6.56E-05 | 6.47E-04 | 0.13 | 2.65E-06 | 5.92E-05 |
| 22 | hsa-miR-934 | 81 | 34 | 2.40 | 6.66E-05 | 6.47E-04 | 0.12 | 4.49E-07 | 1.52E-05 |
| 376 | hsa-miR-142-5p | 697 | 1753 | 0.40 | 6.72E-05 | 6.47E-04 | 0.84 | 6.23E-06 | 9.97E-05 |
| 328 | hsa-miR-574-3p | 1683 | 4334 | 0.39 | 7.04E-05 | 6.71E-04 | 0.91 | 1.75E-10 | 2.98E-08 |
| 135 | hsa-miR-20a* | 145 | 77 | 1.88 | 7.68E-05 | 7.16E-04 | 0.12 | 3.18E-05 | 3.33E-04 |
| 377 | hsa-miR-15a | 4234 | 6578 | 0.64 | 7.69E-05 | 7.16E-04 | 0.78 | 2.58E-03 | 9.86E-03 |
| 162 | hsa-miR-29a | 714 | 1790 | 0.40 | 8.39E-05 | 7.74E-04 | 0.82 | 9.64E-05 | 7.94E-04 |
| 183 | hsa-miR-549 | 60 | 38 | 1.58 | 9.59E-05 | 8.75E-04 | 0.20 | 3.64E-04 | 2.13E-03 |
| 91 | hsa-miR-653 | 39 | 67 | 0.57 | 9.83E-05 | 8.77E-04 | 0.78 | 1.20E-03 | 5.27E-03 |
| 145 | hsa-miR-515-5p | 162 | 102 | 1.60 | 9.77E-05 | 8.77E-04 | 0.14 | 8.70E-04 | 4.14E-03 |
| 76 | hsa-miR-488 | 20 | 46 | 0.43 | 1.02E-04 | 8.94E-04 | 0.84 | 2.75E-05 | 2.95E-04 |
| 378 | hsa-miR-1301 | 216 | 98 | 2.21 | 1.02E-04 | 8.94E-04 | 0.11 | 6.06E-07 | 1.90E-05 |
| 60 | hsa-miR-28-3p | 186 | 289 | 0.65 | 1.05E-04 | 9.08E-04 | 0.82 | 2.89E-03 | 1.06E-02 |
| 51 | hsa-miR-512-5p | 51 | 28 | 1.83 | 1.07E-04 | 9.15E-04 | 0.17 | 6.47E-05 | 5.65E-04 |
| 80 | hsa-miR-105 | 41 | 16 | 2.56 | 1.25E-04 | 1.06E-03 | 0.15 | 1.05E-05 | 1.44E-04 |
| 31 | hsa-miR-425* | 80 | 107 | 0.75 | 1.39E-04 | 1.16E-03 | 0.74 | 1.03E-02 | 2.89E-02 |
| 48 | hsa-miR-595 | 91 | 33 | 2.77 | 1.38E-04 | 1.16E-03 | 0.23 | 8.99E-04 | 4.23E-03 |
| 167 | hsa-miR-214* | 62 | 25 | 2.50 | 1.50E-04 | 1.22E-03 | 0.13 | 3.99E-07 | 1.45E-05 |
| 187 | hsa-miR-302b | 20 | 38 | 0.52 | 1.51E-04 | 1.22E-03 | 0.81 | 1.54E-03 | 6.50E-03 |
| 379 | hsa-miR-551b | 88 | 32 | 2.77 | 1.51E-04 | 1.22E-03 | 0.18 | 1.09E-04 | 8.67E-04 |
| 380 | hsa-miR-26a | 7035 | 12794 | 0.55 | 1.63E-04 | 1.31E-03 | 0.76 | 4.48E-03 | 1.51E-02 |
| 295 | hsa-miR-522* | 152 | 60 | 2.54 | 1.81E-04 | 1.44E-03 | 0.15 | 6.86E-06 | 1.08E-04 |
| 66 | hsa-miR-33a | 104 | 58 | 1.80 | 1.99E-04 | 1.53E-03 | 0.17 | 2.67E-04 | 1.66E-03 |
| 271 | hsa-miR-409-3p | 39 | 130 | 0.30 | 2.00E-04 | 1.53E-03 | 0.85 | 1.23E-06 | 3.35E-05 |
| 381 | hsa-miR-588 | 122 | 72 | 1.70 | 2.01E-04 | 1.53E-03 | 0.16 | 4.33E-04 | 2.39E-03 |
| 382 | hsa-miR-331-3p | 699 | 2688 | 0.26 | 2.00E-04 | 1.53E-03 | 0.82 | 4.65E-05 | 4.53E-04 |
| 17 | hsa-miR-450b-5p | 58 | 34 | 1.69 | 2.06E-04 | 1.53E-03 | 0.17 | 1.69E-04 | 1.18E-03 |
| 383 | hsa-miR-1274b | 630 | 1392 | 0.45 | 2.05E-04 | 1.53E-03 | 0.78 | 9.99E-04 | 4.60E-03 |
| 384 | hsa-miR-301b | 189 | 98 | 1.93 | 2.03E-04 | 1.53E-03 | 0.14 | 4.43E-06 | 8.20E-05 |
| 219 | hsa-miR-520f | 17 | 37 | 0.46 | 2.12E-04 | 1.56E-03 | 0.82 | 1.19E-04 | 8.98E-04 |
| 385 | hsa-miR-15b | 15850 | 25643 | 0.62 | 2.18E-04 | 1.59E-03 | 0.71 | 1.04E-02 | 2.91E-02 |
| 125 | hsa-miR-154 | 16 | 38 | 0.43 | 2.21E-04 | 1.60E-03 | 0.81 | 1.29E-04 | 9.60E-04 |
| 165 | hsa-miR-26b* | 23 | 55 | 0.43 | 2.35E-04 | 1.69E-03 | 0.81 | 2.92E-04 | 1.78E-03 |
| 30 | hsa-miR-216b | 132 | 61 | 2.18 | 2.51E-04 | 1.79E-03 | 0.14 | 2.95E-06 | 6.26E-05 |
| 42 | hsa-miR-624 | 56 | 102 | 0.55 | 2.58E-04 | 1.82E-03 | 0.77 | 3.88E-03 | 1.33E-02 |
| 207 | hsa-miR-1908 | 889 | 3043 | 0.29 | 2.60E-04 | 1.82E-03 | 0.82 | 1.65E-05 | 1.97E-04 |
| 266 | hsa-miR-508-3p | 17 | 45 | 0.38 | 2.67E-04 | 1.86E-03 | 0.83 | 2.05E-05 | 2.32E-04 |
| 38 | hsa-miR-25* | 61 | 88 | 0.69 | 2.72E-04 | 1.87E-03 | 0.76 | 3.49E-03 | 1.22E-02 |
| 189 | hsa-miR-196b | 14 | 38 | 0.37 | 2.73E-04 | 1.87E-03 | 0.83 | 2.55E-05 | 2.77E-04 |
| 262 | hsa-miR-215 | 382 | 705 | 0.54 | 2.76E-04 | 1.87E-03 | 0.83 | 2.01E-05 | 2.30E-04 |
| 61 | hsa-miR-127-5p | 134 | 54 | 2.49 | 2.87E-04 | 1.93E-03 | 0.19 | 4.02E-04 | 2.27E-03 |
| 221 | hsa-miR-1912 | 162 | 105 | 1.55 | 3.09E-04 | 2.06E-03 | 0.15 | 2.29E-04 | 1.49E-03 |
| 71 | hsa-miR-518d-3p | 63 | 31 | 2.03 | 3.14E-04 | 2.08E-03 | 0.22 | 1.23E-03 | 5.30E-03 |
| 109 | hsa-miR-143* | 114 | 54 | 2.12 | 3.17E-04 | 2.08E-03 | 0.16 | 9.14E-05 | 7.68E-04 |

Figure 6 (cont.)

| 386 | hsa-miR-138-1* | 99 | 54 | 1.84 | 3.25E-04 | 2.12E-03 | 0.18 | 2.23E-04 | 1.49E-03 |
|---|---|---|---|---|---|---|---|---|---|
| 178 | hsa-miR-152 | 246 | 321 | 0.77 | 3.45E-04 | 2.24E-03 | 0.75 | 8.24E-03 | 2.45E-02 |
| 387 | hsa-miR-203 | 26 | 48 | 0.55 | 3.52E-04 | 2.26E-03 | 0.79 | 1.33E-03 | 5.72E-03 |
| 388 | hsa-miR-423-3p | 1019 | 2159 | 0.47 | 3.69E-04 | 2.36E-03 | 0.82 | 1.89E-04 | 1.28E-03 |
| 269 | hsa-miR-1324 | 120 | 67 | 1.80 | 3.73E-04 | 2.36E-03 | 0.16 | 1.87E-04 | 1.28E-03 |
| 292 | hsa-miR-625* | 216 | 365 | 0.59 | 3.83E-04 | 2.40E-03 | 0.77 | 1.99E-03 | 7.96E-03 |
| 249 | hsa-miR-219-5p | 56 | 20 | 2.78 | 3.91E-04 | 2.44E-03 | 0.15 | 2.61E-06 | 5.92E-05 |
| 110 | hsa-miR-380* | 81 | 41 | 1.98 | 3.98E-04 | 2.45E-03 | 0.17 | 1.90E-04 | 1.28E-03 |
| 157 | hsa-miR-219-2-3p | 18 | 52 | 0.35 | 4.01E-04 | 2.45E-03 | 0.83 | 1.35E-04 | 9.98E-04 |
| 389 | hsa-miR-376c | 80 | 106 | 0.75 | 4.02E-04 | 2.45E-03 | 0.72 | 2.14E-02 | 5.12E-02 |
| 258 | hsa-miR-564 | 164 | 72 | 2.29 | 4.32E-04 | 2.62E-03 | 0.14 | 1.12E-05 | 1.51E-04 |
| 119 | hsa-let-7a* | 24 | 52 | 0.45 | 4.47E-04 | 2.69E-03 | 0.77 | 4.75E-03 | 1.60E-02 |
| 138 | hsa-miR-1270 | 31 | 67 | 0.47 | 4.51E-04 | 2.69E-03 | 0.79 | 7.42E-04 | 3.74E-03 |
| 242 | hsa-miR-431 | 165 | 77 | 2.14 | 4.61E-04 | 2.72E-03 | 0.18 | 1.97E-03 | 7.96E-03 |
| 324 | hsa-miR-135b | 17 | 37 | 0.45 | 4.62E-04 | 2.72E-03 | 0.83 | 5.79E-05 | 5.34E-04 |
| 55 | hsa-miR-556-5p | 125 | 67 | 1.87 | 4.92E-04 | 2.84E-03 | 0.18 | 1.21E-03 | 5.28E-03 |
| 308 | hsa-miR-455-3p | 170 | 68 | 2.52 | 4.89E-04 | 2.84E-03 | 0.12 | 5.28E-08 | 3.20E-06 |
| 390 | hsa-miR-107 | 1430 | 852 | 1.68 | 4.90E-04 | 2.84E-03 | 0.20 | 2.69E-04 | 1.66E-03 |
| 182 | hsa-miR-490-3p | 87 | 35 | 2.50 | 5.24E-04 | 3.00E-03 | 0.17 | 1.37E-05 | 1.75E-04 |
| 391 | hsa-miR-497* | 115 | 64 | 1.79 | 5.43E-04 | 3.09E-03 | 0.20 | 1.48E-03 | 6.31E-03 |
| 86 | hsa-miR-1284 | 34 | 77 | 0.44 | 5.50E-04 | 3.11E-03 | 0.82 | 8.38E-05 | 7.10E-04 |
| 34 | hsa-miR-607 | 83 | 35 | 2.37 | 5.83E-04 | 3.21E-03 | 0.16 | 2.99E-05 | 3.17E-04 |
| 104 | hsa-miR-570 | 84 | 38 | 2.23 | 5.80E-04 | 3.21E-03 | 0.21 | 6.10E-04 | 3.19E-03 |
| 143 | hsa-let-7d | 2199 | 3407 | 0.65 | 5.81E-04 | 3.21E-03 | 0.74 | 9.01E-03 | 2.60E-02 |
| 392 | hsa-miR-342-3p | 3225 | 7612 | 0.42 | 5.82E-04 | 3.21E-03 | 0.81 | 6.12E-05 | 5.46E-04 |
| 142 | hsa-miR-411* | 52 | 34 | 1.52 | 6.09E-04 | 3.33E-03 | 0.17 | 1.16E-03 | 5.14E-03 |
| 68 | hsa-miR-1283 | 95 | 48 | 1.97 | 6.15E-04 | 3.34E-03 | 0.21 | 5.51E-04 | 2.92E-03 |
| 123 | hsa-miR-188-3p | 139 | 64 | 2.17 | 6.24E-04 | 3.36E-03 | 0.16 | 5.66E-06 | 9.41E-05 |
| 222 | hsa-miR-452* | 331 | 186 | 1.78 | 6.27E-04 | 3.36E-03 | 0.21 | 6.90E-04 | 3.53E-03 |
| 264 | hsa-miR-183 | 374 | 899 | 0.42 | 6.43E-04 | 3.43E-03 | 0.79 | 4.44E-04 | 2.43E-03 |
| 152 | hsa-miR-346 | 64 | 85 | 0.76 | 6.62E-04 | 3.51E-03 | 0.76 | 1.22E-02 | 3.30E-02 |
| 44 | hsa-miR-646 | 237 | 106 | 2.23 | 6.79E-04 | 3.58E-03 | 0.17 | 1.47E-04 | 1.06E-03 |
| 273 | hsa-miR-509-5p | 225 | 98 | 2.30 | 7.15E-04 | 3.74E-03 | 0.17 | 2.53E-04 | 1.59E-03 |
| 36 | hsa-miR-561 | 45 | 23 | 1.94 | 7.45E-04 | 3.85E-03 | 0.21 | 8.36E-04 | 4.03E-03 |
| 148 | hsa-miR-552 | 33 | 72 | 0.46 | 7.41E-04 | 3.85E-03 | 0.80 | 1.23E-04 | 9.23E-04 |
| 194 | hsa-miR-767-5p | 170 | 78 | 2.17 | 7.82E-04 | 3.99E-03 | 0.16 | 9.60E-06 | 1.34E-04 |
| 393 | hsa-miR-766 | 370 | 599 | 0.62 | 7.81E-04 | 3.99E-03 | 0.76 | 3.38E-03 | 1.19E-02 |
| 174 | hsa-miR-587 | 46 | 96 | 0.48 | 8.01E-04 | 4.07E-03 | 0.79 | 1.00E-03 | 4.60E-03 |
| 59 | hsa-miR-593* | 285 | 127 | 2.25 | 8.09E-04 | 4.08E-03 | 0.14 | 1.12E-04 | 8.67E-04 |
| 394 | hsa-miR-29c | 436 | 840 | 0.52 | 8.26E-04 | 4.15E-03 | 0.74 | 2.73E-03 | 1.03E-02 |
| 70 | hsa-miR-491-3p | 85 | 44 | 1.92 | 8.48E-04 | 4.23E-03 | 0.24 | 9.05E-03 | 2.60E-02 |
| 231 | hsa-miR-1265 | 21 | 16 | 1.25 | 8.64E-04 | 4.25E-03 | 0.29 | 1.73E-02 | 4.42E-02 |
| 395 | hsa-miR-1266 | 109 | 64 | 1.69 | 8.57E-04 | 4.25E-03 | 0.19 | 4.01E-04 | 2.27E-03 |
| 396 | hsa-let-7i* | 258 | 164 | 1.57 | 8.66E-04 | 4.25E-03 | 0.24 | 8.56E-03 | 2.51E-02 |
| 163 | hsa-miR-509-3- | 234 | 92 | 2.55 | 8.80E-04 | 4.29E-03 | 0.21 | 7.00E-04 | 3.55E-03 |

Figure 6 (cont.)

| | 5p | | | | | | | | |
|---|---|---|---|---|---|---|---|---|---|
| 103 | hsa-miR-548p | 113 | 55 | 2.07 | 9.13E-04 | 4.40E-03 | 0.20 | 4.73E-04 | 2.57E-03 |
| 261 | hsa-miR-153 | 114 | 62 | 1.85 | 9.08E-04 | 4.40E-03 | 0.19 | 1.01E-04 | 8.19E-04 |
| 397 | hsa-miR-507 | 27 | 44 | 0.61 | 9.26E-04 | 4.44E-03 | 0.75 | 1.05E-02 | 2.92E-02 |
| 214 | hsa-miR-603 | 132 | 68 | 1.95 | 9.46E-04 | 4.51E-03 | 0.21 | 2.29E-04 | 1.49E-03 |
| 398 | hsa-miR-211 | 14 | 27 | 0.53 | 9.69E-04 | 4.59E-03 | 0.81 | 4.96E-03 | 1.65E-02 |
| 399 | hsa-miR-335 | 412 | 870 | 0.47 | 9.83E-04 | 4.63E-03 | 0.81 | 1.72E-04 | 1.18E-03 |
| 279 | hsa-miR-520c-5p | 142 | 64 | 2.21 | 9.90E-04 | 4.64E-03 | 0.17 | 9.79E-05 | 7.98E-04 |
| 317 | hsa-miR-1303 | 36 | 56 | 0.65 | 1.05E-03 | 4.85E-03 | 0.79 | 4.97E-04 | 2.65E-03 |
| 400 | hsa-miR-30e | 261 | 556 | 0.47 | 1.04E-03 | 4.85E-03 | 0.76 | 3.14E-03 | 1.13E-02 |
| 401 | hsa-miR-302d | 16 | 37 | 0.44 | 1.08E-03 | 4.99E-03 | 0.82 | 4.29E-05 | 4.33E-04 |
| 90 | hsa-miR-555 | 39 | 20 | 1.96 | 1.11E-03 | 5.04E-03 | 0.20 | 2.28E-04 | 1.49E-03 |
| 94 | hsa-miR-181a-2* | 107 | 158 | 0.68 | 1.11E-03 | 5.04E-03 | 0.82 | 7.89E-04 | 3.87E-03 |
| 402 | hsa-miR-497 | 180 | 84 | 2.13 | 1.11E-03 | 5.04E-03 | 0.15 | 4.93E-06 | 8.57E-05 |
| 69 | hsa-miR-34b* | 49 | 73 | 0.66 | 1.15E-03 | 5.17E-03 | 0.78 | 3.51E-03 | 1.22E-02 |
| 141 | hsa-miR-1246 | 20 | 48 | 0.42 | 1.15E-03 | 5.17E-03 | 0.78 | 4.33E-04 | 2.39E-03 |
| 349 | hsa-miR-625 | 71 | 144 | 0.49 | 1.16E-03 | 5.17E-03 | 0.74 | 3.75E-03 | 1.30E-02 |
| 149 | hsa-miR-508-5p | 108 | 47 | 2.32 | 1.17E-03 | 5.17E-03 | 0.18 | 9.23E-06 | 1.31E-04 |
| 218 | hsa-let-7e* | 24 | 48 | 0.50 | 1.18E-03 | 5.20E-03 | 0.79 | 7.69E-04 | 3.79E-03 |
| 253 | hsa-miR-1207-5p | 412 | 810 | 0.51 | 1.18E-03 | 5.20E-03 | 0.78 | 3.27E-05 | 3.38E-04 |
| 45 | hsa-miR-505 | 35 | 64 | 0.54 | 1.26E-03 | 5.48E-03 | 0.76 | 7.77E-03 | 2.35E-02 |
| 403 | hsa-miR-891a | 120 | 79 | 1.52 | 1.26E-03 | 5.48E-03 | 0.24 | 2.14E-02 | 5.12E-02 |
| 237 | hsa-miR-365 | 72 | 115 | 0.63 | 1.29E-03 | 5.60E-03 | 0.80 | 5.70E-05 | 5.34E-04 |
| 29 | hsa-miR-606 | 70 | 31 | 2.26 | 1.31E-03 | 5.62E-03 | 0.26 | 5.22E-03 | 1.72E-02 |
| 404 | hsa-miR-933 | 210 | 124 | 1.69 | 1.31E-03 | 5.63E-03 | 0.25 | 3.64E-02 | 7.79E-02 |
| 67 | hsa-miR-139-5p | 131 | 87 | 1.51 | 1.34E-03 | 5.71E-03 | 0.19 | 7.81E-03 | 2.36E-02 |
| 326 | hsa-miR-135a | 15 | 29 | 0.53 | 1.38E-03 | 5.86E-03 | 0.83 | 1.32E-05 | 1.75E-04 |
| 201 | hsa-miR-125a-5p | 198 | 663 | 0.30 | 1.40E-03 | 5.90E-03 | 0.81 | 6.55E-05 | 5.67E-04 |
| 200 | hsa-miR-539 | 19 | 34 | 0.56 | 1.41E-03 | 5.91E-03 | 0.80 | 1.41E-04 | 1.03E-03 |
| 47 | hsa-miR-218-1* | 75 | 38 | 1.98 | 1.46E-03 | 6.11E-03 | 0.19 | 4.61E-05 | 4.53E-04 |
| 226 | hsa-miR-509-3p | 19 | 38 | 0.51 | 1.56E-03 | 6.48E-03 | 0.75 | 8.69E-03 | 2.53E-02 |
| 73 | hsa-miR-1227 | 68 | 134 | 0.50 | 1.63E-03 | 6.66E-03 | 0.80 | 3.97E-04 | 2.27E-03 |
| 132 | hsa-miR-9* | 92 | 54 | 1.71 | 1.63E-03 | 6.66E-03 | 0.21 | 1.08E-03 | 4.82E-03 |
| 405 | hsa-miR-874 | 165 | 109 | 1.51 | 1.63E-03 | 6.66E-03 | 0.23 | 3.17E-03 | 1.14E-02 |
| 177 | hsa-miR-99a | 114 | 196 | 0.58 | 1.66E-03 | 6.74E-03 | 0.75 | 5.55E-03 | 1.81E-02 |
| 406 | hsa-miR-363 | 4232 | 5994 | 0.71 | 1.66E-03 | 6.74E-03 | 0.64 | 5.40E-02 | 1.06E-01 |
| 239 | hsa-miR-1279 | 18 | 41 | 0.43 | 1.69E-03 | 6.82E-03 | 0.80 | 8.19E-05 | 7.01E-04 |
| 126 | hsa-miR-939 | 49 | 88 | 0.56 | 1.71E-03 | 6.86E-03 | 0.77 | 9.98E-04 | 4.60E-03 |
| 336 | hsa-miR-1290 | 16 | 32 | 0.50 | 1.72E-03 | 6.90E-03 | 0.79 | 1.59E-04 | 1.13E-03 |
| 116 | hsa-miR-1321 | 27 | 52 | 0.52 | 1.77E-03 | 7.04E-03 | 0.79 | 3.05E-04 | 1.84E-03 |
| 64 | hsa-miR-525-3p | 62 | 34 | 1.79 | 1.85E-03 | 7.33E-03 | 0.20 | 8.92E-04 | 4.23E-03 |
| 257 | hsa-miR-597 | 70 | 37 | 1.92 | 1.88E-03 | 7.40E-03 | 0.22 | 3.78E-03 | 1.30E-02 |
| 198 | hsa-miR-188-5p | 109 | 52 | 2.09 | 1.90E-03 | 7.45E-03 | 0.20 | 6.25E-05 | 5.52E-04 |

Figure 6 (cont.)

| | | | | | | | | | |
|---|---|---|---|---|---|---|---|---|---|
| 127 | hsa-miR-1226* | 182 | 92 | 1.97 | 1.94E-03 | 7.57E-03 | 0.18 | 1.17E-04 | 8.98E-04 |
| 208 | hsa-miR-200c* | 51 | 66 | 0.77 | 2.02E-03 | 7.85E-03 | 0.73 | 2.67E-02 | 6.12E-02 |
| 407 | hsa-let-7c | 393 | 859 | 0.46 | 2.03E-03 | 7.85E-03 | 0.73 | 5.60E-03 | 1.82E-02 |
| 9 | hsa-miR-496 | 68 | 44 | 1.57 | 2.11E-03 | 8.09E-03 | 0.22 | 8.71E-03 | 2.53E-02 |
| 337 | hsa-miR-214 | 290 | 128 | 2.26 | 2.11E-03 | 8.09E-03 | 0.21 | 8.01E-04 | 3.91E-03 |
| 265 | hsa-miR-671-5p | 62 | 29 | 2.16 | 2.13E-03 | 8.13E-03 | 0.20 | 5.73E-05 | 5.34E-04 |
| 408 | hsa-miR-302e | 23 | 35 | 0.65 | 2.22E-03 | 8.46E-03 | 0.75 | 6.36E-03 | 2.00E-02 |
| 77 | hsa-miR-455-5p | 32 | 54 | 0.58 | 2.26E-03 | 8.50E-03 | 0.73 | 1.39E-02 | 3.66E-02 |
| 245 | hsa-miR-26a-1* | 25 | 54 | 0.47 | 2.27E-03 | 8.50E-03 | 0.78 | 1.83E-03 | 7.48E-03 |
| 347 | hsa-miR-518d-5p | 149 | 79 | 1.89 | 2.27E-03 | 8.50E-03 | 0.23 | 2.41E-03 | 9.36E-03 |
| 409 | hsa-miR-192* | 132 | 85 | 1.55 | 2.28E-03 | 8.50E-03 | 0.20 | 1.25E-02 | 3.34E-02 |
| 305 | hsa-miR-521 | 52 | 32 | 1.64 | 2.34E-03 | 8.70E-03 | 0.24 | 4.23E-03 | 1.44E-02 |
| 293 | hsa-miR-1253 | 78 | 27 | 2.85 | 2.43E-03 | 8.99E-03 | 0.22 | 5.83E-04 | 3.07E-03 |
| 322 | hsa-miR-1247 | 60 | 33 | 1.83 | 2.48E-03 | 9.13E-03 | 0.24 | 7.35E-03 | 2.25E-02 |
| 205 | hsa-miR-513b | 44 | 26 | 1.68 | 2.54E-03 | 9.34E-03 | 0.23 | 1.06E-03 | 4.77E-03 |
| 272 | hsa-miR-629* | 88 | 160 | 0.55 | 2.63E-03 | 9.61E-03 | 0.75 | 3.13E-03 | 1.13E-02 |
| 334 | hsa-miR-135a* | 22 | 46 | 0.47 | 2.66E-03 | 9.68E-03 | 0.77 | 4.95E-04 | 2.65E-03 |
| 410 | hsa-miR-499-5p | 31 | 51 | 0.60 | 2.71E-03 | 9.83E-03 | 0.76 | 4.19E-03 | 1.43E-02 |
| 84 | hsa-miR-517c | 31 | 48 | 0.64 | 2.79E-03 | 1.00E-02 | 0.73 | 1.02E-02 | 2.89E-02 |
| 120 | hsa-miR-620 | 27 | 37 | 0.74 | 2.79E-03 | 1.00E-02 | 0.70 | 3.93E-02 | 8.08E-02 |
| 286 | hsa-miR-151-3p | 583 | 1210 | 0.48 | 2.92E-03 | 1.04E-02 | 0.81 | 5.94E-05 | 5.42E-04 |
| 20 | hsa-miR-224 | 51 | 64 | 0.80 | 2.94E-03 | 1.05E-02 | 0.70 | 2.09E-02 | 5.06E-02 |
| 411 | hsa-let-7b | 775 | 1774 | 0.44 | 2.96E-03 | 1.05E-02 | 0.75 | 2.89E-03 | 1.06E-02 |
| 211 | hsa-miR-492 | 80 | 43 | 1.85 | 3.04E-03 | 1.07E-02 | 0.22 | 1.58E-03 | 6.65E-03 |
| 133 | hsa-miR-769-3p | 23 | 38 | 0.61 | 3.08E-03 | 1.08E-02 | 0.75 | 8.40E-03 | 2.48E-02 |
| 241 | hsa-miR-576-3p | 20 | 43 | 0.47 | 3.09E-03 | 1.08E-02 | 0.80 | 4.05E-04 | 2.28E-03 |
| 124 | hsa-miR-658 | 47 | 88 | 0.54 | 3.18E-03 | 1.11E-02 | 0.76 | 6.58E-04 | 3.40E-03 |
| 277 | hsa-miR-520c-3p | 19 | 31 | 0.61 | 3.19E-03 | 1.11E-02 | 0.78 | 3.98E-04 | 2.27E-03 |
| 412 | hsa-miR-204 | 16 | 29 | 0.55 | 3.24E-03 | 1.12E-02 | 0.77 | 2.91E-03 | 1.06E-02 |
| 413 | hsa-miR-621 | 323 | 148 | 2.18 | 3.32E-03 | 1.14E-02 | 0.21 | 8.44E-04 | 4.05E-03 |
| 209 | hsa-miR-635 | 102 | 52 | 1.95 | 3.38E-03 | 1.16E-02 | 0.23 | 7.50E-04 | 3.75E-03 |
| 414 | hsa-miR-150 | 1364 | 4087 | 0.33 | 3.41E-03 | 1.17E-02 | 0.74 | 6.67E-03 | 2.08E-02 |
| 151 | hsa-miR-1291 | 115 | 62 | 1.86 | 3.46E-03 | 1.18E-02 | 0.25 | 5.73E-03 | 1.85E-02 |
| 415 | hsa-let-7e | 156 | 358 | 0.44 | 3.56E-03 | 1.21E-02 | 0.70 | 1.18E-02 | 3.21E-02 |
| 95 | hsa-miR-1296 | 48 | 23 | 2.09 | 3.61E-03 | 1.22E-02 | 0.24 | 2.00E-03 | 7.96E-03 |
| 416 | hsa-miR-30b | 8037 | 12074 | 0.67 | 3.62E-03 | 1.22E-02 | 0.73 | 1.12E-02 | 3.09E-02 |
| 128 | hsa-miR-495 | 74 | 41 | 1.83 | 3.73E-03 | 1.25E-02 | 0.22 | 9.67E-04 | 4.53E-03 |
| 172 | hsa-miR-450b-3p | 39 | 23 | 1.69 | 3.73E-03 | 1.25E-02 | 0.25 | 6.73E-03 | 2.09E-02 |
| 37 | hsa-miR-1298 | 45 | 27 | 1.65 | 3.76E-03 | 1.25E-02 | 0.26 | 5.96E-03 | 1.90E-02 |
| 159 | hsa-miR-1180 | 69 | 115 | 0.61 | 3.77E-03 | 1.25E-02 | 0.70 | 2.28E-02 | 5.39E-02 |
| 323 | hsa-miR-489 | 197 | 116 | 1.70 | 3.79E-03 | 1.25E-02 | 0.27 | 1.07E-02 | 2.95E-02 |
| 280 | hsa-miR-141* | 80 | 44 | 1.82 | 3.86E-03 | 1.27E-02 | 0.23 | 4.21E-04 | 2.35E-03 |
| 311 | hsa-miR-1278 | 62 | 32 | 1.96 | 3.95E-03 | 1.29E-02 | 0.21 | 7.53E-04 | 3.75E-03 |
| 314 | hsa-miR-34c-3p | 89 | 54 | 1.65 | 4.00E-03 | 1.31E-02 | 0.23 | 5.86E-03 | 1.87E-02 |

Figure 6 (cont.)

| 417 | hsa-miR-126* | 22 | 32 | 0.71 | 4.05E-03 | 1.31E-02 | 0.74 | 7.04E-03 | 2.17E-02 |
|---|---|---|---|---|---|---|---|---|---|
| 418 | hsa-miR-190 | 19 | 35 | 0.54 | 4.13E-03 | 1.34E-02 | 0.78 | 2.48E-03 | 9.51E-03 |
| 199 | hsa-miR-298 | 121 | 64 | 1.88 | 4.17E-03 | 1.35E-02 | 0.25 | 8.20E-03 | 2.45E-02 |
| 419 | hsa-miR-1184 | 193 | 115 | 1.67 | 4.25E-03 | 1.36E-02 | 0.25 | 6.92E-03 | 2.14E-02 |
| 420 | hsa-let-7a | 1045 | 2066 | 0.51 | 4.27E-03 | 1.37E-02 | 0.69 | 3.71E-02 | 7.82E-02 |
| 229 | hsa-miR-632 | 34 | 58 | 0.58 | 4.48E-03 | 1.42E-02 | 0.75 | 4.25E-03 | 1.44E-02 |
| 312 | hsa-miR-186 | 44 | 81 | 0.54 | 4.49E-03 | 1.42E-02 | 0.74 | 1.51E-03 | 6.40E-03 |
| 421 | hsa-miR-125b | 452 | 1903 | 0.24 | 4.47E-03 | 1.42E-02 | 0.77 | 2.48E-04 | 1.58E-03 |
| 57 | hsa-miR-411 | 54 | 33 | 1.64 | 4.59E-03 | 1.44E-02 | 0.24 | 3.43E-03 | 1.20E-02 |
| 268 | hsa-miR-556-3p | 20 | 33 | 0.61 | 4.58E-03 | 1.44E-02 | 0.76 | 2.79E-03 | 1.04E-02 |
| 202 | hsa-miR-548a-3p | 75 | 54 | 1.39 | 4.76E-03 | 1.49E-02 | 0.23 | 1.94E-03 | 7.88E-03 |
| 169 | hsa-miR-1306 | 38 | 55 | 0.69 | 5.07E-03 | 1.57E-02 | 0.66 | 3.89E-02 | 8.04E-02 |
| 341 | hsa-miR-548b-5p | 18 | 32 | 0.56 | 5.05E-03 | 1.57E-02 | 0.77 | 2.98E-04 | 1.81E-03 |
| 422 | hsa-miR-1285 | 265 | 305 | 0.87 | 5.29E-03 | 1.64E-02 | 0.71 | 2.57E-02 | 5.94E-02 |
| 327 | hsa-miR-548d-5p | 19 | 33 | 0.59 | 5.62E-03 | 1.73E-02 | 0.75 | 7.75E-03 | 2.35E-02 |
| 161 | hsa-miR-422a | 149 | 317 | 0.47 | 5.76E-03 | 1.77E-02 | 0.76 | 1.79E-03 | 7.35E-03 |
| 150 | hsa-miR-545* | 34 | 20 | 1.72 | 5.91E-03 | 1.81E-02 | 0.25 | 2.80E-03 | 1.04E-02 |
| 320 | hsa-miR-381 | 95 | 69 | 1.37 | 6.06E-03 | 1.85E-02 | 0.23 | 2.13E-02 | 5.12E-02 |
| 53 | hsa-miR-513a-5p | 52 | 89 | 0.59 | 6.23E-03 | 1.89E-02 | 0.72 | 1.34E-02 | 3.53E-02 |
| 423 | hsa-miR-130b* | 19 | 34 | 0.54 | 6.22E-03 | 1.89E-02 | 0.75 | 1.08E-03 | 4.82E-03 |
| 424 | hsa-miR-542-5p | 94 | 62 | 1.52 | 6.28E-03 | 1.89E-02 | 0.25 | 5.14E-03 | 1.70E-02 |
| 425 | hsa-miR-1228* | 1100 | 1600 | 0.69 | 6.28E-03 | 1.89E-02 | 0.74 | 2.54E-04 | 1.59E-03 |
| 426 | hsa-miR-146b-3p | 74 | 38 | 1.96 | 6.54E-03 | 1.96E-02 | 0.23 | 1.68E-03 | 6.98E-03 |
| 99 | hsa-miR-181d | 32 | 52 | 0.61 | 6.57E-03 | 1.96E-02 | 0.71 | 3.76E-02 | 7.88E-02 |
| 427 | hsa-miR-490-5p | 128 | 84 | 1.51 | 6.62E-03 | 1.97E-02 | 0.26 | 2.24E-02 | 5.33E-02 |
| 115 | hsa-miR-548c-3p | 42 | 27 | 1.56 | 6.72E-03 | 1.99E-02 | 0.27 | 9.54E-03 | 2.73E-02 |
| 428 | hsa-miR-623 | 57 | 32 | 1.81 | 6.97E-03 | 2.06E-02 | 0.25 | 1.06E-03 | 4.77E-03 |
| 330 | hsa-miR-654-3p | 34 | 23 | 1.45 | 7.00E-03 | 2.06E-02 | 0.28 | 1.99E-02 | 4.89E-02 |
| 203 | hsa-miR-92b | 268 | 460 | 0.58 | 7.12E-03 | 2.09E-02 | 0.73 | 1.01E-02 | 2.86E-02 |
| 223 | hsa-miR-146a | 207 | 351 | 0.59 | 7.17E-03 | 2.09E-02 | 0.75 | 2.45E-03 | 9.48E-03 |
| 260 | hsa-miR-432 | 18 | 27 | 0.66 | 7.17E-03 | 2.09E-02 | 0.73 | 1.68E-02 | 4.33E-02 |
| 429 | hsa-let-7i | 599 | 1171 | 0.51 | 7.35E-03 | 2.13E-02 | 0.70 | 1.87E-02 | 4.67E-02 |
| 430 | hsa-miR-760 | 46 | 32 | 1.44 | 7.38E-03 | 2.14E-02 | 0.28 | 3.11E-03 | 1.13E-02 |
| 184 | hsa-miR-802 | 71 | 47 | 1.52 | 7.62E-03 | 2.20E-02 | 0.27 | 8.70E-03 | 2.53E-02 |
| 173 | hsa-miR-517* | 166 | 125 | 1.33 | 7.75E-03 | 2.23E-02 | 0.27 | 4.07E-02 | 8.27E-02 |
| 431 | hsa-miR-616 | 29 | 37 | 0.79 | 7.95E-03 | 2.28E-02 | 0.72 | 3.23E-02 | 7.05E-02 |
| 432 | hsa-miR-541 | 98 | 72 | 1.37 | 8.02E-03 | 2.29E-02 | 0.29 | 4.06E-02 | 8.26E-02 |
| 433 | hsa-miR-124* | 101 | 51 | 1.96 | 8.06E-03 | 2.29E-02 | 0.24 | 2.79E-03 | 1.04E-02 |
| 434 | hsa-miR-1183 | 97 | 66 | 1.46 | 8.11E-03 | 2.30E-02 | 0.26 | 1.01E-03 | 4.60E-03 |
| 435 | hsa-miR-514 | 41 | 58 | 0.71 | 8.20E-03 | 2.32E-02 | 0.71 | 2.19E-02 | 5.22E-02 |
| 436 | hsa-miR-1 | 27 | 51 | 0.52 | 8.37E-03 | 2.36E-02 | 0.76 | 3.21E-03 | 1.15E-02 |
| 437 | hsa-miR-1471 | 126 | 64 | 1.97 | 8.39E-03 | 2.36E-02 | 0.26 | 3.01E-02 | 6.69E-02 |

Figure 6 (cont.)

| | | | | | | | | | |
|---|---|---|---|---|---|---|---|---|---|
| 438 | hsa-miR-758 | 27 | 41 | 0.65 | 8.58E-03 | 2.40E-02 | 0.66 | 7.96E-02 | 1.47E-01 |
| 255 | hsa-miR-519b-5p | 131 | 77 | 1.68 | 8.75E-03 | 2.44E-02 | 0.24 | 2.17E-03 | 8.51E-03 |
| 325 | hsa-miR-518c* | 54 | 66 | 0.82 | 8.81E-03 | 2.45E-02 | 0.69 | 3.06E-02 | 6.75E-02 |
| 284 | hsa-miR-181c* | 63 | 37 | 1.73 | 8.98E-03 | 2.49E-02 | 0.25 | 1.22E-03 | 5.30E-03 |
| 97 | hsa-miR-628-3p | 193 | 369 | 0.52 | 9.07E-03 | 2.51E-02 | 0.78 | 2.13E-03 | 8.40E-03 |
| 439 | hsa-miR-193a-5p | 72 | 119 | 0.60 | 9.22E-03 | 2.54E-02 | 0.73 | 9.75E-03 | 2.79E-02 |
| 440 | hsa-miR-518a-5p | 175 | 127 | 1.38 | 9.27E-03 | 2.54E-02 | 0.26 | 6.11E-02 | 1.18E-01 |
| 35 | hsa-miR-200a* | 66 | 38 | 1.74 | 9.62E-03 | 2.63E-02 | 0.27 | 1.27E-02 | 3.38E-02 |
| 441 | hsa-miR-1250 | 38 | 25 | 1.50 | 1.01E-02 | 2.75E-02 | 0.34 | 3.83E-02 | 7.98E-02 |
| 348 | hsa-miR-148b | 559 | 747 | 0.75 | 1.03E-02 | 2.79E-02 | 0.70 | 1.34E-02 | 3.53E-02 |
| 442 | hsa-miR-149* | 561 | 770 | 0.73 | 1.03E-02 | 2.80E-02 | 0.72 | 2.72E-03 | 1.02E-02 |
| 62 | hsa-miR-1233 | 81 | 52 | 1.55 | 1.05E-02 | 2.82E-02 | 0.24 | 3.31E-03 | 1.17E-02 |
| 192 | hsa-miR-1302 | 36 | 23 | 1.55 | 1.05E-02 | 2.82E-02 | 0.27 | 8.55E-03 | 2.51E-02 |
| 443 | hsa-miR-138-2* | 61 | 31 | 1.96 | 1.05E-02 | 2.82E-02 | 0.25 | 1.34E-03 | 5.73E-03 |
| 444 | hsa-miR-518e | 74 | 46 | 1.61 | 1.10E-02 | 2.93E-02 | 0.29 | 2.26E-02 | 5.35E-02 |
| 445 | hsa-miR-205 | 51 | 68 | 0.75 | 1.11E-02 | 2.96E-02 | 0.70 | 3.20E-02 | 7.02E-02 |
| 101 | hsa-miR-208b | 64 | 43 | 1.49 | 1.13E-02 | 3.01E-02 | 0.26 | 3.32E-03 | 1.17E-02 |
| 54 | hsa-miR-92a | 11829 | 17008 | 0.70 | 1.15E-02 | 3.05E-02 | 0.65 | 9.51E-02 | 1.67E-01 |
| 287 | hsa-miR-942 | 25 | 37 | 0.69 | 1.15E-02 | 3.05E-02 | 0.71 | 2.82E-02 | 6.37E-02 |
| 236 | hsa-miR-548j | 19 | 38 | 0.50 | 1.17E-02 | 3.09E-02 | 0.77 | 6.40E-04 | 3.33E-03 |
| 446 | hsa-let-7g | 383 | 860 | 0.45 | 1.19E-02 | 3.13E-02 | 0.66 | 3.67E-02 | 7.80E-02 |
| 447 | hsa-miR-663b | 87 | 48 | 1.82 | 1.24E-02 | 3.24E-02 | 0.27 | 1.53E-02 | 3.98E-02 |
| 58 | hsa-miR-454 | 125 | 69 | 1.81 | 1.25E-02 | 3.26E-02 | 0.29 | 8.14E-03 | 2.44E-02 |
| 267 | hsa-miR-362-3p | 227 | 416 | 0.55 | 1.28E-02 | 3.34E-02 | 0.72 | 8.03E-03 | 2.42E-02 |
| 212 | hsa-miR-885-3p | 202 | 317 | 0.64 | 1.30E-02 | 3.38E-02 | 0.73 | 2.27E-03 | 8.87E-03 |
| 185 | hsa-miR-1267 | 44 | 54 | 0.81 | 1.32E-02 | 3.40E-02 | 0.69 | 3.15E-02 | 6.92E-02 |
| 448 | hsa-miR-106a* | 140 | 91 | 1.54 | 1.32E-02 | 3.40E-02 | 0.31 | 4.14E-02 | 8.36E-02 |
| 168 | hsa-miR-24-1* | 91 | 69 | 1.31 | 1.36E-02 | 3.48E-02 | 0.31 | 8.21E-02 | 1.50E-01 |
| 329 | hsa-miR-186* | 100 | 67 | 1.49 | 1.36E-02 | 3.48E-02 | 0.25 | 3.23E-02 | 7.05E-02 |
| 449 | hsa-miR-140-3p | 20591 | 33992 | 0.61 | 1.38E-02 | 3.52E-02 | 0.69 | 3.59E-02 | 7.72E-02 |
| 21 | hsa-miR-32* | 29 | 22 | 1.35 | 1.41E-02 | 3.59E-02 | 0.35 | 6.47E-02 | 1.23E-01 |
| 450 | hsa-miR-302b* | 27 | 47 | 0.58 | 1.42E-02 | 3.59E-02 | 0.77 | 7.32E-03 | 2.25E-02 |
| 451 | hsa-miR-611 | 107 | 74 | 1.45 | 1.42E-02 | 3.60E-02 | 0.26 | 8.14E-02 | 1.49E-01 |
| 452 | hsa-miR-26a-2* | 16 | 27 | 0.60 | 1.42E-02 | 3.60E-02 | 0.77 | 6.25E-03 | 1.97E-02 |
| 246 | hsa-miR-571 | 47 | 37 | 1.26 | 1.45E-02 | 3.66E-02 | 0.29 | 2.47E-03 | 9.51E-03 |
| 121 | hsa-miR-548n | 32 | 22 | 1.48 | 1.47E-02 | 3.69E-02 | 0.29 | 2.00E-02 | 4.89E-02 |
| 248 | hsa-miR-103-as | 140 | 92 | 1.52 | 1.48E-02 | 3.71E-02 | 0.29 | 4.47E-02 | 8.95E-02 |
| 299 | hsa-miR-553 | 25 | 38 | 0.65 | 1.51E-02 | 3.75E-02 | 0.72 | 5.83E-03 | 1.87E-02 |
| 453 | hsa-miR-1208 | 90 | 58 | 1.55 | 1.54E-02 | 3.83E-02 | 0.26 | 1.23E-02 | 3.31E-02 |
| 193 | hsa-miR-671-3p | 42 | 58 | 0.73 | 1.56E-02 | 3.86E-02 | 0.67 | 8.01E-02 | 1.48E-01 |
| 134 | hsa-miR-147b | 35 | 25 | 1.39 | 1.57E-02 | 3.87E-02 | 0.32 | 6.15E-02 | 1.18E-01 |
| 454 | hsa-miR-548d-3p | 50 | 36 | 1.41 | 1.57E-02 | 3.87E-02 | 0.31 | 3.97E-02 | 8.13E-02 |
| 171 | hsa-miR-1248 | 33 | 21 | 1.59 | 1.59E-02 | 3.90E-02 | 0.27 | 1.65E-02 | 4.26E-02 |

Figure 6 (cont.)

| 102 | hsa-miR-99b | 181 | 243 | 0.75 | 1.63E-02 | 4.00E-02 | 0.70 | 2.08E-02 | 5.06E-02 |
|---|---|---|---|---|---|---|---|---|---|
| 455 | hsa-miR-339-5p | 532 | 1017 | 0.52 | 1.64E-02 | 4.01E-02 | 0.73 | 1.03E-02 | 2.89E-02 |
| 166 | hsa-miR-1825 | 47 | 75 | 0.63 | 1.66E-02 | 4.05E-02 | 0.69 | 3.38E-02 | 7.35E-02 |
| 456 | hsa-miR-1256 | 64 | 41 | 1.58 | 1.67E-02 | 4.05E-02 | 0.27 | 1.91E-02 | 4.74E-02 |
| 197 | hsa-miR-1225-5p | 68 | 118 | 0.57 | 1.69E-02 | 4.10E-02 | 0.71 | 1.72E-02 | 4.40E-02 |
| 92 | hsa-miR-568 | 70 | 45 | 1.56 | 1.71E-02 | 4.13E-02 | 0.29 | 1.22E-02 | 3.30E-02 |
| 254 | hsa-miR-369-3p | 29 | 55 | 0.53 | 1.73E-02 | 4.16E-02 | 0.73 | 4.78E-03 | 1.60E-02 |
| 457 | hsa-miR-1282 | 15 | 25 | 0.59 | 1.75E-02 | 4.22E-02 | 0.74 | 2.31E-02 | 5.41E-02 |
| 458 | hsa-miR-1202 | 245 | 148 | 1.66 | 1.76E-02 | 4.22E-02 | 0.25 | 8.64E-02 | 1.56E-01 |
| 342 | hsa-miR-222* | 64 | 45 | 1.43 | 1.81E-02 | 4.32E-02 | 0.28 | 1.77E-03 | 7.34E-03 |
| 224 | hsa-miR-183* | 101 | 210 | 0.48 | 1.82E-02 | 4.33E-02 | 0.75 | 2.67E-03 | 1.01E-02 |
| 459 | hsa-miR-1323 | 42 | 37 | 1.16 | 1.87E-02 | 4.44E-02 | 0.30 | 1.90E-02 | 4.72E-02 |
| 460 | hsa-miR-1244 | 15 | 26 | 0.58 | 1.87E-02 | 4.44E-02 | 0.71 | 2.18E-02 | 5.21E-02 |
| 281 | hsa-miR-194* | 46 | 59 | 0.78 | 1.91E-02 | 4.51E-02 | 0.66 | 7.43E-02 | 1.39E-01 |
| 247 | hsa-miR-199b-5p | 27 | 42 | 0.64 | 1.94E-02 | 4.57E-02 | 0.72 | 1.28E-02 | 3.39E-02 |
| 49 | hsa-miR-499-3p | 86 | 56 | 1.54 | 1.97E-02 | 4.63E-02 | 0.28 | 2.69E-02 | 6.13E-02 |
| 50 | hsa-miR-513a-3p | 36 | 30 | 1.21 | 1.99E-02 | 4.65E-02 | 0.33 | 4.12E-02 | 8.34E-02 |
| 461 | hsa-miR-324-3p | 719 | 981 | 0.73 | 2.02E-02 | 4.70E-02 | 0.72 | 1.32E-02 | 3.51E-02 |
| 462 | hsa-miR-519d | 61 | 39 | 1.55 | 2.02E-02 | 4.70E-02 | 0.27 | 1.81E-02 | 4.55E-02 |
| 463 | hsa-miR-30e* | 46 | 60 | 0.77 | 2.02E-02 | 4.70E-02 | 0.70 | 2.06E-02 | 5.01E-02 |
| 228 | hsa-miR-146a* | 80 | 50 | 1.60 | 2.07E-02 | 4.79E-02 | 0.32 | 6.11E-02 | 1.18E-01 |
| 234 | hsa-miR-92b* | 131 | 191 | 0.69 | 2.11E-02 | 4.88E-02 | 0.71 | 9.89E-04 | 4.60E-03 |
| 344 | hsa-miR-1307 | 79 | 117 | 0.68 | 2.12E-02 | 4.89E-02 | 0.71 | 2.78E-02 | 6.30E-02 |
| 464 | hsa-miR-129* | 45 | 67 | 0.67 | 2.13E-02 | 4.90E-02 | 0.69 | 2.98E-02 | 6.64E-02 |
| 252 | hsa-miR-769-5p | 30 | 37 | 0.83 | 2.16E-02 | 4.95E-02 | 0.68 | 4.76E-02 | 9.43E-02 |

Figure 7  Up-regulated miRNAs a) Up-regulated miRNAs hsa-miR-491-5p, hsa-miR-128, hsa-miR-582-3p, hsa-miR-22, hsa-miR-15a, hsa-miR-28-3p, hsa-miR-425*, hsa-miR-25*, hsa-miR-152, hsa-miR-376c, hsa-miR-346, hsa-miR-181a-2*, hsa-miR-363, hsa-miR-200c*, hsa-miR-224, hsa-miR-30b, hsa-miR-1285, hsa-miR-1228*, hsa-miR-518c*, hsa-miR-149*, hsa-miR-205, hsa-miR-885-3p, hsa-miR-99b, hsa-miR-324-3p, hsa-miR-92b*, hsa-miR-1307, hsa-miR-1538, hsa-miR-589*, hsa-miR-936, hsa-miR-1275, hsa-miR-518f, hsa-miR-1909, hsa-miR-1231, hsa-miR-505*, hsa-miR-18b*, hsa-miR-379*, hsa-miR-424, hsa-miR-15b*, hsa-miR-483-5p, hsa-miR-27a, hsa-miR-551a, hsa-miR-770-5p, hsa-miR-1303, hsa-miR-34b*, hsa-miR-1306, hsa-miR-514, hsa-miR-1267, hsa-miR-671-3p, hsa-miR-194*, hsa-miR-30e*, hsa-miR-129*, hsa-miR-1269, hsa-miR-99a*, hsa-miR-302e, hsa-miR-517c, hsa-miR-620, hsa-miR-126*, hsa-miR-432, hsa-miR-616, hsa-miR-758, hsa-miR-942, hsa-miR-553, hsa-miR-199b-5p, hsa-miR-769-5p, hsa-miR-515-3p, hsa-miR-379, hsa-miR-615-3p, hsa-miR-593, hsa-miR-1204, hsa-let-7b*, hsa-miR-1294, hsa-miR-1238, hsa-miR-92a-2*, hsa-miR-601, hsa-miR-609, hsa-miR-185*, hsa-let-7f-1*, hsa-miR-19b, hsa-let-7d*, hsa-miR-425, hsa-miR-1260, hsa-miR-192, hsa-miR-23a, hsa-miR-185, hsa-miR-23b, hsa-miR-744, hsa-miR-484, hsa-miR-296-5p, hsa-miR-30c, hsa-miR-664, hsa-miR-145, hsa-miR-151-5p, hsa-miR-720, hsa-miR-30a, hsa-miR-16, hsa-miR-194, hsa-miR-19a, hsa-miR-1281, hsa-miR-629, hsa-miR-423-5p, hsa-miR-7-1*, hsa-miR-532-3p, hsa-miR-93*, hsa-miR-340, hsa-miR-182, hsa-miR-328, hsa-miR-30d, hsa-miR-197, hsa-miR-361-5p, hsa-miR-28-5p, hsa-miR-191, hsa-miR-1274a, hsa-miR-223, hsa-let-7f, hsa-miR-25, hsa-miR-199a-5p, hsa-miR-142-5p, hsa-miR-574-3p, hsa-miR-29a, hsa-miR-26a, hsa-miR-331-3p, hsa-miR-1274b, hsa-miR-15b, hsa-miR-624, hsa-miR-1908, hsa-miR-215, hsa-miR-423-3p, hsa-miR-625*, hsa-miR-342-3p, hsa-miR-183, hsa-miR-766, hsa-miR-29c, hsa-miR-335, hsa-miR-30e, hsa-miR-625, hsa-miR-1207-5p, hsa-miR-365, hsa-miR-125a-5p, hsa-miR-1227, hsa-miR-99a, hsa-let-7c, hsa-miR-629*, hsa-miR-151-3p, hsa-let-7b, hsa-miR-150, hsa-let-7e, hsa-miR-1180, hsa-let-7a, hsa-miR-125b, hsa-miR-422a, hsa-miR-513a-5p, hsa-miR-92b, hsa-miR-146a, hsa-let-7i, hsa-miR-628-3p, hsa-miR-193a-5p, hsa-let-7g, hsa-miR-362-3p, hsa-miR-140-3p, hsa-miR-339-5p, hsa-miR-1225-5p, hsa-miR-183*, hsa-miR-18a*, hsa-miR-342-5p, hsa-miR-297, hsa-miR-580, hsa-miR-548m, hsa-miR-483-3p, hsa-miR-302f, hsa-miR-30c-1*, hsa-miR-373, hsa-miR-193b*, hsa-miR-653, hsa-miR-409-3p, hsa-miR-26b*, hsa-miR-219-2-3p, hsa-let-7a*, hsa-miR-1270, hsa-miR-1284, hsa-miR-552, hsa-miR-587, hsa-miR-505, hsa-miR-939, hsa-miR-1321, hsa-miR-455-5p, hsa-miR-26a-1*, hsa-miR-499-5p, hsa-miR-658, hsa-miR-632, hsa-miR-186, hsa-miR-181d, hsa-miR-1, hsa-miR-1825, hsa-miR-369-3p, hsa-miR-140-5p, hsa-miR-548e, hsa-miR-1224-5p, hsa-miR-892a, hsa-miR-302a, hsa-miR-1261, hsa-miR-132*, hsa-miR-548i, hsa-miR-488, hsa-miR-302b, hsa-miR-520f, hsa-miR-154, hsa-miR-508-3p, hsa-miR-196b, hsa-miR-203, hsa-miR-135b, hsa-miR-507, hsa-miR-211, hsa-miR-302d, hsa-miR-1246, hsa-let-7e*, hsa-miR-135a, hsa-miR-539, hsa-miR-509-3p, hsa-miR-1279, hsa-miR-1290, hsa-miR-135a*, hsa-miR-769-3p, hsa-miR-576-3p, hsa-miR-520c-3p, hsa-miR-204, hsa-miR-190, hsa-miR-556-3p, hsa-miR-548b-5p, hsa-miR-548d-5p, hsa-miR-130b*, hsa-miR-548j, hsa-miR-302b*, hsa-miR-26a-2*, hsa-miR-1282, hsa-miR-1244, hsa-miR-206, hsa-miR-613, hsa-miR-382 b) Strong up-regulated miRNAs hsa-miR-491-5p, hsa-miR-128, hsa-miR-582-3p, hsa-miR-22, hsa-miR-15a, hsa-miR-28-3p, hsa-miR-425*, hsa-miR-25*, hsa-miR-152, hsa-miR-376c, hsa-miR-346, hsa-miR-181a-2*, hsa-miR-363, hsa-miR-200c*, hsa-miR-224, hsa-miR-30b, hsa-miR-1285, hsa-miR-1228*, hsa-miR-518c*, hsa-miR-149*, hsa-miR-205, hsa-miR-885-3p, hsa-miR-99b, hsa-miR-324-3p, hsa-miR-92b*, hsa-miR-1307, hsa-miR-1538, hsa-miR-589*, hsa-miR-936, hsa-miR-1275, hsa-miR-518f, hsa-miR-1909, hsa-miR-1231, hsa-miR-505*, hsa-miR-18b*, hsa-miR-379*, hsa-miR-424, hsa-miR-15b*, hsa-miR-483-5p, hsa-miR-27a, hsa-miR-551a, hsa-miR-770-5p, hsa-miR-1303, hsa-miR-34b*, hsa-miR-1306, hsa-miR-514, hsa-miR-1267, hsa-miR-671-3p, hsa-miR-194*, hsa-miR-30e*, hsa-miR-129*, hsa-miR-1269, hsa-miR-99a*

Figure 8    Down-regulated miRNAs a) Down-regulated miRNAs hsa-miR-545, hsa-miR-33b, hsa-miR-1251, hsa-miR-654-5p, hsa-miR-32, hsa-let-7g*, hsa-miR-1272, hsa-miR-330-3p, hsa-miR-217, hsa-miR-24-2*, hsa-miR-196a*, hsa-miR-650, hsa-miR-20a*, hsa-miR-515-5p, hsa-miR-1301, hsa-miR-522*, hsa-miR-33a, hsa-miR-588, hsa-miR-301b, hsa-miR-216b, hsa-miR-127-5p, hsa-miR-1912, hsa-miR-143*, hsa-miR-138-1*, hsa-miR-1324, hsa-miR-564, hsa-miR-431, hsa-miR-556-5p, hsa-miR-455-3p, hsa-miR-107, hsa-miR-497*, hsa-miR-188-3p, hsa-miR-452*, hsa-miR-646, hsa-miR-509-5p, hsa-miR-767-5p, hsa-miR-593*, hsa-miR-1266, hsa-let-7i*, hsa-miR-509-3-5p, hsa-miR-548p, hsa-miR-153, hsa-miR-603, hsa-miR-520c-5p, hsa-miR-497, hsa-miR-891a, hsa-miR-933, hsa-miR-139-5p, hsa-miR-9*, hsa-miR-874, hsa-miR-188-5p, hsa-miR-1226*, hsa-miR-214, hsa-miR-518d-5p, hsa-miR-192*, hsa-miR-621, hsa-miR-635, hsa-miR-1291, hsa-miR-489, hsa-miR-34c-3p, hsa-miR-298, hsa-miR-1184, hsa-miR-542-5p, hsa-miR-490-5p, hsa-miR-124*, hsa-miR-1471, hsa-miR-519b-5p, hsa-miR-1233, hsa-miR-454, hsa-miR-106a*, hsa-miR-103-as, hsa-miR-1208, hsa-miR-1202, hsa-miR-499-3p, hsa-miR-374a, hsa-miR-199b-3p, hsa-miR-377, hsa-miR-96, hsa-miR-574-5p, hsa-miR-124, hsa-miR-20b, hsa-miR-144*, hsa-miR-891b, hsa-miR-640, hsa-miR-34a*, hsa-miR-554, hsa-miR-604, hsa-miR-523, hsa-miR-367*, hsa-miR-566, hsa-miR-612, hsa-miR-518a-3p, hsa-miR-558, hsa-miR-221*, hsa-miR-596, hsa-miR-409-5p, hsa-miR-139-3p, hsa-miR-1305, hsa-miR-31*, hsa-miR-633, hsa-miR-934, hsa-miR-549, hsa-miR-512-5p, hsa-miR-595, hsa-miR-214*, hsa-miR-551b, hsa-miR-450b-5p, hsa-miR-518d-3p, hsa-miR-219-5p, hsa-miR-380*, hsa-miR-490-3p, hsa-miR-607, hsa-miR-570, hsa-miR-411*, hsa-miR-1283, hsa-miR-491-3p, hsa-miR-508-5p, hsa-miR-606, hsa-miR-218-1*, hsa-miR-525-3p, hsa-miR-597, hsa-miR-496, hsa-miR-671-5p, hsa-miR-521, hsa-miR-1253, hsa-miR-1247, hsa-miR-492, hsa-miR-495, hsa-miR-141*, hsa-miR-1278, hsa-miR-411, hsa-miR-146b-3p, hsa-miR-623, hsa-miR-802, hsa-miR-181c*, hsa-miR-200a*, hsa-miR-138-2*, hsa-miR-518e, hsa-miR-663b, hsa-miR-1256, hsa-miR-568, hsa-miR-519d, hsa-miR-146a*, hsa-miR-559, hsa-miR-137, hsa-miR-516b, hsa-miR-105, hsa-miR-561, hsa-miR-555, hsa-miR-513b, hsa-miR-1296, hsa-miR-450b-3p, hsa-miR-1298, hsa-miR-545*, hsa-miR-548c-3p, hsa-miR-1250, hsa-miR-1302, hsa-miR-1248, hsa-miR-19a*, hsa-miR-548a-3p, hsa-miR-381, hsa-miR-517*, hsa-miR-541, hsa-miR-1183, hsa-miR-518a-5p, hsa-miR-24-1*, hsa-miR-186*, hsa-miR-611, hsa-miR-410, hsa-miR-503, hsa-miR-518b, hsa-miR-627, hsa-miR-103, hsa-miR-548o, hsa-miR-518e*, hsa-miR-216a, hsa-miR-1288, hsa-miR-20a, hsa-miR-301a, hsa-miR-96*, hsa-miR-421, hsa-miR-106a, hsa-miR-17, hsa-miR-660, hsa-miR-93, hsa-miR-208b, hsa-miR-548d-3p, hsa-miR-222*, hsa-miR-487b, hsa-miR-34c-5p, hsa-miR-376b, hsa-miR-30d*, hsa-miR-1265, hsa-miR-654-3p, hsa-miR-760, hsa-miR-32*, hsa-miR-571, hsa-miR-548n, hsa-miR-147b, hsa-miR-1323, hsa-miR-513a-3p, hsa-miR-548a-5p, hsa-miR-544, hsa-miR-1276, hsa-miR-133a, hsa-miR-655, hsa-miR-517a, hsa-miR-23a*, hsa-miR-219-1-3p b) Strong down-regulated miRNAs hsa-miR-545, hsa-miR-33b, hsa-miR-1251, hsa-miR-654-5p, hsa-miR-32, hsa-let-7g*, hsa-miR-1272, hsa-miR-330-3p, hsa-miR-217, hsa-miR-24-2*, hsa-miR-196a*, hsa-miR-650, hsa-miR-20a*, hsa-miR-515-5p, hsa-miR-1301, hsa-miR-522*, hsa-miR-33a, hsa-miR-588, hsa-miR-301b, hsa-miR-216b, hsa-miR-127-5p, hsa-miR-1912, hsa-miR-143*, hsa-miR-138-1*, hsa-miR-1324, hsa-miR-564, hsa-miR-431, hsa-miR-556-5p, hsa-miR-455-3p, hsa-miR-107, hsa-miR-497*, hsa-miR-188-3p, hsa-miR-452*, hsa-miR-646, hsa-miR-509-5p, hsa-miR-767-5p, hsa-miR-593*, hsa-miR-1266, hsa-let-7i*, hsa-miR-509-3-5p, hsa-miR-548p, hsa-miR-153, hsa-miR-603, hsa-miR-520c-5p, hsa-miR-497, hsa-miR-891a, hsa-miR-933, hsa-miR-139-5p, hsa-miR-9*, hsa-miR-874, hsa-miR-188-5p, hsa-miR-1226*, hsa-miR-214, hsa-miR-518d-5p, hsa-miR-192*, hsa-miR-621, hsa-miR-635, hsa-miR-1291, hsa-miR-489, hsa-miR-34c-3p, hsa-miR-298, hsa-miR-1184, hsa-miR-542-5p, hsa-miR-490-5p, hsa-miR-124*, hsa-miR-1471, hsa-miR-519b-5p, hsa-miR-1233, hsa-miR-454, hsa-miR-106a*, hsa-miR-103-as, hsa-miR-1208, hsa-miR-1202, hsa-miR-499-3p, hsa-miR-374a, hsa-miR-199b-3p, hsa-miR-377, hsa-miR-96, hsa-miR-574-5p, hsa-miR-124, hsa-miR-20b, hsa-miR-144*, hsa-miR-891b, hsa-miR-640, hsa-miR-34a*, hsa-miR-554, hsa-miR-604, hsa-miR-523, hsa-miR-367*, hsa-miR-566, hsa-miR-612, hsa-miR-518a-3p, hsa-miR-558, hsa-miR-221*, hsa-miR-596, hsa-miR-409-5p, hsa-miR-139-3p, hsa-miR-1305, hsa-miR-31*, hsa-miR-633, hsa-miR-934, hsa-miR-549, hsa-miR-512-5p, hsa-miR-595, hsa-miR-214*, hsa-miR-551b, hsa-miR-450b-5p, hsa-miR-518d-3p, hsa-miR-219-5p, hsa-miR-380*, hsa-miR-490-3p, hsa-miR-607, hsa-miR-570, hsa-miR- Figure 8 (Cont.)
411*, hsa-miR-1283, hsa-miR-491-3p, hsa-miR-508-5p, hsa-miR-606, hsa-miR-218-1*, hsa-miR-525-3p, hsa-miR-597, hsa-miR-496, hsa-miR-671-5p, hsa-miR-521, hsa-miR-1253, hsa-miR-1247, hsa-miR-492, hsa-miR-495, hsa-miR-141*, hsa-miR-1278, hsa-miR-411, hsa-miR-146b-3p, hsa-miR-623, hsa-miR-802, hsa-miR-181c*, hsa-miR-200a*, hsa-miR-138-2*, hsa-miR-518e, hsa-miR-663b, hsa-miR-1256, hsa-miR-568, hsa-miR-519d, hsa-miR-146a*, hsa-miR-559, hsa-miR-137

Figure 9

| Signature | SEQ ID-NO | miRNA | Acc | Spec | Sens | Bal. Acc |
|---|---|---|---|---|---|---|
| SNRCC-695 | 10, 81 | hsa-let-7d*, hsa-miR-192 | 83.1% | 82.2% | 87.7% | 84.9% |
| SNRCC-696 | 10, 82 | hsa-let-7d*, hsa-miR-664 | 87.5% | 87.0% | 90.4% | 88.7% |
| SNRCC-697 | 10, 23 | hsa-let-7d*, hsa-miR-654-5p | 91.8% | 91.5% | 93.5% | 92.5% |
| SNRCC-698 | 10, 16 | hsa-let-7d*, hsa-miR-891b | 93.6% | 93.4% | 94.6% | 94.0% |
| SNRCC-699 | 10, 52 | hsa-let-7d*, hsa-miR-604 | 92.5% | 92.7% | 91.9% | 92.3% |
| SNRCC-700 | 10, 46 | hsa-let-7d*, hsa-miR-302f | 85.1% | 85.5% | 83.1% | 84.3% |
| SNRCC-701 | 10, 85 | hsa-let-7d*, hsa-miR-483-3p | 91.1% | 91.4% | 90.0% | 90.7% |
| SNRCC-702 | 10, 22 | hsa-let-7d*, hsa-miR-934 | 88.7% | 88.0% | 92.7% | 90.3% |
| SNRCC-703 | 11, 18 | hsa-miR-19b, hsa-miR-1260 | 78.5% | 75.9% | 91.5% | 83.7% |
| SNRCC-704 | 11, 81 | hsa-miR-19b, hsa-miR-192 | 80.5% | 81.7% | 74.2% | 78.0% |
| SNRCC-705 | 11, 82 | hsa-miR-19b, hsa-miR-664 | 75.3% | 71.7% | 93.5% | 82.6% |
| SNRCC-706 | 11, 5 | hsa-miR-19b, hsa-miR-1251 | 84.5% | 84.8% | 83.1% | 83.9% |
| SNRCC-707 | 11, 23 | hsa-miR-19b, hsa-miR-654-5p | 92.7% | 92.8% | 92.3% | 92.6% |
| SNRCC-708 | 11, 4 | hsa-miR-19b, hsa-miR-640 | 89.2% | 91.7% | 76.2% | 83.9% |
| SNRCC-709 | 11, 3 | hsa-miR-19b, hsa-miR-523 | 83.5% | 83.3% | 84.6% | 83.9% |
| SNRCC-710 | 11, 28 | hsa-miR-19b, hsa-miR-548m | 87.7% | 88.3% | 84.2% | 86.3% |
| SNRCC-711 | 11, 19 | hsa-miR-19b, hsa-miR-221* | 84.1% | 83.9% | 85.0% | 84.5% |
| SNRCC-712 | 11, 52 | hsa-miR-19b, hsa-miR-604 | 93.7% | 94.5% | 89.6% | 92.1% |
| SNRCC-713 | 11, 85 | hsa-miR-19b, hsa-miR-483-3p | 80.9% | 79.2% | 89.6% | 84.4% |
| SNRCC-714 | 11, 39 | hsa-miR-19b, hsa-miR-373 | 83.7% | 84.1% | 81.9% | 83.0% |
| SNRCC-715 | 11, 22 | hsa-miR-19b, hsa-miR-934 | 87.7% | 88.3% | 85.0% | 86.6% |
| SNRCC-716 | 18, 81 | hsa-miR-1260, hsa-miR-192 | 80.2% | 79.5% | 83.5% | 81.5% |
| SNRCC-717 | 18, 82 | hsa-miR-1260, hsa-miR-664 | 76.7% | 72.3% | 98.8% | 85.6% |
| SNRCC-718 | 18, 5 | hsa-miR-1260, hsa-miR-1251 | 82.6% | 82.3% | 84.2% | 83.3% |
| SNRCC-719 | 18, 23 | hsa-miR-1260, hsa-miR-654-5p | 89.6% | 89.8% | 88.1% | 89.0% |
| SNRCC-720 | 18, 4 | hsa-miR-1260, hsa-miR-640 | 91.7% | 92.5% | 87.7% | 90.1% |
| SNRCC-721 | 18, 3 | hsa-miR-1260, hsa-miR-523 | 85.1% | 86.5% | 78.1% | 82.3% |
| SNRCC-722 | 18, 24 | hsa-miR-1260, hsa-miR-554 | 80.8% | 80.2% | 83.8% | 82.0% |
| SNRCC-723 | 18, 28 | hsa-miR-1260, hsa-miR-548m | 90.0% | 91.0% | 85.0% | 88.0% |
| SNRCC-724 | 18, 12 | hsa-miR-1260, hsa-miR-518a-3p | 85.6% | 85.2% | 87.3% | 86.3% |
| SNRCC-725 | 18, 52 | hsa-miR-1260, hsa-miR-604 | 91.0% | 91.0% | 91.2% | 91.1% |
| SNRCC-726 | 18, 46 | hsa-miR-1260, hsa-miR-302f | 87.8% | 89.5% | 78.8% | 84.2% |
| SNRCC-727 | 18, 85 | hsa-miR-1260, hsa-miR-483-3p | 86.6% | 85.4% | 93.1% | 89.2% |
| SNRCC-728 | 18, 39 | hsa-miR-1260, hsa-miR-373 | 83.0% | 83.0% | 83.1% | 83.1% |
| SNRCC-729 | 18, 22 | hsa-miR-1260, hsa-miR-934 | 85.4% | 85.7% | 84.2% | 85.0% |

Figure 9 (cont.)

| | | | | | | |
|---|---|---|---|---|---|---|
| SNRCC-730 | 8, 81 | hsa-miR-34a*, hsa-miR-192 | 93.7% | 95.5% | 85.0% | 90.2% |
| SNRCC-731 | 8, 82 | hsa-miR-34a*, hsa-miR-664 | 94.2% | 95.2% | 89.2% | 92.2% |
| SNRCC-732 | 8, 23 | hsa-miR-34a*, hsa-miR-654-5p | 91.1% | 91.4% | 89.6% | 90.5% |
| SNRCC-733 | 8, 24 | hsa-miR-34a*, hsa-miR-554 | 91.6% | 92.7% | 86.2% | 89.4% |
| SNRCC-734 | 8, 28 | hsa-miR-34a*, hsa-miR-548m | 94.1% | 94.5% | 91.9% | 93.2% |
| SNRCC-735 | 8, 52 | hsa-miR-34a*, hsa-miR-604 | 94.4% | 94.8% | 92.3% | 93.6% |
| SNRCC-736 | 8, 46 | hsa-miR-34a*, hsa-miR-302f | 92.3% | 92.3% | 92.3% | 92.3% |
| SNRCC-737 | 8, 85 | hsa-miR-34a*, hsa-miR-483-3p | 93.5% | 94.1% | 90.4% | 92.2% |
| SNRCC-738 | 8, 39 | hsa-miR-34a*, hsa-miR-373 | 93.7% | 94.0% | 91.9% | 93.0% |
| SNRCC-739 | 8, 22 | hsa-miR-34a*, hsa-miR-934 | 91.2% | 92.3% | 85.8% | 89.0% |
| SNRCC-740 | 81, 82 | hsa-miR-192, hsa-miR-664 | 76.8% | 77.4% | 73.8% | 75.6% |
| SNRCC-741 | 81, 5 | hsa-miR-192, hsa-miR-1251 | 83.2% | 83.9% | 79.2% | 81.6% |
| SNRCC-742 | 81, 23 | hsa-miR-192, hsa-miR-654-5p | 85.4% | 85.2% | 86.5% | 85.8% |
| SNRCC-743 | 81, 4 | hsa-miR-192, hsa-miR-640 | 90.0% | 92.5% | 77.3% | 84.9% |
| SNRCC-744 | 81, 16 | hsa-miR-192, hsa-miR-891b | 89.9% | 89.4% | 92.3% | 90.9% |
| SNRCC-745 | 81, 3 | hsa-miR-192, hsa-miR-523 | 78.9% | 80.5% | 70.4% | 75.5% |
| SNRCC-746 | 81, 24 | hsa-miR-192, hsa-miR-554 | 91.7% | 94.0% | 80.0% | 87.0% |
| SNRCC-747 | 81, 28 | hsa-miR-192, hsa-miR-548m | 85.0% | 86.6% | 76.9% | 81.8% |
| SNRCC-748 | 81, 12 | hsa-miR-192, hsa-miR-518a-3p | 84.6% | 84.8% | 83.5% | 84.2% |
| SNRCC-749 | 81, 19 | hsa-miR-192, hsa-miR-221* | 81.1% | 80.0% | 86.9% | 83.5% |
| SNRCC-750 | 81, 52 | hsa-miR-192, hsa-miR-604 | 94.9% | 95.8% | 90.8% | 93.3% |
| SNRCC-751 | 81, 46 | hsa-miR-192, hsa-miR-302f | 77.9% | 79.5% | 70.0% | 74.7% |
| SNRCC-752 | 81, 85 | hsa-miR-192, hsa-miR-483-3p | 81.7% | 80.7% | 86.9% | 83.8% |
| SNRCC-753 | 81, 39 | hsa-miR-192, hsa-miR-373 | 87.1% | 90.6% | 69.2% | 79.9% |
| SNRCC-754 | 81, 22 | hsa-miR-192, hsa-miR-934 | 84.9% | 86.2% | 78.5% | 82.3% |
| SNRCC-755 | 82, 5 | hsa-miR-664, hsa-miR-1251 | 86.8% | 86.2% | 89.6% | 87.9% |
| SNRCC-756 | 82, 23 | hsa-miR-664, hsa-miR-654-5p | 88.7% | 87.0% | 97.3% | 92.2% |
| SNRCC-757 | 82, 4 | hsa-miR-664, hsa-miR-640 | 91.8% | 92.6% | 88.1% | 90.3% |
| SNRCC-758 | 82, 16 | hsa-miR-664, hsa-miR-891b | 90.5% | 91.7% | 84.6% | 88.1% |
| SNRCC-759 | 82, 3 | hsa-miR-664, hsa-miR-523 | 85.5% | 85.5% | 85.4% | 85.5% |
| SNRCC-760 | 82, 24 | hsa-miR-664, hsa-miR-554 | 82.5% | 83.5% | 77.7% | 80.6% |
| SNRCC-761 | 82, 28 | hsa-miR-664, hsa-miR-548m | 90.3% | 90.7% | 88.1% | 89.4% |
| SNRCC-762 | 82, 12 | hsa-miR-664, hsa-miR-518a-3p | 88.3% | 88.0% | 89.6% | 88.8% |
| SNRCC-763 | 82, 19 | hsa-miR-664, hsa-miR-221* | 81.3% | 80.4% | 85.8% | 83.1% |
| SNRCC-764 | 82, 52 | hsa-miR-664, hsa-miR-604 | 93.5% | 93.9% | 91.9% | 92.9% |
| SNRCC-765 | 82, 46 | hsa-miR-664, hsa-miR-302f | 84.7% | 85.2% | 82.3% | 83.7% |
| SNRCC-766 | 82, 85 | hsa-miR-664, hsa-miR-483-3p | 86.1% | 85.5% | 89.6% | 87.5% |
| SNRCC-767 | 82, 39 | hsa-miR-664, hsa-miR-373 | 85.2% | 86.1% | 80.4% | 83.3% |
| SNRCC-768 | 82, 22 | hsa-miR-664, hsa-miR-934 | 81.5% | 83.3% | 72.7% | 78.0% |
| SNRCC-769 | 5, 23 | hsa-miR-1251, hsa-miR-654-5p | 91.0% | 92.3% | 84.6% | 88.4% |
| SNRCC-770 | 5, 16 | hsa-miR-1251, hsa-miR-891b | 94.1% | 93.8% | 95.4% | 94.6% |
| SNRCC-771 | 5, 24 | hsa-miR-1251, hsa-miR-554 | 88.0% | 88.4% | 85.8% | 87.1% |
| SNRCC-772 | 5, 28 | hsa-miR-1251, hsa-miR-548m | 87.5% | 87.0% | 90.4% | 88.7% |
| SNRCC-773 | 5, 12 | hsa-miR-1251, hsa-miR-518a-3p | 85.3% | 85.8% | 82.7% | 84.2% |
| SNRCC-774 | 5, 19 | hsa-miR-1251, hsa-miR-221* | 86.2% | 86.4% | 85.0% | 85.7% |
| SNRCC-775 | 5, 46 | hsa-miR-1251, hsa-miR-302f | 85.9% | 87.6% | 77.3% | 82.4% |

Figure 9 (cont.)

| | | | | | | |
|---|---|---|---|---|---|---|
| SNRCC-776 | 5, 85 | hsa-miR-1251, hsa-miR-483-3p | 85.0% | 85.8% | 81.2% | 83.5% |
| SNRCC-777 | 5, 22 | hsa-miR-1251, hsa-miR-934 | 82.7% | 82.5% | 83.5% | 83.0% |
| SNRCC-778 | 23, 4 | hsa-miR-654-5p, hsa-miR-640 | 85.8% | 87.2% | 78.5% | 82.8% |
| SNRCC-779 | 23, 16 | hsa-miR-654-5p, hsa-miR-891b | 94.9% | 93.9% | 100.0% | 97.0% |
| SNRCC-780 | 23, 3 | hsa-miR-654-5p, hsa-miR-523 | 87.8% | 87.9% | 87.7% | 87.8% |
| SNRCC-781 | 23, 28 | hsa-miR-654-5p, hsa-miR-548m | 87.1% | 87.6% | 84.6% | 86.1% |
| SNRCC-782 | 23, 12 | hsa-miR-654-5p, hsa-miR-518a-3p | 87.4% | 88.6% | 81.2% | 84.9% |
| SNRCC-783 | 23, 19 | hsa-miR-654-5p, hsa-miR-221* | 87.8% | 89.9% | 76.9% | 83.4% |
| SNRCC-784 | 23, 52 | hsa-miR-654-5p, hsa-miR-604 | 90.6% | 91.5% | 86.2% | 88.8% |
| SNRCC-785 | 23, 46 | hsa-miR-654-5p, hsa-miR-302f | 87.7% | 87.7% | 88.1% | 87.9% |
| SNRCC-786 | 23, 85 | hsa-miR-654-5p, hsa-miR-483-3p | 81.7% | 80.2% | 89.2% | 84.7% |
| SNRCC-787 | 23, 39 | hsa-miR-654-5p, hsa-miR-373 | 85.3% | 84.5% | 88.8% | 86.7% |
| SNRCC-788 | 4, 16 | hsa-miR-640, hsa-miR-891b | 93.1% | 93.8% | 89.6% | 91.7% |
| SNRCC-789 | 4, 24 | hsa-miR-640, hsa-miR-554 | 92.8% | 93.9% | 87.7% | 90.8% |
| SNRCC-790 | 4, 28 | hsa-miR-640, hsa-miR-548m | 91.1% | 91.4% | 90.0% | 90.7% |
| SNRCC-791 | 4, 12 | hsa-miR-640, hsa-miR-518a-3p | 92.1% | 93.7% | 83.8% | 88.8% |
| SNRCC-792 | 4, 52 | hsa-miR-640, hsa-miR-604 | 90.1% | 92.1% | 80.0% | 86.1% |
| SNRCC-793 | 4, 46 | hsa-miR-640, hsa-miR-302f | 86.2% | 88.5% | 74.6% | 81.6% |
| SNRCC-794 | 4, 85 | hsa-miR-640, hsa-miR-483-3p | 86.9% | 87.6% | 83.5% | 85.5% |
| SNRCC-795 | 4, 22 | hsa-miR-640, hsa-miR-934 | 92.3% | 93.1% | 88.5% | 90.8% |
| SNRCC-796 | 16, 3 | hsa-miR-891b, hsa-miR-523 | 90.1% | 88.9% | 96.2% | 92.5% |
| SNRCC-797 | 16, 24 | hsa-miR-891b, hsa-miR-554 | 94.6% | 95.2% | 91.2% | 93.2% |
| SNRCC-798 | 16, 28 | hsa-miR-891b, hsa-miR-548m | 88.7% | 89.2% | 86.2% | 87.7% |
| SNRCC-799 | 16, 12 | hsa-miR-891b, hsa-miR-518a-3p | 88.9% | 88.2% | 92.3% | 90.2% |
| SNRCC-800 | 16, 52 | hsa-miR-891b, hsa-miR-604 | 95.3% | 96.1% | 91.5% | 93.8% |
| SNRCC-801 | 16, 46 | hsa-miR-891b, hsa-miR-302f | 94.8% | 95.3% | 92.3% | 93.8% |
| SNRCC-802 | 16, 85 | hsa-miR-891b, hsa-miR-483-3p | 90.4% | 90.4% | 90.4% | 90.4% |
| SNRCC-803 | 16, 39 | hsa-miR-891b, hsa-miR-373 | 93.9% | 93.8% | 94.6% | 94.2% |
| SNRCC-804 | 16, 22 | hsa-miR-891b, hsa-miR-934 | 86.5% | 86.4% | 86.5% | 86.5% |
| SNRCC-805 | 3, 24 | hsa-miR-523, hsa-miR-554 | 86.6% | 86.8% | 85.4% | 86.1% |
| SNRCC-806 | 3, 28 | hsa-miR-523, hsa-miR-548m | 86.4% | 86.1% | 88.1% | 87.1% |
| SNRCC-807 | 3, 12 | hsa-miR-523, hsa-miR-518a-3p | 80.6% | 81.6% | 75.8% | 78.7% |
| SNRCC-808 | 3, 19 | hsa-miR-523, hsa-miR-221* | 83.8% | 82.0% | 93.1% | 87.5% |
| SNRCC-809 | 3, 46 | hsa-miR-523, hsa-miR-302f | 81.8% | 82.3% | 79.2% | 80.8% |
| SNRCC-810 | 3, 85 | hsa-miR-523, hsa-miR-483-3p | 80.6% | 78.2% | 92.7% | 85.4% |
| SNRCC-811 | 3, 22 | hsa-miR-523, hsa-miR-934 | 88.0% | 87.7% | 90.0% | 88.8% |
| SNRCC-812 | 24, 28 | hsa-miR-554, hsa-miR-548m | 87.6% | 89.3% | 78.8% | 84.1% |
| SNRCC-813 | 24, 12 | hsa-miR-554, hsa-miR-518a-3p | 86.1% | 85.8% | 87.7% | 86.8% |
| SNRCC-814 | 24, 19 | hsa-miR-554, hsa-miR-221* | 86.9% | 88.6% | 78.5% | 83.5% |
| SNRCC-815 | 24, 52 | hsa-miR-554, hsa-miR-604 | 91.6% | 93.0% | 84.6% | 88.8% |
| SNRCC-816 | 24, 46 | hsa-miR-554, hsa-miR-302f | 84.4% | 84.7% | 83.1% | 83.9% |
| SNRCC-817 | 24, 85 | hsa-miR-554, hsa-miR-483-3p | 82.9% | 83.8% | 78.5% | 81.1% |
| SNRCC-818 | 24, 39 | hsa-miR-554, hsa-miR-373 | 83.4% | 85.1% | 75.0% | 80.0% |
| SNRCC-819 | 28, 12 | hsa-miR-548m, hsa-miR-518a-3p | 89.6% | 90.3% | 85.8% | 88.0% |
| SNRCC-820 | 28, 19 | hsa-miR-548m, hsa-miR-221* | 86.4% | 87.3% | 81.9% | 84.6% |
| SNRCC-821 | 28, 52 | hsa-miR-548m, hsa-miR-604 | 91.1% | 92.4% | 84.2% | 88.3% |

Figure 9 (cont.)

| | | | | | | |
|---|---|---|---|---|---|---|
| SNRCC-822 | 28, 46 | hsa-miR-548m, hsa-miR-302f | 91.5% | 94.2% | 77.7% | 86.0% |
| SNRCC-823 | 28, 85 | hsa-miR-548m, hsa-miR-483-3p | 86.1% | 85.8% | 87.7% | 86.7% |
| SNRCC-824 | 28, 39 | hsa-miR-548m, hsa-miR-373 | 77.8% | 77.5% | 79.2% | 78.4% |
| SNRCC-825 | 28, 22 | hsa-miR-548m, hsa-miR-934 | 86.7% | 86.1% | 89.6% | 87.9% |
| SNRCC-826 | 12, 19 | hsa-miR-518a-3p, hsa-miR-221* | 79.4% | 78.3% | 84.6% | 81.5% |
| SNRCC-827 | 12, 52 | hsa-miR-518a-3p, hsa-miR-604 | 87.8% | 87.6% | 88.8% | 88.2% |
| SNRCC-828 | 12, 46 | hsa-miR-518a-3p, hsa-miR-302f | 82.5% | 83.2% | 78.8% | 81.0% |
| SNRCC-829 | 12, 85 | hsa-miR-518a-3p, hsa-miR-483-3p | 88.1% | 88.9% | 84.2% | 86.5% |
| SNRCC-830 | 12, 39 | hsa-miR-518a-3p, hsa-miR-373 | 84.7% | 84.5% | 85.8% | 85.2% |
| SNRCC-831 | 19, 52 | hsa-miR-221*, hsa-miR-604 | 91.2% | 93.5% | 79.6% | 86.6% |
| SNRCC-832 | 19, 46 | hsa-miR-221*, hsa-miR-302f | 87.8% | 86.4% | 95.0% | 90.7% |
| SNRCC-833 | 19, 85 | hsa-miR-221*, hsa-miR-483-3p | 83.5% | 83.0% | 86.2% | 84.6% |
| SNRCC-834 | 19, 39 | hsa-miR-221*, hsa-miR-373 | 80.9% | 83.3% | 68.8% | 76.1% |
| SNRCC-835 | 52, 46 | hsa-miR-604, hsa-miR-302f | 89.7% | 90.7% | 85.0% | 87.8% |
| SNRCC-836 | 52, 85 | hsa-miR-604, hsa-miR-483-3p | 90.1% | 91.5% | 82.7% | 87.1% |
| SNRCC-837 | 52, 39 | hsa-miR-604, hsa-miR-373 | 91.2% | 93.7% | 78.5% | 86.1% |
| SNRCC-838 | 52, 22 | hsa-miR-604, hsa-miR-934 | 90.1% | 91.3% | 83.8% | 87.6% |
| SNRCC-839 | 46, 85 | hsa-miR-302f, hsa-miR-483-3p | 77.5% | 78.5% | 72.7% | 75.6% |
| SNRCC-840 | 46, 39 | hsa-miR-302f, hsa-miR-373 | 79.0% | 80.5% | 71.5% | 76.0% |
| SNRCC-841 | 46, 22 | hsa-miR-302f, hsa-miR-934 | 87.8% | 86.9% | 92.3% | 89.6% |
| SNRCC-842 | 85, 39 | hsa-miR-483-3p, hsa-miR-373 | 74.2% | 71.8% | 86.5% | 79.2% |
| SNRCC-843 | 85, 22 | hsa-miR-483-3p, hsa-miR-934 | 77.0% | 75.6% | 84.2% | 79.9% |
| SNRCC-844 | 39, 22 | hsa-miR-373, hsa-miR-934 | 81.1% | 80.2% | 85.8% | 83.0% |

COMPLEX SETS OF MIRNAS AS NON-INVASIVE BIOMARKERS FOR KIDNEY CANCER

This application is a 35 U.S.C. 371 National Phase Entry Application of the International Application No. PCT/EP2012/065277, filed on Mar. 8, 20121, which claims priority to European Patent Application EP11178149.8, filed on 19 Aug. 2011, the disclosures of which are incorporated herein by reference in their entirety.

TECHNICAL FIELD OF THE INVENTION

The present invention relates to a method for diagnosing and/or prognosing of kidney cancer based on the determination of expression profiles of sets of miRNAs representative for kidney cancer compared to a reference. Furthermore, the present invention relates to sets of polynucleotides and/or primer pairs for detecting sets of miRNAs for diagnosing and/or prognosing of kidney cancer in a biological sample from a subject. Further, the present invention relates to means for diagnosing and/or prognosing of kidney cancer comprising said sets of primer pairs and/or polynucleotides. In addition, the present invention relates to a kit for diagnosing and/or prognosing of kidney cancer comprising means for determining expression profiles of sets of miRNAs representative for kidney cancer and at least one reference. Further, the present invention relates to use of polynucleotides and/or primer pairs for diagnosing and/or prognosing of kidney cancer in a biological samples of a subject.

BACKGROUND OF THE INVENTION

Today, biomarkers play a key role in early diagnosis, risk stratification, and therapeutic management of various diseases. While progress in biomarker research has accelerated over the last 5 years, the clinical translation of disease biomarkers as endpoints in disease management and as the foundation for diagnostic products still poses a challenge.

MicroRNAs (miRNAs) are a new class of biomarkers. They represent a group of small noncoding RNAs that regulate gene expression at the posttranslational level by degrading or blocking translation of messenger RNA (mRNA) targets. MiRNAs are important players when it comes to regulate cellular functions and in several diseases, including cancer.

So far, miRNAs have been extensively studied in tissue material. It has been found that miRNAs are expressed in a highly tissue-specific manner. Disease-specific expression of miRNAs have been reported in many human cancers employing primarily tissue material as the miRNA source. In this context miRNAs expression profiles were found to be useful in identifying the tissue of origin for cancers of unknown primary origin.

Since recently it is known that miRNAs are not only present in tissues but also in other body fluid samples, including human blood. Nevertheless, the mechanism why miRNAs are found in body fluids, especially in blood, or their function in these body fluids is not understood yet.

Various miRNA biomarkers found in tissue material have been proposed to be correlated with certain diseases, e.g. cancer. However, there is still a need for novel miRNAs as biomarkers for the detection and/or prediction of these and other types of diseases. Especially desirable are non-invasive biomarkers, that allow for quick, easy and cost-effective diagnosis/prognosis which cause only minimal stress for the patient eliminating the need for surgical intervention Particularly, the potential role of miRNAs as non-invasive biomarkers for the diagnosis and/or prognosis of kidney cancer has not been systematically evaluated yet. In addition, many of the miRNA biomarkers presently available for diagnosing and/or prognosing of diseases have shortcomings such as reduced sensitivity, not sufficient specificity or do not allow timely diagnosis or represent invasive biomarkers. Accordingly, there is still a need for novel and efficient miRNAs or sets of miRNAs as markers, effective methods and kits for the non-invasive diagnosis and/or prognosis of diseases such as kidney cancer.

The inventors of the present invention assessed for the first time the expression of miRNAs on a whole-genome level in subjects with kidney cancer as non-invasive biomarkers from body fluids, preferably in blood. They surprisingly found that miRNAs are significantly dysregulated in blood of kidney cancer subjects in comparison to healthy controls and thus, miRNAs are appropriated non-invasive biomarkers for diagnosing and/or prognosing of kidney cancer. This finding is surprising, since there is nearly no overlap of the miRNA biomarkers found in blood and the miRNA biomarkers found in tissue material representing the origin of the disease. The inventors of the present invention surprisingly found miRNA biomarkers in body fluids, especially in blood, that have not been found to be correlated to kidney cancer when tissues material was used for this kind of analysis. Therefore, the inventors of the invention identified for the first time miRNAs as non-invasive surrogate biomarkers for diagnosis and/or prognosis of kidney cancer. The inventors of the present invention identified single miRNAs which predict kidney cancer with high specificity, sensitivity and accuracy. The inventors of the present invention also pursued a multiple biomarker strategy, thus implementing sets of miRNA biomarkers for diagnosing and/or prognosing of kidney cancer leading to added specificity, sensitivity, accuracy and predictive power, thereby circumventing limitations of single biomarker. In detail, by using a machine learning algorithms, they identified unique sets of miRNAs (miRNA signatures) that allow for non-invasive diagnosis of kidney cancer with even higher power, indicating that sets of miRNAs (miRNA signatures) derived from a body fluid sample, such as blood from a subject (e.g. human) can be used as novel non-invasive biomarkers.

SUMMARY OF THE INVENTION

In a first aspect, the invention provides a method for diagnosing and/or prognosing of kidney cancer comprising the steps of:
(i) determining an expression profile of a set comprising at least two miRNAs representative for kidney cancer in a body fluid sample from a subject, and
(ii) comparing said expression profile to a reference, wherein the comparison of said expression profile to said reference allows for the diagnosis and/or prognosis of kidney cancer, In a second aspect, the invention provides a set comprising polynucleotides for detecting a set comprising at least two miRNAs for diagnosing and/or prognosing of kidney cancer in a body fluid sample from a subject.

In a third aspect, the invention provides a use of a set of polynucleotides according to the second aspect of the invention for diagnosing and/or prognosing kidney cancer in a subject In a fourth aspect, the invention provides a set of primer pairs for determining the expression level of a set of miRNAs in a body fluid sample of a subject suffering or suspected of suffering from kidney cancer.

In a fifth aspect, the invention provides a use of set of primer pairs according to the fourth aspect of the invention for diagnosing and/or prognosing kidney cancer in a subject In a sixth aspect, the invention provides means for diagnosing and/or prognosing of kidney cancer in a body fluid sample of a subject comprising:
(i) a set of at least two polynucleotides according to the second aspect of the invention or
(ii) a set of primer pairs according the fourth aspect of the invention.

In a seventh aspect, the invention provides a kit for diagnosing and/or prognosing of kidney cancer comprising
(i) means for determining an expression profile of a set comprising at least two miRNAs representative for kidney cancer in a body fluid sample from a subject, and
(ii) at least one reference.

In an eighth aspect, the invention provides a set of miRNAs in a body fluid sample isolated from a subject for diagnosing and/or prognosing of kidney cancer.

In a ninth aspect, the invention provides a use of a set of miRNAs according to the eighth aspect of the invention for diagnosing and/or prognosing of kidney cancer in a subject, This summary of the invention does not necessarily describe all features of the invention.

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

To practice the present invention, unless otherwise indicated, conventional methods of chemistry, biochemistry, and recombinant DNA techniques are employed which are explained in the literature in the field (cf., e.g., *Molecular Cloning: A Laboratory Manual, 2$^{nd}$ Edition*, J. Sambrook et al. eds., Cold Spring Harbor Laboratory Press, Cold Spring Harbor 1989).

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and in the appended claims, the singular forms "a", "an", and "the" include plural referents, unless the content clearly dictates otherwise. For example, the term "a test compound" also includes "test compounds".

The terms "microRNA" or "miRNA" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences (e.g. biotin stretches). The miRNAs regulate gene expression and are encoded by genes from whose DNA they are transcribed but miRNAs are not translated into protein (i.e. miRNAs are noncoding RNAs). The genes encoding miRNAs are longer than the processed mature miRNA molecules. The miRNAs are first transcribed as primary transcripts or pri-miRNAs with a cap and poly-A tail and processed to short, 70 nucleotide stem-loop structures known as pre-miRNAs in the cell nucleus. This processing is performed in animals by a protein complex known as the Microprocessor complex consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC. This strand is known as the guide strand and is selected by the argonaute protein, the catalytically active RNase in the RISC, on the basis of the stability of the 5' end. The remaining strand, known as the miRNA*, anti-guide (anti-strand), or passenger strand, is degraded as a RISC substrate. Therefore, the miRNA*s are derived from the same hairpin structure like the "normal" miRNAs. So if the "normal" miRNA is then later called the "mature miRNA" or "guide strand", the miRNA* is the "anti-guide strand" or "passenger strand".

The terms "microRNA*" or "miRNA*" refer to single-stranded RNA molecules of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally labels and/or elongated sequences (e.g. biotin stretches). The "miRNA*s", also known as the "anti-guide strands" or "passenger strands", are mostly complementary to the "mature miRNAs" or "guide strands", but have usually single-stranded overhangs on each end. There are usually one or more mispairs and there are sometimes extra or missing bases causing single-stranded "bubbles". The miRNA*s are likely to act in a regulatory fashion as the miRNAs (see also above). In the context of the present invention, the terms "miRNA" and "miRNA*" are interchangeable used. The present invention encompasses (target) miRNAs which are dysregulated in biological samples such as blood or tissue of kidney cancer patients in comparison to healthy controls. Said (target) miRNAs are preferably selected from the group consisting of SEQ ID NO: 1 to 357 or SEQ ID NO: 1 to 465.

The term "miRBase" refers to a well established repository of validated miRNAs. The miRBase (www.mirbase.org) is a searchable database of published miRNA sequences and annotation. Each entry in the miRBase Sequence database represents a predicted hairpin portion of a miRNA transcript (termed mir in the database), with information on the location and sequence of the mature miRNA sequence (termed miR). Both hairpin and mature sequences are available for searching and browsing, and entries can also be retrieved by name, keyword, references and annotation. All sequence and annotation data are also available for download.

As used herein, the term "nucleotides" refers to structural components, or building blocks, of DNA and RNA. Nucleotides consist of a base (one of four chemicals: adenine, thymine, guanine, and cytosine) plus a molecule of sugar and one of phosphoric acid. The term "nucleosides" refers to glycosylamine consisting of a nucleobase (often referred to simply base) bound to a ribose or deoxyribose sugar. Examples of nucleosides include cytidine, uridine, adenosine, guanosine, thymidine and inosine. Nucleosides can be phosphorylated by specific kinases in the cell on the sugar's primary alcohol group (—CH2-OH), producing nucleotides, which are the molecular building blocks of DNA and RNA.

The term "polynucleotide", as used herein, means a molecule of at least 10 nucleotides and of not more than 35 nucleotides covalently linked together. Preferably, the polynucleotides of the present invention are molecules of 10 to 33 nucleotides or 15 to 30 nucleotides in length, more preferably of 17 to 27 nucleotides or 18 to 26 nucleotides in length, i.e. 10, 11, 12, 13, 14, 15, 16, 17, 18, 19, 20, 21, 22, 23, 24, 25, 26, 27, 28, 29, 30, 31, 32, 33, 34, or 35 nucleotides in length, not including optionally spacer elements and/or elongation elements described below. The depiction of a single strand of a polynucleotide also defines the sequence of the complementary strand. Polynucleotides may be single stranded or double stranded, or may contain portions of both double stranded and single stranded sequences. The term "polynucleotide" means a polymer of deoxyribonucleotide or ribonucleotide bases and includes DNA and RNA molecules, both sense and anti-sense strands. In detail, the polynucleotide may be DNA, both cDNA and genomic DNA, RNA, cRNA or a hybrid, where the polynucleotide sequence may contain combinations of deoxyribonucleotide or ribonucleotide bases, and combinations of bases including uracil, adenine, thymine, cytosine, guanine, inosine, xanthine, hypoxanthine, isocytosine and isoguanine Polynucleotides may be obtained by chemical synthesis methods or by recombinant methods.

In the context of the present invention, a polynucleotide as a single polynucleotide strand provides a probe (e.g. miRNA capture probe) that is capable of binding to, hybridizing with, or detecting a target of complementary sequence, such as a nucleotide sequence of a miRNA or miRNA*, through one or more types of chemical bonds, usually through complementary base pairing, usually through hydrogen bond formation. Polynucleotides in their function as probes may bind target sequences, such as nucleotide sequences of miRNAs or miRNAs*, lacking complete complementarity with the polynucleotide sequences depending upon the stringency of the hybridization condition. There may be any number of base pair mismatches which will interfere with hybridization between the target sequence, such as a nucleotide sequence of a miRNA or miRNA*, and the single stranded polynucleotide described herein. However, if the number of mutations is so great that no hybridization can occur under even the least stringent hybridization conditions, the sequences are no complementary sequences. The present invention encompasses polynucleotides in form of single polynucleotide strands as probes for binding to, hybridizing with or detecting complementary sequences of (target) miRNAs for diagnosing and/or prognosing of kidney cancer. Said (target) miRNAs are preferably selected from the group consisting of SEQ ID NO: 1 to 357 or SEQ ID NO: 1 to 465.

Because of the conservation of miRNAs among species, for example between humans and other mammals, e.g. animals such as mice, monkey or rat, the polynucleotide(s) of the invention may not only be suitable for detecting a miRNA(s) of a specific species, e.g. a human miRNA, but may also be suitable for detecting the respective miRNA orthologue(s) in another species, e.g. in another mammal, e.g. animal such as mouse or rat.

The term "antisense", as used herein, refers to nucleotide sequences which are complementary to a specific DNA or RNA sequence. The term "antisense strand" is used in reference to a nucleic acid strand that is complementary to the "sense" strand.

The term "label", as used herein, means a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and other entities which can be made detectable. A label may be incorporated into nucleic acids at any position, e.g. at the 3' or 5' end or internally. The polynucleotide for detecting a miRNA (polynucleotide probe) and/or the miRNA itself may be labeled. For detection purposes, the miRNA(s) or miRNA*(s) may be employed unlabeled, directly labeled, or indirectly labeled, such as with biotin to which a streptavidin complex may later bind.

The term "stringent hybridization conditions", as used herein, means conditions under which a first nucleotide sequence (e.g. polynucleotide in its function as a probe for detecting a miRNA or miRNA*) will hybridize to a second nucleotide sequence (e.g. target sequence such as nucleotide sequence of a miRNA or miRNA*), such as in a complex mixture of nucleotide sequences. Stringent conditions are sequence-dependent and will be different in different circumstances.

Stringent conditions may be selected to be about 5 to 10° C. lower than the thermal melting point (Tm) for the specific sequence at a defined ionic strength, pH. The Tm may be the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, such as about 0.01 to 1.0 M sodium ion concentration (or other salts) at pH 7.0 to 8.3 and the temperature is at least about 20° C. for short probes (e.g. about 10-35 nucleotides) and up to 60° C. for long probes (e.g. greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.; or 6×SSPE, 10% formamide, 0.01%, Tween 20, 0.1×TE buffer, 0.5 mg/ml BSA, 0.1 mg/ml herring sperm DNA, incubating at 42° C. with wash in 05×SSPE and 6×SSPE at 45° C.

The term "sensitivity", as used herein, means a statistical measure of how well a binary classification test correctly identifies a condition, for example how frequently it correctly classifies a heart and cardiovascular system disease into the correct type out of two or more possible types (e.g. heart and cardiovascular system disease type and healthy type). The sensitivity for class A is the proportion of cases that are determined to belong to class "A" by the test out of the cases that are in class "A". A theoretical, optimal prediction can achieve 100% sensitivity (i.e. predict all patients from the sick group as sick).

The term "specificity", as used herein, means a statistical measure of how well a binary classification test correctly identifies a condition, for example how frequently it correctly classifies a heart and cardiovascular system disease into the correct type out of two or more possible types. The specificity for class A is the proportion of cases that are determined to belong to class "not A" by the test out of the cases that are in class "not A". A theoretical, optimal prediction can achieve 100% specificity (i.e. not predict anyone from the healthy group as sick).

The term "accuracy", as used herein, means a statistical measure for the correctness of classification or identification of sample types. The accuracy is the proportion of true results (both true positives and true negatives).

The term "Receiver operating characteristic (ROC) curves" means a graphical measure of sensitivity (y-axis) vs. 1−specificity (x-axis) for a clinical test. An important measure of the accuracy of the clinical test is the area under the ROC curve value (AUC value). If this area is equal to 1.0 then this test is 100% accurate because both the sensitivity and specificity are 1.0 so there are no false positives and no false negatives. On the other hand a test that cannot discriminate that is the diagonal line from 0.0 to 1.1. The ROC area for this line is 0.5. ROC curve areas (AUC-values) are typically between 0.5 and 1.0, but also ROC values below 0.5 can—according to information theory—be as good, if the result is interpreted inversely. Therefore, according to the present invention an AUC-value close to 1 (e.g. 0.95) represents the same good measure for a clinical test as an AUC-value close to 0 (e.g. 0.05).

The term "biological sample", as used in the context of the present invention, refers to any biological sample containing miRNA(s). Said biological sample may be a biological fluid, tissue, cell(s) or mixtures thereof. For example, biological samples encompassed by the present invention are body fluids, tissue (e.g. section or explant) samples, cell culture samples, cell kidney samples, single cell samples, collection of single cell samples, blood samples (e.g. whole blood or a blood fraction such as serum or plasma), urine samples, or samples from other peripheral sources. Said biological samples may be mixed or pooled, e.g. a biological sample may be a mixture of blood and urine samples. A "biological sample" may be provided by removing cell(s), cell kidneys, an explant, or a section from a subject suspected to be affected by kidney cancer, but may also be provided by using a previously isolated sample. For example, a tissue sample may be removed from a subject suspected to be affected by kidney cancers by conventional biopsy techniques or a blood sample may be taken from a subject suspected to be affected by kidney cancer by conventional blood collection techniques. The biological sample, e.g. tissue or blood sample, may be obtained from a subject suspected to be affected by kidney cancer prior to initiation of the therapeutic treatment, during the therapeutic treatment and/or after the therapeutic treatment.

The term "body fluid sample", as used in the context of the present invention, refers to liquids originating from the body of a subject. Said body fluid samples include, but are not limited to, blood, urine, sputum, breast milk, cerebrospinal fluid, amniotic fluid, bronchial lavage, colostrum, seminal fluid, cerumen (earwax), endolymph, perilymph, gastric juice, mucus, peritoneal fluid, pleural fluid, saliva, sebum (skin oil), semen, sweat, tears, vaginal secretion, vomit including components or fractions thereof. Said body fluid samples may be mixed or pooled, e.g. a body fluid sample may be a mixture of blood and urine samples or blood and tissue material. A "body fluid sample" may be provided by removing a body liquid from a subject, but may also be provided by using previously isolated sample material.

Preferably, the body fluid sample from a subject (e.g. human or animal) has a volume of between 0.1 and 20 ml, more preferably of between 0.5 and 10 ml, more preferably between 1 and 8 ml and most preferably between 2 and 5 ml, i.e. 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

In the context of the present invention said "body fluid sample" allows for a non-invasive diagnosis/and or prognosis of a subject.

The term "blood sample", as used in the context of the present invention, refers to a blood sample originating from a subject. The "blood sample" may be derived by removing blood from a subject by conventional blood collecting techniques, but may also be provided by using previously isolated and/or stored blood samples. For example a blood sample may be whole blood, plasma, serum, blood cells, PBMC (peripheral blood mononuclear cells), blood cellular fractions including or comprising red blood cells (erythrocytes), white blood cells (leukocytes), platelets (thrombocytes), or blood collected in blood collection tubes (e.g. EDTA-, heparin-, citrate-, PAXgene-, Tempus-tubes) including components or fractions thereof. For example, a blood sample may be taken from a subject suspected to be affected or to be suspected to be affected by kidney cancer, prior to initiation of a therapeutic treatment, during the therapeutic treatment and/or after the therapeutic treatment.

Preferably, the blood sample from a subject (e.g. human or animal) has a volume of between 0.1 and 20 ml, more preferably of between 0.5 and 10 ml, more preferably between 1 and 8 ml and most preferably between 2 and 5 ml, i.e. 0.1, 0.2, 0.3, 0.4, 0.5, 0.6, 0.7, 0.8, 0.9, 1, 2, 2.5, 3, 4, 5, 6, 7, 8, 9, 10, 11, 12, 13, 14, 15, 16, 17, 18, 19, or 20 ml.

In the context of the present invention said "body fluid sample" allows for a non-invasive diagnosis/and or prognosis of a subject.

Preferably, when the blood sample is collected from the subject the RNA-fraction, especially the the miRNA fraction, is guarded against degradation. For this purpose special collection tubes (e.g. PAXgene RNA tubes from Preanalytix, Tempus Blood RNA tubes from Applied Biosystems) or additives (e.g. RNAlater from Ambion, RNAsin from Promega) that stabilize the RNA fraction and/or the miRNA fraction are employed.

The biological sample, preferably the body fluid sample may be from a subject (e.g. human or mammal) that has been therapeutically treated or that has not been therapeutically treated. In one embodiment, the therapeutical treatment is monitored on the basis of the detection of the miRNA or set of miRNAs by the polynucleotide or set of polynucleotides of the invention. It is also preferred that total RNA or a subfraction thereof, isolated (e.g. extracted) from a biological sample of a subject (e.g. human or animal), is used for detecting the miRNA or set of miRNAs by the polynucleotide or set of polynucleotides or primer pairs of the invention.

The term "non-invasive", as used in the context of the present invention, refers to methods for obtaining a biological sample, particularly a body fluid sample, without the need for an invasive surgical intervention or invasive medical procedure. In the context of the present invention, a blood drawn represents a non-invasive procedure, therefore a blood-based test (utilizing blood or fractions thereof) is a non-invasive test. Other body fluid samples for non-invasive tests are e.g. urine, sputum, tears, mothers mild, cerumen, sweat, saliva, vaginal secretion, vomit, etc.

The term "minimal invasive", as used in the context of the present invention, refers to methods for obtaining a biological sample, particularly a body fluid sample, with a minimal need for an invasive surgical intervention or invasive medical procedure.

The term "biomarker", as used in the context of the present invention, represents a characteristic that can be objectively measured and evaluated as an indicator of normal and disease processes or pharmacological responses. A biomarker is a parameter that can be used to measure the onset or the progress of disease or the effects of treatment. The parameter can be chemical, physical or biological.

The term "surrogate biomarker", as used in the context of the present invention, represents biomarker intended to substitute for a clinical endpoint. It is a measure of a clinical condition or a measure of effect of a certain treatment that may correlate with the real clinical condition (e.g. healthy, diseased) but doesn't necessarily have a guaranteed relationship. An ideal surrogate biomarker is a laboratory substitute for a clinically meaningful result, and should lie directly in the causal pathway linking disease to outcome. Surrogate biomarkers are used when the primary endpoint is undesired (e.g. death). A commonly used example is cholesterol: while elevated cholesterol levels increase the likelihood for heart disease, the relationship is not linear—many people with normal cholesterol develop heart disease, and many with high cholesterol do not. "Death from heart disease" is the endpoint of interest, but "cholesterol" is the surrogate biomarker.

The term "diagnosis" as used in the context of the present invention refers to the process of determining a possible disease or disorder and therefore is a process attempting to define the (clinical) condition of a subject. The determination of the expression level of a set of miRNAs according to the present invention correlates with the (clinical) condition of a subject. Preferably, the diagnosis comprises (i) determining the occurrence/presence of kidney cancer, (ii) monitoring the course of kidney cancer, (iii) staging of kidney cancer, (iv) measuring the response of a patient with kidney cancer to therapeutic intervention, and/or (v) segmentation of a subject suffering from kidney cancer.

The term "prognosis" as used in the context of the present invention refers to describing the likelihood of the outcome or course of a disease or a disorder. Preferably, the prognosis comprises (i) identifying of a subject who has a risk to develop kidney cancer, (ii) predicting/estimating the occurrence, preferably the severity of occurrence of kidney cancer, and/or (iii) predicting the response of a subject with kidney cancer to therapeutic intervention.

The term "(clinical) condition" (biological state or health state), as used herein, means a status of a subject that can be described by physical, mental or social criteria. It includes so-called "healthy" and "diseased" conditions. For the definition of "healthy" and "diseased" conditions it is referred to the international classification of diseases (ICD) of the WHO (http://www.int/classifications/icd/en/index.html). When one condition is compared according to a preferred embodiment of the method of the present invention, it is understood that said condition is kidney cancer or a specific form of kidney cancer. When two or more conditions are compared according to another preferred embodiment of the method of the present invention, it is understood that this is possible for all conditions that can be defined and is not limited to a comparison of a diseased versus healthy comparison and extends to multiway comparison, under the proviso that at least one condition is kidney cancers, preferably a specific form of kidney cancer.

The term "miRNA expression profile" as used in the context of the present invention, represents the determination of the miRNA expression level or a measure that correlates with the miRNA expression level in a biological sample. The miRNA expression profile may be generated by any convenient means, e.g. nucleic acid hybridization (e.g. to a microarray, bead-based methods), nucleic acid amplification (PCR, RT-PCR, qRT-PCR, high-throughput RT-PCR), ELISA for quantitation, next generation sequencing (e.g. ABI SOLID, Illumina Genome Analyzer, Roche/454 GS FLX), flow cytometry (e.g. LUMINEX, Firefly Bioworks) and the like, that allow the analysis of differential miRNA expression levels between samples of a subject (e.g. diseased) and a control subject (e.g. healthy, reference sample). The sample material measure by the aforementioned means may be total RNA, labeled total RNA, amplified total RNA, cDNA, labeled cDNA, amplified cDNA, miRNA, labeled miRNA, amplified miRNA or any derivatives that may be generated from the aforementioned RNA/DNA species. By determining the miRNA expression profile, each miRNA is represented by a numerical value. The higher the value of an individual miRNA, the higher is the expression level of said miRNA, or the lower the value of an individual miRNA, the lower is the expression level of said miRNA.

The "miRNA expression profile", as used herein, represents the expression level/expression data of a single miRNA or a collection of expression levels of at least two miRNAs, preferably of least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more, or up to all known miRNAs.

The term "differential expression" of miRNAs as used herein, means qualitative and/or quantitative differences in the temporal and/or local miRNA expression patterns, e.g. within and/or among biological samples, body fluid samples, cells, or within blood. Thus, a differentially expressed miRNA may qualitatively have its expression altered, including an activation or inactivation in, for example, blood from a diseases subject versus blood from a healthy subject. The difference in miRNA expression may also be quantitative, e.g. in that expression is modulated, i.e. either up-regulated, resulting in an increased amount of miRNA, or down-regulated, resulting in a decreased amount of miRNA. The degree to which miRNA expression differs need only be large enough to be quantified via standard expression characterization techniques, e.g. by quantitative hybridization (e.g. to a microarray, to beads), amplification (PCR, RT-PCR, qRT-PCR, high-throughput RT-PCR), ELISA for quantitation, next generation sequencing (e.g. ABI SOLID, Illumina Genome Analyzer, Roche 454 GS FL), flow cytometry (e.g. LUMINEX, Firefly Bioworks) and the like.

Nucleic acid hybridization may be performed using a microarray/biochip or in situ hybridization. In situ hybridization is preferred for the analysis of a single miRNA or a set comprising a low number of miRNAs (e.g. a set of at least 2 to 50 miRNAs such as a set of 2, 5, 10, 20, 30, or 40 miRNAs). The microarray/biochip, however, allows the analysis of a single miRNA as well as a complex set of miRNAs (e.g. a all known miRNAs or subsets thereof).

For nucleic acid hybridization, for example, the polynucleotides (probes) according to the present invention with complementarity to the corresponding miRNAs to be detected are attached to a solid phase to generate a microarray/biochip (e.g. 357 (465) polynucleotides (probes) which are complementary to the 357 (465) miRNAs having SEQ ID NO: 1 to 357 or SEQ ID NO: 1 to 465. Said microarray/biochip is then incubated with a biological sample containing miRNAs, isolated (e.g. extracted) from the body fluid sample such as blood sample from a subject such as a human or an animal, which may be labelled, e.g. fluorescently labelled, or unlabelled. Quantification of the expression level of the miRNAs may then be carried out e.g. by direct read out of a label or by additional manipulations, e.g. by use of a polymerase reaction (e.g. template directed primer extension, MPEA-Assay, RAKE-assay) or a ligation reaction to incorporate or add labels to the captured miRNAs.

Alternatively, the polynucleotides which are at least partially complementary (e.g. a set of chimeric polynucleotides with each a first stretch being complementary to a set of miRNA sequences and a second stretch complementary to capture probes bound to a solid surface (e.g. beads, Luminex beads)) to miRNAs having SEQ ID NO: 1 to 357 or SEQ ID NO: 1 to 465. are contacted with the biological sample containing miRNAs (e.g a body fluid sample, preferably a blood sample) in solution to hybridize. Afterwards, the hybridized duplexes are pulled down to the surface (e.g a plurality of beads) and successfully captured miRNAs are quantitatively determined (e.g. FlexmiR-assay, FlexmiR v2 detection assays from Luminex, Firefly Bioworks Assay).

Nucleic acid amplification may be performed using real time polymerase chain reaction (RT-PCR) such as real time quantitative polymerase chain reaction (RT qPCR). The standard real time polymerase chain reaction (RT-PCR) is preferred for the analysis of a single miRNA or a set comprising a low number of miRNAs (e.g. a set of at least 2 to 50 miRNAs such as a set of 2, 5, 10, 20, 30, or 40 miRNAs), whereas high-throughput RT-PCR technologies (e.g. OpenArray from Applied Biosystems, SmartPCR from Wafergen, Biomark System from Fluidigm) are also able to measure large sets (e.g a set of 10, 20, 30, 50, 80, 100, 200 or more) to all known miRNAs in a high parallel fashion. RT-PCR is particularly suitable for detecting low abandoned miRNAs.

The aforesaid real time polymerase chain reaction (RT-PCR) may include the following steps: (i) extracting the total RNA from a biological sample or body fluid sample such as a blood sample (e.g. whole blood, serum, or plasma) of a subjects such as human or animal, and obtaining cDNA samples by RNA reverse transcription (RT) reaction using universal or miRNA-specific primers; or collecting a body fluid sample such as urine or blood sample (e.g. whole blood, serum, or plasma) of a patient such as human or animal, and conducting reverse transcriptase reaction using universal or miRNA-specific primers (e.g. looped RT-primers) within the body fluid sample such as urine or blood sample (e.g. whole blood, serum, or plasma) being a buffer so as to prepare directly cDNA samples, (ii) designing miRNA-specific cDNA forward primers and providing universal reverse primers to amplify the cDNA via polymerase chain reaction (PCR), (iii) adding a fluorescent dye (e.g. SYBR Green) or a fluorescent probe (e.g. Taqman probe) probe to conduct PCR, and (iv) detecting the miRNA(s) level in the body fluid sample such as urine or blood sample (e.g. whole blood, serum, or plasma).

A variety of kits and protocols to determine an expression profile by real time polymerase chain reaction (RT-PCR) such as real time quantitative polymerase chain reaction (RT qPCR) are available. For example, reverse transcription of miRNAs may be performed using the TaqMan MicroRNA Reverse Transcription Kit (Applied Biosystems) according to manufacturer's recommendations. Briefly, miRNA may be combined with dNTPs, MultiScribe reverse transcriptase and the primer specific for the target miRNA. The resulting cDNA may be diluted and may be used for PCR reaction. The PCR may be performed according to the manufacturer's recommendation (Applied Biosystems). Briefly, cDNA may be combined with the TaqMan assay specific for the target miRNA and PCR reaction may be performed using ABI7300. Alternative kits are available from Ambion, Roche, Qiagen, Invitrogen, SABiosciences, Exiqon etc.

The term "subject", as used in the context of the present invention, means a patient or individual or mammal suspected to be affected by kidney cancer. The patient may be diagnosed to be affected by kidney cancer, i.e. diseased, or may be diagnosed to be not affected by kidney cancer, i.e. healthy. The subject may also be diagnosed to be affected by a specific form of kidney cancer. The subject may further be diagnosed to develop kidney cancer or a specific form of kidney cancer as the inventors of the present invention surprisingly found that miRNAs representative for kidney cancer are already present in the biological sample, e.g. blood sample, before kidney cancer occurs or during the early stage of kidney cancer. It should be noted that a subject that is diagnosed as being healthy, i.e. not suffering from kidney cancer or from a specific form of kidney cancer, may possibly suffer from another disease not tested/known. The subject may be any mammal, including both a human and another mammal, e.g. an animal such as a rabbit, mouse, rat, or monkey. Human subjects are particularly preferred. Therefore, the miRNA from a subject may be a human miRNA or a miRNA from another mammal, e.g. an animal miRNA such as a mouse, monkey or rat miRNA, or the miRNAs comprised in a set may be human miRNAs or miRNAs from another mammal, e.g. animal miRNAs such as mouse, monkey or rat miRNAs.

The term "control subject", as used in the context of the present invention, may refer to a subject known to be affected with kidney cancer (positive control), i.e. diseased, or to a subject known to be not affected with kidney cancer (negative control), i.e. healthy. It may also refer to a subject known to be effected by another disease/condition (see definition "(clinical) condition"). It should be noted that a control subject that is known to be healthy, i.e. not suffering from kidney cancer, may possibly suffer from another disease not tested/known. The control subject may be any mammal, including both a human and another mammal, e.g. an animal such as a rabbit, mouse, rat, or monkey. Human "control subjects" are particularly preferred.

The term "set comprising at least two miRNAs representative for kidney cancer", as used herein, refers to refers to at least two fixed defined miRNAs comprised in a set which are known to be differential (differentially expressed) between subjects (e.g. humans or other mammals such as animals) suffering from kidney cancer (diseased state) and control subjects (e.g. humans or other mammals such as animals and are, thus, representative for kidney cancer. Said "set comprising at least two miRNAs representative for kidney cancer" are preferably selected from the group consisting of SEQ ID NO: 1 to 357 or SEQ ID NO: 1 to 465, a fragment thereof, and a sequence having at least 80% sequence identity thereto.

The term "kidney cancer", as used herein refers to cancer of the kidney. This includes, but not limited to, renal cell carcinoma (RCC), Transitional Cell Carcinoma, Wilms' Tumor and Renal Sarcoma. In a preferred embodiment, kidney cancer refers to a renal cell carcinoma (RCC).

In the United States, kidney cancer accounts for approximately 3% of all adult cancers. According to the American Cancer Society, about 32,000 new cases are diagnosed and about 12,000 people die from the disease annually. Kidney cancer occurs most often in people between the ages of 50 and 70, and affects men almost twice as often as women. Smokers develop renal cell carcinoma about twice as often as nonsmokers and develop cancer of the renal pelvis about 4 times as often. Not smoking is the most effective way to prevent kidney cancer and it is estimated that the elimination of smoking would reduce the rate of renal pelvis cancer by one-half and the rate of renal cell carcinoma by one-third.

Several types of cancer can develop in the kidneys. Renal cell carcinoma (RCC), the most common form, accounts for approximately 85% of all cases. In RCC, cancerous (malignant) cells develop in the lining of the kidney's tubules and grow into a mass called a tumor. In most cases, a single tumor develops, although more than one tumor can develop within one or both kidneys.

Early diagnosis of kidney cancer is important. As with most types of cancer, the earlier the tumor is discovered, the better a patient's chances for survival. Tumors discovered at an early stage often respond well to treatment. Survival rates in such cases are high. Tumors that have grown large or spread (metastasized) through the bloodstream or lymphatic system to other parts of the body are more difficult to treat and present an increased risk for mortality.

If the physician suspects RCC, a series of examinations, procedures, and laboratory tests are performed to confirm the diagnosis. Usually, one or more imaging tests are performed to obtain pictures of the kidney(s) and locate abnormalities. More than half of all patients with RCC have blood in the urine (hematuria). Often this blood is present in small amounts or diffused in the urine so that it cannot be seen with the naked eye (called microscopic hematuria). To detect hematuria, a chemical test of the urine is performed. On occasion, cells found in the urine are examined under a microscope for abnormalities. RCC tumors are made up of cancerous (malignant) cells that grow into a mass. If a tumor is found through imaging or other procedures, a cell sample may be taken for microscopic examination. Physicians usually avoid performing needle biopsies of suspected kidney tumors because of the risk for bleeding or other complications.

Due to the shortcomings of current state of the art diagnosis for kidney cancer, there is an urgent need for better, non-invasive tests to further diagnosis and prognosis options for patients.

The inventors of the present invention surprisingly found that miRNAs are significantly dysregulated in body fluid samples such as blood of kidney cancer subjects in comparison to a cohort of controls (healthy subjects) and thus, miRNAs are appropriated biomarkers for diagnosing and/or prognosing of kidney cancer in a non-invasive fashion or minimal-invasive fashion. Furthermore, the sets of miRNAs of the present invention lead to high performance in diagnosing and/or prognosing of kidney cancer, thus expose very high specificity, sensitivity and accuracy. They succeeded in determining the miRNAs that are differentially regulated in body fluid samples from patients having kidney cancer compared to a cohort of controls (healthy subjects) (see experimental section for experimental details). Additionally, the inventors of the present invention performed hypothesis tests (e.g. t-test, limma-test) or other measurements (e.g. AUC, mutual information) on the expression level of the found miRNAs, in all controls (healthy subjects) and subjects suffering from kidney cancer. These tests resulted in a significance value (p-value) for each miRNA. This p-value is a measure for the diagnostic power of each of these single miRNAs to discriminate, for example, between the two clinical conditions: controls (healthy subjects), i.e. not suffering from kidney cancer, or diseased, i.e. suffering from kidney cancer. Since a manifold of tests are carried out, one for each miRNA, the p-values may be too optimistic and, thus, over-estimate the actual discriminatory power. Hence, the p-values are corrected for multiple testing by the Benjamini Hochberg approach.

An overview of the miRNAs that are found to be significantly differentially regulated in biological samples of kidney cancer and that performed best according to t-test, limma-test or AUC is provided in FIG. 1 or FIG. 6 (Experimental details: SEQ ID NO: sequence identification number, miRNA: identifier of the miRNA according to miRBase, median g1: median intensity obtained from microarray analysis for healthy controls, median g2: median intensity obtained from microarray analysis for individuals with kidney cancer, qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment.). The miRNAs, i.e. miRNAs according to SEQ ID NO: 1 to 357 or SEQ ID NO: 1 to 465, are sorted in order of their t-test significance as described in more detail in the experimental section (see ttest_adjp=adjusted p-value calculated according to ttest). It should be noted that the lower the ttest_adjp value of a single miRNA, the higher is the diagnostic power of said miRNA for diagnosing and/or prognosing of kidney cancer.

The significantly differentially regulated miRNAs are either up-regulated (see FIG. 7a) or strong up-regulated (see FIG. 7b) or alternatively down-regulated (see FIG. 8a) or strong down-regulated (see FIG. 8b) in biological samples of kidney cancer as compared to healthy controls.

Usually the diagnostic power of a single miRNA biomarker is not sufficient to reach high accuracy, specificity and sensitivity for discrimination between healthy subjects (controls) and subjects suffering from kidney cancer, hence no simple threshold method can be used for diagnosis and/or prognosis.

Therefore, the inventors of the present invention employed more than one miRNA biomarker, i.e. sets of miRNA biomarkers (signatures), to further increase and/or improve the performance for diagnosing and/or prognosing of subjects suffering from kidney cancer. This leads to a significant increase in sensitivity, specificity and accuracy when compared to the prior art.

In order to be able to discriminate, for example, between two or more clinical conditions, e.g. healthy and suffering from kidney cancer, for a defined set of miRNA biomarkers, the inventors of the present invention applied a machine learning approach (e.g. t-test, AUC, support vector machine, hierarchical clustering, or k-means) which leads to an algorithm that is trained by reference data (i.e. data of reference miRNA expression profiles from the two clinical conditions, e.g. healthy and suffering from kidney cancer, for the defined set of miRNA markers) to discriminate between the two statistical classes (i.e. two clinical conditions, e.g. healthy or suffering from kidney cancer).

The inventors of the present invention surprisingly found that this approach yields in miRNA sets (signatures) that provide high diagnostic accuracy, specificity and sensitivity in the determination of kidney cancer in patients (see FIG. 2 or FIG. 5b or FIG. 9). Said miRNA sets (signatures) comprise at least two miRNAs, wherein the nucleotide sequences of said miRNAs are preferably selected from the group consisting of SEQ ID NO: 1 to 357 or SEQ ID NO: 1 to 465.

An exemplarily approach to arrive at miRNA sets/signatures that correlate with kidney cancer is summarized below:

Step 1: Total RNA (or subfractions thereof) is extracted from the biological sample, e.g. a body fluid sample, preferably a blood sample (including plasma, serum, PBMC or other blood fractions), using suitable kits and/or purification methods.

Step 2: From the respective samples the quantity (expression level) of one miRNA or sets of at least two miRNAs, e.g. selected from the group consisting of SEQ ID NO: 1 to 357 or SEQ ID NO: 1 to 465, is measured using experimental techniques. These techniques include but are not restricted to array based approaches, amplification methods (PCR, RT-PCR, qPCR), sequencing, next generation sequencing, flow cytometry and/or mass spectroscopy.

Step 3: In order to gather information on the diagnostic/prognostic value and the redundancy of each of the single miRNA biomarkers, mathematical methods are applied. These methods include, but are not restricted to, basic mathematic approaches (e.g. Fold Quotients, Signal to Noise ratios, Correlation), statistical methods as hypothesis tests (e.g. t-test, Wilcoxon-Mann-Whitney test), the Area under the Receiver operator Characteristics Curve, information theory approaches, (e.g. the Mutual Information, Cross-entropy), probability theory (e.g. joint and conditional probabilities) or combinations and modifications of the previously mentioned methods.

Step 4: The information gathered in step 3 is used to estimate for each miRNA biomarker the diagnostic content or value. Usually, however, this diagnostic value is too small to get a highly accurate diagnosis with accuracy rates, specificities and sensitivities beyond the 90% barrier.

The diagnostic content of the miRNAs suitable for diagnosing/prognosing kidney cancer is exemplarily listed in FIG. 1 or FIG. 6 (Experimental details: SEQ ID NO: sequence identification number, miRNA: identifier of the miRNA according to miRBase, median g1: median intensity obtained from microarray analysis for healthy controls, median g2: median intensity obtained from microarray analysis for subjects with kidney cancer, qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment.). This Figure includes the miRNAs according to SEQ ID NO: 1 to 357 or SEQ ID NO: 1 to 465.

Step 5: In order to increase the performance for diagnosing/prognosing of subjects suffering from kidney cancer, more than one miRNA biomarker needs to be employed. Thus statistical learning/machine learning/bioinformatics/computational approaches are applied for set selection in order to select/define sets of miRNA biomarkers (e.g. comprising miRNAs SEQ ID NO: 1 to 357 or SEQ ID NO: 1 to 465) that are tailored for the detection of kidney cancer. These techniques include, but are not restricted to, Wrapper subset selection techniques (e.g. forward step-wise, backward step-wise, combinatorial approaches, optimization approaches), filter subset selection methods (e.g. the methods mentioned in Step 3), principal component analysis, or combinations and modifications of such methods (e.g. hybrid approaches).

Step 6: The subsets, selected/defined in Step 5, which may range from only a small number (at least two for the set) to all measured biomarkers is then used to carry out a diagnosis/prognosis of kidney cancer. To this end, statistical learning/machine learning/bioinformatics/computational approaches are applied that include but are not restricted to any type of supervised or unsupervised analysis: classification techniques (e.g. naïve Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

Step 7: By combination of subset selection (Step 5) and machine learning (Step 6) an algorithm or mathematical function for diagnosing/prognosing kidney cancer is obtained. This algorithm or mathematical function is applied to a miRNA expression profile of a subject to be diagnosed for kidney cancer.

In a first aspect, the present invention relates to a method for diagnosing and/or prognosing of kidney cancer comprising the steps of:

(i) determining an expression profile of a set comprising at least two miRNAs representative for kidney cancer in a body fluid sample from a subject, and (ii) comparing said expression profile to a reference, wherein the comparison of said expression profile to said reference allows for the diagnosis and/or prognosis of kidney cancer, It is preferred that kidney cancer is renal cell carcinoma (RCC)

It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

Preferably, the set comprising at least two miRNAs is from the group consisting of SEQ ID NO: 1 to 357 or SEQ ID NO: 1 to 465.

It is preferred that the set comprising at least two miRNAs is selected from the set of miRNAs listed in FIG. 2 or FIG. 5b or FIG. 9.

It is preferred that the set comprising at least two miRNAs comprises at least one set of miRNAs listed in FIG. 2 or FIG. 5b or FIG. 9.

Preferably, the set comprising at least two miRNAs comprises at least one up-regulated miRNA listed in FIG. 7a or comprises at least one down-regulated miRNAs listed in FIG. 8a. More preferably, the set comprising at least two miRNAs comprises at least one up-regulated miRNA listed in FIG. 7b or comprises at least one down-regulated miR-NAs listed in FIG. 8b. It is further preferred, that the set comprising at least two miRNAs comprises at least one up-regulated miRNA listed in FIG. 7a and further comprises at least one down-regulated miRNAs listed in FIG. 8a.

It is preferred that the determining the expression profile of a set comprising at least two miRNAs is for or is representative for assessing the response of the immune system in a body fluid sample, preferably in a blood sample, of the subject having of suspected of having kidney cancer.

Thus, it is preferred that the method for diagnosing and/or prognosing of kidney cancer comprises the steps of:
  (i) determining an expression profile (expression profile data) of a set comprising, essentially consisting of, or consisting of at least two miRNAs representative for kidney cancer in a blood sample from a subject (e.g. a human or another mammal such as an animal), and
  (ii) comparing said expression profile (expression profile data) to a reference, wherein the comparison of said expression profile (expression profile data) to said reference allows for the diagnosis and/or prognosis of kidney cancer.

Thus, for analysis of a body fluid sample (e.g. blood sample) in step (i) of the method of the present invention, an expression profile of a set comprising at least two miRNAs which are known to be differential between subjects (e.g. humans or other mammals such as animals) having or being suspected to have kidney cancer or a special form of kidney cancer (diseased state) and subjects (e.g. humans or other mammals such as animals) not having kidney cancer or a special form of kidney cancer (healthy/control state) and are, thus, representative for kidney cancer, is determined, wherein the nucleotide sequences of said miRNAs are) preferably selected from the group consisting of SEQ ID NO: 1 to 357 or SEQ ID NO: 1 to 465, a fragment thereof, and a sequence having at least 80% sequence identity thereto.

It is more particularly preferred that an expression profile of a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more, or comprising/consisting of 357 (465) miRNAs, representative for kidney cancer in a body fluid sample (e.g. a blood sample) from a subject (e.g. a human or another mammal such as an animal) is determined in the step (i) of the method of the present invention, wherein the nucleotide sequences of said miRNAs are selected from the group consisting of
  (i) a nucleotide sequence according to SEQ ID NO: 1 to 357 or SEQ ID NO: 1 to 465,
  (ii) a nucleotide sequence that is a fragment of the nucleotide sequence according to (i), preferably, a nucleotide sequence that is a fragment which is between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequence according to (i), and
  (iii) a nucleotide sequence that has at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequence according to (i) or nucleotide sequence fragment according to (ii).

Additionally, it is more particularly preferred that an expression profile of a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more, or comprising/consisting of 357 (465) miRNAs, representative for kidney cancer in a body fluid sample (e.g. a blood sample) from a subject (e.g. a human or another mammal such as an animal) is determined in the step (i) of the method of the present invention, wherein the set comprising at least two miRNAs is selected from the group consisting of
  (i) a set of miRNAs listed in FIG. 2 or FIG. 5b or FIG. 9
  (ii) a combination of at least 2 sets of miRNAs listed in FIG. 2 or FIG. 5b or FIG. 9
  (iii) nucleotide sequences that are fragments of the nucleotide sequence according to (i) or (ii), preferably, nucleotide sequences that are fragments which are between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the nucleotide sequences according to (i) or (ii), and
  (iv) nucleotide sequences that have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the nucleotide sequences according to (i) or (ii) or nucleotide sequence fragments according to (iii).

It is particularly preferred that the nucleotide sequences as defined in (iv) have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity over a continuous stretch of at least 10, 11, 12, 13, 14, 15, 16, 17, 18, 19, 20 or more nucleotides, preferably over the whole length, to the nucleotide sequences of the nucleotides according to (i) or (ii) or nucleotide fragments according to (iii).

Furthermore, according to the present invention, a first diagnosis and/or prognosis of kidney cancer can be performed employing, as disclosed, miRNA-detection in a body fluid sample, e.g. in blood, followed by a second diagnosis and/or prognosis that is based on other methods (e.g. other biomarkers and/or imaging methods).

Furthermore, according to the present invention, the set comprising at least two miRNAs for diagnosing and/or prognosing kidney cancer in a body fluid sample, e.g. blood sample, from a patient, e.g. human or animal, may be established on one experimental platform (e.g. microarray/biochip), while for routine diagnosis/prognosis another experimental platform (e.g. qPCR) may be chosen.

Subsequent to the determination of an expression profile (of expression profile data) of a set comprising at least two miRNAs representative for kidney cancer as defined above in a body fluid sample (e.g. blood sample) from a patient (e.g. human or animal) in step (i) of the method for diagnosing and/or prognosing of kidney cancer of the present invention, said method further comprises the step (ii) of comparing said expression profile (expression profile data) to a reference, wherein the comparison of said expression profile (expression profile data) to said reference allows for the diagnosis and/or prognosis of kidney cancer.

The subject (e.g. human or another mammal (e.g. animal)) to be diagnosed with the method of the present invention may suffer, may be suspected to suffer or may not suffer from kidney cancer. The subject (e.g. human or another mammal (e.g. animal)) to be diagnosed with the method of the present invention may suffer from a specific type of kidney cancer. It is also possible to determine, whether the subject (e.g. human or another mammal (e.g. animal) to be diagnosed will develop kidney cancer as the inventors of the present invention surprisingly found that miRNAs representative for kidney cancer are already present in the body fluid sample, e.g. blood sample, before kidney cancer occurs or during the early stage of kidney cancer.

The reference may be the reference (e.g. reference expression profile (data)) of a healthy condition (i.e. not kidney cancer), may be the reference (e.g. reference expression profile (data)) of a diseased condition (i.e. kidney cancer) or may be the reference (e.g. reference expression profiles (data)) of at least two conditions from which at least one condition is a diseased condition (i.e. kidney cancer). For example, (i) one condition may be a healthy condition (i.e. not kidney cancer) and one condition may be a diseased condition (i.e. kidney cancer), or (ii) one condition may be a diseased condition (e.g. a specific form of kidney cancer) and one condition may be another diseased condition (i.e. specific form of kidney cancer, or other timepoint of treatment, other therapeutic treatment).

Further, the reference may be the reference expression profiles (data) of essentially the same, preferably the same, set of miRNAs of step (i), preferably in a body fluid sample originated from the same source (e.g. urine, or blood such as serum, plasma, or blood cells) as the body fluid sample from the subject (e.g. human or animal) to be tested, but obtained from subjects (e.g. human or animal) known to not suffer from kidney cancer and from subjects (e.g. human or animal) known to suffer from kidney cancer (e.g. kidney cancer, e.g. kidney cancer that has been therapeutically treated).

Preferably, both the reference expression profile and the expression profile of step (i) are determined in the same body fluid sample, e.g. urine, or blood sample including a whole blood, a blood serum sample, blood plasma sample or a blood cell sample (e.g. erythrocytes, leukocytes and/or thrombocytes). It is understood that the reference expression profile is not necessarily obtained from a single subject known to be affected by kidney cancer or known to be not affected by kidney cancer (e.g. healthy subject, such as healthy human or animal, or diseased subject, such as diseased human or animal) but may be an average reference expression profile of a plurality of subjects known to be affected by kidney cancer or known to be not affected by kidney cancer (e.g. healthy subjects, such as healthy humans or animals, or diseased subjects, such as diseased humans or animals), e.g. at least 2 to 200 subjects, more preferably at least 10 to 150 subjects, and most preferably at least 20 to 100 subjects, (e.g. healthy subject, such as healthy human or animal, or diseased subject, such as diseased human or animal). The expression profile and the reference expression profile may be obtained from a subject/patient of the same species (e.g. human or animal), or may be obtained from a subject/patient of a different species (e.g. human or animal). Preferably, the expression profile is obtained from a subject known to be affected by kidney cancer or known to be not affected by kidney cancer of the same species (e.g. human or animal), of the same gender (e.g. female or male) and/or of a similar age/phase of life (e.g. infant, young child, juvenile, adult) as the subject (e.g. human or animal) to be tested or diagnosed.

Thus, in a preferred embodiment of the method of the present invention, the reference is a reference expression profile (data) of at least one subject, preferably the reference is an average expression profile (data) of at least 2 to 200 subjects, more preferably of at least 10 to 150 subjects, and most preferably of at least 20 to 100 subjects, with one known clinical condition which is kidney cancer or a specific form of kidney cancer, or which is not kidney cancer or a specific form of kidney cancer (i.e. healthy/healthiness), wherein the reference expression profile is the profile of a set comprising at least two miRNAs that have nucleotide sequences that essentially correspond (are essentially identical), preferably that correspond (are identical), to the nucleotide sequences of the miRNAs of step (i). Preferably, the reference expression profile is the profile of a set comprising at least two miRNAs that have nucleotide sequences that essentially correspond (are essentially identical), preferably that correspond (are identical), to the nucleotide sequences of the miRNAs selected from the group consisting of SEQ ID NO: 1 to 357 or SEQ ID NO: 1 to 465, a fragment thereof, and a sequence having at least 80% sequence identity thereto of step (i).

The comparison of the expression profile of the patient to be diagnosed (e.g. human or animal) to the (average) reference expression profile may then allow for diagnosing and/or prognosing of kidney cancer or a specific form of kidney cancer (step (ii)), either the subject/patient (e.g. human or animal) to be diagnosed is healthy, i.e. not suffering from kidney cancer, or diseased, i.e. suffering from kidney cancer or a specific form of kidney cancer.

The comparison of the expression profile of the subject (e.g. human or animal) to be diagnosed to said reference expression profile(s) may then allow for the diagnosis and/or prognosis of kidney cancer (step (ii)), either the subject (e.g. human or animal) to be diagnosed is healthy, i.e. not suffering from kidney cancer, or the subject (e.g. human or animal) is diseased, i.e. suffering from kidney cancer.

The comparison of the expression profile of the patient (e.g. human or animal) to be diagnosed to said reference expression profiles may then allow for the diagnosis/prognosis of a specific form of kidney cancer (step (ii)), e.g. whether the patient to be diagnosed suffers from kidney cancer.

In a particularly preferred embodiment of the method of the present invention, the reference is an algorithm or mathematical function. Preferably, the algorithm or mathematical function is obtained on the basis of reference expression profiles (data) of at least 2 to 200 subjects, more preferably of at least 10 to 150 subjects, and most preferably of at least 20 to 100 subjects, with two known clinical conditions from which one is kidney cancer, wherein the reference expression profiles is the profile of a set comprising at least two miRNAs that have nucleotide sequences that essentially correspond (are essentially identical), preferably that correspond (are identical), to the nucleotide sequences of the miRNAs of step (i). Preferably, is the profile of a set comprising at least two miRNAs that have nucleotide sequences that essentially correspond (are essentially identical), preferably that correspond (are identical), to the nucleotide sequences of the miRNAs selected from the group consisting of SEQ ID NO: 1 to 357 or SEQ ID NO: 1 to 465, a fragment thereof, and a sequence having at least 80% sequence identity thereto of step (i).

It is preferred that the algorithm or mathematical function is obtained using a machine learning approach.

Machine learning approaches may include but are not limited to supervised or unsupervised analysis: classification techniques (e.g. naïve Bayes, Linear Discriminant Analysis, Quadratic Discriminant Analysis Neural Nets, Tree based approaches, Support Vector Machines, Nearest Neighbour Approaches), Regression techniques (e.g. linear Regression, Multiple Regression, logistic regression, probit regression, ordinal logistic regression ordinal Probit-Regression, Poisson Regression, negative binomial Regression, multinomial logistic Regression, truncated regression), Clustering techniques (e.g. k-means clustering, hierarchical clustering, PCA), Adaptations, extensions, and combinations of the previously mentioned approaches.

The inventors of the present invention surprisingly found that the application/use of a machine learning approach (e.g. t-test, AUC, support vector machine, hierarchical clustering, or k-means) leads to the obtainment of an algorithm or mathematical function that is trained by the reference expression profile(s) or reference expression profile data mentioned above (e.g. trained by the miRNA reference expression profile (data) of a diseased condition (i.e. kidney cancer or a specific form of kidney cancer), for example, obtained from subjects (e.g. humans or animals) known to suffer from kidney cancer or from a specific form of kidney cancer (i.e. being diseased) and/or a trained by the miRNA reference expression profile (data) of a healthy condition (i.e. not kidney cancer or a specific form of kidney cancer), for example, obtained from subjects (e.g. humans or animals) known to not suffer from kidney cancer or from a specific form of kidney cancer and that this allows a better (i) discrimination between the at least two (e.g. 2 or 3) clinical conditions (the at least two statistical classes, e.g. the two conditions healthy or suffering from kidney cancer or the two clinical conditions suffering from a specific form of kidney cancer or suffering from another specific form of kidney cancer or at least three clinical conditions, e.g. the three clinical conditions healthy, suffering from a specific form of kidney cancer or suffering from another specific form of kidney cancer or (ii) decision whether the at least one clinical condition (the one condition healthy or suffering from kidney cancer is present. In this way, the performance for diagnosing/prognosing of individuals suffering from kidney cancer can be increased (see also experimental section for details).

Thus, in a preferred embodiment of the method of the present invention, the algorithm or mathematical function is obtained using a machine learning approach, wherein said algorithm or mathematical function is trained by a reference expression profile (data) of at least 2 to 200 subjects, more preferably of at least 10 to 150 subjects, and most preferably of at least 20 to 100 subjects with two known clinical condition for which one is kidney cancer or a specific form of kidney cancer, wherein the reference expression profile is the profile of a set comprising at least two miRNAs that have nucleotide sequences that essentially correspond (are essentially identical), preferably that correspond (are identical), to the nucleotide sequences of the miRNAs of step (i), preferably to decide whether the at least one clinical condition which is kidney cancer or a specific form of kidney cancer.

Further, for instance, the machine learning approach may be applied to the reference expression profiles (data) of a set comprising at least 2 miRNAs (e.g. 10 miRNAs such as miRNAs according to SEQ ID NO: 1 to 10) of at least one subject (e.g. human or animal) known to suffer from kidney cancer and of at least one subject (e.g. human or animal) known to be healthy and may led to the obtainment of an algorithm or mathematical function. This algorithm or mathematical function may then be applied to a miRNA expression profile of the same at least 2 miRNAs as mentioned above (e.g. 10 miRNAs such as miRNAs according to SEQ ID NO: 1 to 10) of a subject (e.g. human or animal) to be diagnosed for kidney cancer and, thus, may then allow to discriminate whether the subject (e.g. human or animal) tested is healthy, i.e. not suffering from kidney cancer, or diseased, i.e. suffering from kidney cancer.

Additionally the algorithm may be trained to discriminate between more than 2 (e.g. 3, 4, 5 or more) clinical conditions from which at least one is kidney cancer.

Preferably, the reference and optionally the expression profile (data) of the miRNA(s) representative for kidney cancer is (are) stored in a database, e.g. an internet database, a centralized, and/or a decentralized database. It is preferred that the reference, e.g. mathematical function or algorithm, is comprised in a computer program, e.g. saved on a data carrier.

The above mentioned method is for diagnosing kidney cancer in a subject, e.g. a human or another mammal such as an animal. Preferably, the diagnosis comprises (i) determining the occurrence/presence of kidney cancer, (ii) monitoring the course of kidney cancer, (iii) staging of kidney cancer, (iv) measuring the response of a patient with kidney cancer to therapeutic intervention, and/or (v) segmentation of a subject suffering from kidney cancer.

Further, the above mentioned method is for prognosis of kidney cancer in a subject, a human or another mammal such as an animal. Preferably, the prognosis comprises (i) identifying of a subject who has a risk to develop kidney cancer, (ii) predicting/estimating the occurrence, preferably the severity of occurrence of kidney cancer, and/or (iii) predicting the response of a subject with kidney cancer to therapeutic intervention.

Further, in a preferred embodiment of the method of the present invention, for determining an expression profile of the set comprising at least two miRNAs representative for kidney cancer in a body fluid sample from a subject comprises a set of miRNAs listed in FIG. 2 or FIG. 5*b* or FIG. 9.

For example, said set comprising 30 miRNAs representative for kidney cancer in a body fluid sample from a subject comprises a set of miRNAs listed in FIG. 2 or FIG. 5b or FIG. 9. Alternatively, said set comprising 29, 28, 27, 26, 25, 24, 23, 22, 21, 20, 19, 18, 17, 16, 15, 14, 13, 12, 11, 10, 9, 8, 7, 6, 5, 4 or 3 miRNAs comprises a set of miRNAs listed in FIG. 2 or FIG. 5b or FIG. 9.

For example, said set comprising 30 miRNAs representative for kidney cancer in a body fluid sample from a subject comprises a set of miRNAs listed in FIG. 2 or FIG. 5b or FIG. 9. For example, said set comprising 25 miRNAs representative for kidney cancer in a body fluid sample from a subject comprises a set of miRNAs listed in FIG. 2 or FIG. 5b or FIG. 9. For example, said set comprising 20 miRNAs representative for kidney cancer in a body fluid sample from a subject comprises a set of miRNAs listed in FIG. 2 or FIG. 5b or FIG. 9. For example, said set comprising 15 miRNAs representative for kidney cancer in a body fluid sample from a subject comprises a set of miRNAs listed in FIG. 2 or FIG. 5b or FIG. 9. For example, said set comprising 10 miRNAs representative for kidney cancer in a body fluid sample from a subject comprises a set of miRNAs listed in FIG. 2 or FIG. 5b or FIG. 9. For example, said set comprising 5 miRNAs representative for kidney cancer in a body fluid sample from a subject comprises a set of miRNAs listed in FIG. 2 or FIG. 5b or FIG. 9.

Further, in another preferred embodiment of the method of the present invention, for determining an expression profile of the set comprising at least two miRNAs representative for kidney cancer in a body fluid sample from a subject comprises combinations of sets of miRNAs listed in FIG. 2 or FIG. 5b or FIG. 9.

For example, said set comprising 30 miRNAs representative for kidney cancer in a body fluid sample from a subject comprises at least 2 sets of miRNAs listed in FIG. 2 or FIG. 5b or FIG. 9. Alternatively, said set comprising 29, 28, 27, 26, 25, 24, 23, 22, 21, 20, 19, 18, 17, 16, 15, 14, 13, 12, 11, 10, 9, 8, 7, 6, 5 or 4 miRNAs comprises a least 2 sets of miRNAs listed in FIG. 2 or FIG. 5b or FIG. 9.

For example, said set comprising 30 miRNAs representative for kidney cancer in a body fluid sample from a subject comprises a least 2 sets of miRNAs listed in FIG. 2 or FIG. 5b or FIG. 9. For example, said set comprising 25 miRNAs representative for kidney cancer in a body fluid sample from a subject comprises a least 2 sets of miRNAs listed in FIG. 2 or FIG. 5b or FIG. 9. For example, said set comprising 20 miRNAs representative for kidney cancer in a body fluid sample from a subject comprises a least 2 sets of miRNAs listed in FIG. 2 or FIG. 5b or FIG. 9. For example, said set comprising 15 miRNAs representative for kidney cancer in a body fluid sample from a subject comprises a least 2 sets of miRNAs listed in FIG. 2 or FIG. 5b or FIG. 9. For example, said set comprising 10 miRNAs representative for kidney cancer in a body fluid sample from a subject comprises a least 2 sets of miRNAs listed in FIG. 2 or FIG. 5b or FIG. 9. For example, said set comprising 5 miRNAs representative for kidney cancer in a body fluid sample from a subject comprises a least 2 sets of miRNAs listed in FIG. 2 or FIG. 5b or FIG. 9.

In a second aspect, the invention relates to a set comprising polynucleotides for detecting a set comprising at least two miRNAs for diagnosing and/or prognosing of kidney cancer in a body fluid sample from a subject.

It is preferred that kidney cancer is renal cell carcinoma (RCC)

It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

Preferably, the nucleotide sequences of the set comprising at least two miRNAs for diagnosing and/or prognosing of kidney cancer in a body fluid sample, e.g. blood sample, from a patient, e.g. human or animal, are selected from the group consisting of SEQ ID NO: 1 to 357 or SEQ ID NO: 1 to 465.

It is preferred that the set comprising at least two miRNAs is selected from the sets of miRNAs listed in FIG. 2 or FIG. 5b or FIG. 9.

Preferably, the set comprising polynucleotides for detecting a set comprising at least two miRNAs for diagnosing and/or prognosing of kidney cancer comprises polynucleotides for detecting at least one up-regulated miRNA listed in FIG. 7a or for detecting at least one down-regulated miRNAs listed in FIG. 8a. More preferably, the set comprises polynucleotides for detecting at least one up-regulated miRNA listed in FIG. 7b or comprises polynucleotides for detecting at least one down-regulated miRNAs listed in FIG. 8b. It is further preferred, that the set comprises polynucleotides for detecting at least one up-regulated miRNA listed in FIG. 7a and further comprises polynucleotides for detecting at least one down-regulated miRNAs listed in FIG. 8a.

It is preferred that (i) the polynucleotides comprised in the set of the present invention are complementary to the miRNAs comprised in the set, wherein the nucleotide sequences of said miRNAs are preferably selected from the group consisting of SEQ ID NO: 1 to 357 or SEQ ID NO: 1 to 465, (ii) the polynucleotides comprised in the set are fragments of the polynucleotides comprised in the set according to (i), preferably the polynucleotides comprised in the set are fragments which are between 1 and 12, more preferably between 1 and 8, and most preferably between 1 and 5 or 1 and 3, i.e. 1, 2, 3, 4, 5, 6, 7, 8, 9, 10, 11, or 12, nucleotides shorter than the polynucleotides comprised in the set according to (i), or (iii) the polynucleotides comprised in the set have at least 80%, preferably at least 85%, more preferably at least 90%, and most preferably at least 95% or 99%, i.e. 80, 81, 82, 83, 84, 85, 86, 87, 88, 89, 90, 91, 92, 93, 94, 95, 96, 97, 98, or 99%, sequence identity to the polynucleotide sequences of the polynucleotides comprised in the set according to (i) or polynucleotide fragments comprised in the set according to (ii).

It is preferred that the polynucleotides of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40 or more miRNAs, or comprising/consisting of 357 (465) miRNAs and wherein the nucleotide sequences of said miRNAs are selected from the group consisting of SEQ ID NO: 1 to 357 or SEQ ID NO: 1 to 465.

It is preferred that the polynucleotides of the present invention are for detecting a set comprising, essentially consisting of, or consisting of at least 2 miRNAs, wherein the set comprising, miRNAs is selected from the set listed in FIG. 2 or FIG. 5*b* or FIG. 9.

It is preferred that the polynucleotides of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40 or more miRNAs, or comprising/consisting of 357 (465) miRNAs and wherein the set of miRNAs comprises at least one of the sets listed in FIG. 2 or FIG. 5*b* or FIG. 9.

For the body fluid sample (e.g. blood sample) analysis, it may be required that a set of polynucleotides (probes) capable of detecting a fixed defined set of miRNAs are attached to a solid support, bead, substrate, surface, platform, or matrix, e.g. biochip, which may be used for body fluid sample (e.g. blood sample) analysis. For example, if the fixed defined set of miRNAs for diagnosing kidney cancer comprises or consists of 20 miRNAs, polynucleotides capable of detecting these 20 miRNAs are attached to a solid support, substrate, surface, platform or matrix, e.g. biochip, in order to perform the diagnostic sample analysis.

Alternatively, it may be required that a set of chimeric polynucleotides (probes) capable of detecting a fixed defined set of miRNAs it contacted in solution with a sample containing miRNAs derived from a body fluid sample. The chimeric polynucleotide may comprise of a first sequence stretch that is complementary to a miRNA and a second sequence stretch that allows to pull down the chimeric polynucleotide-miRNA-duplexes to one or more solid supports (e.g. a set of beads for determining the set of miRNAs). For example, a set of 20 chimeric polynucleotides capable of detecting 20 miRNAs are contacted with sample containing miRNAs derived from a body fluid sample in order to form duplexes that can be pulled down to 20 different species of beads and detected thereon.

For example, the polynucleotides of the present invention are for detecting a set of 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 miRNAs wherein the set of miRNAs comprises at least one of the set of miRNAs listed in FIG. 2 or FIG. 5*b* or FIG. 9.

For example, the polynucleotides of the present invention are for detecting a set of 30 miRNAs wherein the set of miRNAs comprises at least one of the sets of miRNAs listed in FIG. 2 or FIG. 5*b* or FIG. 9.

For example, the polynucleotides of the present invention are for detecting a set of 25 miRNAs wherein the set of miRNAs comprises at least one of the sets of miRNAs listed in FIG. 2 or FIG. 5*b* or FIG. 9.

For example, the polynucleotides of the present invention are for detecting a set of 20 miRNAs wherein the set of miRNAs comprises at least one of the sets of miRNAs listed in FIG. 2 or FIG. 5*b* or FIG. 9.

For example, the polynucleotides of the present invention are for detecting a set of 15 miRNAs wherein the set of miRNAs comprises at least one of the sets of miRNAs listed in FIG. 2 or FIG. 5*b* or FIG. 9.

For example, the polynucleotides of the present invention are for detecting a set of 10 miRNAs wherein the set of miRNAs comprises at least one of the sets of miRNAs listed in FIG. 2 or FIG. 5*b* or FIG. 9.

For example, the polynucleotides of the present invention are for detecting a set of 5 miRNAs wherein the set of miRNAs comprises at least one of the sets of miRNAs listed in FIG. 2 or FIG. 5*b* or FIG. 9.

In a third aspect, the invention relates to the use of set of polynucleotides according to the second aspect of the invention for diagnosing and/or prognosing kidney cancer in a subject It is preferred that kidney cancer is renal cell carcinoma (RCC)

In a fourth aspect, the invention relates to a set of at least two primer pairs for determining the expression level of a set of miRNAs in a body fluid sample of a subject suffering or suspected of suffering from kidney cancer.

It is preferred that kidney cancer is renal cell carcinoma (RCC)

It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

Preferably, that the set comprising at least two miRNAs for diagnosing and/or prognosing of kidney cancer in a body fluid sample, e.g. blood sample, from a subject, e.g. patient, human or animal, are selected from the group consisting of SEQ ID NO: 1 to 357 or SEQ ID NO: 1 to 465.

It is preferred that the set comprising at least two miRNAs is selected from the sets of miRNAs listed in FIG. 2 or FIG. 5*b* or FIG. 9.

It is preferred that the set of at least two primer pairs for determining the expression level of a set of miRNAs in a body fluid sample of a subject suffering or suspected of suffering from kidney cancer are primer pairs that are specific for at least one miRNA selected from the group consisting of SEQ ID 1 to 357 or SEQ ID NO: 1 to 465.

It is preferred that the set of at least two primer pairs for determining the expression level of a set of miRNAs in a body fluid sample of a subject suffering or suspected of suffering from kidney cancer are primer pairs that are specific for at least one set of miRNAs listed in FIG. 2 or FIG. 5*b* or FIG. 9.

Preferably, the set of least two primer pairs for determining the expression level comprises primer pairs for determining at least one up-regulated miRNA listed in FIG. 7*a* or comprises primer pairs for determining at least one down-regulated miRNAs listed in FIG. 8*a*. More preferably, the set of least two primer pairs for determining the expression level comprises primer pairs for determining at least one up-regulated miRNA listed in FIG. 7*b* or comprises at least one down-regulated miRNAs listed in FIG. 8*b*. It is further preferred, that the set comprises primer pairs for determining at least one up-regulated miRNA listed in FIG. 7*a* and further comprises primer pairs for determining at least one down-regulated miRNAs listed in FIG. 8*a*.

It is preferred that the set of at least two primer pairs of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 36, 37, 38, 39, 40 or more miRNAs, or comprising/consisting of 357 (465) miRNAs and wherein the nucleotide sequences of said miRNAs are selected from the group consisting of SEQ ID NO: 1 to 357 or SEQ ID NO: 1 to 465.

It is preferred that the set of at least two primer pairs of the present invention are for detecting a set comprising, essentially consisting of, or consisting of at least 2 miRNAs, wherein the set comprising, miRNAs is selected from the set listed in FIG. 2 or FIG. 5b or FIG. 9.

It is preferred that the set of at least two primer pairs of the present invention are for detecting a set comprising, essentially consisting of, or consisting of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 36, 37, 38, 39, 40 or more miRNAs, or comprising/consisting of 357 (465) miRNAs and wherein the set of miRNAs comprises at least one of the sets listed in FIG. 2 or FIG. 5b or FIG. 9.

For example, the set of at least two primer pairs of the present invention are for detecting a set of 40 or 39 or 38 or 37 or 36 or 35 or 34 or 33 or 32 or 31 or 30 or 29 or 28 or 27 or 26 or 25 or 24 or 23 or 22 or 21 or 20 or 19 or 18 or 17 or 16 or 15 or 14 or 13 or 12 or 11 or 10 or 9 or 8 or 7 or 6 or 5 or 4 or 3 or 2 miRNAs wherein the set of miRNAs comprises at least one of the set of miRNAs listed in FIG. 2 or FIG. 5b or FIG. 9.

For example, the set of primer pairs of the present invention are for detecting a set of 30 miRNAs wherein the set of miRNAs comprises at least one of the sets of miRNAs listed in FIG. 2 or FIG. 5b or FIG. 9. For example, the set of primer pairs of the present invention are for detecting a set of 25 miRNAs wherein the set of miRNAs comprises at least one of the sets of miRNAs listed in FIG. 2 or FIG. 5b or FIG. 9. For example, the set of primer pairs of the present invention are for detecting a set of 20 miRNAs wherein the set of miRNAs comprises at least one of the sets of miRNAs listed in FIG. 2 or FIG. 5b or FIG. 9. For example, the set of primer pairs of the present invention are for detecting a set of 15 miRNAs wherein the set of miRNAs comprises at least one of the sets of miRNAs listed in FIG. 2 or FIG. 5b or FIG. 9. For example, the set of primer pairs of the present invention are for detecting a set of 10 miRNAs wherein the set of miRNAs comprises at least one of the sets of miRNAs listed in FIG. 2 or FIG. 5b or FIG. 9.

Preferably, the said primer pairs may be used for amplifying cDNA transcripts of the set of miRNAs selected from the group consisting of SEQ ID NO: 1 to 357 or SEQ ID NO: 1 to 465. Furthermore, the said primer pairs may be used for amplifying cDNA transcripts of the set of miRNAs listed in FIG. 2 or FIG. 5b or FIG. 9

It is understood that the primer pairs for detecting a set of miRNAs may consist of specific and or non-specific primers. Additionally, the set of primer pairs may be complemented by other substances or reagents (e.g. buffers, enzymes, dye, labelled probes) known to the skilled in the art for conducting real time polymerase chain reaction (RT-PCR)

In a fifth aspect, the invention relates to the use of a set of primer pairs according to the fourth aspect of the invention for diagnosing and/or prognosing kidney cancer in a subject It is preferred that kidney cancer is renal cell carcinoma (RCC)

In a sixth aspect, the invention relates to means for diagnosing and/or prognosing of kidney cancer in a body fluid sample of a subject.

Preferably, the invention relates to means for diagnosing and/or prognosing of kidney cancer in a body fluid sample of a subject comprising
(i) a set of at least two polynucleotides according to the second aspect of the invention or
(ii) a set of at least two primer pairs according the fourth aspect of the invention.

It is preferred that kidney cancer is renal cell carcinoma (RCC)

It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

Preferably, that the set of at least two polynucleotides or the set of at least 2 primer pairs are for detecting a set comprising at least two miRNAs for diagnosing and/or prognosing of kidney cancer in a body fluid sample, e.g. blood sample, from a subject, e.g. patient, human or animal, wherein the set of miRNAs is selected from the group consisting of SEQ ID NO: 1 to 357 or SEQ ID NO: 1 to 465.

It is preferred that the set of at least two polynucleotides or the set of at least 2 primer pairs are for detecting a set comprising at least two miRNAs for diagnosing and/or prognosing of kidney cancer in a body fluid sample, e.g. blood sample, from a subject, e.g. patient, human or animal, wherein the set of miRNAs is selected from the sets of miRNAs listed in FIG. 2 or FIG. 5b or FIG. 9.

It is preferred that the set of at least two primer pairs for determining the expression level of a set of miRNAs in a body fluid sample of a subject suffering or suspected of suffering from kidney cancer are primer pairs that are specific for at least two miRNAs selected from the group consisting of SEQ ID NO: 1 to 357 or SEQ ID NO: 1 to 465.

It is preferred that the set of at least two primer pairs for determining the expression level of a set of miRNAs in a body fluid sample of a subject suffering or suspected of suffering from kidney cancer are primer pairs that are specific for at least one set of miRNAs listed in FIG. 2 or FIG. 5b or FIG. 9.

It is preferred that the subject is a mammal including both a human and another mammal, e.g. an animal such as a mouse, a rat, a rabbit, or a monkey. It is particularly preferred that the subject is a human.

The present invention provides means for diagnosing and/or prognosing of kidney cancer comprising a set comprising, essentially consisting of, or consisting of at least two polynucleotides (probes) according to the second aspect of the present invention, e.g. a polynucleotide for detecting a set comprising, essentially consisting of, or consisting of at least 2 polynucleotides, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or up to 357 (465) or more polynucleotides for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 or 357 (465) miRNAs or all known miRNAs, wherein the nucleotide sequence of said miRNAs are preferably selected from the group consisting of SEQ ID NO: 1 to 357 or SEQ ID NO: 1 to 465 or SEQ ID NO: 1 to 465 or SEQ ID NO: 1 to 465 or SEQ ID NO: 1 to 465, a fragment thereof, and a sequence having at least 80% sequence identity thereto.

The means for diagnosing and/or prognosing of kidney cancer comprises, essentially consists of, or consists of a solid support, substrate, surface, platform or matrix comprising a set comprising, essentially consisting of, or consisting of at least two polynucleotides (probes) according to the second aspect of the present invention, e.g. a solid support, substrate, surface, platform or matrix comprising at least 2 polynucleotides, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more polynucleotides, or comprising/consisting of 357 (465) polynucleotides for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more miRNAs, or comprising/consisting of 357 (465) miRNAs, wherein the nucleotide sequence said miRNAs are preferably selected from the group consisting of SEQ ID NO: 1 to 357 or SEQ ID NO: 1 to 465, a fragment thereof, and a sequence having at least 80% sequence identity thereto. Preferably, the above mentioned polynucleotide(s) is (are) attached or immobilized to the solid support, substrate, surface, platform or matrix. It is possible to include appropriate controls for non-specific hybridization on the solid support, substrate, surface, platform or matrix.

Additionally, the means for diagnosing and/or prognosing of kidney cancer comprises, essentially consists of, or consists of a solid support, substrate, surface, platform or matrix comprising a set comprising, essentially consisting of, or consisting of at least two polynucleotides (probes) according to the second aspect of the present invention, e.g. a solid support, substrate, surface, platform or matrix comprising at least 2 polynucleotides, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more polynucleotides, or comprising/consisting of 357 (465) polynucleotides for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more miRNAs, or comprising/consisting of 357 (465) miRNAs, wherein the set of miRNAs comprises at least one set of miRNAs listed in FIG. 2 or FIG. 5b or FIG. 9. Preferably, the above mentioned polynucleotides are attached or immobilized to the solid support, substrate, surface, platform or matrix. It is possible to include appropriate controls for non-specific hybridization on the solid support, substrate, surface, platform or matrix.

It is particularly preferred that said means for diagnosing and/or prognosing of kidney cancer comprise, essentially consists of, or consists of a microarray/biochip comprising at least two polynucleotides according to the second aspect of the present invention.

It is also preferred that said means for diagnosing and/or prognosing of kidney cancer comprise, essentially consists of, or consists of a set of beads comprising a at least two polynucleotides according to the second aspect of the present invention. It is especially preferred that the beads are employed within a flow cytometer setup or a setup for analysing magnetic beads for diagnosing and/or prognosing of kidney cancer, e.g. in a LUMINEX system (www.luminexcorp.com)

Additionally, the present invention provides means for diagnosing and/or prognosing of kidney cancer comprising a set comprising, essentially consisting of, or consisting of at least two primer pairs according to the fourth aspect of the present invention, e.g. of at least 2 primer pairs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or up to 357 (465) or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 357 (465) miRNAs or all known miRNAs, wherein the nucleotide sequence of said miRNA or the nucleotide sequences of said miRNAs is (are) preferably selected from the group consisting of SEQ ID NO: 1 to 357 or SEQ ID NO: 1 to 465, a fragment thereof, and a sequence having at least 80% sequence identity thereto.

Also, the present invention provides means for diagnosing and/or prognosing of kidney cancer comprising a set comprising, essentially consisting of, or consisting of at least two primer pairs according to the fourth aspect of the present invention, e.g. of at least 2 primer pairs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or up to 357 (465) or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or 357 (465) miRNAs or all known miRNAs, wherein the set of miRNAs comprises at least one set of miRNAs listed in FIG. 2 or FIG. 5b or FIG. 9.

In a seventh aspect, the invention relates to a kit for diagnosing and/or prognosing of kidney cancer in a subject.

Preferably, the invention relates to a kit for diagnosing and/or prognosing of kidney cancer comprising
(i) means for determining an expression profile of a set comprising at least two miRNAs representative for kidney cancer in a body fluid sample from a subject, and
(ii) at least one reference.

It is preferred that kidney cancer is renal cell carcinoma (RCC)

It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

The present invention provides a kit for diagnosing and/or prognosing of kidney cancer comprising
(i) means for determining an expression profile of a set comprising, essentially consisting of, or consisting of at least two miRNAs (e.g. human miRNAs or miRNAs from another mammal such as an animal (e.g. mouse miRNA or rat miRNAs)), preferably comprising, essentially consisting of, or consisting of at least 2 or up to 357 (465) or more polynucleotides or alternatively a set of at least 2 or up to 357 (465) or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more or 357 (465) miRNAs or all known miRNAs, representative for kidney cancer in a biological sample (e.g. a body fluid samples or a blood sample) from a subject (e.g. human or animal), wherein the nucleotide sequence of said miRNA or the nucleotide sequences of said miRNAs is (are) preferably selected from the group consisting of SEQ ID NO: 1 to 357 or SEQ ID NO: 1 to 465, a fragment thereof, and a sequence having at least 80% sequence identity thereto; and (ii) at least one reference.

The present invention provides a kit for diagnosing and/or prognosing of kidney cancer comprising (i) means for determining an expression profile of a set comprising, essentially consisting of, or consisting of at least two miRNAs (e.g. human miRNAs or miRNAs from another mammal such as an animal (e.g. mouse miRNA or rat miRNAs)), preferably comprising, essentially consisting of, or consisting of at least 2 or up to 357 (465) or more polynucleotides or alternatively a set of at least 2 or up to 357 (465) or more primer pairs for detecting a set comprising, essentially consisting of, or consisting of at least 2 miRNAs, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more or 357 (465) miRNAs or all known miRNAs, representative for kidney cancer in a biological sample (e.g. a body fluid samples or a blood sample) from a subject (e.g. human or animal), wherein the set of miRNAs comprises at least one of the set of miRNAs listed in FIG. 2 or FIG. 5b or FIG. 9.

(ii) at least one reference.

Said means may comprise a set comprising, essentially consisting of, or consisting of at least two polynucleotides according to the second aspect of the present invention, a set of at least 2 primer pairs according to the fourth aspect of the invention; means according to the sixth aspect of the present invention; primers suitable to perform reverse transcriptase reaction and/or real time polymerase chain reaction such as quantitative polymerase chain reaction; and/or means for conducting next generation sequencing.

It is particularly preferred that said kit comprises (ia) a set comprising, essentially consisting of, or consisting of at least two polynucleotides according to the second aspect of the present invention, or a set of primer pairs according to the fourth aspect of the invention and (ib) optionally at least one of the means selected from the group consisting of: at least one biological sample, for example, tissue sample or body fluid sample, e.g. a blood sample, e.g. whole blood, serum, plasma, or blood cells, of a subject (e.g. human or animal), at least one sample of total RNA extracted from said biological sample, for example, body fluid sample, tissue sample or blood sample, e.g. whole blood, serum, plasma, or blood cells, of a patient (e.g. human or animal), and means to extract RNA from a body fluid sample, e.g. blood sample, e.g. for determining an expression profile of a set comprising, essentially consisting of, or consisting of at least two miRNAs representative for kidney cancer in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 357 or SEQ ID NO: 1 to 465, a fragment thereof, and a sequence having at least 80% sequence identity thereto.

It is more particularly preferred that said kit comprises (ia) a solid support, substrate, surface, platform or matrix (e.g a microarray of a set of beads) according to the third aspect of the present invention comprising a polynucleotide or a set comprising, essentially consisting of, or consisting of at least two polynucleotides according of the first aspect of the present invention, and (ib) optionally at least one of the means selected from the group consisting of: at least one body fluid sample, for example, tissue or blood sample, e.g. serum, plasma, or blood cells, from a patient (e.g. human or animal), at least one sample of total RNA (or fractions thereof, e.g. miRNA) extracted from a body fluid sample, for example, tissue or blood sample, e.g. serum, plasma, or blood cells, from a patient (e.g. human or animal), means to extract total RNA (or fractions thereof, e.g. miRNA) from a body fluid sample (e.g. blood sample), means for input/injection of a body fluid sample (e.g. blood sample), positive controls for the hybridization experiment, means for holding the solid support, substrate, platform or matrix comprising the polynucleotide(s) (probe(s)), means for labelling the isolated miRNA (e.g. NTP/biotin-NTP), means for hybridization, means to carry out enzymatic reactions (e.g. exonuclease I and/or Klenow enzyme) means for washing steps, means for detecting the hybridization signal, and mean for analysing the detected hybridization signal, e.g. for determining an expression profile of a miRNA or a set comprising, essentially consisting of, or consisting of at least two miRNAs representative for kidney cancer in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 357 or SEQ ID NO: 1 to 465, a fragment thereof, and a sequence having at least 80% sequence identity thereto.

Preferably, the above mentioned set comprising, essentially consisting of, or consisting of at least two polynucleotides are attached or immobilized to the solid support, substrate, surface, platform or matrix, e.g. to a microarray or to a set of beads.

Preferably, the above mentioned set comprising, essentially consisting of, or consisting of at least two polynucleotides is (are) attached or immobilized to microarray/biochip.

It is particularly preferred that said kit comprises (ia) a miRNA-specific primer for reverse transcription of miRNA in miRNA-specific cDNA for a single miRNA (e.g. human miRNA or miRNA from another mammal such as an animal (e.g. mouse or rat miRNA)) or at least two miRNA-specific primers for reverse transcription of miRNAs in miRNA-specific cDNAs for at least 2 miRNAs (e.g. human miRNAs or miRNAs from another mammal such as an animal (e.g. mouse or rat miRNAs)), preferably for at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more, or 357 (465) miRNAs (e.g. human miRNAs or miRNAs from another mammal such as an animal (e.g. mouse or rat miRNAs)), comprised in a set of miRNAs, wherein the nucleotide sequence of said miRNA or the nucleotide sequences of said miRNAs is (are) preferably selected from the group consisting of SEQ ID NO: 1 to 357 or SEQ ID NO: 1 to 465, and (ib) preferably, a primer set comprising a forward primer which is specific for the cDNA obtained from the miRNA and an universal reverse primer for amplifying the cDNA obtained from the miRNA via real time polymerase chain reaction (RT-PCR) such as real time quantitative polymerase chain reaction (RT qPCR) for the single cDNA obtained from the miRNA or at least two primer sets comprising a forward primer which is specific for the single cDNA obtained from the miRNA and an universal reverse primer for amplifying the cDNA obtained from the miRNA via real time polymerase chain reaction (RT-PCR) such as real time quantitative polymerase chain reaction (RT qPCR) for at least 2, preferably for at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more or 357 (465) cDNAs obtained from the miRNAs comprised in the set of miRNAs, wherein preferably said cDNA is complementary to the nucleotide sequence of the miRNA or said cDNAs are complementary to the nucleotide sequences of the miRNAs selected from the group consisting of SEQ ID NO: 1 to 357 or SEQ ID NO: 1 to 465, and (ic) optionally at least one of the means selected from the group consisting of: at least one body fluid sample, for example, tissue or blood sample, e.g. serum, plasma, or blood cells, from a patient (e.g. human or animal), at least one sample of total RNA (or fractions thereof, e.g. miRNA) extracted from a body fluid sample, for example, tissue or blood sample, e.g. serum, plasma, or blood cells, form a patient (e.g. human or animal), means to extract total RNA (or fractions thereof, e.g. miRNA) from a body fluid sample (e.g. blood sample), additional means to carry out the reverse transcriptase reaction (miRNA in cDNA) (e.g. reverse transcriptase (RT) enzyme, puffers, dNTPs, RNAse inhibitor), additional means to carry out real time polymerase chain reaction (RT-PCR) such as real time quantitative PCR (RT qPCR) (e.g. enzymes, puffers, water), means for labelling (e.g. fluorescent label and/or quencher), positive controls for reverse transcriptase reaction and real time PCR, and means for analysing the real time polymerase chain reaction (RT-PCR) result, e.g. for determining an expression profile of a miRNA or a set comprising, essentially consisting of, or consisting of at least 2, preferably comprising, essentially consisting of, or consisting of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more, or 357 (465) miRNAs representative for kidney cancer in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 357 or SEQ ID NO: 1 to 465, a fragment thereof, and a sequence having at least 80% sequence identity thereto.

The primer as defined above may also be an oligo-dT primer, e.g. if the miRNA comprises a polyA tail (e.g. as a result of a miRNA elongation, for example, subsequent to RNA extraction) or a miRNA specific looped RT primer (Please amend/adapted if required).

It is also preferred that said kit comprises means for conducting next generation sequencing in order to determine an expression profile of a (single) miRNA or a set comprising, essentially consisting of, or consisting of at least 2 miRNAs representative for kidney cancer in a body fluid sample (e.g. blood sample) from a patient (e.g. human or animal), wherein the nucleotide sequence of said miRNA or the nucleotide sequences of said miRNAs is (are) preferably selected from the group consisting of SEQ ID NO: 1 to 357 or SEQ ID NO: 1 to 465, a fragment thereof, and a sequence having at least 80% sequence identity thereto. Preferably, said kit further comprises means selected from the group consisting of: at least one body fluid sample, for example, tissue or blood sample, e.g. blood serum, blood plasma, or blood cells from a patient (e.g. human or animal), at least one sample of total RNA (or fractions thereof, e.g. miRNA) extracted from the body fluid sample (e.g. tissue or blood sample) of a patient (e.g. human or animal), and means to extract total RNA (or fractions thereof, e.g. miRNA) from a body fluid sample (e.g. blood sample).

The above mentioned kits further comprise at least one reference (ii). A comparison to said reference may allow for the diagnosis and/or prognosis of kidney cancer. Said reference may be the reference (e.g. reference expression profile (data)) of a healthy condition (i.e. not kidney cancer or a specific form of kidney cancer), may be the reference (e.g. reference expression profile (data)) of a diseased condition (i.e. kidney cancer), or may be the reference (e.g. reference expression (data)) of at least two conditions from which at least one condition is a diseased condition (i.e. kidney cancer).

It is preferred that said reference is a reference expression profile (data) of at least one subject (e.g. human or animal), preferably the reference is an average expression profile (data) of at least 2 to 200 subjects, more preferably at least 10 to 150 subjects, and most preferably at least 20 to 100 subjects, with one known clinical condition which is kidney cancer or a specific form of kidney cancer, or which is not kidney cancer or not a specific form of kidney cancer (i.e. healthy/healthiness), wherein the reference expression profile of a set comprising at least two miRNAs that have nucleotide sequences that essentially correspond (are essentially identical), preferably that correspond (are identical), to the nucleotide sequences of the miRNAs which expression profile is determined by the means of (i).

It is also preferred that said reference are (average) reference expression profiles (data) of at least two subjects, preferably of at least 2 to 200 subjects, more preferably of at least 10 to 150 subjects, and most preferably of at least 20 to 100 subjects, with at least two known clinical conditions, preferably at least 2 to 5, more preferably at least 2 to 4 (i.e. at least 2, 3, 4, or 5) known clinical conditions, from which at least one is kidney cancer), wherein the reference expression profiles are the profiles of a set comprising at least two miRNAs that have nucleotide sequences that essentially correspond (are essentially identical), preferably that correspond (are identical), to the nucleotide sequences of the miRNAs which expression profile is determined by the means of (i).

It is preferred that the reference is generated from expression profiles (data) obtained from 2 clinical conditions, which are kidney cancer and healthy control.

Preferably, (i) the (average) reference expression profile (data), which is provided with the kit, is determined in the same type of body fluid sample (e.g. blood and/or urine sample) and/or obtained from (control) subject(s) of the same species, gender and/or of similar age/stage of life, or (ii) the (average) reference expression profiles (data), which are provided with the kit, are determined in the same type of body fluid sample (e.g. blood and/or urine sample) and/or are obtained from (control) subject(s) of the same species, gender and/or of similar age/stage of life.

Said reference, preferably said (average) reference expression profile(s) (data) may be comprised in an information leaflet (e.g. for comparing tested single reference miRNA biomarkers with the expression profile data of a patient to be diagnosed) or saved on a data carrier (e.g. for comparing tested sets of miRNA biomarkers with the expression profile data of a patient to be diagnosed). Said reference, preferably said (average) reference expression profile(s) (data) may also be comprised in a computer program which is saved on a data carrier. The kit may alternatively comprise an access code which allows the access to a database, e.g. an internet database, a centralized or a decentralized database, where said reference, preferably said (average) reference expression profile(s) (data) is (are) comprised.

It is particularly preferred that the reference is an algorithm or mathematical function.

Preferably the algorithm or mathematical function is obtained from a reference expression profile (data) of at least one subject, preferably the algorithm or mathematical function is obtained from an average reference expression profile (data) of at least 2 to 200 subjects, more preferably of at least 10 to 150 subjects, and most preferably of at least 20 to 100 subjects, i.e. of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with one known clinical condition which is kidney cancer or a specific form of kidney cancer, or which is not kidney cancer or a specific form of kidney cancer (i.e. healthy/healthiness), wherein the reference expression profile is the profile of a single miRNA that has a nucleotide sequence that essentially corresponds (is essentially identical), preferably that corresponds (is identical), to the nucleotide sequence of the miRNA which expression profile is determined by the means of (i), or is the profile of a set comprising at least two miRNAs that have nucleotide sequences that essentially correspond (are essentially identical), preferably that correspond (are identical), to the nucleotide sequences of the miRNAs which expression profile is determined by the means of (i).

It is also preferred that the algorithm or mathematical function is obtained from (average) reference expression profiles (data) of at least two subjects, preferably of at least 2 to 200 subjects, more preferably of at least 10 to 150 subjects, and most preferably of at least 20 to 100 subjects, i.e. of at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 subjects, with at least two known clinical conditions, preferably at least 2 to 5, more preferably at least 2 to 4 (i.e. at least 2, 3, 4, or 5) known clinical conditions, from which at least one is kidney cancer, wherein the reference expression profiles are the profiles of a single miRNA that has a nucleotide sequence that essentially corresponds (is essentially identical), preferably that corresponds (is identical), to the nucleotide sequence of the miRNA which expression profile is determined by the means of (i) or are the profiles of a set comprising at least two miRNAs that have nucleotide sequences that essentially correspond (are essentially identical), preferably that correspond (are identical), to the nucleotide sequences of the miRNAs which expression profile is determined by the means of (i).

It is preferred that the algorithm or mathematical function is obtained using a machine learning approach (see second aspect of the present invention).

Preferably, the algorithm or mathematical function is saved on a data carrier comprised in the kit or the computer program, wherein the algorithm or mathematical function is comprised, is saved on a data carrier comprised in the kit. Said kit may alternatively comprise an access code which allows the access to an internet page, where the algorithm or mathematical function is saved or where the computer program, wherein the algorithm or mathematical function is comprised, can be downloaded.

Preferably, the algorithm or mathematical function is saved on a data carrier or the algorithm or mathematical function is comprised in a computer program which is saved on a data carrier. Said kit may alternatively comprise an access code which allows the access to a database or an internet page, where the algorithm or mathematical function is comprised, or where a computer program comprising the algorithm or mathematical function can be downloaded.

More than one reference may be comprised in the kit, e.g. 2, 3, 4, 5, or more references. For example, the kit may comprise reference data, preferably (average) reference expression profile(s) (data), which may be comprised in an information leaflet or saved on a data carrier. In addition, the kit may comprise more than one algorithm or mathematical function, e.g. two algorithms or mathematical functions, e.g. one trained to discriminate between a healthy condition and kidney cancer and one trained to discriminate between specific forms of kidney cancer, e.g. comprised in a computer program, preferably stored on a data carrier.

In an eighth aspect, the invention relates to a set of miRNAs isolated from a body fluid sample from a subject for diagnosing and/or prognosing of kidney cancer, wherein the miRNAs are selected from the group consisting of SEQ ID NO: 1 to 357 or SEQ ID NO: 1 to 465.

It is preferred that kidney cancer is renal cell carcinoma (RCC)

It is preferred that the body fluid sample is a blood sample, particularly preferred it is a whole blood, a blood cell, a PBMC, a serum, a plasma or a leukocyte sample, more particularly preferred it is a leukocyte-containing sample or a leukocyte-, erythrocyte- and/or a platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

It is preferred that the predetermined set of miRNAs comprises miRNAs that are differentially regulated in blood samples from kidney cancer patients as compared to healthy controls.

Preferably, the predetermined set comprising at least two miRNAs that are differentially regulated in blood samples from kidney cancer patients as compared to healthy controls is selected from the set of miRNAs listed in FIG. 2 or FIG. 5b or FIG. 9.

It is preferred that the predetermined set comprising at least two miRNAs that are differentially regulated in blood samples from kidney cancer patients as compared to healthy controls comprises at least one set of miRNAs listed in FIG. 2 or FIG. 5b or FIG. 9

Preferably, the set of miRNAs isolated from a body fluid sample comprises at least one up-regulated miRNA listed in FIG. 7a or comprises at least one down-regulated miRNAs listed in FIG. 8a. More preferably, the of miRNAs isolated from a body fluid sample comprises at least one up-regulated miRNA listed in FIG. 7b or comprises at least one down-regulated miRNAs listed in FIG. 8b. It is further preferred, that of miRNAs isolated from a body fluid sample at least two miRNAs comprises at least one up-regulated miRNA listed in FIG. 7 and further comprises at least one down-regulated miRNAs listed in FIG. 8.

In a ninth aspect, the invention relates to the use of a set of miRNAs according to the eighth aspect of the invention for diagnosing and/or prognosing of kidney cancer in a subject, In a further aspect, the present invention relates to a method for determining the status and/or the response of the immune system in a subject having or suspected of having kidney cancer, comprising the steps of:
(i.) determining an expression profile of a set comprising at least two miRNAs representative for the status and/or the response of the immune system in a body fluid sample from a subject, and
(ii) comparing said expression profile to a reference, wherein the comparison of said expression profile to said reference allows for determining the status and/or the response of the immune system in said subject It is preferred that the body fluid sample is a blood sample, particularly preferred it is a whole blood, PBMC, serum, plasma or leukocyte sample, more particularly preferred it is a blood cell sample, preferably a leukocyte-, erythrocyte and/or platelet-containing sample.

It is further preferred that the body fluid sample is a blood sample that has been collected under conditions where the RNA-fraction is guarded against degradation, preferably the blood sample is collected in a PAXgene (RNA) Tube.

It is preferred that the subject is a mammal including both a human and another mammal, e.g. an animal such as a mouse, a rat, a rabbit, or a monkey. It is particularly preferred that the subject is a human.

Preferably, the set comprising at least two miRNAs is from the group consisting of SEQ ID NO: 1 to 465.

It is preferred that the set comprising at least two miRNAs is selected from the set of miRNAs listed in FIG. 2 or FIG. 9.

It is preferred that the set comprising at least two miRNAs comprises at least one set of miRNAs listed in FIG. 2 or FIG. 9.

Preferably, the set comprising at least two miRNAs in the method for determining the status and/or the response of the immune system in a subject having or suspected of having kidney cancer comprises at least one up-regulated miRNA listed in FIG. 7a or comprises at least one down-regulated miRNAs listed in FIG. 8a. More preferably, the set comprising at least two miRNAs comprises at least one up-regulated miRNA listed in FIG. 7b or comprises at least one down-regulated miRNAs listed in FIG. 8b. It is further preferred, that the set comprising at least two miRNAs comprises at least one up-regulated miRNA listed in FIG. 7a and further comprises at least one down-regulated miRNAs listed in FIG. 8a.

It is preferred that the determining the expression profile of a set comprising at least two miRNAs selected from the group consisting of SEQ ID NO: 1 to 465 is for or is representative for determining the status and/or the response of the immune system in a body fluid sample, preferably in a blood sample, of the subject having of suspected of having kidney cancer.

It is further preferred that the determination of the status and/or the response of the immune system in a body fluid sample or blood sample, allows for a diagnosis in the subject having or suspected of having kidney cancer.

Preferably, the determination of the status and/or the response of the immune system in a body fluid sample or blood sample, allows for a treatment decision in said subject.

In a further aspect, the present invention relates to a method for diagnosing and/or prognosing of kidney cancer comprising the steps of:
(i) providing a set comprising at least two polynucleotides according to the second aspect of the present invention for detecting a set comprising at least two miRNAs representative for kidney cancer in a body fluid sample (e.g. blood sample) from a patient (e.g. human or animal),
wherein the nucleotide sequence of said miRNA or the nucleotide sequences of said miRNAs is (are) preferably selected from the group consisting of SEQ ID NO: 1 to 357 or SEQ ID NO: 1 to 465, a fragment thereof, and a sequence having at least 80% sequence identity thereto,
(ii) using the polynucleotide(s) provided in (i) for determining an miRNA expression profile in a body fluid sample (e.g. blood sample) from a patient (e.g. human or animal) with an unknown clinical condition,
(iii) comparing said expression profile to a reference,
(iv) diagnosing or prognosing the clinical condition of the patient (e.g. human or animal) on the basis of said comparison.

The term "patient with an unknown clinical condition" refers to a patient (e.g. human or animal) which may suffer from kidney cancer (i.e. diseased patient) or may not suffer from kidney cancer (i.e. healthy patient). The patient (e.g. human or animal) to be diagnosed may further suffer from a specific type of kidney cancer. It is also possible to determine, whether the patient (e.g. human or animal) to be diagnosed will develop the above mentioned disease as the inventors of the present invention surprisingly found that miRNAs representative for kidney cancer are already present in the body fluid sample, e.g. blood sample, before kidney cancer occurs or during the early stage of kidney cancer. It should be noted that a patient that is diagnosed as being healthy, i.e. not suffering from kidney cancer, may possibly suffer from another disease not tested/known.

In summary, the present invention is composed of the following items:
1. A method for diagnosing and/or prognosing of kidney cancer comprising the steps of:
    (i) determining an expression profile of a set comprising at least two miRNAs representative for kidney cancer in a body fluid sample from a subject, and
    (ii) comparing said expression profile to a reference, wherein the comparison of said expression profile to said reference allows for the diagnosis and/or prognosis of kidney cancer,
    wherein the nucleotide sequences of the miRNAs comprised in the set are selected from the group consisting of SEQ ID NO: 1 to 357 or SEQ ID NO: 1 to 465, a fragment thereof, and a sequence having at least 80% sequence identity thereto.
2. The method of item 1, wherein kidney cancer is renal cell carcinoma (RCC)
3. The method of item 1 or 2, wherein the body fluid sample is a blood sample.
4. The method of item 2 or 3, wherein the blood sample is selected from whole blood, PBMC, serum, plasma, a leukocyte sample, a blood cell sample, a leukocyte-, erythrocyte- and/or platelet-containing sample.
5. The method of any of the items 1 to 4, wherein the set of miRNAs comprises at least one of the sets of miRNAs listed in FIG. 2 or FIG. 5b or FIG. 9.
6. The method of any of the items 1 to 5, wherein the set of miRNAs comprises at least one up-regulated miRNA listed in FIG. 7a or 7b.

7. The method of any of the items 1 to 5, wherein the set of miRNAs comprises at least one down-regulated miRNA listed in FIG. 8a or 8b.
8. The method of any of the items 1 to 5, wherein the set of miRNAs comprises at least one up-regulated miRNA listed in FIG. 7a or 7b and at least one down-regulated miRNA listed in FIG. 8a or 8b.
9. The method according to any of the items 1 to 8, wherein the reference are reference expression profiles of at least two subjects with at least two known clinical conditions from which at least one is kidney cancer, wherein the reference expression profiles are the profiles of a set comprising at least two miRNAs that have nucleotide sequences that correspond to the nucleotide sequences of the miRNAs of step (i).
10. The method according to any of the items 1 to 8, wherein the reference is an algorithm or mathematical function that is obtained from reference expression profiles of at least two subjects with at least two known clinical conditions from which at least one is kidney cancer, wherein the reference expression profiles are the profiles of a set comprising at least two miRNAs that have nucleotide sequences that correspond to the nucleotide sequences of the miRNAs of step (i).
11. A set comprising polynucleotides for detecting a set comprising at least two miRNAs for diagnosing and/or prognosing of kidney cancer in a body fluid sample from a subject, wherein the nucleotide sequences of the miRNAs comprised in the set are selected from the group consisting of SEQ ID NO: 1 to 357 or SEQ ID NO: 1 to 465.
12. The set comprising polynucleotides of item 11, wherein kidney cancer is renal cell carcinoma (RCC)
13. The set comprising polynucleotides of any of the items 11 to 12 wherein the body fluid sample is a blood sample
14. The set comprising polynucleotides of item 13, wherein the blood sample is selected from whole blood, PBMC, serum, plasma, a leukocyte sample, a blood cell sample, a leukocyte-, erythrocyte- and/or platelet-containing sample.
15. The set comprising polynucleotides of any of the items 11 to 14, wherein set comprising at least two miRNAs is selected form the set of miRNAs listed in FIG. 2 or FIG. 5b or FIG. 9.
16. The set comprising polynucleotides of any of the items 11 to 14, wherein the nucleotide sequences of the miRNAs comprised in the set are selected from the set of miRNAs listed in FIG. 2 or FIG. 5b or FIG. 7.
17. The set comprising polynucleotides of any of the items 11 to 16, wherein the set of miRNAs comprises at least one up-regulated miRNA listed in FIG. 7a or 7b.
18. The set comprising polynucleotides of any of the items 11 to 16, wherein the set of miRNAs comprises at least one down-regulated miRNA listed in FIG. 8a or 8b.
19. The set comprising polynucleotides of any of the items 11 to 16, wherein the set of miRNAs comprises at least one up-regulated miRNA listed in FIG. 7a or 7b and at least one down-regulated miRNA listed in FIG. 8a or 8b
20. The set comprising polynucleotides according to any of the items 11 to 19, wherein
   (i) the polynucleotides comprised in the set are complementary to the miRNAs comprised in the set according to items 11 or 19,
   (ii) the polynucleotides comprised in the set are fragments of the polynucleotides comprised in the set according to (i), or
   (iii) the polynucleotides comprised in the set have at least 80% sequence identity to the polynucleotide sequences of the polynucleotides comprised in the set according to (i) or polynucleotide fragments comprised in the set according to (ii).
21. Use of set of polynucleotides according to any of the items 11 to 20 for diagnosing and/or prognosing kidney cancer in a subject
22. A set of at least two primer pairs for determining the expression level of a set of miRNAs in a body fluid sample of a subject suffering or suspected of suffering from kidney cancer, wherein the primer pairs are specific for at least two miRNAs selected from the group consisting of SEQ ID NO: 1 to 357 or SEQ ID NO: 1 to 465
23. The set of primer pairs of item 22, wherein kidney cancer is renal cell carcinoma (RCC)
24. The set of primer pairs of items 22 or 23, wherein the body fluid sample is a blood sample.
25. The set of primer pairs of item 24, wherein the blood sample is selected from whole blood, PBMC, serum, plasma, a leukocyte sample, a blood cell sample, a leukocyte-, erythrocyte- and/or platelet-containing sample.
26. The set of primer pairs of any of the items 22 to 25, wherein the sets of miRNAs comprises at least one of the sets of miRNAs listed in FIG. 2 or FIG. 5b or FIG. 9.
27. The set of primer pairs of any of the items 22 to 26, wherein the set of miRNAs comprises at least one up-regulated miRNA listed in FIG. 7a or 7b.
28. The set of primer pairs of any of the items 22 to 26, wherein the set of miRNAs comprises at least one down-regulated miRNA listed in FIG. 8a or 8b.
29. The set of primer pairs of any of the items 22 to 26, wherein the set of miRNAs comprises at least one up-regulated miRNA listed in FIG. 7a or 7b and at least one down-regulated miRNA listed in FIG. 8a or 8b.
30. Use of set of primer pairs according to any of the items 22 to 29 for diagnosing and/or prognosing kidney cancer in a subject
31. Means for diagnosing and/or prognosing of kidney cancer in a body fluid sample of a subject comprising:
   (i) a set of at least two polynucleotides according to any of the items 11 to 19 or
   (ii) a set of primer pairs according to any of the items 21 to 27.
32. The means of item 29, wherein said means comprise a biochip, a RT-PCT system, a PCR-system, a flow cytometer or a next generation sequencing system.
33. The means of item 31 or 32, wherein kidney cancer is renal cell carcinoma (RCC)
34. The means of any of the items 31 or 33, wherein the body fluid sample is a blood sample.
35. The means of item 34, wherein the blood sample is selected from whole blood, PBMC, serum, plasma, a leukocyte sample, a blood cell sample, a leukocyte-, erythrocyte- and/or platelet-containing sample.
36. A kit for diagnosing and/or prognosing of kidney cancer comprising
   (i) means for determining an expression profile of a set comprising at least two miRNAs representative for kidney cancer in a body fluid sample from a subject, and
   (ii) at least one reference.
37. The kit of item 36, wherein the nucleotide sequences of said miRNAs are selected from the group consisting of SEQ ID NO: 1 to 357 or SEQ ID NO: 1 to 465, a fragment thereof, and a sequence having at least 80% sequence identity thereto.
38. The kit of items 36 or 37, wherein said kit comprises the means according to any of the items 31 to 35.
39. A set of miRNAs isolated from a body fluid sample from a subject for diagnosing and/or prognosing of kidney cancer, wherein the miRNAs are selected from the group consisting of SEQ ID NO: 1 to 357 or SEQ ID NO: 1 to 465

40. The set of miRNAs of item 39, wherein kidney cancer is renal cell carcinoma (RCC)
41. The set of miRNAs of item 39 or 40, wherein the body fluid sample is a blood sample.
42. The set of miRNAs of item 41, wherein the blood sample is selected from whole blood, PBMC, serum, plasma, a leukocyte sample, a blood cell sample, a leukocyte-, erythrocyte- and/or platelet-containing sample.
43. The set of miRNAs of items 39 to 42, wherein the set of miRNAs comprises at least one of the sets of miRNAs listed in FIG. 2 or FIG. 5b or FIG. 9.
44. The set of miRNAs of any of the items 39 to 43, wherein the set of miRNAs comprises at least one up-regulated miRNA listed in FIG. 7a or 7b.
45. The set of miRNAs of any of the items 39 to 43, wherein the set of miRNAs comprises at least one down-regulated miRNA listed in FIG. 8a or 8b.
46. The set of miRNAs of any of the items 39 to 43, wherein the set of miRNAs comprises at least one up-regulated miRNA listed in FIG. 7a or 7b and at least one down-regulated miRNA listed in FIG. 8a or 8b.
47. Use of a set of miRNAs according to any of the items 39 to 46 for diagnosing and/or prognosing of kidney cancer in a subject.
48. A method for determining the status and/or the response of the immune system in a subject having or suspected of having kidney cancer, comprising the steps of:
   (i.) determining an expression profile of a set comprising at least two miRNAs representative for the status and/or the response of the immune system in a body fluid sample from a subject, and
   (ii.) comparing said expression profile to a reference, wherein the comparison of said expression profile to said reference allows for determining the status and/or the response of the immune system in said subject
   wherein the miRNAs comprised in the set are selected from the group consisting of SEQ ID NO: 1 588, a fragment thereof, and a sequence having at least 80% sequence identity thereto.
49. The method of item 48, wherein kidney cancer is renal cell carcinoma (RCC)
50. The method of item 48 or 49, wherein the body fluid sample is a blood sample.
51. The method of item 50, wherein the blood sample is selected from whole blood, PBMC, serum, plasma, a leukocyte sample, a blood cell sample, a leukocyte-, erythrocyte- and/or platelet-containing sample.
52. The method of any of the items 48 to 51, wherein the set of miRNAs comprises at least one of the sets of miRNAs listed in FIG. 2 or FIG. 5b or FIG. 7.
53. The method of any of the items 48 to 52, wherein the set of miRNAs comprises at least one up-regulated miRNA listed in FIG. 7a or 7b.
54. The method of any of the items 48 to 52, wherein the set of miRNAs comprises at least one down-regulated miRNA listed in FIG. 8a or 8b.
55. The method of any of the items 48 to 52, wherein the set of miRNAs comprises at least one up-regulated miRNA listed in FIG. 7a or 7b and at least one down-regulated miRNA listed in FIG. 8a or 8b.
56. The method according to any of the items 48 to 55, wherein the reference are reference expression profiles of at least two subjects with at least two known clinical conditions from which at least one is kidney cancer, wherein the reference expression profiles are the profiles of a set comprising at least two miRNAs that have nucleotide sequences that correspond to the nucleotide sequences of the miRNAs of step (i).
57. The method according to any of the items 48 to 55 wherein the reference is an algorithm or mathematical function that is obtained from reference expression profiles of at least two subjects with at least two known clinical conditions from which at least one is kidney cancer, wherein the reference expression profiles are the profiles of a set comprising at least two miRNAs that have nucleotide sequences that correspond to the nucleotide sequences of the miRNAs of step (i).

BRIEF DESCRIPTION OF THE DRAWINGS

FIG. 1: MiRNAs for diagnosis or prognosis of kidney cancer. Experimental data obtained for analysis of miRNAs according to SEQ ID NO: 1 to 357. Experimental details: SEQ ID NO: sequence identification number, miRNA: identifier of the miRNA according to miRBase, median g1: median intensity obtained from microarray analysis for healthy controls, median g2: median intensity obtained from microarray analysis for individuals with renal cell carcinoma (RCC), qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment.

FIG. 2: Sets of miRNAS (miRNA-signatures SNRCC-1 to SNRCC-694) that allow for effective diagnosis and/or prognosis of kidney cancer when differentiating renal cell carcinoma (RCC) and healthy controls. Experimental details: SEQ ID NO: sequence identification number, miRNA: identifier of the miRNA according to miRBase, Acc=accuracy, Spec=specificity, Sens=sensitivity.

FIG. 5: Further sets of miRNAS (miRNA-signatures SNRCC-lin1 to SNRCC-lin9 and SNRCC-rbf1 to SNRCC-rbf9) that allow for effective diagnosis and/or prognosis of kidney cancer when differentiating RCC and healthy controls//5a: Graphical representation of Accuracy, Balanced Accuracy, Sensitivity and Specificity in relation to the number of miRNA-biomarkers within the sets of miRNAs (miRNA-signatures)//5b: Experimental details: miRNA-signatures (SNRCC-lin1 to SNRCC-lin9 and SNRCC-rbf1 to SNRCC-rbf9), # of miRNA contained in the miRNA-Signature; miRNA: identifier of the miRNA according to miRBase, Accuracy in percent.

FIG. 6: MiRNAs for diagnosis or prognosis of kidney cancer. Experimental data obtained for analysis of miRNAs according to SEQ ID NO: 1 to 465. Experimental details: SEQ ID NO: sequence identification number, miRNA: identifier of the miRNA according to miRBase, median g1: median intensity obtained from microarray analysis for healthy controls, median g2: median intensity obtained from microarray analysis for individuals with kidney cancer (RCC), qmedian: ratio of median g1/median g2, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment FIG. 7: miRNAs that are up-regulated in kidney cancer compared to healthy controls that allow for effective diagnosis and/or prognosis of kidney cancer (RCC). With a) miRNAs that are up-regulated in kidney cancer, b) miRNAs that are strong up-regulated in kidney cancer (Fold Change>1.5) compared to healthy controls that allow for effective diagnosis and/or prognosis of kidney cancer.

FIG. 8: miRNAs that are down-regulated in kidney cancer compared to healthy controls that allow for effective diagnosis and/or prognosis of kidney cancer. With a) miRNAs that are down-regulated in kidney cancer, b) miRNAs that are strong down-regulated in kidney cancer (Fold Change>1.5) compared to healthy controls that allow for effective diagnosis and/or prognosis of kidney cancer.

FIG. 9: Further sets of miRNAs (miRNA-signatures SNRCC-695 to SNRCC-844) that allow for effective diagnosis and/or prognosis of kidney cancer when differentiating kidney cancer and healthy controls. With miRNA signatures SNRCC-695 to SNRCC-844; SEQ ID NO: sequence identification number; miRNAs contained in the respective miRNA-Signature with miRNA identifier according to miRBase; Accuracy, Specificity, Sensitivity and Balanced Accuracy (Bal.Acc.) in percent.

EXAMPLES

Figure 3:
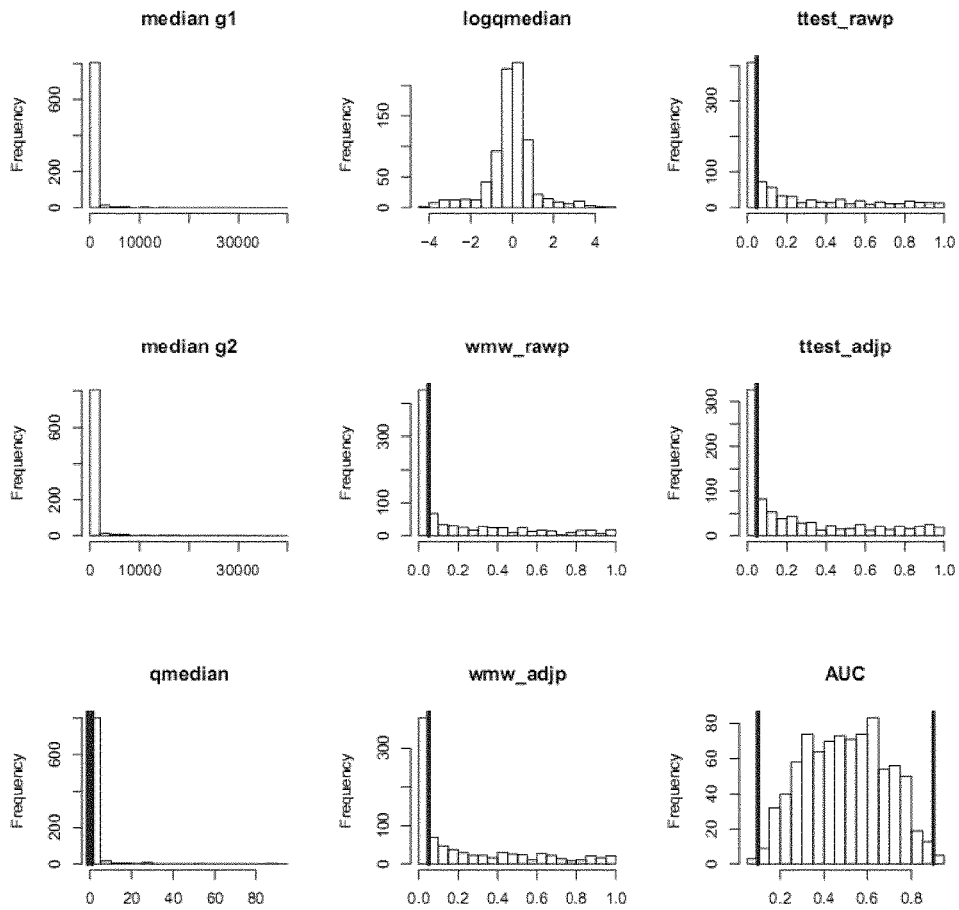
FIG. 3: Graphical representation of the experimental data on miRNAs for diagnosis or prognosis of kidney cancer. The histograms show the distribution curve obtained when 862 miRNAs biomarkers were analysed on microarrays. The thick lines separate the high informative miRNA biomarkers for diagnosis or prognosis of renal cell carcinoma (RCC) in comparison to healthy controls from the non-informative ones. Experimental details: median g1: median intensity obtained from microarray analysis for healthy controls, median g2: median intensity obtained from microarray analysis for individuals with RCC, qmedian: ratio of median g1/median g2, logqmedian: log of qmedian, ttest_rawp: p-value obtained when applying t-test, ttest_adjp: adjusted p-value in order to reduce false discovery rate by Benjamini-Hochberg adjustment, AUC: Area under the curve, limma_rawp: p-value obtained when applying limma-test, limma_adjp: adjusted p-value in order to reduce false discovery rate by Benjamini-Hochberg adjustment.
Figure 4:
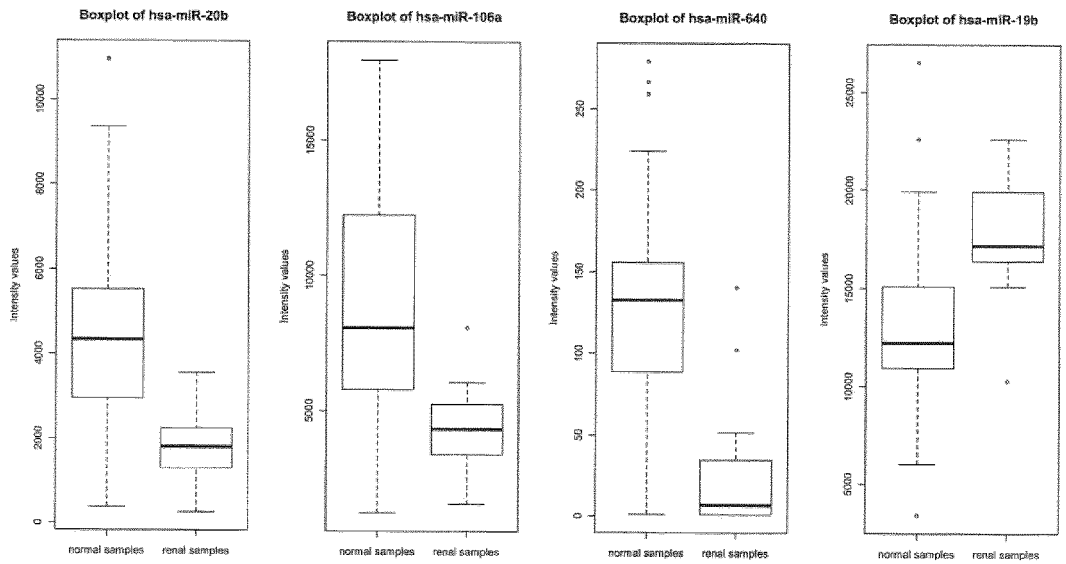
FIG. 4: Boxplot of the experimental data of selected miRNAs suitable for diagnosis or prognosis of renal cell carcinoma (RCC). Y-axis: intensity values corresponding to the expression level of the miRNAs, x-axis left: normal samples (healthy controls), right: RCC samples (patients with RCC)

The Examples are designed in order to further illustrate the present invention and serve a better understanding. They are not to be construed as limiting the scope of the invention in any way.

Materials and Methods

Samples

All blood donors participating in this study have given their written informed consent. The patient samples have been prepared at the Institute for Human Genetics at University Saarland (Homburg/Saar, Germany). Besides the samples of diseased patients, also normal (healthy) control samples were provided. Further normal control samples were provided by 3 other institutions. Alltogether, 16 renal cell carcinoma samples (RCC) and 70 healthy control samples were analysed. The RCC samples were characterized as Fuhrman grade G2 and G3 with tumor sizes between 3.1 and 8.9 cm.

miRNA Extraction and Microarray Screening

Blood of patients has been extracted as previously described [1]. In brief, 2.5 to 5 ml blood was extracted in PAXgene Blood RNA tubes (BD, Franklin Lakes, N.J. USA) and centrifuged at 5000×g for 10 min at room temperature. The miRNeasy kit (Qiagen GmbH, Hilden) was used to isolate total RNA including miRNA from the resuspended pellet according to manufacturer's instructions. The eluted RNA was stored at −70° C.

All samples were shipped overnight on dry ice and analyzed with the Geniom RT Analyzer (febit biomed GmbH, Heidelberg, Germany) at the in-house genomic service department using the Geniom Biochip miRNA Homo sapiens. Each array contains 7 replicates of about 863 miRNAs and miRNA* sequences as annotated in the Sanger miRBase releases 14.0. On-chip sample labeling with biotin was carried out by microfluidic-based primer extension labeling of miRNAs (MPEA [2]). Following hybridization for 16 hours at 42° C., the biochip was washed and a program for signal enhancement was carried out. All steps from sample loading to miRNA detection were processed without any manual intervention and inside the machine. The detection pictures were evaluated using the Geniom Wizard Software. For each feature, the median signal intensity was calculated. Following a background correction step, the median of the 7 replicates of each miRNA was computed. To normalize the data across different arrays, quantile normalization [3] was applied and all further analyses were carried out using the normalized and background subtracted intensity values.

Statistical Analysis

To estimate the value of single miRNAs, t-tests (unpaired, two-tailed) were carried out. The resulting p-values have been adjusted for multiple testing by Benjamini-Hochberg adjustment [4, 5]. In addition to this single biomarker analysis, we performed supervised classification of samples by using Support Vector Machines (SVM [6]) as implemented in the R e1071 package [7]. As parameters, we evaluated different kernel methods including linear, polynomial (degree 2 to 5), sigmoid and radial basis function kernels. The cost parameter was sampled from 0.01 to 10 in decimal powers. As subset selection technique, a filter approach based on t-test was carried out. In each iteration, the s miRNAs with lowest p-values were computed on the training set in each fold of a standard 10-fold cross validation, where s was sampled in regular intervals between 2 and 300. The respective subset was used to train the SVM and to carry out the prediction of the test samples in the cross validation. To compute probabilities for classes instead of class labels, a regression approach based on the output of the support vectors has been applied. To test for overtraining, non-parametric permutation tests have been applied. All computations were carried out using R [7], a freely available language for statistical tasks.

REFERENCES

1. Keller A, Leidinger P, Borries A, Wendschlag A, Wucherpfennig F, Scheffler M, Huwer H, Lenhof H P, Meese E: miRNAs in lung cancer—studying complex fingerprints in patient's blood cells by microarray experiments. BMC Cancer 2009, 9:353.
2. Vorwerk S, Ganter K, Cheng Y, Hoheisel J, Stahler P F, Beier M: Micro fluidic-based enzymatic on-chip labeling of miRNAs. N Biotechnol 2008, 25(2-3):142-149.
3. Bolstad B M, Irizarry R A, Astrand M, Speed T P: A comparison of normalization methods for high density oligonucleotide array data based on variance and bias. Bioinformatics 2003, 19(2):185-193.
4. Benjamini Y, Drai D, Elmer G, Kafkafi N, Golani I: Controlling the false discovery rate in behavior genetics research. Behav Brain Res 2001, 125(1-2):279-284.
5. Hochberg Y: A sharper bonferroni procedure for multiple tests of significance. Biometrica 1988, 75:185-193.
6. Vapnik V: The nature of statistical learning theory. 2nd edition edn. New York: Springer; 2000.
7. Team R: R: A Language and Environment for Statistical Computing. In. Vienna: R Foundation for Statistical Computing; 2008.

The invention claimed is:

1. A method for diagnosing and/or prognosing of kidney cancer comprising the steps of:
(i) determining an expression profile of a set comprising at least two miRNAs representative for kidney cancer in all blood cells of leukocytes, erythrocytes, and platelets without the acellular portion of a blood sample from a subject, and
(ii) comparing said expression profile to a reference, wherein the comparison of said expression profile to said reference allows for the diagnosis and/or prognosis of kidney cancer,
wherein kidney cancer is a renal cell carcinoma and the nucleotide sequences of the miRNAs comprised in the set are selected from the group consisting of SEQ ID NO: 1 to 465.

2. The method of claim 1, wherein the set of miRNAs comprises at least one of the sets of miRNAs listed in FIG. 2 or FIG. 9.

3. The method of claim 1, wherein the set of miRNAs comprises at least one up-regulated miRNA listed in FIG. 7a or 7b and/or at least one down-regulated miRNA listed in FIG. 8a or 8b.

4. A kit for diagnosing and/or prognosing of kidney cancer comprising
(i) means for determining an expression profile of a set comprising at least two miRNAs representative for kidney cancer in all blood cells of leukocytes, erythrocytes, and platelets without the acellular portion of a blood sample from a subject comprising:
  (a) a set of at least two polynucleotides or set of at least two primer pairs for detecting a set comprising at least two miRNAs for diagnosing and/or prognosing of kidney cancer in a blood sample from a subject, wherein the nucleotide sequences of the miRNAs comprised in the set are selected from the group consisting of SEQ ID NO: 1 to 465,
  (b) a biochip, a RT-PCR system, a PCR-system, a flow cytometer, a bead-based multiplex system or a next generation sequencing system,
and
(ii) at least one reference
wherein kidney cancer is a renal cell carcinoma.

5. The method of claim 1, wherein the expression profile of the miRNA s is determined comprising the steps:
  (i) extracting total RNA from all blood cells of leukocytes, erythrocytes, and platelets without the acellular portion of said blood sample,
  (ii) reverse-transcribing the total RNA into cDNA, and
  (iii) amplifying the cDNA and thereby detecting the miRNA levels in all blood cells of leukocytes, erythrocytes, and platelets without the acellular portion of said blood sample.

6. The kit of claim 4, wherein the reference is determined in the same type of blood sample as the subject to be diagnosed and/or prognosed.

* * * * *

SEQUENCE LISTING

<160> NUMBER OF SEQ ID NOS: 465

<210> SEQ ID NO 1
<211> LENGTH: 23
<212> TYPE: RNA
<213> ORGANISM: Homo sapiens

<400> SEQUENCE: 1
aaaagugcuu acagugcagg uag                                              23

<210> SEQ ID NO 2
<211> LENGTH: 23
<212> TYPE: RNA
<213> ORGANISM: Homo sapiens

<400> SEQUENCE: 2
caaagugcuc auagugcagg uag                                              23

<210> SEQ ID NO 3
<211> LENGTH: 23
<212> TYPE: RNA
<213> ORGANISM: Homo sapiens

<400> SEQUENCE: 3
gaacgcgcuu cccuauagag ggu                                              23

<210> SEQ ID NO 4
<211> LENGTH: 21
<212> TYPE: RNA
<213> ORGANISM: Homo sapiens

<400> SEQUENCE: 4
augauccagg aaccugccuc u                                                21

<210> SEQ ID NO 5
<211> LENGTH: 21
<212> TYPE: RNA
<213> ORGANISM: Homo sapiens

<400> SEQUENCE: 5
acucuagcug ccaaaggcgc u                                                21

<210> SEQ ID NO 6
<211> LENGTH: 23
<212> TYPE: RNA
<213> ORGANISM: Homo sapiens

<400> SEQUENCE: 6
uaaagugcuu auagugcagg uag                                              23

<210> SEQ ID NO 7
<211> LENGTH: 23
<212> TYPE: RNA
<213> ORGANISM: Homo sapiens

<400> SEQUENCE: 7
caaagugcuu acagugcagg uag                                              23

<210> SEQ ID NO 8
<211> LENGTH: 22
<212> TYPE: RNA
<213> ORGANISM: Homo sapiens

<400> SEQUENCE: 8

-continued

```
caaucagcaa guauacugcc cu                                          22

<210> SEQ ID NO 9
<211> LENGTH: 22
<212> TYPE: RNA
<213> ORGANISM: Homo sapiens

<400> SEQUENCE: 9
ugaguauuac auggccaauc uc                                          22

<210> SEQ ID NO 10
<211> LENGTH: 22
<212> TYPE: RNA
<213> ORGANISM: Homo sapiens

<400> SEQUENCE: 10
cuauacgacc ugcugccuuu cu                                          22

<210> SEQ ID NO 11
<211> LENGTH: 23
<212> TYPE: RNA
<213> ORGANISM: Homo sapiens

<400> SEQUENCE: 11
ugugcaaauc caugcaaaac uga                                         23

<210> SEQ ID NO 12
<211> LENGTH: 22
<212> TYPE: RNA
<213> ORGANISM: Homo sapiens

<400> SEQUENCE: 12
gaaagcgcuu cccuuugcug ga                                          22

<210> SEQ ID NO 13
<211> LENGTH: 22
<212> TYPE: RNA
<213> ORGANISM: Homo sapiens

<400> SEQUENCE: 13
aucuggaggu aagaagcacu uu                                          22

<210> SEQ ID NO 14
<211> LENGTH: 22
<212> TYPE: RNA
<213> ORGANISM: Homo sapiens

<400> SEQUENCE: 14
acuguugcua auaugcaacu cu                                          22

<210> SEQ ID NO 15
<211> LENGTH: 23
<212> TYPE: RNA
<213> ORGANISM: Homo sapiens

<400> SEQUENCE: 15
caaagugcug uucgugcagg uag                                         23

<210> SEQ ID NO 16
<211> LENGTH: 22
<212> TYPE: RNA
<213> ORGANISM: Homo sapiens
```

```
<400> SEQUENCE: 16
ugcaacuuac cugagucauu ga                                              22

<210> SEQ ID NO 17
<211> LENGTH: 22
<212> TYPE: RNA
<213> ORGANISM: Homo sapiens

<400> SEQUENCE: 17
uuuugcaaua uguuccugaa ua                                              22

<210> SEQ ID NO 18
<211> LENGTH: 18
<212> TYPE: RNA
<213> ORGANISM: Homo sapiens

<400> SEQUENCE: 18
aucccaccuc ugccacca                                                   18

<210> SEQ ID NO 19
<211> LENGTH: 22
<212> TYPE: RNA
<213> ORGANISM: Homo sapiens

<400> SEQUENCE: 19
accuggcaua caauguagau uu                                              22

<210> SEQ ID NO 20
<211> LENGTH: 21
<212> TYPE: RNA
<213> ORGANISM: Homo sapiens

<400> SEQUENCE: 20
caagucacua gugguuccgu u                                               21

<210> SEQ ID NO 21
<211> LENGTH: 22
<212> TYPE: RNA
<213> ORGANISM: Homo sapiens

<400> SEQUENCE: 21
caauuuagug ugugugauau uu                                              22

<210> SEQ ID NO 22
<211> LENGTH: 22
<212> TYPE: RNA
<213> ORGANISM: Homo sapiens

<400> SEQUENCE: 22 ugcuacuac uggagacacu gg                                               22

<210> SEQ ID NO 23
<211> LENGTH: 22
<212> TYPE: RNA
<213> ORGANISM: Homo sapiens

<400> SEQUENCE: 23
uggugggccg cagaacaugu gc                                              22

<210> SEQ ID NO 24
<211> LENGTH: 21
<212> TYPE: RNA
<213> ORGANISM: Homo sapiens
```

```
<400> SEQUENCE: 24
gcuaguccug acucagccag u                                              21

<210> SEQ ID NO 25
<211> LENGTH: 23
<212> TYPE: RNA
<213> ORGANISM: Homo sapiens

<400> SEQUENCE: 25
cuaauaguau cuaccacaau aaa                                            23

<210> SEQ ID NO 26
<211> LENGTH: 22
<212> TYPE: RNA
<213> ORGANISM: Homo sapiens

<400> SEQUENCE: 26
uugagaauga ugaaucauua gg                                             22

<210> SEQ ID NO 27
<211> LENGTH: 21
<212> TYPE: RNA
<213> ORGANISM: Homo sapiens

<400> SEQUENCE: 27
uaaagugcug acagugcaga u                                              21

<210> SEQ ID NO 28
<211> LENGTH: 21
<212> TYPE: RNA
<213> ORGANISM: Homo sapiens

<400> SEQUENCE: 28
caaagguauu ugugguuuuu g                                              21

<210> SEQ ID NO 29
<211> LENGTH: 21
<212> TYPE: RNA
<213> ORGANISM: Homo sapiens

<400> SEQUENCE: 29
aaacuacuga aaaucaaaga u                                              21

<210> SEQ ID NO 30
<211> LENGTH: 22
<212> TYPE: RNA
<213> ORGANISM: Homo sapiens

<400> SEQUENCE: 30
aaaucucugc aggcaaaugu ga                                             22

<210> SEQ ID NO 31
<211> LENGTH: 22
<212> TYPE: RNA
<213> ORGANISM: Homo sapiens

<400> SEQUENCE: 31
aucgggaaug ucguguccgc cc                                             22

<210> SEQ ID NO 32
<211> LENGTH: 22
<212> TYPE: RNA
```

```
<213> ORGANISM: Homo sapiens

<400> SEQUENCE: 32
ggagacgcgg cccuguugga gu                                              22

<210> SEQ ID NO 33
<211> LENGTH: 23
<212> TYPE: RNA
<213> ORGANISM: Homo sapiens

<400> SEQUENCE: 33
agcagcauug uacagggcua uga                                             23

<210> SEQ ID NO 34
<211> LENGTH: 21
<212> TYPE: RNA
<213> ORGANISM: Homo sapiens

<400> SEQUENCE: 34
guucaaaucc agaucuauaa c                                               21

<210> SEQ ID NO 35
<211> LENGTH: 22
<212> TYPE: RNA
<213> ORGANISM: Homo sapiens

<400> SEQUENCE: 35
caucuuaccg gacagugcug ga                                              22

<210> SEQ ID NO 36
<211> LENGTH: 22
<212> TYPE: RNA
<213> ORGANISM: Homo sapiens

<400> SEQUENCE: 36
caaaguuuaa gauccuugaa gu                                              22

<210> SEQ ID NO 37
<211> LENGTH: 22
<212> TYPE: RNA
<213> ORGANISM: Homo sapiens

<400> SEQUENCE: 37
uucauucggc uguccagaug ua                                              22

<210> SEQ ID NO 38
<211> LENGTH: 21
<212> TYPE: RNA
<213> ORGANISM: Homo sapiens

<400> SEQUENCE: 38
aggcggagac uugggcaauu g                                               21

<210> SEQ ID NO 39
<211> LENGTH: 23
<212> TYPE: RNA
<213> ORGANISM: Homo sapiens

<400> SEQUENCE: 39
gaagugcuuc gauuuugggg ugu                                             23

<210> SEQ ID NO 40
<211> LENGTH: 23
```

```
<212> TYPE: RNA
<213> ORGANISM: Homo sapiens

<400> SEQUENCE: 40
agguuacccg agcaacuuug cau                                              23

<210> SEQ ID NO 41
<211> LENGTH: 23
<212> TYPE: RNA
<213> ORGANISM: Homo sapiens

<400> SEQUENCE: 41
uaaggugcau cuagugcaga uag                                              23

<210> SEQ ID NO 42
<211> LENGTH: 21
<212> TYPE: RNA
<213> ORGANISM: Homo sapiens

<400> SEQUENCE: 42
cacaagguau ugguauuacc u                                                21

<210> SEQ ID NO 43
<211> LENGTH: 21
<212> TYPE: RNA
<213> ORGANISM: Homo sapiens

<400> SEQUENCE: 43
aauggcgcca cuaggguugu g                                                21

<210> SEQ ID NO 44
<211> LENGTH: 19
<212> TYPE: RNA
<213> ORGANISM: Homo sapiens

<400> SEQUENCE: 44
aagcagcugc cucugaggc                                                   19

<210> SEQ ID NO 45
<211> LENGTH: 22
<212> TYPE: RNA
<213> ORGANISM: Homo sapiens

<400> SEQUENCE: 45
cgucaacacu ugcugguuuc cu                                               22

<210> SEQ ID NO 46
<211> LENGTH: 17
<212> TYPE: RNA
<213> ORGANISM: Homo sapiens

<400> SEQUENCE: 46
uaauugcuuc cauguuu                                                     17

<210> SEQ ID NO 47
<211> LENGTH: 22
<212> TYPE: RNA
<213> ORGANISM: Homo sapiens

<400> SEQUENCE: 47
augguuccgu caagcaccau gg                                               22

<210> SEQ ID NO 48
```

```
<211> LENGTH: 21
<212> TYPE: RNA
<213> ORGANISM: Homo sapiens

<400> SEQUENCE: 48
gaagugugcc gguguguguc u                                              21

<210> SEQ ID NO 49
<211> LENGTH: 22
<212> TYPE: RNA
<213> ORGANISM: Homo sapiens

<400> SEQUENCE: 49
aacaucacag caagucugug cu                                             22

<210> SEQ ID NO 50
<211> LENGTH: 23
<212> TYPE: RNA
<213> ORGANISM: Homo sapiens

<400> SEQUENCE: 50
uaaauuucac cuuucugaga agg                                            23

<210> SEQ ID NO 51
<211> LENGTH: 23
<212> TYPE: RNA
<213> ORGANISM: Homo sapiens

<400> SEQUENCE: 51
cacucagccu ugagggcacu uuc                                            23

<210> SEQ ID NO 52
<211> LENGTH: 19
<212> TYPE: RNA
<213> ORGANISM: Homo sapiens

<400> SEQUENCE: 52
aggcugcgga auucaggac                                                 19

<210> SEQ ID NO 53
<211> LENGTH: 18
<212> TYPE: RNA
<213> ORGANISM: Homo sapiens

<400> SEQUENCE: 53
uucacaggga ggugucau                                                  18

<210> SEQ ID NO 54
<211> LENGTH: 22
<212> TYPE: RNA
<213> ORGANISM: Homo sapiens

<400> SEQUENCE: 54
uauugcacuu gucccggccu gu                                             22

<210> SEQ ID NO 55
<211> LENGTH: 22
<212> TYPE: RNA
<213> ORGANISM: Homo sapiens

<400> SEQUENCE: 55
gaugagcuca uuguaauaug ag                                             22
```

```
<210> SEQ ID NO 56
<211> LENGTH: 21
<212> TYPE: RNA
<213> ORGANISM: Homo sapiens

<400> SEQUENCE: 56
aagccugccc ggcuccucgg g                                        21

<210> SEQ ID NO 57
<211> LENGTH: 21
<212> TYPE: RNA
<213> ORGANISM: Homo sapiens

<400> SEQUENCE: 57
uaguagaccg uauagcguac g                                        21

<210> SEQ ID NO 58
<211> LENGTH: 23
<212> TYPE: RNA
<213> ORGANISM: Homo sapiens

<400> SEQUENCE: 58
uagugcaaua uugcuuauag ggu                                      23

<210> SEQ ID NO 59
<211> LENGTH: 25
<212> TYPE: RNA
<213> ORGANISM: Homo sapiens

<400> SEQUENCE: 59
aggcaccagc caggcauugc ucagc                                    25

<210> SEQ ID NO 60
<211> LENGTH: 22
<212> TYPE: RNA
<213> ORGANISM: Homo sapiens

<400> SEQUENCE: 60
cacuagauug ugagcuccug ga                                       22

<210> SEQ ID NO 61
<211> LENGTH: 22
<212> TYPE: RNA
<213> ORGANISM: Homo sapiens

<400> SEQUENCE: 61
cugaagcuca gagggcucug au                                       22

<210> SEQ ID NO 62
<211> LENGTH: 20
<212> TYPE: RNA
<213> ORGANISM: Homo sapiens

<400> SEQUENCE: 62
ugagcccugu ccucccgcag                                          20

<210> SEQ ID NO 63
<211> LENGTH: 22
<212> TYPE: RNA
<213> ORGANISM: Homo sapiens

<400> SEQUENCE: 63
cuggcccucu cugcccuucc gu                                       22
```

<210> SEQ ID NO 64
<211> LENGTH: 22
<212> TYPE: RNA
<213> ORGANISM: Homo sapiens

<400> SEQUENCE: 64
gaaggcgcuu cccuuuagag cg                                              22

<210> SEQ ID NO 65
<211> LENGTH: 20
<212> TYPE: RNA
<213> ORGANISM: Homo sapiens

<400> SEQUENCE: 65
gugcauugcu guugcauugc                                                 20

<210> SEQ ID NO 66
<211> LENGTH: 21
<212> TYPE: RNA
<213> ORGANISM: Homo sapiens

<400> SEQUENCE: 66
gugcauugua guugcauugc a                                               21

<210> SEQ ID NO 67
<211> LENGTH: 22
<212> TYPE: RNA
<213> ORGANISM: Homo sapiens

<400> SEQUENCE: 67
ucuacagugc acgugucucc ag                                              22

<210> SEQ ID NO 68
<211> LENGTH: 22
<212> TYPE: RNA
<213> ORGANISM: Homo sapiens

<400> SEQUENCE: 68
ucuacaaagg aaagcgcuuu cu                                              22

<210> SEQ ID NO 69
<211> LENGTH: 23
<212> TYPE: RNA
<213> ORGANISM: Homo sapiens

<400> SEQUENCE: 69
uaggcagugu cauuagcuga uug                                             23

<210> SEQ ID NO 70
<211> LENGTH: 22
<212> TYPE: RNA
<213> ORGANISM: Homo sapiens

<400> SEQUENCE: 70
cuuaugcaag auucccuucu ac                                              22

<210> SEQ ID NO 71
<211> LENGTH: 21
<212> TYPE: RNA
<213> ORGANISM: Homo sapiens

<400> SEQUENCE: 71
caaagcgcuu cccuuuggag c                                               21

<210> SEQ ID NO 72
<211> LENGTH: 22
<212> TYPE: RNA
<213> ORGANISM: Homo sapiens

<400> SEQUENCE: 72
uaaucucagc uggcaacugu ga                                              22

<210> SEQ ID NO 73
<211> LENGTH: 20
<212> TYPE: RNA
<213> ORGANISM: Homo sapiens

<400> SEQUENCE: 73
cgugccaccc uuuuccccag                                                 20

<210> SEQ ID NO 74
<211> LENGTH: 22
<212> TYPE: RNA
<213> ORGANISM: Homo sapiens

<400> SEQUENCE: 74
accguggcuu ucgauuguua cu                                              22

<210> SEQ ID NO 75
<211> LENGTH: 22
<212> TYPE: RNA
<213> ORGANISM: Homo sapiens

<400> SEQUENCE: 75
acaguagagg gaggaaucgc ag                                              22

<210> SEQ ID NO 76
<211> LENGTH: 21
<212> TYPE: RNA
<213> ORGANISM: Homo sapiens

<400> SEQUENCE: 76
uugaaaggcu auuucuuggu c                                               21

<210> SEQ ID NO 77
<211> LENGTH: 22
<212> TYPE: RNA
<213> ORGANISM: Homo sapiens

<400> SEQUENCE: 77
uaugugccuu uggacuacau cg                                              22

<210> SEQ ID NO 78
<211> LENGTH: 19
<212> TYPE: RNA
<213> ORGANISM: Homo sapiens

<400> SEQUENCE: 78
ugagcugcug uaccaaaau                                                  19

<210> SEQ ID NO 79
<211> LENGTH: 22
<212> TYPE: RNA
<213> ORGANISM: Homo sapiens

<400> SEQUENCE: 79

-continued agugggggaac ccuuccauga gg                                    22

<210> SEQ ID NO 80
<211> LENGTH: 23
<212> TYPE: RNA
<213> ORGANISM: Homo sapiens

<400> SEQUENCE: 80
ucaaaugcuc agacuccugu ggu                                    23

<210> SEQ ID NO 81
<211> LENGTH: 21
<212> TYPE: RNA
<213> ORGANISM: Homo sapiens

<400> SEQUENCE: 81
cugaccuaug aauugacagc c                                      21

<210> SEQ ID NO 82
<211> LENGTH: 23
<212> TYPE: RNA
<213> ORGANISM: Homo sapiens

<400> SEQUENCE: 82
uauucauuua uccccagccu aca                                    23

<210> SEQ ID NO 83
<211> LENGTH: 23
<212> TYPE: RNA
<213> ORGANISM: Homo sapiens

<400> SEQUENCE: 83
guccaguuuu cccaggaauc ccu                                    23

<210> SEQ ID NO 84
<211> LENGTH: 22
<212> TYPE: RNA
<213> ORGANISM: Homo sapiens

<400> SEQUENCE: 84
aucgugcauc cuuuuagagu gu                                     22

<210> SEQ ID NO 85
<211> LENGTH: 21
<212> TYPE: RNA
<213> ORGANISM: Homo sapiens

<400> SEQUENCE: 85
ucacuccucu ccucccgucu u                                      21

<210> SEQ ID NO 86
<211> LENGTH: 22
<212> TYPE: RNA
<213> ORGANISM: Homo sapiens

<400> SEQUENCE: 86
ucuauacaga cccuggcuuu uc                                     22

<210> SEQ ID NO 87
<211> LENGTH: 19
<212> TYPE: RNA
<213> ORGANISM: Homo sapiens

<400> SEQUENCE: 87

-continued

| | |
|---|---|
| auggauaagg cuuuggcuu | 19 |

<210> SEQ ID NO 88
<211> LENGTH: 21
<212> TYPE: RNA
<213> ORGANISM: Homo sapiens

<400> SEQUENCE: 88

| | |
|---|---|
| aggaggcagc gcucucagga c | 21 |

<210> SEQ ID NO 89
<211> LENGTH: 23
<212> TYPE: RNA
<213> ORGANISM: Homo sapiens

<400> SEQUENCE: 89

| | |
|---|---|
| cggcccgggc ugcugcuguu ccu | 23 |

<210> SEQ ID NO 90
<211> LENGTH: 21
<212> TYPE: RNA
<213> ORGANISM: Homo sapiens

<400> SEQUENCE: 90

| | |
|---|---|
| aggguaagcu gaaccucuga u | 21 |

<210> SEQ ID NO 91
<211> LENGTH: 21
<212> TYPE: RNA
<213> ORGANISM: Homo sapiens

<400> SEQUENCE: 91

| | |
|---|---|
| guguugaaac aaucucuacu g | 21 |

<210> SEQ ID NO 92
<211> LENGTH: 20
<212> TYPE: RNA
<213> ORGANISM: Homo sapiens

<400> SEQUENCE: 92

| | |
|---|---|
| auguauaaau guauacacac | 20 |

<210> SEQ ID NO 93
<211> LENGTH: 22
<212> TYPE: RNA
<213> ORGANISM: Homo sapiens

<400> SEQUENCE: 93

| | |
|---|---|
| aaaaguaauu gcgaguuuua cc | 22 |

<210> SEQ ID NO 94
<211> LENGTH: 22
<212> TYPE: RNA
<213> ORGANISM: Homo sapiens

<400> SEQUENCE: 94

| | |
|---|---|
| accacugacc guugacugua cc | 22 |

<210> SEQ ID NO 95
<211> LENGTH: 22
<212> TYPE: RNA
<213> ORGANISM: Homo sapiens

```
<400> SEQUENCE: 95
uuagggcccu ggcuccaucu cc                                              22

<210> SEQ ID NO 96
<211> LENGTH: 22
<212> TYPE: RNA
<213> ORGANISM: Homo sapiens

<400> SEQUENCE: 96
auaauacaug guuaaccucu uu                                              22

<210> SEQ ID NO 97
<211> LENGTH: 21
<212> TYPE: RNA
<213> ORGANISM: Homo sapiens

<400> SEQUENCE: 97
ucuaguaaga guggcagucg a                                               21

<210> SEQ ID NO 98
<211> LENGTH: 22
<212> TYPE: RNA
<213> ORGANISM: Homo sapiens

<400> SEQUENCE: 98
uuuucaacuc uaaugggaga ga                                              22

<210> SEQ ID NO 99
<211> LENGTH: 23
<212> TYPE: RNA
<213> ORGANISM: Homo sapiens

<400> SEQUENCE: 99
aacauucauu guugucggug ggu                                             23

<210> SEQ ID NO 100
<211> LENGTH: 22
<212> TYPE: RNA
<213> ORGANISM: Homo sapiens

<400> SEQUENCE: 100
cugggagagg guuguuuacu cc                                              22

<210> SEQ ID NO 101
<211> LENGTH: 22
<212> TYPE: RNA
<213> ORGANISM: Homo sapiens

<400> SEQUENCE: 101
auaagacgaa caaaagguuu gu                                              22

<210> SEQ ID NO 102
<211> LENGTH: 22
<212> TYPE: RNA
<213> ORGANISM: Homo sapiens

<400> SEQUENCE: 102
cacccguaga accgaccuug cg                                              22

<210> SEQ ID NO 103
<211> LENGTH: 22
<212> TYPE: RNA
<213> ORGANISM: Homo sapiens
```

-continued

```
<400> SEQUENCE: 103
uagcaaaaac ugcaguuacu uu                                              22

<210> SEQ ID NO 104
<211> LENGTH: 22
<212> TYPE: RNA
<213> ORGANISM: Homo sapiens

<400> SEQUENCE: 104
cgaaaacagc aauuaccuuu gc                                              22

<210> SEQ ID NO 105
<211> LENGTH: 25
<212> TYPE: RNA
<213> ORGANISM: Homo sapiens

<400> SEQUENCE: 105
gcugggcagg gcuucugagc uccuu                                           25

<210> SEQ ID NO 106
<211> LENGTH: 22
<212> TYPE: RNA
<213> ORGANISM: Homo sapiens

<400> SEQUENCE: 106
aaucaugugc agugccaaua ug                                              22

<210> SEQ ID NO 107
<211> LENGTH: 22
<212> TYPE: RNA
<213> ORGANISM: Homo sapiens

<400> SEQUENCE: 107
gggagccagg aaguauugau gu                                              22

<210> SEQ ID NO 108
<211> LENGTH: 22
<212> TYPE: RNA
<213> ORGANISM: Homo sapiens

<400> SEQUENCE: 108
cgggguuuug agggcgagau ga                                              22

<210> SEQ ID NO 109
<211> LENGTH: 22
<212> TYPE: RNA
<213> ORGANISM: Homo sapiens

<400> SEQUENCE: 109
ggugcagugc ugcaucucug gu                                              22

<210> SEQ ID NO 110
<211> LENGTH: 22
<212> TYPE: RNA
<213> ORGANISM: Homo sapiens

<400> SEQUENCE: 110
ugguugacca uagaacaugc gc                                              22

<210> SEQ ID NO 111
<211> LENGTH: 22
<212> TYPE: RNA
```

<213> ORGANISM: Homo sapiens

<400> SEQUENCE: 111
uuauaauaca accugauaag ug                                    22

<210> SEQ ID NO 112
<211> LENGTH: 22
<212> TYPE: RNA
<213> ORGANISM: Homo sapiens

<400> SEQUENCE: 112
aaaaguaauu gcggauuuug cc                                    22

<210> SEQ ID NO 113
<211> LENGTH: 26
<212> TYPE: RNA
<213> ORGANISM: Homo sapiens

<400> SEQUENCE: 113
gaugaugaug gcagcaaauu cugaaa                                26

<210> SEQ ID NO 114
<211> LENGTH: 21
<212> TYPE: RNA
<213> ORGANISM: Homo sapiens

<400> SEQUENCE: 114
uaaaguaaau augcaccaaa a                                     21

<210> SEQ ID NO 115
<211> LENGTH: 22
<212> TYPE: RNA
<213> ORGANISM: Homo sapiens

<400> SEQUENCE: 115
caaaaaucuc aauuacuuuu gc                                    22

<210> SEQ ID NO 116
<211> LENGTH: 18
<212> TYPE: RNA
<213> ORGANISM: Homo sapiens

<400> SEQUENCE: 116
cagggaggug aaugugau                                         18

<210> SEQ ID NO 117
<211> LENGTH: 21
<212> TYPE: RNA
<213> ORGANISM: Homo sapiens

<400> SEQUENCE: 117
cacugugucc uuucugcgua g                                     21

<210> SEQ ID NO 118
<211> LENGTH: 23
<212> TYPE: RNA
<213> ORGANISM: Homo sapiens

<400> SEQUENCE: 118
uaagugcuuc cauguuuugg uga                                   23

<210> SEQ ID NO 119
<211> LENGTH: 21

```
<212> TYPE: RNA
<213> ORGANISM: Homo sapiens

<400> SEQUENCE: 119
cuauacaauc uacugucuuu c                                        21

<210> SEQ ID NO 120
<211> LENGTH: 20
<212> TYPE: RNA
<213> ORGANISM: Homo sapiens

<400> SEQUENCE: 120
auggagauag auauagaaau                                          20

<210> SEQ ID NO 121
<211> LENGTH: 22
<212> TYPE: RNA
<213> ORGANISM: Homo sapiens

<400> SEQUENCE: 121
caaaaguaau uuggauuuu gu                                        22

<210> SEQ ID NO 122
<211> LENGTH: 20
<212> TYPE: RNA
<213> ORGANISM: Homo sapiens

<400> SEQUENCE: 122
uacaguauag augauguacu                                          20

<210> SEQ ID NO 123
<211> LENGTH: 21
<212> TYPE: RNA
<213> ORGANISM: Homo sapiens

<400> SEQUENCE: 123
cucccacaug caggguuugc a                                        21

<210> SEQ ID NO 124
<211> LENGTH: 25
<212> TYPE: RNA
<213> ORGANISM: Homo sapiens

<400> SEQUENCE: 124
ggcggaggga aguagguccg uuggu                                    25

<210> SEQ ID NO 125
<211> LENGTH: 22
<212> TYPE: RNA
<213> ORGANISM: Homo sapiens

<400> SEQUENCE: 125
uagguuaucc guguugccuu cg                                       22

<210> SEQ ID NO 126
<211> LENGTH: 24
<212> TYPE: RNA
<213> ORGANISM: Homo sapiens

<400> SEQUENCE: 126 ugggagcug aggcucuggg ggug                                      24

<210> SEQ ID NO 127
```

```
<211> LENGTH: 26
<212> TYPE: RNA
<213> ORGANISM: Homo sapiens

<400> SEQUENCE: 127
gugagggcau gcaggccugg augggg                                              26

<210> SEQ ID NO 128
<211> LENGTH: 22
<212> TYPE: RNA
<213> ORGANISM: Homo sapiens

<400> SEQUENCE: 128
aaacaaacau ggugcacuuc uu                                                  22

<210> SEQ ID NO 129
<211> LENGTH: 18
<212> TYPE: RNA
<213> ORGANISM: Homo sapiens

<400> SEQUENCE: 129
gucccuguuc aggcgcca                                                       18

<210> SEQ ID NO 130
<211> LENGTH: 22
<212> TYPE: RNA
<213> ORGANISM: Homo sapiens

<400> SEQUENCE: 130
ugcuaugcca acauauugcc au                                                  22

<210> SEQ ID NO 131
<211> LENGTH: 22
<212> TYPE: RNA
<213> ORGANISM: Homo sapiens

<400> SEQUENCE: 131
uauugcacau uacuaaguug ca                                                  22

<210> SEQ ID NO 132
<211> LENGTH: 22
<212> TYPE: RNA
<213> ORGANISM: Homo sapiens

<400> SEQUENCE: 132
auaaagcuag auaaccgaaa gu                                                  22

<210> SEQ ID NO 133
<211> LENGTH: 23
<212> TYPE: RNA
<213> ORGANISM: Homo sapiens

<400> SEQUENCE: 133
cugggaucuc cggggucuug guu                                                 23

<210> SEQ ID NO 134
<211> LENGTH: 22
<212> TYPE: RNA
<213> ORGANISM: Homo sapiens

<400> SEQUENCE: 134
gugugcggaa augcuucugc ua                                                  22
```

```
<210> SEQ ID NO 135
<211> LENGTH: 22
<212> TYPE: RNA
<213> ORGANISM: Homo sapiens

<400> SEQUENCE: 135
acugcauuau gagcacuuaa ag                                              22

<210> SEQ ID NO 136
<211> LENGTH: 22
<212> TYPE: RNA
<213> ORGANISM: Homo sapiens

<400> SEQUENCE: 136
uuauaaagca augagacuga uu                                              22

<210> SEQ ID NO 137
<211> LENGTH: 21
<212> TYPE: RNA
<213> ORGANISM: Homo sapiens

<400> SEQUENCE: 137 agggccccccc cucaauccug u                                              21

<210> SEQ ID NO 138
<211> LENGTH: 23
<212> TYPE: RNA
<213> ORGANISM: Homo sapiens

<400> SEQUENCE: 138
cuggagauau ggaagagcug ugu                                             23

<210> SEQ ID NO 139
<211> LENGTH: 22
<212> TYPE: RNA
<213> ORGANISM: Homo sapiens

<400> SEQUENCE: 139
aguuuugcau aguugcacua ca                                              22

<210> SEQ ID NO 140
<211> LENGTH: 22
<212> TYPE: RNA
<213> ORGANISM: Homo sapiens

<400> SEQUENCE: 140
cgcaggggcc gggugcucac cg                                              22

<210> SEQ ID NO 141
<211> LENGTH: 19
<212> TYPE: RNA
<213> ORGANISM: Homo sapiens

<400> SEQUENCE: 141
aauggauuuu uggagcagg                                                  19

<210> SEQ ID NO 142
<211> LENGTH: 22
<212> TYPE: RNA
<213> ORGANISM: Homo sapiens

<400> SEQUENCE: 142
uauguaacac gguccacuaa cc                                              22
```

```
<210> SEQ ID NO 143
<211> LENGTH: 22
<212> TYPE: RNA
<213> ORGANISM: Homo sapiens

<400> SEQUENCE: 143
agagguagua gguugcauag uu                                              22

<210> SEQ ID NO 144
<211> LENGTH: 23
<212> TYPE: RNA
<213> ORGANISM: Homo sapiens

<400> SEQUENCE: 144
uaaggugcau cuagugcagu uag                                             23

<210> SEQ ID NO 145
<211> LENGTH: 24
<212> TYPE: RNA
<213> ORGANISM: Homo sapiens

<400> SEQUENCE: 145
uucuccaaaa gaaagcacuu ucug                                            24

<210> SEQ ID NO 146
<211> LENGTH: 19
<212> TYPE: RNA
<213> ORGANISM: Homo sapiens

<400> SEQUENCE: 146
gugaggacuc gggaggugg                                                  19

<210> SEQ ID NO 147
<211> LENGTH: 21
<212> TYPE: RNA
<213> ORGANISM: Homo sapiens

<400> SEQUENCE: 147
cuguacaggc cacugccuug c                                               21

<210> SEQ ID NO 148
<211> LENGTH: 21
<212> TYPE: RNA
<213> ORGANISM: Homo sapiens

<400> SEQUENCE: 148
aacaggugac ugguuagaca a                                               21

<210> SEQ ID NO 149
<211> LENGTH: 23
<212> TYPE: RNA
<213> ORGANISM: Homo sapiens

<400> SEQUENCE: 149
uacuccagag ggcgucacuc aug                                             23

<210> SEQ ID NO 150
<211> LENGTH: 22
<212> TYPE: RNA
<213> ORGANISM: Homo sapiens

<400> SEQUENCE: 150
ucaguaaaug uuuauuagau ga                                              22
```

<210> SEQ ID NO 151
<211> LENGTH: 24
<212> TYPE: RNA
<213> ORGANISM: Homo sapiens

<400> SEQUENCE: 151
uggcccugac ugaagaccag cagu                                          24

<210> SEQ ID NO 152
<211> LENGTH: 23
<212> TYPE: RNA
<213> ORGANISM: Homo sapiens

<400> SEQUENCE: 152
ugucugcccg caugccugcc ucu                                           23

<210> SEQ ID NO 153
<211> LENGTH: 22
<212> TYPE: RNA
<213> ORGANISM: Homo sapiens

<400> SEQUENCE: 153
ugccuacuga gcugaaacac ag                                            22

<210> SEQ ID NO 154
<211> LENGTH: 22
<212> TYPE: RNA
<213> ORGANISM: Homo sapiens

<400> SEQUENCE: 154
ucaggcucag uccccucccg au                                            22

<210> SEQ ID NO 155
<211> LENGTH: 17
<212> TYPE: RNA
<213> ORGANISM: Homo sapiens

<400> SEQUENCE: 155
ucucgcuggg gccucca                                                  17

<210> SEQ ID NO 156
<211> LENGTH: 23
<212> TYPE: RNA
<213> ORGANISM: Homo sapiens

<400> SEQUENCE: 156
uagcagcggg aacaguucug cag                                           23

<210> SEQ ID NO 157
<211> LENGTH: 22
<212> TYPE: RNA
<213> ORGANISM: Homo sapiens

<400> SEQUENCE: 157
agaauugugg cuggacaucu gu                                            22

<210> SEQ ID NO 158
<211> LENGTH: 23
<212> TYPE: RNA
<213> ORGANISM: Homo sapiens

<400> SEQUENCE: 158

```
uguaaacauc cuacacucuc agc                                        23

<210> SEQ ID NO 159
<211> LENGTH: 22
<212> TYPE: RNA
<213> ORGANISM: Homo sapiens

<400> SEQUENCE: 159
uuuccggcuc gcgugggugu gu                                         22

<210> SEQ ID NO 160
<211> LENGTH: 22
<212> TYPE: RNA
<213> ORGANISM: Homo sapiens

<400> SEQUENCE: 160
aaucguacag ggucauccac uu                                         22

<210> SEQ ID NO 161
<211> LENGTH: 22
<212> TYPE: RNA
<213> ORGANISM: Homo sapiens

<400> SEQUENCE: 161
acuggacuua gggucagaag gc                                         22

<210> SEQ ID NO 162
<211> LENGTH: 22
<212> TYPE: RNA
<213> ORGANISM: Homo sapiens

<400> SEQUENCE: 162
uagcaccauc ugaaaucggu ua                                         22

<210> SEQ ID NO 163
<211> LENGTH: 22
<212> TYPE: RNA
<213> ORGANISM: Homo sapiens

<400> SEQUENCE: 163
uacugcagac guggcaauca ug                                         22

<210> SEQ ID NO 164
<211> LENGTH: 23
<212> TYPE: RNA
<213> ORGANISM: Homo sapiens

<400> SEQUENCE: 164
uacugcauca ggaacugauu gga                                        23

<210> SEQ ID NO 165
<211> LENGTH: 22
<212> TYPE: RNA
<213> ORGANISM: Homo sapiens

<400> SEQUENCE: 165
ccuguucucc auuacuuggc uc                                         22

<210> SEQ ID NO 166
<211> LENGTH: 18
<212> TYPE: RNA
<213> ORGANISM: Homo sapiens

<400> SEQUENCE: 166
```

-continued uccagugccc uccucucc                                                    18

<210> SEQ ID NO 167
<211> LENGTH: 22
<212> TYPE: RNA
<213> ORGANISM: Homo sapiens

<400> SEQUENCE: 167
ugccugucua cacuugcugu gc                                               22

<210> SEQ ID NO 168
<211> LENGTH: 22
<212> TYPE: RNA
<213> ORGANISM: Homo sapiens

<400> SEQUENCE: 168
ugccuacuga gcugauauca gu                                               22

<210> SEQ ID NO 169
<211> LENGTH: 18
<212> TYPE: RNA
<213> ORGANISM: Homo sapiens

<400> SEQUENCE: 169
acguuggcuc ugguggug                                                    18

<210> SEQ ID NO 170
<211> LENGTH: 22
<212> TYPE: RNA
<213> ORGANISM: Homo sapiens

<400> SEQUENCE: 170
caagcucgcu ucuaugdguc ug                                               22

<210> SEQ ID NO 171
<211> LENGTH: 27
<212> TYPE: RNA
<213> ORGANISM: Homo sapiens

<400> SEQUENCE: 171
accuucuugu auaagcacug ugcuaaa                                          27

<210> SEQ ID NO 172
<211> LENGTH: 22
<212> TYPE: RNA
<213> ORGANISM: Homo sapiens

<400> SEQUENCE: 172
uugggaucau uuugcaucca ua                                               22

<210> SEQ ID NO 173
<211> LENGTH: 22
<212> TYPE: RNA
<213> ORGANISM: Homo sapiens

<400> SEQUENCE: 173
ccucuagaug gaagcacugu cu                                               22

<210> SEQ ID NO 174
<211> LENGTH: 21
<212> TYPE: RNA
<213> ORGANISM: Homo sapiens

```
<400> SEQUENCE: 174
uuuccauagg ugaugaguca c                                           21

<210> SEQ ID NO 175
<211> LENGTH: 23
<212> TYPE: RNA
<213> ORGANISM: Homo sapiens

<400> SEQUENCE: 175
ugagugugug ugugugagug ugu                                         23

<210> SEQ ID NO 176
<211> LENGTH: 22
<212> TYPE: RNA
<213> ORGANISM: Homo sapiens

<400> SEQUENCE: 176
auucugcauu uuuagcaagu uc                                          22

<210> SEQ ID NO 177
<211> LENGTH: 22
<212> TYPE: RNA
<213> ORGANISM: Homo sapiens

<400> SEQUENCE: 177
aacccguaga uccgaucuug ug                                          22

<210> SEQ ID NO 178
<211> LENGTH: 21
<212> TYPE: RNA
<213> ORGANISM: Homo sapiens

<400> SEQUENCE: 178
ucagugcaug acagaacuug g                                           21

<210> SEQ ID NO 179
<211> LENGTH: 22
<212> TYPE: RNA
<213> ORGANISM: Homo sapiens

<400> SEQUENCE: 179
acugcaguga aggcacuugu ag                                          22

<210> SEQ ID NO 180
<211> LENGTH: 23
<212> TYPE: RNA
<213> ORGANISM: Homo sapiens

<400> SEQUENCE: 180
uuuggcacua gcacauuuuu gcu                                         23

<210> SEQ ID NO 181
<211> LENGTH: 22
<212> TYPE: RNA
<213> ORGANISM: Homo sapiens

<400> SEQUENCE: 181
uguaaacauc cucgacugga ag                                          22

<210> SEQ ID NO 182
<211> LENGTH: 22
<212> TYPE: RNA
<213> ORGANISM: Homo sapiens
```

<400> SEQUENCE: 182
caaccuggag gacuccaugc ug                                              22

<210> SEQ ID NO 183
<211> LENGTH: 21
<212> TYPE: RNA
<213> ORGANISM: Homo sapiens

<400> SEQUENCE: 183
ugacaacuau ggaugagcuc u                                               21

<210> SEQ ID NO 184
<211> LENGTH: 23
<212> TYPE: RNA
<213> ORGANISM: Homo sapiens

<400> SEQUENCE: 184
caguaacaaa gauucauccu ugu                                             23

<210> SEQ ID NO 185
<211> LENGTH: 21
<212> TYPE: RNA
<213> ORGANISM: Homo sapiens

<400> SEQUENCE: 185
ccuguugaag uguaaucccc a                                               21

<210> SEQ ID NO 186
<211> LENGTH: 21
<212> TYPE: RNA
<213> ORGANISM: Homo sapiens

<400> SEQUENCE: 186
aauauaacac agauggccug u                                               21

<210> SEQ ID NO 187
<211> LENGTH: 23
<212> TYPE: RNA
<213> ORGANISM: Homo sapiens

<400> SEQUENCE: 187
uaagugcuuc cauguuuuag uag                                             23

<210> SEQ ID NO 188
<211> LENGTH: 22
<212> TYPE: RNA
<213> ORGANISM: Homo sapiens

<400> SEQUENCE: 188
aaggagcuca cagucuauug ag                                              22

<210> SEQ ID NO 189
<211> LENGTH: 22
<212> TYPE: RNA
<213> ORGANISM: Homo sapiens

<400> SEQUENCE: 189
uagguaguuu ccuguuguug gg                                              22

<210> SEQ ID NO 190
<211> LENGTH: 23
<212> TYPE: RNA

```
<213> ORGANISM: Homo sapiens

<400> SEQUENCE: 190
aggcagugua guuagcugau ugc                                           23

<210> SEQ ID NO 191
<211> LENGTH: 22
<212> TYPE: RNA
<213> ORGANISM: Homo sapiens

<400> SEQUENCE: 191
gagugccuuc uuuuggagcg uu                                            22

<210> SEQ ID NO 192
<211> LENGTH: 21
<212> TYPE: RNA
<213> ORGANISM: Homo sapiens

<400> SEQUENCE: 192
uugggacaua cuuaugcuaa a                                             21

<210> SEQ ID NO 193
<211> LENGTH: 21
<212> TYPE: RNA
<213> ORGANISM: Homo sapiens

<400> SEQUENCE: 193
uccgguucuc agggcuccac c                                             21

<210> SEQ ID NO 194
<211> LENGTH: 23
<212> TYPE: RNA
<213> ORGANISM: Homo sapiens

<400> SEQUENCE: 194
ugcaccaugg uugucugagc aug                                           23

<210> SEQ ID NO 195
<211> LENGTH: 22
<212> TYPE: RNA
<213> ORGANISM: Homo sapiens

<400> SEQUENCE: 195
uucaccaccu ucuccaccca gc                                            22

<210> SEQ ID NO 196
<211> LENGTH: 21
<212> TYPE: RNA
<213> ORGANISM: Homo sapiens

<400> SEQUENCE: 196
uggguuuacg uugggagaac u                                             21

<210> SEQ ID NO 197
<211> LENGTH: 22
<212> TYPE: RNA
<213> ORGANISM: Homo sapiens

<400> SEQUENCE: 197
guggguacgg cccagugggg gg                                            22

<210> SEQ ID NO 198
<211> LENGTH: 21
```

```
<212> TYPE: RNA
<213> ORGANISM: Homo sapiens

<400> SEQUENCE: 198
caucccuugc augguggagg g                                                 21

<210> SEQ ID NO 199
<211> LENGTH: 24
<212> TYPE: RNA
<213> ORGANISM: Homo sapiens

<400> SEQUENCE: 199
agcagaagca gggagguucu ccca                                              24

<210> SEQ ID NO 200
<211> LENGTH: 22
<212> TYPE: RNA
<213> ORGANISM: Homo sapiens

<400> SEQUENCE: 200
ggagaaauua uccuuggugu gu                                                22

<210> SEQ ID NO 201
<211> LENGTH: 24
<212> TYPE: RNA
<213> ORGANISM: Homo sapiens

<400> SEQUENCE: 201
ucccugagac ccuuuaaccu guga                                              24

<210> SEQ ID NO 202
<211> LENGTH: 22
<212> TYPE: RNA
<213> ORGANISM: Homo sapiens

<400> SEQUENCE: 202
caaaacuggc aauuacuuuu gc                                                22

<210> SEQ ID NO 203
<211> LENGTH: 22
<212> TYPE: RNA
<213> ORGANISM: Homo sapiens

<400> SEQUENCE: 203
uauugcacuc gucccggccu cc                                                22

<210> SEQ ID NO 204
<211> LENGTH: 22
<212> TYPE: RNA
<213> ORGANISM: Homo sapiens

<400> SEQUENCE: 204
cucuagaggg aagcgcuuuc ug                                                22

<210> SEQ ID NO 205
<211> LENGTH: 22
<212> TYPE: RNA
<213> ORGANISM: Homo sapiens

<400> SEQUENCE: 205
uucacaagga ggugucauuu au                                                22

<210> SEQ ID NO 206
```

```
<211> LENGTH: 22
<212> TYPE: RNA
<213> ORGANISM: Homo sapiens

<400> SEQUENCE: 206
uacccauugc auaucggagu ug                                              22

<210> SEQ ID NO 207
<211> LENGTH: 21
<212> TYPE: RNA
<213> ORGANISM: Homo sapiens

<400> SEQUENCE: 207
cggcggggac ggcgauuggu c                                               21

<210> SEQ ID NO 208
<211> LENGTH: 22
<212> TYPE: RNA
<213> ORGANISM: Homo sapiens

<400> SEQUENCE: 208
cgucuuaccc agcaguguuu gg                                              22

<210> SEQ ID NO 209
<211> LENGTH: 23
<212> TYPE: RNA
<213> ORGANISM: Homo sapiens

<400> SEQUENCE: 209
acuugggcac ugaaacaaug ucc                                             23

<210> SEQ ID NO 210
<211> LENGTH: 22
<212> TYPE: RNA
<213> ORGANISM: Homo sapiens

<400> SEQUENCE: 210
acaguagucu gcacauuggu ua                                              22

<210> SEQ ID NO 211
<211> LENGTH: 23
<212> TYPE: RNA
<213> ORGANISM: Homo sapiens

<400> SEQUENCE: 211
aggaccugcg ggacaagauu cuu                                             23

<210> SEQ ID NO 212
<211> LENGTH: 22
<212> TYPE: RNA
<213> ORGANISM: Homo sapiens

<400> SEQUENCE: 212
aggcagcggg guguagugga ua                                              22

<210> SEQ ID NO 213
<211> LENGTH: 22
<212> TYPE: RNA
<213> ORGANISM: Homo sapiens

<400> SEQUENCE: 213 gggugggggau uuguugcauu ac                                             22
```

```
<210> SEQ ID NO 214
<211> LENGTH: 22
<212> TYPE: RNA
<213> ORGANISM: Homo sapiens

<400> SEQUENCE: 214
cacacacugc aauuacuuuu gc                                              22

<210> SEQ ID NO 215
<211> LENGTH: 22
<212> TYPE: RNA
<213> ORGANISM: Homo sapiens

<400> SEQUENCE: 215
cuauacaacc uacugccuuc cc                                              22

<210> SEQ ID NO 216
<211> LENGTH: 22
<212> TYPE: RNA
<213> ORGANISM: Homo sapiens

<400> SEQUENCE: 216
gaaguuguuc gugguggauu cg                                              22

<210> SEQ ID NO 217
<211> LENGTH: 22
<212> TYPE: RNA
<213> ORGANISM: Homo sapiens

<400> SEQUENCE: 217
uauguaacau gguccacuaa cu                                              22

<210> SEQ ID NO 218
<211> LENGTH: 22
<212> TYPE: RNA
<213> ORGANISM: Homo sapiens

<400> SEQUENCE: 218
cuauacggcc uccuagcuuu cc                                              22

<210> SEQ ID NO 219
<211> LENGTH: 22
<212> TYPE: RNA
<213> ORGANISM: Homo sapiens

<400> SEQUENCE: 219
aagugcuucc uuuuagaggg uu                                              22

<210> SEQ ID NO 220
<211> LENGTH: 22
<212> TYPE: RNA
<213> ORGANISM: Homo sapiens

<400> SEQUENCE: 220
aucacacaaa ggcaacuuuu gu                                              22

<210> SEQ ID NO 221
<211> LENGTH: 22
<212> TYPE: RNA
<213> ORGANISM: Homo sapiens

<400> SEQUENCE: 221
uacccagagc augcagugug aa                                              22
```

```
<210> SEQ ID NO 222
<211> LENGTH: 22
<212> TYPE: RNA
<213> ORGANISM: Homo sapiens

<400> SEQUENCE: 222
cucaucugca aagaaguaag ug                                                  22

<210> SEQ ID NO 223
<211> LENGTH: 22
<212> TYPE: RNA
<213> ORGANISM: Homo sapiens

<400> SEQUENCE: 223
ugagaacuga auuccauggg uu                                                  22

<210> SEQ ID NO 224
<211> LENGTH: 22
<212> TYPE: RNA
<213> ORGANISM: Homo sapiens

<400> SEQUENCE: 224
gugaauuacc gaagggccau aa                                                  22

<210> SEQ ID NO 225
<211> LENGTH: 22
<212> TYPE: RNA
<213> ORGANISM: Homo sapiens

<400> SEQUENCE: 225
agaguugagu cuggacgucc cg                                                  22

<210> SEQ ID NO 226
<211> LENGTH: 22
<212> TYPE: RNA
<213> ORGANISM: Homo sapiens

<400> SEQUENCE: 226 ugauuggua c gucugugggu ag                                                 22

<210> SEQ ID NO 227
<211> LENGTH: 22
<212> TYPE: RNA
<213> ORGANISM: Homo sapiens

<400> SEQUENCE: 227
aagugcuguc auagcugagg uc                                                  22

<210> SEQ ID NO 228
<211> LENGTH: 22
<212> TYPE: RNA
<213> ORGANISM: Homo sapiens

<400> SEQUENCE: 228
ccucugaaau ucaguucuuc ag                                                  22

<210> SEQ ID NO 229
<211> LENGTH: 19
<212> TYPE: RNA
<213> ORGANISM: Homo sapiens

<400> SEQUENCE: 229
gugucugcuu ccuguggga                                                      19
```

```
<210> SEQ ID NO 230
<211> LENGTH: 22
<212> TYPE: RNA
<213> ORGANISM: Homo sapiens

<400> SEQUENCE: 230
uuaucagaau cuccagggu ac                                              22

<210> SEQ ID NO 231
<211> LENGTH: 22
<212> TYPE: RNA
<213> ORGANISM: Homo sapiens

<400> SEQUENCE: 231
caggaugugg ucaaguguug uu                                             22

<210> SEQ ID NO 232
<211> LENGTH: 22
<212> TYPE: RNA
<213> ORGANISM: Homo sapiens

<400> SEQUENCE: 232
uuuggucccc uucaaccagc ug                                             22

<210> SEQ ID NO 233
<211> LENGTH: 22
<212> TYPE: RNA
<213> ORGANISM: Homo sapiens

<400> SEQUENCE: 233
uggagagaaa ggcaguuccu ga                                             22

<210> SEQ ID NO 234
<211> LENGTH: 22
<212> TYPE: RNA
<213> ORGANISM: Homo sapiens

<400> SEQUENCE: 234
agggacggga cgcggugcag ug                                             22

<210> SEQ ID NO 235
<211> LENGTH: 21
<212> TYPE: RNA
<213> ORGANISM: Homo sapiens

<400> SEQUENCE: 235
uggacugccc ugaucuggag a                                              21

<210> SEQ ID NO 236
<211> LENGTH: 22
<212> TYPE: RNA
<213> ORGANISM: Homo sapiens

<400> SEQUENCE: 236
aaaaguaauu gcggucuuug gu                                             22

<210> SEQ ID NO 237
<211> LENGTH: 22
<212> TYPE: RNA
<213> ORGANISM: Homo sapiens

<400> SEQUENCE: 237
```
uaaugccccu aaaaauccuu au                                          22

<210> SEQ ID NO 238
<211> LENGTH: 22
<212> TYPE: RNA
<213> ORGANISM: Homo sapiens

<400> SEQUENCE: 238
ugcccuaaau gccccuucug gc                                          22

<210> SEQ ID NO 239
<211> LENGTH: 17
<212> TYPE: RNA
<213> ORGANISM: Homo sapiens

<400> SEQUENCE: 239
ucauauugcu ucuuucu                                                17

<210> SEQ ID NO 240
<211> LENGTH: 23
<212> TYPE: RNA
<213> ORGANISM: Homo sapiens

<400> SEQUENCE: 240
aaugacacga ucacucccgu uga                                         23

<210> SEQ ID NO 241
<211> LENGTH: 22
<212> TYPE: RNA
<213> ORGANISM: Homo sapiens

<400> SEQUENCE: 241
aagaugugga aaaauuggaa uc                                          22

<210> SEQ ID NO 242
<211> LENGTH: 21
<212> TYPE: RNA
<213> ORGANISM: Homo sapiens

<400> SEQUENCE: 242
ugucuugcag gccgucaugc a                                           21

<210> SEQ ID NO 243
<211> LENGTH: 22
<212> TYPE: RNA
<213> ORGANISM: Homo sapiens

<400> SEQUENCE: 243
caaagcgcuc cccuuuagag gu                                          22

<210> SEQ ID NO 244
<211> LENGTH: 20
<212> TYPE: RNA
<213> ORGANISM: Homo sapiens

<400> SEQUENCE: 244
uaaggcacgc ggugaaugcc                                             20

<210> SEQ ID NO 245
<211> LENGTH: 22
<212> TYPE: RNA
<213> ORGANISM: Homo sapiens

<400> SEQUENCE: 245
ccuauucuug guuacuugca cg    22

<210> SEQ ID NO 246
<211> LENGTH: 21
<212> TYPE: RNA
<213> ORGANISM: Homo sapiens

<400> SEQUENCE: 246
ugaguuggcc aucugaguga g    21

<210> SEQ ID NO 247
<211> LENGTH: 23
<212> TYPE: RNA
<213> ORGANISM: Homo sapiens

<400> SEQUENCE: 247
cccaguguuu agacuaucug uuc    23

<210> SEQ ID NO 248
<211> LENGTH: 23
<212> TYPE: RNA
<213> ORGANISM: Homo sapiens

<400> SEQUENCE: 248
ucauagcccu guacaaugcu gcu    23

<210> SEQ ID NO 249
<211> LENGTH: 21
<212> TYPE: RNA
<213> ORGANISM: Homo sapiens

<400> SEQUENCE: 249
ugauugucca aacgcaauuc u    21

<210> SEQ ID NO 250
<211> LENGTH: 22
<212> TYPE: RNA
<213> ORGANISM: Homo sapiens

<400> SEQUENCE: 250
ugucaguuug ucaaauaccc ca    22

<210> SEQ ID NO 251
<211> LENGTH: 23
<212> TYPE: RNA
<213> ORGANISM: Homo sapiens

<400> SEQUENCE: 251
cagugcaaua guauugucaa agc    23

<210> SEQ ID NO 252
<211> LENGTH: 22
<212> TYPE: RNA
<213> ORGANISM: Homo sapiens

<400> SEQUENCE: 252
ugagaccucu ggguucugag cu    22

<210> SEQ ID NO 253
<211> LENGTH: 21
<212> TYPE: RNA
<213> ORGANISM: Homo sapiens

```
<400> SEQUENCE: 253
uggcagggag gcugggaggg g                                               21

<210> SEQ ID NO 254
<211> LENGTH: 21
<212> TYPE: RNA
<213> ORGANISM: Homo sapiens

<400> SEQUENCE: 254
aauaauacau gguugaucuu u                                               21

<210> SEQ ID NO 255
<211> LENGTH: 22
<212> TYPE: RNA
<213> ORGANISM: Homo sapiens

<400> SEQUENCE: 255
cucuagaggg aagcgcuuuc ug                                              22

<210> SEQ ID NO 256
<211> LENGTH: 23
<212> TYPE: RNA
<213> ORGANISM: Homo sapiens

<400> SEQUENCE: 256 cgcaucccu agggcauugg ugu                                              23

<210> SEQ ID NO 257
<211> LENGTH: 22
<212> TYPE: RNA
<213> ORGANISM: Homo sapiens

<400> SEQUENCE: 257
ugugucacuc gaugaccacu gu                                              22

<210> SEQ ID NO 258
<211> LENGTH: 19
<212> TYPE: RNA
<213> ORGANISM: Homo sapiens

<400> SEQUENCE: 258
aggcacggug ucagcaggc                                                  19

<210> SEQ ID NO 259
<211> LENGTH: 22
<212> TYPE: RNA
<213> ORGANISM: Homo sapiens

<400> SEQUENCE: 259
cagugguuuu acccuauggu ag                                              22

<210> SEQ ID NO 260
<211> LENGTH: 23
<212> TYPE: RNA
<213> ORGANISM: Homo sapiens

<400> SEQUENCE: 260
ucuuggagua ggucauuggg ugg                                             23

<210> SEQ ID NO 261
<211> LENGTH: 22
<212> TYPE: RNA
<213> ORGANISM: Homo sapiens
```

```
<400> SEQUENCE: 261
uugcauaguc acaaaaguga uc                                           22

<210> SEQ ID NO 262
<211> LENGTH: 21
<212> TYPE: RNA
<213> ORGANISM: Homo sapiens

<400> SEQUENCE: 262
augaccuaug aauugacaga c                                            21

<210> SEQ ID NO 263
<211> LENGTH: 22
<212> TYPE: RNA
<213> ORGANISM: Homo sapiens

<400> SEQUENCE: 263
cccugugccc ggcccacuuc ug                                           22

<210> SEQ ID NO 264
<211> LENGTH: 22
<212> TYPE: RNA
<213> ORGANISM: Homo sapiens

<400> SEQUENCE: 264
uauggcacug guagaauuca cu                                           22

<210> SEQ ID NO 265
<211> LENGTH: 23
<212> TYPE: RNA
<213> ORGANISM: Homo sapiens

<400> SEQUENCE: 265
aggaagcccu ggaggggcug gag                                          23

<210> SEQ ID NO 266
<211> LENGTH: 23
<212> TYPE: RNA
<213> ORGANISM: Homo sapiens

<400> SEQUENCE: 266
ugauuguagc cuuuuggagu aga                                          23

<210> SEQ ID NO 267
<211> LENGTH: 22
<212> TYPE: RNA
<213> ORGANISM: Homo sapiens

<400> SEQUENCE: 267
aacacaccua uucaaggauu ca                                           22

<210> SEQ ID NO 268
<211> LENGTH: 22
<212> TYPE: RNA
<213> ORGANISM: Homo sapiens

<400> SEQUENCE: 268
auauuaccau uagcucaucu uu                                           22

<210> SEQ ID NO 269
<211> LENGTH: 24
<212> TYPE: RNA
```

```
<213> ORGANISM: Homo sapiens

<400> SEQUENCE: 269
ccagacagaa uucuaugcac uuuc                                           24

<210> SEQ ID NO 270
<211> LENGTH: 23
<212> TYPE: RNA
<213> ORGANISM: Homo sapiens

<400> SEQUENCE: 270
uccaguacca cgugucaggg cca                                            23

<210> SEQ ID NO 271
<211> LENGTH: 22
<212> TYPE: RNA
<213> ORGANISM: Homo sapiens

<400> SEQUENCE: 271
gaauguugcu cggugaaccc cu                                             22

<210> SEQ ID NO 272
<211> LENGTH: 22
<212> TYPE: RNA
<213> ORGANISM: Homo sapiens

<400> SEQUENCE: 272
guucucccaa cguaagccca gc                                             22

<210> SEQ ID NO 273
<211> LENGTH: 21
<212> TYPE: RNA
<213> ORGANISM: Homo sapiens

<400> SEQUENCE: 273
uacugcagac aguggcaauc a                                              21

<210> SEQ ID NO 274
<211> LENGTH: 21
<212> TYPE: RNA
<213> ORGANISM: Homo sapiens

<400> SEQUENCE: 274
gcgacccacu cuugguuucc a                                              21

<210> SEQ ID NO 275
<211> LENGTH: 22
<212> TYPE: RNA
<213> ORGANISM: Homo sapiens

<400> SEQUENCE: 275
aaaaacugag acuacuuuug ca                                             22

<210> SEQ ID NO 276
<211> LENGTH: 21
<212> TYPE: RNA
<213> ORGANISM: Homo sapiens

<400> SEQUENCE: 276
gaaagcgcuu cucuuuagag g                                              21

<210> SEQ ID NO 277
<211> LENGTH: 22
```

```
<212> TYPE: RNA
<213> ORGANISM: Homo sapiens

<400> SEQUENCE: 277
aaagugcuuc cuuuuagagg gu                                              22

<210> SEQ ID NO 278
<211> LENGTH: 22
<212> TYPE: RNA
<213> ORGANISM: Homo sapiens

<400> SEQUENCE: 278
ccaaaacugc aguuacuuuu gc                                              22

<210> SEQ ID NO 279
<211> LENGTH: 22
<212> TYPE: RNA
<213> ORGANISM: Homo sapiens

<400> SEQUENCE: 279
cucuagaggg aagcacuuuc ug                                              22

<210> SEQ ID NO 280
<211> LENGTH: 22
<212> TYPE: RNA
<213> ORGANISM: Homo sapiens

<400> SEQUENCE: 280
caucuuccag uacaguguug ga                                              22

<210> SEQ ID NO 281
<211> LENGTH: 22
<212> TYPE: RNA
<213> ORGANISM: Homo sapiens

<400> SEQUENCE: 281
ccaguggggc ugcuguuauc ug                                              22

<210> SEQ ID NO 282
<211> LENGTH: 22
<212> TYPE: RNA
<213> ORGANISM: Homo sapiens

<400> SEQUENCE: 282
cagcagcaau ucauguuuug aa                                              22

<210> SEQ ID NO 283
<211> LENGTH: 17
<212> TYPE: RNA
<213> ORGANISM: Homo sapiens

<400> SEQUENCE: 283 guggggaga ggcuguc                                                     17

<210> SEQ ID NO 284
<211> LENGTH: 22
<212> TYPE: RNA
<213> ORGANISM: Homo sapiens

<400> SEQUENCE: 284
aaccaucgac cguugagugg ac                                              22

<210> SEQ ID NO 285
```

```
<211> LENGTH: 22
<212> TYPE: RNA
<213> ORGANISM: Homo sapiens

<400> SEQUENCE: 285
ucguaccgug aguaauaaug cg                                              22

<210> SEQ ID NO 286
<211> LENGTH: 21
<212> TYPE: RNA
<213> ORGANISM: Homo sapiens

<400> SEQUENCE: 286
cuagacugaa gcuccuugag g                                               21

<210> SEQ ID NO 287
<211> LENGTH: 22
<212> TYPE: RNA
<213> ORGANISM: Homo sapiens

<400> SEQUENCE: 287
ucuucucugu uuuggccaug ug                                              22

<210> SEQ ID NO 288
<211> LENGTH: 23
<212> TYPE: RNA
<213> ORGANISM: Homo sapiens

<400> SEQUENCE: 288
gcaaagcaca cggccugcag aga                                             23

<210> SEQ ID NO 289
<211> LENGTH: 23
<212> TYPE: RNA
<213> ORGANISM: Homo sapiens

<400> SEQUENCE: 289
uaauacugcc ggguaaugau gga                                             23

<210> SEQ ID NO 290
<211> LENGTH: 22
<212> TYPE: RNA
<213> ORGANISM: Homo sapiens

<400> SEQUENCE: 290
uggucuagga uuguuggagg ag                                              22

<210> SEQ ID NO 291
<211> LENGTH: 21
<212> TYPE: RNA
<213> ORGANISM: Homo sapiens

<400> SEQUENCE: 291
aucacauugc cagggauuac c                                               21

<210> SEQ ID NO 292
<211> LENGTH: 22
<212> TYPE: RNA
<213> ORGANISM: Homo sapiens

<400> SEQUENCE: 292
gacuauagaa cuuuccccu ca                                               22
```

```
<210> SEQ ID NO 293
<211> LENGTH: 21
<212> TYPE: RNA
<213> ORGANISM: Homo sapiens

<400> SEQUENCE: 293
agagaagaag aucagccugc a                                             21

<210> SEQ ID NO 294
<211> LENGTH: 23
<212> TYPE: RNA
<213> ORGANISM: Homo sapiens

<400> SEQUENCE: 294
ugaggggcag agagcgagac uuu                                           23

<210> SEQ ID NO 295
<211> LENGTH: 22
<212> TYPE: RNA
<213> ORGANISM: Homo sapiens

<400> SEQUENCE: 295
cucuagaggg aagcgcuuuc ug                                            22

<210> SEQ ID NO 296
<211> LENGTH: 22
<212> TYPE: RNA
<213> ORGANISM: Homo sapiens

<400> SEQUENCE: 296
aggggcuggc uuuccucugg uc                                            22

<210> SEQ ID NO 297
<211> LENGTH: 20
<212> TYPE: RNA
<213> ORGANISM: Homo sapiens

<400> SEQUENCE: 297
cuuccucguc ugucugcccc                                               20

<210> SEQ ID NO 298
<211> LENGTH: 22
<212> TYPE: RNA
<213> ORGANISM: Homo sapiens

<400> SEQUENCE: 298
aucauagagg aaaauccaug uu                                            22

<210> SEQ ID NO 299
<211> LENGTH: 21
<212> TYPE: RNA
<213> ORGANISM: Homo sapiens

<400> SEQUENCE: 299
aaaacgguga gauuuuguuu u                                             21

<210> SEQ ID NO 300
<211> LENGTH: 21
<212> TYPE: RNA
<213> ORGANISM: Homo sapiens

<400> SEQUENCE: 300
aucacauugc cagggauuuc c                                             21
```

```
<210> SEQ ID NO 301
<211> LENGTH: 19
<212> TYPE: RNA
<213> ORGANISM: Homo sapiens

<400> SEQUENCE: 301
gggcgccugu gaucccaac                                                    19

<210> SEQ ID NO 302
<211> LENGTH: 22
<212> TYPE: RNA
<213> ORGANISM: Homo sapiens

<400> SEQUENCE: 302
cuggacugag ccgugcuacu gg                                                22

<210> SEQ ID NO 303
<211> LENGTH: 20
<212> TYPE: RNA
<213> ORGANISM: Homo sapiens

<400> SEQUENCE: 303
aggaauguuc cuucuuugcc                                                   20

<210> SEQ ID NO 304
<211> LENGTH: 21
<212> TYPE: RNA
<213> ORGANISM: Homo sapiens

<400> SEQUENCE: 304
agggguscua ucgugauug a                                                  21

<210> SEQ ID NO 305
<211> LENGTH: 22
<212> TYPE: RNA
<213> ORGANISM: Homo sapiens

<400> SEQUENCE: 305
aacgcacuuc ccuuuagagu gu                                                22

<210> SEQ ID NO 306
<211> LENGTH: 21
<212> TYPE: RNA
<213> ORGANISM: Homo sapiens

<400> SEQUENCE: 306
auguaugugu gcaugugcau g                                                 21

<210> SEQ ID NO 307
<211> LENGTH: 23
<212> TYPE: RNA
<213> ORGANISM: Homo sapiens

<400> SEQUENCE: 307
uuauugcuua agaauacgcg uag                                               23

<210> SEQ ID NO 308
<211> LENGTH: 21
<212> TYPE: RNA
<213> ORGANISM: Homo sapiens

<400> SEQUENCE: 308
gcaguccaug ggcauauaca c                                                 21
```

```
<210> SEQ ID NO 309
<211> LENGTH: 22
<212> TYPE: RNA
<213> ORGANISM: Homo sapiens

<400> SEQUENCE: 309
cgaaucauua uuugcugcuc ua                                              22

<210> SEQ ID NO 310
<211> LENGTH: 22
<212> TYPE: RNA
<213> ORGANISM: Homo sapiens

<400> SEQUENCE: 310
uccgagccug ggucucccuc uu                                              22

<210> SEQ ID NO 311
<211> LENGTH: 22
<212> TYPE: RNA
<213> ORGANISM: Homo sapiens

<400> SEQUENCE: 311
uaguacugug cauaucaucu au                                              22

<210> SEQ ID NO 312
<211> LENGTH: 22
<212> TYPE: RNA
<213> ORGANISM: Homo sapiens

<400> SEQUENCE: 312
caaagaauuc uccuuuuggg cu                                              22

<210> SEQ ID NO 313
<211> LENGTH: 22
<212> TYPE: RNA
<213> ORGANISM: Homo sapiens

<400> SEQUENCE: 313
ucagcaaaca uuuauugugu gc                                              22

<210> SEQ ID NO 314
<211> LENGTH: 22
<212> TYPE: RNA
<213> ORGANISM: Homo sapiens

<400> SEQUENCE: 314
aaucacuaac cacacggcca gg                                              22

<210> SEQ ID NO 315
<211> LENGTH: 21
<212> TYPE: RNA
<213> ORGANISM: Homo sapiens

<400> SEQUENCE: 315
ucguggccug gucuccauua u                                               21

<210> SEQ ID NO 316
<211> LENGTH: 23
<212> TYPE: RNA
<213> ORGANISM: Homo sapiens

<400> SEQUENCE: 316
```

```
aucaacagac auuaauuggg cgc                                            23

<210> SEQ ID NO 317
<211> LENGTH: 22
<212> TYPE: RNA
<213> ORGANISM: Homo sapiens

<400> SEQUENCE: 317
uuuagagacg gggucuugcu cu                                             22

<210> SEQ ID NO 318
<211> LENGTH: 19
<212> TYPE: RNA
<213> ORGANISM: Homo sapiens

<400> SEQUENCE: 318
aguguggcuu ucuuagagc                                                 19

<210> SEQ ID NO 319
<211> LENGTH: 22
<212> TYPE: RNA
<213> ORGANISM: Homo sapiens

<400> SEQUENCE: 319
cuuggcaccu agcaagcacu ca                                             22

<210> SEQ ID NO 320
<211> LENGTH: 22
<212> TYPE: RNA
<213> ORGANISM: Homo sapiens

<400> SEQUENCE: 320
uauacaaggg caagcucucu gu                                             22

<210> SEQ ID NO 321
<211> LENGTH: 22
<212> TYPE: RNA
<213> ORGANISM: Homo sapiens

<400> SEQUENCE: 321
gugagucucu aagaaaagag ga                                             22

<210> SEQ ID NO 322
<211> LENGTH: 22
<212> TYPE: RNA
<213> ORGANISM: Homo sapiens

<400> SEQUENCE: 322
acccgucccg uucguccccg ga                                             22

<210> SEQ ID NO 323
<211> LENGTH: 22
<212> TYPE: RNA
<213> ORGANISM: Homo sapiens

<400> SEQUENCE: 323
gugacaucac auauacggca gc                                             22

<210> SEQ ID NO 324
<211> LENGTH: 23
<212> TYPE: RNA
<213> ORGANISM: Homo sapiens

<400> SEQUENCE: 324
```

-continued uauggcuuuu cauuccuaug uga                                          23

<210> SEQ ID NO 325
<211> LENGTH: 23
<212> TYPE: RNA
<213> ORGANISM: Homo sapiens

<400> SEQUENCE: 325
ucucuggagg gaagcacuuu cug                                          23

<210> SEQ ID NO 326
<211> LENGTH: 23
<212> TYPE: RNA
<213> ORGANISM: Homo sapiens

<400> SEQUENCE: 326
uauggcuuuu uauuccuaug uga                                          23

<210> SEQ ID NO 327
<211> LENGTH: 22
<212> TYPE: RNA
<213> ORGANISM: Homo sapiens

<400> SEQUENCE: 327
aaaaguaauu gugguuuuug cc                                           22

<210> SEQ ID NO 328
<211> LENGTH: 22
<212> TYPE: RNA
<213> ORGANISM: Homo sapiens

<400> SEQUENCE: 328
cacgcucaug cacacaccca ca                                           22

<210> SEQ ID NO 329
<211> LENGTH: 22
<212> TYPE: RNA
<213> ORGANISM: Homo sapiens

<400> SEQUENCE: 329
gcccaaaggu gaauuuuuug gg                                           22

<210> SEQ ID NO 330
<211> LENGTH: 22
<212> TYPE: RNA
<213> ORGANISM: Homo sapiens

<400> SEQUENCE: 330
uaugucugcu gaccaucacc uu                                           22

<210> SEQ ID NO 331
<211> LENGTH: 22
<212> TYPE: RNA
<213> ORGANISM: Homo sapiens

<400> SEQUENCE: 331
uggaauguaa ggaagugugu gg                                           22

<210> SEQ ID NO 332
<211> LENGTH: 22
<212> TYPE: RNA
<213> ORGANISM: Homo sapiens

```
<400> SEQUENCE: 332
ggauaucauc auauacugua ag                                              22

<210> SEQ ID NO 333
<211> LENGTH: 24
<212> TYPE: RNA
<213> ORGANISM: Homo sapiens

<400> SEQUENCE: 333
ucagaacaaa ugccgguucc caga                                            24

<210> SEQ ID NO 334
<211> LENGTH: 22
<212> TYPE: RNA
<213> ORGANISM: Homo sapiens

<400> SEQUENCE: 334
uauagggauu ggagccgugg cg                                              22

<210> SEQ ID NO 335
<211> LENGTH: 22
<212> TYPE: RNA
<213> ORGANISM: Homo sapiens

<400> SEQUENCE: 335
cuauacaauc uauugccuuc cc                                              22

<210> SEQ ID NO 336
<211> LENGTH: 19
<212> TYPE: RNA
<213> ORGANISM: Homo sapiens

<400> SEQUENCE: 336
uggauuuuug gaucaggga                                                  19

<210> SEQ ID NO 337
<211> LENGTH: 22
<212> TYPE: RNA
<213> ORGANISM: Homo sapiens

<400> SEQUENCE: 337
acagcaggca cagacaggca gu                                              22

<210> SEQ ID NO 338
<211> LENGTH: 19
<212> TYPE: RNA
<213> ORGANISM: Homo sapiens

<400> SEQUENCE: 338
ugucucugcu gggguuucu                                                  19

<210> SEQ ID NO 339
<211> LENGTH: 22
<212> TYPE: RNA
<213> ORGANISM: Homo sapiens

<400> SEQUENCE: 339
cggcaacaag aaacugccug ag                                              22

<210> SEQ ID NO 340
<211> LENGTH: 22
<212> TYPE: RNA
<213> ORGANISM: Homo sapiens
```

```
<400> SEQUENCE: 340
cuuucaguca gauguuugcu gc                                              22

<210> SEQ ID NO 341
<211> LENGTH: 22
<212> TYPE: RNA
<213> ORGANISM: Homo sapiens

<400> SEQUENCE: 341
aaaaguaauu gugguuuugg cc                                              22

<210> SEQ ID NO 342
<211> LENGTH: 22
<212> TYPE: RNA
<213> ORGANISM: Homo sapiens

<400> SEQUENCE: 342
cucaguagcc aguguagauc cu                                              22

<210> SEQ ID NO 343
<211> LENGTH: 22
<212> TYPE: RNA
<213> ORGANISM: Homo sapiens

<400> SEQUENCE: 343
aagacgggag gaaagaaggg ag                                              22

<210> SEQ ID NO 344
<211> LENGTH: 22
<212> TYPE: RNA
<213> ORGANISM: Homo sapiens

<400> SEQUENCE: 344
acucggcgug gcgucggucg ug                                              22

<210> SEQ ID NO 345
<211> LENGTH: 20
<212> TYPE: RNA
<213> ORGANISM: Homo sapiens

<400> SEQUENCE: 345
uaaagagccc uguggagaca                                                 20

<210> SEQ ID NO 346
<211> LENGTH: 20
<212> TYPE: RNA
<213> ORGANISM: Homo sapiens

<400> SEQUENCE: 346
gugucugggc ggacagcugc                                                 20

<210> SEQ ID NO 347
<211> LENGTH: 22
<212> TYPE: RNA
<213> ORGANISM: Homo sapiens

<400> SEQUENCE: 347
cucuagaggg aagcacuuuc ug                                              22

<210> SEQ ID NO 348
<211> LENGTH: 22
<212> TYPE: RNA
```

<213> ORGANISM: Homo sapiens

<400> SEQUENCE: 348
ucagugcauc acagaacuuu gu                                            22

<210> SEQ ID NO 349
<211> LENGTH: 21
<212> TYPE: RNA
<213> ORGANISM: Homo sapiens

<400> SEQUENCE: 349 aggggggaaag uucuauaguc c                                            21

<210> SEQ ID NO 350
<211> LENGTH: 22
<212> TYPE: RNA
<213> ORGANISM: Homo sapiens

<400> SEQUENCE: 350
aucgugcauc ccuuuagagu gu                                            22

<210> SEQ ID NO 351
<211> LENGTH: 21
<212> TYPE: RNA
<213> ORGANISM: Homo sapiens

<400> SEQUENCE: 351
ugguagacua uggaacguag g                                             21

<210> SEQ ID NO 352
<211> LENGTH: 22
<212> TYPE: RNA
<213> ORGANISM: Homo sapiens

<400> SEQUENCE: 352
gggguuccug gggaugggau uu                                            22

<210> SEQ ID NO 353
<211> LENGTH: 21
<212> TYPE: RNA
<213> ORGANISM: Homo sapiens

<400> SEQUENCE: 353
uucacagugg cuaaguuccg c                                             21

<210> SEQ ID NO 354
<211> LENGTH: 22
<212> TYPE: RNA
<213> ORGANISM: Homo sapiens

<400> SEQUENCE: 354
ucacaaguca ggcucuuggg ac                                            22

<210> SEQ ID NO 355
<211> LENGTH: 22
<212> TYPE: RNA
<213> ORGANISM: Homo sapiens

<400> SEQUENCE: 355
ugugagguug gcauuguugu cu                                            22

<210> SEQ ID NO 356
<211> LENGTH: 20

```
<212> TYPE: RNA
<213> ORGANISM: Homo sapiens

<400> SEQUENCE: 356
aggguguuuc ucucaucucu                                                      20

<210> SEQ ID NO 357
<211> LENGTH: 22
<212> TYPE: RNA
<213> ORGANISM: Homo sapiens

<400> SEQUENCE: 357
uacgucaucg uugucaucgu ca                                                   22

<210> SEQ ID NO 358
<211> LENGTH: 22
<212> TYPE: RNA
<213> ORGANISM: Homo sapiens

<400> SEQUENCE: 358
ugcggggcua gggcuaacag ca                                                   22

<210> SEQ ID NO 359
<211> LENGTH: 21
<212> TYPE: RNA
<213> ORGANISM: Homo sapiens

<400> SEQUENCE: 359
ucgaggagcu cacagucuag u                                                    21

<210> SEQ ID NO 360
<211> LENGTH: 22
<212> TYPE: RNA
<213> ORGANISM: Homo sapiens

<400> SEQUENCE: 360
uagcagcacg uaaauauugg cg                                                   22

<210> SEQ ID NO 361
<211> LENGTH: 22
<212> TYPE: RNA
<213> ORGANISM: Homo sapiens

<400> SEQUENCE: 361
uguaacagca acuccaugug ga                                                   22

<210> SEQ ID NO 362
<211> LENGTH: 23
<212> TYPE: RNA
<213> ORGANISM: Homo sapiens

<400> SEQUENCE: 362
ugugcaaauc uaugcaaaac uga                                                  23

<210> SEQ ID NO 363
<211> LENGTH: 17
<212> TYPE: RNA
<213> ORGANISM: Homo sapiens

<400> SEQUENCE: 363
ucgccuccuc cucuccc                                                         17

<210> SEQ ID NO 364
```

```
<211> LENGTH: 22
<212> TYPE: RNA
<213> ORGANISM: Homo sapiens

<400> SEQUENCE: 364
caacaaauca cagucugcca ua                                              22

<210> SEQ ID NO 365
<211> LENGTH: 22
<212> TYPE: RNA
<213> ORGANISM: Homo sapiens

<400> SEQUENCE: 365
ccucccacac ccaaggcuug ca                                              22

<210> SEQ ID NO 366
<211> LENGTH: 22
<212> TYPE: RNA
<213> ORGANISM: Homo sapiens

<400> SEQUENCE: 366
acugcugagc uagcacuucc cg                                              22

<210> SEQ ID NO 367
<211> LENGTH: 21
<212> TYPE: RNA
<213> ORGANISM: Homo sapiens

<400> SEQUENCE: 367
ucacagugaa ccggucucuu u                                               21

<210> SEQ ID NO 368
<211> LENGTH: 24
<212> TYPE: RNA
<213> ORGANISM: Homo sapiens

<400> SEQUENCE: 368
uuuggcaaug guagaacuca cacu                                            24

<210> SEQ ID NO 369
<211> LENGTH: 22
<212> TYPE: RNA
<213> ORGANISM: Homo sapiens

<400> SEQUENCE: 369
uguaaacauc cccgacugga ag                                              22

<210> SEQ ID NO 370
<211> LENGTH: 23
<212> TYPE: RNA
<213> ORGANISM: Homo sapiens

<400> SEQUENCE: 370
caacggaauc ccaaaagcag cug                                             23

<210> SEQ ID NO 371
<211> LENGTH: 22
<212> TYPE: RNA
<213> ORGANISM: Homo sapiens

<400> SEQUENCE: 371
ugagguagua gauuguauag uu                                              22
```

```
<210> SEQ ID NO 372
<211> LENGTH: 22
<212> TYPE: RNA
<213> ORGANISM: Homo sapiens

<400> SEQUENCE: 372
uaacugguug aacaacugaa cc                                              22

<210> SEQ ID NO 373
<211> LENGTH: 22
<212> TYPE: RNA
<213> ORGANISM: Homo sapiens

<400> SEQUENCE: 373
cauugcacuu gucucggucu ga                                              22

<210> SEQ ID NO 374
<211> LENGTH: 22
<212> TYPE: RNA
<213> ORGANISM: Homo sapiens

<400> SEQUENCE: 374
aagcugccag uugaagaacu gu                                              22

<210> SEQ ID NO 375
<211> LENGTH: 23
<212> TYPE: RNA
<213> ORGANISM: Homo sapiens

<400> SEQUENCE: 375
cccaguguuc agacuaccug uuc                                             23

<210> SEQ ID NO 376
<211> LENGTH: 21
<212> TYPE: RNA
<213> ORGANISM: Homo sapiens

<400> SEQUENCE: 376
cauaaaguag aaagcacuac u                                               21

<210> SEQ ID NO 377
<211> LENGTH: 22
<212> TYPE: RNA
<213> ORGANISM: Homo sapiens

<400> SEQUENCE: 377
uagcagcaca uaaugguuug ug                                              22

<210> SEQ ID NO 378
<211> LENGTH: 24
<212> TYPE: RNA
<213> ORGANISM: Homo sapiens

<400> SEQUENCE: 378
uugcagcugc cugggaguga cuuc                                            24

<210> SEQ ID NO 379
<211> LENGTH: 21
<212> TYPE: RNA
<213> ORGANISM: Homo sapiens

<400> SEQUENCE: 379
gcgacccaua cuugguuuca g                                               21
```

```
<210> SEQ ID NO 380
<211> LENGTH: 22
<212> TYPE: RNA
<213> ORGANISM: Homo sapiens

<400> SEQUENCE: 380
uucaaguaau ccaggauagg cu                                              22

<210> SEQ ID NO 381
<211> LENGTH: 21
<212> TYPE: RNA
<213> ORGANISM: Homo sapiens

<400> SEQUENCE: 381
uuggccacaa uggguuagaa c                                               21

<210> SEQ ID NO 382
<211> LENGTH: 21
<212> TYPE: RNA
<213> ORGANISM: Homo sapiens

<400> SEQUENCE: 382
gccccugggc cuauccuaga a                                               21

<210> SEQ ID NO 383
<211> LENGTH: 17
<212> TYPE: RNA
<213> ORGANISM: Homo sapiens

<400> SEQUENCE: 383
ucccuguucg ggcgcca                                                    17

<210> SEQ ID NO 384
<211> LENGTH: 23
<212> TYPE: RNA
<213> ORGANISM: Homo sapiens

<400> SEQUENCE: 384
cagugcaaug auauugucaa agc                                             23

<210> SEQ ID NO 385
<211> LENGTH: 22
<212> TYPE: RNA
<213> ORGANISM: Homo sapiens

<400> SEQUENCE: 385
uagcagcaca ucaugguuua ca                                              22

<210> SEQ ID NO 386
<211> LENGTH: 22
<212> TYPE: RNA
<213> ORGANISM: Homo sapiens

<400> SEQUENCE: 386
gcuacuucac aacaccaggg cc                                              22

<210> SEQ ID NO 387
<211> LENGTH: 22
<212> TYPE: RNA
<213> ORGANISM: Homo sapiens

<400> SEQUENCE: 387
gugaaauguu uaggaccacu ag                                              22
```

```
<210> SEQ ID NO 388
<211> LENGTH: 23
<212> TYPE: RNA
<213> ORGANISM: Homo sapiens

<400> SEQUENCE: 388
agcucggucu gaggccccuc agu                                        23

<210> SEQ ID NO 389
<211> LENGTH: 21
<212> TYPE: RNA
<213> ORGANISM: Homo sapiens

<400> SEQUENCE: 389
aacauagagg aaauuccacg u                                          21

<210> SEQ ID NO 390
<211> LENGTH: 23
<212> TYPE: RNA
<213> ORGANISM: Homo sapiens

<400> SEQUENCE: 390
agcagcauug uacagggcua uca                                        23

<210> SEQ ID NO 391
<211> LENGTH: 22
<212> TYPE: RNA
<213> ORGANISM: Homo sapiens

<400> SEQUENCE: 391
caaaccacac uguggaguua ga                                         22

<210> SEQ ID NO 392
<211> LENGTH: 23
<212> TYPE: RNA
<213> ORGANISM: Homo sapiens

<400> SEQUENCE: 392
ucucacacag aaaucgcacc cgu                                        23

<210> SEQ ID NO 393
<211> LENGTH: 22
<212> TYPE: RNA
<213> ORGANISM: Homo sapiens

<400> SEQUENCE: 393
acuccagccc cacagccuca gc                                         22

<210> SEQ ID NO 394
<211> LENGTH: 22
<212> TYPE: RNA
<213> ORGANISM: Homo sapiens

<400> SEQUENCE: 394
uagcaccauu ugaaaucggu ua                                         22

<210> SEQ ID NO 395
<211> LENGTH: 23
<212> TYPE: RNA
<213> ORGANISM: Homo sapiens

<400> SEQUENCE: 395
```
ccucagggcu guagaacagg gcu                                            23

<210> SEQ ID NO 396
<211> LENGTH: 22
<212> TYPE: RNA
<213> ORGANISM: Homo sapiens

<400> SEQUENCE: 396
cugcgcaagc uacugccuug cu                                             22

<210> SEQ ID NO 397
<211> LENGTH: 21
<212> TYPE: RNA
<213> ORGANISM: Homo sapiens

<400> SEQUENCE: 397
uuuugcaccu uuuggaguga a                                              21

<210> SEQ ID NO 398
<211> LENGTH: 22
<212> TYPE: RNA
<213> ORGANISM: Homo sapiens

<400> SEQUENCE: 398
uucccuuugu cauccuucgc cu                                             22

<210> SEQ ID NO 399
<211> LENGTH: 23
<212> TYPE: RNA
<213> ORGANISM: Homo sapiens

<400> SEQUENCE: 399
ucaagagcaa uaacgaaaaa ugu                                            23

<210> SEQ ID NO 400
<211> LENGTH: 22
<212> TYPE: RNA
<213> ORGANISM: Homo sapiens

<400> SEQUENCE: 400
uguaaacauc cuugacugga ag                                             22

<210> SEQ ID NO 401
<211> LENGTH: 23
<212> TYPE: RNA
<213> ORGANISM: Homo sapiens

<400> SEQUENCE: 401
uaagugcuuc cauguuugag ugu                                            23

<210> SEQ ID NO 402
<211> LENGTH: 21
<212> TYPE: RNA
<213> ORGANISM: Homo sapiens

<400> SEQUENCE: 402
cagcagcaca cugugguuug u                                              21

<210> SEQ ID NO 403
<211> LENGTH: 22
<212> TYPE: RNA
<213> ORGANISM: Homo sapiens

<400> SEQUENCE: 403

-continued ugcaacgaac cugagccacu ga          22

<210> SEQ ID NO 404
<211> LENGTH: 22
<212> TYPE: RNA
<213> ORGANISM: Homo sapiens

<400> SEQUENCE: 404
ugugcgcagg gagaccucuc cc          22

<210> SEQ ID NO 405
<211> LENGTH: 22
<212> TYPE: RNA
<213> ORGANISM: Homo sapiens

<400> SEQUENCE: 405
cugcccuggc ccgagggacc ga          22

<210> SEQ ID NO 406
<211> LENGTH: 22
<212> TYPE: RNA
<213> ORGANISM: Homo sapiens

<400> SEQUENCE: 406
aauugcacgg uauccaucug ua          22

<210> SEQ ID NO 407
<211> LENGTH: 22
<212> TYPE: RNA
<213> ORGANISM: Homo sapiens

<400> SEQUENCE: 407
ugagguagua gguuguaugg uu          22

<210> SEQ ID NO 408
<211> LENGTH: 17
<212> TYPE: RNA
<213> ORGANISM: Homo sapiens

<400> SEQUENCE: 408
uaagugcuuc caugcuu          17

<210> SEQ ID NO 409
<211> LENGTH: 22
<212> TYPE: RNA
<213> ORGANISM: Homo sapiens

<400> SEQUENCE: 409
cugccaauuc cauaggucac ag          22

<210> SEQ ID NO 410
<211> LENGTH: 21
<212> TYPE: RNA
<213> ORGANISM: Homo sapiens

<400> SEQUENCE: 410
uuaagacuug cagugauguu u           21

<210> SEQ ID NO 411
<211> LENGTH: 22
<212> TYPE: RNA
<213> ORGANISM: Homo sapiens

```
<400> SEQUENCE: 411
ugagguagua gguugugugg uu                                              22

<210> SEQ ID NO 412
<211> LENGTH: 22
<212> TYPE: RNA
<213> ORGANISM: Homo sapiens

<400> SEQUENCE: 412
uucccuuugu cauccaugc cu                                               22

<210> SEQ ID NO 413
<211> LENGTH: 21
<212> TYPE: RNA
<213> ORGANISM: Homo sapiens

<400> SEQUENCE: 413
ggcuagcaac agcgcuuacc u                                               21

<210> SEQ ID NO 414
<211> LENGTH: 22
<212> TYPE: RNA
<213> ORGANISM: Homo sapiens

<400> SEQUENCE: 414
ucucccaacc cuuguaccag ug                                              22

<210> SEQ ID NO 415
<211> LENGTH: 22
<212> TYPE: RNA
<213> ORGANISM: Homo sapiens

<400> SEQUENCE: 415
ugagguagga gguuguauag uu                                              22

<210> SEQ ID NO 416
<211> LENGTH: 22
<212> TYPE: RNA
<213> ORGANISM: Homo sapiens

<400> SEQUENCE: 416
uguaaacauc cuacacucag cu                                              22

<210> SEQ ID NO 417
<211> LENGTH: 21
<212> TYPE: RNA
<213> ORGANISM: Homo sapiens

<400> SEQUENCE: 417
cauuauuacu uuugguacgc g                                               21

<210> SEQ ID NO 418
<211> LENGTH: 22
<212> TYPE: RNA
<213> ORGANISM: Homo sapiens

<400> SEQUENCE: 418
ugauauguuu gauauauuag gu                                              22

<210> SEQ ID NO 419
<211> LENGTH: 23
<212> TYPE: RNA
<213> ORGANISM: Homo sapiens
```

-continued

```
<400> SEQUENCE: 419
ccugcagcga cuugauggcu ucc                                            23

<210> SEQ ID NO 420
<211> LENGTH: 22
<212> TYPE: RNA
<213> ORGANISM: Homo sapiens

<400> SEQUENCE: 420
ugagguagua gguuguauag uu                                             22

<210> SEQ ID NO 421
<211> LENGTH: 22
<212> TYPE: RNA
<213> ORGANISM: Homo sapiens

<400> SEQUENCE: 421
ucccugagac ccuaacuugu ga                                             22

<210> SEQ ID NO 422
<211> LENGTH: 22
<212> TYPE: RNA
<213> ORGANISM: Homo sapiens

<400> SEQUENCE: 422
ucugggcaac aaagugagac cu                                             22

<210> SEQ ID NO 423
<211> LENGTH: 21
<212> TYPE: RNA
<213> ORGANISM: Homo sapiens

<400> SEQUENCE: 423
acucuuuccc uguugcacua c                                              21

<210> SEQ ID NO 424
<211> LENGTH: 23
<212> TYPE: RNA
<213> ORGANISM: Homo sapiens

<400> SEQUENCE: 424
ucggggauca ucaugucacg aga                                            23

<210> SEQ ID NO 425
<211> LENGTH: 21
<212> TYPE: RNA
<213> ORGANISM: Homo sapiens

<400> SEQUENCE: 425
gugggcgggg gcaggugugu g                                              21

<210> SEQ ID NO 426
<211> LENGTH: 22
<212> TYPE: RNA
<213> ORGANISM: Homo sapiens

<400> SEQUENCE: 426
ugcccugugg acucaguucu gg                                             22

<210> SEQ ID NO 427
<211> LENGTH: 20
<212> TYPE: RNA
```

```
<213> ORGANISM: Homo sapiens

<400> SEQUENCE: 427
ccauggaucu ccaggugggu                                              20

<210> SEQ ID NO 428
<211> LENGTH: 23
<212> TYPE: RNA
<213> ORGANISM: Homo sapiens

<400> SEQUENCE: 428
aucccuugca ggggcuguug ggu                                          23

<210> SEQ ID NO 429
<211> LENGTH: 22
<212> TYPE: RNA
<213> ORGANISM: Homo sapiens

<400> SEQUENCE: 429
ugagguagua guuugugcug uu                                           22

<210> SEQ ID NO 430
<211> LENGTH: 20
<212> TYPE: RNA
<213> ORGANISM: Homo sapiens

<400> SEQUENCE: 430
cggcucuggg ucugugggga                                              20

<210> SEQ ID NO 431
<211> LENGTH: 22
<212> TYPE: RNA
<213> ORGANISM: Homo sapiens

<400> SEQUENCE: 431
agucauugga ggguuugagc ag                                           22

<210> SEQ ID NO 432
<211> LENGTH: 22
<212> TYPE: RNA
<213> ORGANISM: Homo sapiens

<400> SEQUENCE: 432
uggugggcac agaaucugga cu                                           22

<210> SEQ ID NO 433
<211> LENGTH: 22
<212> TYPE: RNA
<213> ORGANISM: Homo sapiens

<400> SEQUENCE: 433
cguguucaca gcggaccuug au                                           22

<210> SEQ ID NO 434
<211> LENGTH: 27
<212> TYPE: RNA
<213> ORGANISM: Homo sapiens

<400> SEQUENCE: 434
cacuguaggu gauggugaga gugggca                                      27

<210> SEQ ID NO 435
<211> LENGTH: 21
```

-continued

<212> TYPE: RNA
<213> ORGANISM: Homo sapiens

<400> SEQUENCE: 435
auugacacuu cugugaguag a                                     21

<210> SEQ ID NO 436
<211> LENGTH: 22
<212> TYPE: RNA
<213> ORGANISM: Homo sapiens

<400> SEQUENCE: 436
uggaauguaa agaaguaugu au                                    22

<210> SEQ ID NO 437
<211> LENGTH: 22
<212> TYPE: RNA
<213> ORGANISM: Homo sapiens

<400> SEQUENCE: 437
gcccgcgugu ggagccaggu gu                                    22

<210> SEQ ID NO 438
<211> LENGTH: 22
<212> TYPE: RNA
<213> ORGANISM: Homo sapiens

<400> SEQUENCE: 438
uuugugaccu gguccacuaa cc                                    22

<210> SEQ ID NO 439
<211> LENGTH: 22
<212> TYPE: RNA
<213> ORGANISM: Homo sapiens

<400> SEQUENCE: 439
ugggucuuug cgggcgagau ga                                    22

<210> SEQ ID NO 440
<211> LENGTH: 20
<212> TYPE: RNA
<213> ORGANISM: Homo sapiens

<400> SEQUENCE: 440
cugcaaaggg aagcccuuuc                                       20

<210> SEQ ID NO 441
<211> LENGTH: 21
<212> TYPE: RNA
<213> ORGANISM: Homo sapiens

<400> SEQUENCE: 441
acggugcugg auguggccuu u                                     21

<210> SEQ ID NO 442
<211> LENGTH: 21
<212> TYPE: RNA
<213> ORGANISM: Homo sapiens

<400> SEQUENCE: 442
agggagggac gggggcugug c                                     21

<210> SEQ ID NO 443

```
<211> LENGTH: 22
<212> TYPE: RNA
<213> ORGANISM: Homo sapiens

<400> SEQUENCE: 443
gcuauuucac gacaccaggg uu                                              22

<210> SEQ ID NO 444
<211> LENGTH: 21
<212> TYPE: RNA
<213> ORGANISM: Homo sapiens

<400> SEQUENCE: 444
aaagcgcuuc ccuucagagu g                                               21

<210> SEQ ID NO 445
<211> LENGTH: 22
<212> TYPE: RNA
<213> ORGANISM: Homo sapiens

<400> SEQUENCE: 445
uccuucauuc caccggaguc ug                                              22

<210> SEQ ID NO 446
<211> LENGTH: 22
<212> TYPE: RNA
<213> ORGANISM: Homo sapiens

<400> SEQUENCE: 446
ugagguagua guuuguacag uu                                              22

<210> SEQ ID NO 447
<211> LENGTH: 22
<212> TYPE: RNA
<213> ORGANISM: Homo sapiens

<400> SEQUENCE: 447
gguggcccgg ccgugccuga gg                                              22

<210> SEQ ID NO 448
<211> LENGTH: 22
<212> TYPE: RNA
<213> ORGANISM: Homo sapiens

<400> SEQUENCE: 448
cugcaaugua agcacuucuu ac                                              22

<210> SEQ ID NO 449
<211> LENGTH: 21
<212> TYPE: RNA
<213> ORGANISM: Homo sapiens

<400> SEQUENCE: 449
uaccacaggg uagaaccacg g                                               21

<210> SEQ ID NO 450
<211> LENGTH: 22
<212> TYPE: RNA
<213> ORGANISM: Homo sapiens

<400> SEQUENCE: 450
acuuuaacau ggaagugcuu uc                                              22
```

```
<210> SEQ ID NO 451
<211> LENGTH: 23
<212> TYPE: RNA
<213> ORGANISM: Homo sapiens

<400> SEQUENCE: 451
gcgaggaccc cucgggucu gac                                              23

<210> SEQ ID NO 452
<211> LENGTH: 22
<212> TYPE: RNA
<213> ORGANISM: Homo sapiens

<400> SEQUENCE: 452
ccuauucuug auuacuuguu uc                                              22

<210> SEQ ID NO 453
<211> LENGTH: 20
<212> TYPE: RNA
<213> ORGANISM: Homo sapiens

<400> SEQUENCE: 453
ucacuguuca gacaggcgga                                                 20

<210> SEQ ID NO 454
<211> LENGTH: 22
<212> TYPE: RNA
<213> ORGANISM: Homo sapiens

<400> SEQUENCE: 454
caaaaaccac aguuucuuuu gc                                              22

<210> SEQ ID NO 455
<211> LENGTH: 23
<212> TYPE: RNA
<213> ORGANISM: Homo sapiens

<400> SEQUENCE: 455
ucccuguccu ccaggagcuc acg                                             23

<210> SEQ ID NO 456
<211> LENGTH: 22
<212> TYPE: RNA
<213> ORGANISM: Homo sapiens

<400> SEQUENCE: 456
aggcauugac uucucacuag cu                                              22

<210> SEQ ID NO 457
<211> LENGTH: 20
<212> TYPE: RNA
<213> ORGANISM: Homo sapiens

<400> SEQUENCE: 457
ucguuugccu uuuucugcuu                                                 20

<210> SEQ ID NO 458
<211> LENGTH: 21
<212> TYPE: RNA
<213> ORGANISM: Homo sapiens

<400> SEQUENCE: 458
gugccagcug caguggggga g                                               21
```

```
<210> SEQ ID NO 459
<211> LENGTH: 22
<212> TYPE: RNA
<213> ORGANISM: Homo sapiens

<400> SEQUENCE: 459
ucaaaacuga ggggcauuuu cu                                              22

<210> SEQ ID NO 460
<211> LENGTH: 26
<212> TYPE: RNA
<213> ORGANISM: Homo sapiens

<400> SEQUENCE: 460
aaguaguugg uuuguaugag augguu                                          26

<210> SEQ ID NO 461
<211> LENGTH: 20
<212> TYPE: RNA
<213> ORGANISM: Homo sapiens

<400> SEQUENCE: 461
acugccccag gugcugcugg                                                 20

<210> SEQ ID NO 462
<211> LENGTH: 22
<212> TYPE: RNA
<213> ORGANISM: Homo sapiens

<400> SEQUENCE: 462
caaagugccu cccuuuagag ug                                              22

<210> SEQ ID NO 463
<211> LENGTH: 22
<212> TYPE: RNA
<213> ORGANISM: Homo sapiens

<400> SEQUENCE: 463
cuuucagucg gauguuuaca gc                                              22

<210> SEQ ID NO 464
<211> LENGTH: 22
<212> TYPE: RNA
<213> ORGANISM: Homo sapiens

<400> SEQUENCE: 464
aagcccuuac cccaaaaagu au                                              22

<210> SEQ ID NO 465
<211> LENGTH: 23
<212> TYPE: RNA
<213> ORGANISM: Homo sapiens

<400> SEQUENCE: 465
acugcccuaa gugcuccuuc ugg                                             23
```